US011732262B2

(12) United States Patent
Luangsay et al.

(10) Patent No.: US 11,732,262 B2
(45) Date of Patent: Aug. 22, 2023

(54) USE OF FUBP1 INHIBITORS FOR TREATING HEPATITIS B VIRUS INFECTION

(71) Applicants: Hoffmann—La Roche, Inc., Little Falls, NJ (US); CENTRE LEON BERARD, Lyons (FR); UNIVERSITE CLAUDE BERNARD LYON I, Villeurbanne (FR); CENTRE NATIONAL DE LA RECHERCHE SCIENTIFIQUE, Paris (FR); INSERM—INSTITUT NATIONAL DE LA SANTE ET DE LA RECHERCHE MEDICALE, Paris (FR)

(72) Inventors: Souphalone Luangsay, Basel (CH); Barbara Testoni, Lyons (FR); Fabien Zoulim, Lyons (FR); Soren Ottosen, Horsholm (DK); Lykke Pedersen, Horsholm (DK)

( * ) Notice: Subject to any disclaimer, the term of this patent is extended or adjusted under 35 U.S.C. 154(b) by 0 days.

(21) Appl. No.: 17/063,610

(22) Filed: Oct. 5, 2020

(65) Prior Publication Data

US 2021/0024934 A1 Jan. 28, 2021

Related U.S. Application Data

(63) Continuation of application No. PCT/EP2019/058664, filed on Apr. 5, 2019.

(30) Foreign Application Priority Data

Apr. 5, 2018 (EP) .................................... 18165897

(51) Int. Cl.

| | |
|---|---|
| ***C12N 15/113*** | (2010.01) |
| ***A61P 31/20*** | (2006.01) |
| ***A61K 31/4745*** | (2006.01) |
| ***A61K 31/496*** | (2006.01) |
| ***A61K 31/7125*** | (2006.01) |

(52) U.S. Cl.

CPC ........ *C12N 15/113* (2013.01); *A61K 31/4745* (2013.01); *A61K 31/496* (2013.01); *A61K 31/7125* (2013.01); *A61P 31/20* (2018.01)

(58) Field of Classification Search

None

See application file for complete search history.

(56) References Cited

U.S. PATENT DOCUMENTS 5,580,760 A * 12/1996 Levens .............. C07K 14/4705 435/372
8,349,809 B2 1/2013 Brown
8,513,207 B2 8/2013 Brown
2005/0238706 A1 10/2005 Ahmad et al.
2008/0113351 A1 * 5/2008 Naito ........................ A61P 5/26 536/23.1

FOREIGN PATENT DOCUMENTS

EP 2742135 A1 6/2014
WO 93/07883 A1 4/1993
WO 98/39352 A1 9/1998
WO 99/14226 A2 3/1999
WO 2000/047599 A1 8/2000
WO 00/66604 A2 11/2000
WO 01/23613 A1 4/2001
WO 2004017940 A2 3/2004
WO 2004027061 A1 4/2004
WO 2004/046160 A2 6/2004
WO 2005/014806 A2 2/2005
WO 2006/082053 A1 8/2006
WO 2007/031091 A2 3/2007
WO 2007/090071 A2 8/2007
WO 2007/134181 A2 11/2007
WO 2007/146511 A2 12/2007
WO 2008/113832 A2 9/2008
WO 2008/150729 A2 12/2008
WO 2008/154401 A2 12/2008
WO 2009/006478 A2 1/2009
WO 2010/036698 A1 4/2010
WO 2010/077578 A1 7/2010
WO 2011/017521 A2 2/2011
WO 2011/047312 A1 4/2011
WO 2011/156202 A1 12/2011
WO 2012/024170 A2 2/2012
WO 2012/055362 A1 5/2012
WO 2012/143379 A1 10/2012
WO 2012/145697 A1 10/2012
WO 2013/003520 A1 1/2013
WO 2013/033230 A1 3/2013
WO 2013/154798 A1 10/2013
WO 2013/159109 A1 10/2013
WO 2014/076196 A1 5/2014
WO 2014/179620 A1 11/2014
WO 2014/179629 A2 11/2014
WO 2014/207232 A1 12/2014
WO 2015/173208 A2 11/2015
WO 2016/055601 A1 4/2016
WO 2016054421 A1 4/2016
WO 2016100975 A1 6/2016
WO 2016/127002 A1 8/2016

(Continued)

OTHER PUBLICATIONS

Dixit et al. J Virol 89:7905-7921, pp. 1-28 (Year: 2015).*

(Continued)

*Primary Examiner* — Brian Whiteman

(57) ABSTRACT

The present invention relates to a FUBP1 inhibitor for use in treatment of an HBV infection, in particular a chronic HBV infection. The invention in particular relates to the use of FUBP1 inhibitors for destabilizing cccDNA, such as HBV cccDNA. The invention also relates to nucleic acid molecules, such as oligonucleotides including siRNA, shRNA and antisense oligonucleotides, which are complementary to FUBP1 and capable of reducing a FUBP1 mRNA. Also comprised in the present invention is a pharmaceutical composition and its use in the treatment and/or prevention of a HBV infection.

10 Claims, 6 Drawing Sheets

Specification includes a Sequence Listing.

(56) References Cited

FOREIGN PATENT DOCUMENTS

| | | | |
|---|---|---|---|
| WO | 2017/015175 | A1 | 1/2017 |
| WO | 2017/027350 | A2 | 2/2017 |
| WO | 2017/178656 | A1 | 10/2017 |
| WO | 2017/216390 | A1 | 12/2017 |
| WO | 2017216391 | A1 | 12/2017 |
| WO | 2019/193165 | A1 | 10/2019 |

OTHER PUBLICATIONS

Zhang et al. J. Virol 82:5761-5773, pp. 1-27 (Year: 2008).*
Szabo et al. Pathology Oncology Research Vo. 10, pp. 5-11 (Year: 2004).*
Ansel et al., "Pharmaceutical Dosage Forms and Drug Delivery Systems," Williams & Wilkins, 6th Edition pp. 105-116, 194-200; 1456-1457 (1995) (41 pages).
B Hirt, "Selective extraction of polyoma DNA from infected mouse cell cultures", J Mol Biol., vol. 26(2), Jun. 1967, pp. 365-369. doi: 10.1016/0022-2836(67)90307-5.
Bastin, R.J. et al., Salt Selection and Optimisation Procedures for Pharmaceutical New Chemical Entities, Organic Process Research & Development, (2000), vol. 4, pp. 427-435.
Bergstrom DE, "Unnatural nucleosides with unusual base pairing properties", Current Protocols in Nucleic Acid Chemistry, 2009, Suppl. 37 1.4.1, 32 pgs.
Biessen et al., "Targeted delivery of oligodeoxynucleotides to parenchymal liver cells in vivo," Biochem J., 1999, vol. 340, pp. 783-792, 10 pages.
Caruthers et al., "Chemical Synthesis of Deoxyoligonucleotides by the Phosphoramidite Method," Methods Enzymol. 154: 287-313 (1987) (27 pages).
Chang, Mei-Hwei, "Hepatitis B virus infection," Elsevier, Seminars in Fetal Neonatal Medicine, 2007, vol. 12, pp. 160-167, 8 pages.
Dawei Cai, et al., "A southern blot assay for detection of hepatitis B virus covalently closed circular DNA from cell cultures", Methods Mol Biol. vol. 1030, 2013, pp. 151-161, doi: 10.1007/978-1-62703-484-5_13.
Deleavey, GF et al., "Designing Chemically Modified Oligonucleotides for Targeted Gene Silencing," Chemistry and Biology, 2012, vol. 19(8), pp. 937-954, 18 pages.
Duff, et al., "Intrabody tissue-specific delivery of antisense conjugates in animals: ligand-linker—antisense oligomer conjugates," Methods Enzvmol, Dec. 3, 20001, 313:297-321.
Freier, S.M. et al., The ups and downs of nucleic acid duplex stability: structure-stability studies on chemically-modified DNA:RN A duplexes, Nucleic Acids Research, 1997, vol. 25(22), pp. 4429-4443.
Gennaro, AR et al., "Remington's Pharmaceutical Sciences," Mack Publishing Company, 17th ed., 1985, 9 pages.
Guo et al. 2016 Sci Rep 6: 2552.
Hansen et al., "Entropy titration. A Calorimetric Method for the Determination of t..G0 (K), t..h0 and t..S0 1, "Chemical Communications. 36-38, (1965) (3 pages).
Hirao, I et al., "Natural versus Artificial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.
Holdgate et al., "Measurements of Binding Thermodynamics in Drug Discovery," Drug Discov Today. 10(22):1543-1550 (2005) (8 pages).
International Preliminary Report on Patentability received for PCT Patent Application No. PCT/EP2019/058664 , dated Oct. 15, 2020, 8 pages.
Jobst et al., "Selective sugar binding to the carbohydrate recognition domains of the rat hepatic and macrophage asialoglycoprotein receptors," J Biol Chem, Mar. 22, 1996, 271(12):6686-6693.
Ladner et al. 1997 Antimicrobial Agents and Chemotherapy 41(8) 171-1720.
Langer, R, "New Methods of Drug Delivery," Science, 1990, vol. 249, issue 4976, pp. 1527-1533, 7 pages.
Masakazu Kakuni, et al., "Chimeric Mice with Humanized Livers: A Unique Tool for in Vivo and in Vitro Enzyme Induction Studies", Int. J. Mol. Sci., vol. 15, 2014, pp. 58-74; doi: 10.3390/ijms15010058.
McTigue et al., "Sequence-Dependent Thermodynamic Parameters for Locked Nucleic Acid (LNA)-DNA Duplex Formation," Biochemistry. 43(18):5388-5405 (2004) (18 pages).
Mergny, JL et al., "Analysis of Thermal Melting Curves," Oligonucleotides, 2003, vol. 13(6), pp. 515-537, 23 pages.
Mitsuoka et al., "A bridged nucleic acid, 2',4'-BNA COC: synthesis of fully modified oligonucleotides bearing thymine, 5 methylcytosine, adenine and guanine 2',4'-BNA COC monomers and RNA-selective nucleic-acid recognition," Nucleic Acids Research, Mar. 2009, 37(4):1225-1238, 14 pgs.
Morita et al., "2'-O,4'-C-Ethylene-Bridged Nucleic Acids (ENA): Highly Nuclease-Resistant and Thermodynamically Stable Oligonucleotides for Antisense Drug," Bioorg Med Chem Lett. 12(1): 73-76 (2002) (4 pages).
Ramdzan et al., 2-D DIGE profiling of hepatocellular carcinoma tissues identified isoforms of far upstream binding protein (FUBP) as novel candidates in liver carcinogenesis, 2008, Proteomics, vol. 8, pp. 5086-5096, 11 pages.
Santa Lucia, JJr., "A unified view of polymer, dumbbell, and oligonucleotide DNA nearest-neighborthermodynamics," Proc Nall Acad Sci USA, 1998, 95(4), pp. 1460-1465, 6 pages.
Seth et al., "Synthesis and Biophysical Evaluation of 2',4'-Constrained 2'0-Methoxyethyl and 2',4'- Constrained 2'0-Ethvl Nucleic Acid Analo??lles," J. Org. Chem., 2010, 75:1569-1581.
Soan and Yang, "Construction of shRNA lentiviral vector", North American Journal of Medical Sciences, vol. 2. No. 12, Dec. 2010.
Stephen Locarnini, et al., "Molecular genetics of HBV infection", Review Antivir Ther., vol. 15 Suppl 3, 2010, pp. 3-14. doi: 10.3851/IMP1619.
Sugimoto, N. et al., Thermodynamic Parameters to Predict Stability of RNA/DNA Hybrid Duplexes, Biochemistry, 1995, vol. 34(35), pp. 11211-11216.
Tringali et al. 2012 Journal of Pharmacy and Pharmacology vol. 64, p. 360-365.
Uhlmann, E., Recent advances in the medicinal chemistry of antisense olignonucleotides, Current Opinion in Drug Discovery & Development, 2000, vol. 3, No. 2, pp. 203-213.
Wan et al., "The Medicinal Chemistry of Therapeutic Oligonucleotides," J Med Chem. 59(21):9645-9667 (2016) (23 pages).
Yan, et al., "HBVcircle: A novel tool to investigate hepatitis B virus covalently closed circular DNA", J Hepatol . Jun. 2017;66(6):1149-1157. doi: 10.1016/j.jhep.2017.02.004. Epub Feb. 14, 2017.
Alweiss et al., The Role of cccDNA in HBV Maintenance, 2017, Viruses, vol. 9, No. 156, pp. 1-12, 13 pages.
Hauck et al., Pyrazolo[1,5a]pyrimidines as a new class of FUSE binding protein 1 (FUBP1) inhibitors, Bioorganic & Medicinal Chemistry, 2016, vol. 24, No. 22, pp. 5717-5729, 13 pages.
Hosseini et al., Camptothecin and its analog SN-38, the active metabolite of irinotecan, inhibit binding of the transcriptional regulator and oncoprotein FUBP1to its DNA target sequence FUSE, Biochemical Pharmacology, 2017, vol. 146, pp. 53-62, 10 pages.
Huth et al., NMR-Driven Discovery of Benzoylanthranilic Acid Inhibitors of Far Upstream Element Binding Protein Binding to the Human Oncogene c-myc Promoter, 2004, J Med. Chem., vol. 47, pp. 4851-4857, 7 pages.
Rabenhorst et al., Overexpression of the Far Upstream Element Binding Protein 1 in Hepatocellular Carcinoma is Required for Tumor Growth, 2009, Hepatology, vol. 50, pp. 1121-1129, 9 pages.
Sun et al., Involvement of PUF60 in Transcriptional and Post-transcriptional Regulation of Hepatitis B Virus Pregenomic RNA Expression, 2017, Scientific Reports, vol. 7:12874, pp. 1-15, 15 pages.
Xiong et al., Fuse-binding protein 1 is a target of the EZH@ inhibitor GSK343, in osteosarcoma cells, 2016, International Journal of Oncology, vol. 49, pp. 623-628, 6 pages.

(56) References Cited

OTHER PUBLICATIONS

Zhang et al., Far upstream element binding protein 1: a commander of transcription, translation and beyond, 2013, Oncogene, vol. 32, pp. 2907-2916, 10 pages.
Zhang et al., Knockdown of FUSE binding protein 1 enhances the sensitivity of epithelial ovarian cancer cells to carboplatin, 2017, Oncology Letters, vol. 14, pp. 5819-5824, 5 pages.
Zubaidah: "2-D DIGE profiling of hepatocellular carcinoma tissues identified isoforms of far upstream binding proteins (FUBP) as novel candidates in liver carcinogenesis," Proteomics, 2008, vol. 8, pp. 5086-5096, 11 pages.
International Search Report for International Application No. PCT/EP2019/058664, dated Jul. 2, 2019, 3 pages.
Malz et al., "Overexpression of far upstream element binding proteins: a mechanism regulating proliferation and migration in liver cancer cells" Hepatology, vol. 50, Issue 4, 2009, pp. 1130-1139.
Scoles et al., "Antisense oligonucleotides: A primer", Neurol Genet, 5(2):e323, Apr. 1, 2019, 10 pages.
Swayze et al., "Antisense oligonucleotides containing locked nucleic acid improve potency but cause significant hepatotoxicity in animals", Nucleic Acids Res, vol. 35(2), 2007, pp. 687-700.
Flanagan W. M et al. Effects of oligonucleotide length, mismatches and mRNA levels on C-5 propyne-modified antisense potency. Nucleic Acids Research, vol. 24, Issue 15, Aug. 1, 1996, pp. 2936-2941, https://doi. org/10.1093/nar/24.15.2936.
FUBP1 far upstream element binding protein 1 [Homo sapiens (human)], www.ncbi.nlm.nih.gov/gene/8880, Mar. 16, 2023, 8 pgs.
Karaki et al., Antisense Oligonucleotides, A Novel Developing Targeting Therapy. Antisense Therapy. 2019, doi: 10.5772/intechopen.82105, 2018, 18 pgs.
Ozcan et al., Preclinical and clinical development of siRNA-based therapeutics. Advanced Drug Delivery Reviews, 2015, 87, 108-119. doi: 10.1016/j.addr.2015.01.007, 26 pgs.
Holen, et al., Positional effects of short interfering RNAs targeting the human coagulation trigger Tissue Factor. Nucleic Acids Research, 2002, v.30, No. 8, p. 1757-1766. doi:10.1093/nar/30.8.1757, see p. 1761 left col. par.3, p. 1765 left col. par. 2, 10 p. .
Reynolds et al., Rational siRNA design for RNA Interference. Nature Biotechnology, 2004, v.22, p. 326-330, see p. 326 left col. par.1, fig.1, 5 p. .

* cited by examiner

Conj 1=

Conj 2=

SEQUENCE LISTING

<160> NUMBER OF SEQ ID NOS: 90

<210> SEQ ID NO 1
<211> LENGTH: 35056
<212> TYPE: DNA
<213> ORGANISM: homo sapiens

<400> SEQUENCE: 1

```
gcgcaagaat gtaatagagc ttcgacggcc gccatttct ttctttctta gctgttagct      60

gagaggaagt ctctgaacag gcggcagcgg ctcttatagt gcaaccatgg cagactattc     120

aacagtgcct cccccctctt ctggctcagc tggtggcggt ggtggcggcg gtggtggtgg     180

aggagttaac gacgctttca aagatgcact gcagagagcc cggcaggtaa gtgtggaccg     240

cgcggcggaa tcccgaaagc tcacggtaat tggccgctga ctgagtaggc cgctacccct     300

aagcgcatga ggaagaggaa agaggtgttc ttccgggctg aaatgtgaag agacacgttt     360
```

-continued

```
ccccatgttg gtaataacga ttagagacca gaacccagtt ttgtgttctt ggtgcctaat    420
ccacttagaa ccccgacgcg tgctacgcaa agaaggcctg aagtctttct cccgcttctg    480
cggcactcgc gtgtctccag tgagctagtt tagataaaga tcctcttcca ggggataaag    540
cgcagttagt ttcacacaat ttaatggaag gttctggtaa tgagtttggg aaagaactag    600
ggtctgtcct ggagccatag caagggaagg gatttatcat taaagtagcc tttacagctc    660
atttccgttc tctctcgcaa ttaaaaccgc tttcagtacc attcaccgtc acacctctac    720
aaggaaggga cttgaaagca gcctttttct gggcgggatt tacgtgtcag tctgttccac    780
cagtccgccc cccttatttc tcaaaatggc ctcaggccca ttataccaga ggtttcaatt    840
tgaatctgcc tctcagttca gagtcgtaaa ctgaccagac ctctttgtat tacgtagtgc    900
gtgcatttgc cctgaaggca ccactttccc agacgaaagc tgttaaaata gtgcgtgtat    960
tccaggaaaa taaaagatac cttaatttga actttacatt cttagatagt cccctaatat   1020
atttaacatt tcaaaatgta tggtgttggt atagatttgc atgtaagcaa aagaatccta   1080
ttctctgtga cactatgcat attgtactag gtgctgggca tttttacta gttttaagct   1140
aatgataatt agaaaccagt gttgtgctgt gttttcgttg cattaggagt tcacttagtt   1200
aactttttac cgggacagtt gaaggaacat tgagtcaaaa ttagaattca taaaatccgt   1260
tgtaacacat ctaatgtgaa cgcattataa acatgtacct gtactttttt ataaccagaa   1320
atactaggag tagtcaacaa aaggtcatca ttaatattag ttctgcggtt ttttccacgt   1380
aatttaagaa attctgaaca tgtttagcaa caagcatata actatgacaa acactcttag   1440
cgtgttttat tagattgatt tgtaaaactt aagggaacta ttttatttac tggaaccaac   1500
tattttattt taccagaacc agcacattgg attaattggt atcgcacact gtaggtagat   1560
actggagttt tgttttgttt tgtttgagac ggagtctccc tctgtcgccc agactggagt   1620
gcagtggtgc gatctcgtcc cactgcaacc tctgcctccc ggcttcaagc aattctcctg   1680
cctcagcctc ccgagtagct gggattacag gcgcccgcca ccatgcccgg ctaatttttt   1740
gtgttttttt tgtttgtttg tttgttttca gtagagacag ggtttcacca tgctggccag   1800
gctggtctcg aactcctgac ctcgtgatcc gcccgtcttg gcctcccaaa gctgggatta   1860
caggcgtgag ccgctgcgcc cggccttgtt ttttttcgtt tgtttgtttt aatgcatgaa   1920
ttgtttccta ctaagaagct atgatatagt tccttgacca aatgcagatg aacaggatta   1980
tctgattaat actttaacga gagcagacaa aatatggata tttaattcat ccacttgctt   2040
tataagtgtt tatagagttt gttaggaggg gatgcccaat ttcctaagta aaggtgatat   2100
atgagcaaga cattataaaa tgaaagagag tttggccagt gaagaaaaga agcagcatgc   2160
gcagaggtgt ggggacttga gggaatggca aggacccaga agtgaagtcg ctagaagatg   2220
ggggtgggag gacgtgaaac gaggcaagga aaggtacaag cggatccaga tactggaaga   2280
ccttgtgttg caatgcttta attaaaaatt ggatttcagg ccgggtacgg tggctcacgc   2340
ctgtagtccc agcactttgg gaggctgagg caggcagatc acttgaagtc ggagtttaag   2400
accagcctgg ccaacatggt gaaaccccat ctttacaaaa aatacaaaaa gtagccgggc   2460
ttggtggcct gtgcctgtag tcctagctac ttgggaggct gaggcacaag aaccgcttca   2520
acctgggaag tggaggttgc agtgagtgga gatcacgctg ctgcactcca gcctggtcat   2580
agagcgagac cctgtctcaa aaaaaaaaaa attggatttt attattaggc taagccataa   2640
tttctttata cttcttaaaa tatagaaatt gttggcaaat tgtgaaattt attgttgtat   2700
aatgctaata gatcagttgt cctgatgtct ttgctgtaat gatttcttta taaaaatgat   2760
```

-continued

```
cttaaatctg agctccctaa ctttagtttt tgcctggaat tacccattac atttgatgat   2820
atctctaaat gtcagttgta gctgttactc tgatgatata agtggaatat acagaagcgt   2880
acttagacaa aagttaggtt aatatctgaa ctacttcctc cttgtgtatt taagagaata   2940
ttgacttaag tttctagaat cctcaactaa tcctaagttt attttctttg tctagaatac   3000
tatgctgttt ttgtttttgg aaggaagaga tataggcata gtttcctgct ctcaaggagc   3060
ttcaaaggct gtaccagtgg ggatgccatt ggtattttta gctggatagt tgttattcag   3120
aaaagcagga caagtaatta tgattcctgg tccgtacctg gtaatgccag taatgttaac   3180
tctagctggt tgttgacatc tggtcattta gttgccaatc ttcttttttt ttttctggct   3240
tttatgtgaa atttttagat ttttataata tcctgagcta aattcaacac agggacacca   3300
gattgctgct ttagttcagg gtttccagcc tgtgcactta agaaatttat ttttgtgtat   3360
atcaagctgt aactccagag attgggattg tttgattggg tctttagcag tggtactaat   3420
agcaacttct gtctctagaa cattggaaaa ttaaaatgtg tttatctacc gtttttttcc   3480
tcgaggttat atgaaggtag aaatgaatca gactagatga ttagctaagc gagactatta   3540
accctcatcc cttcccctct agacaactat gaaattagtc attatgtatt cgatccttct   3600
tgcagtctct tctctgacag ttataaaagt gatttaggct gcataatgtt gtttgaatga   3660
aatgaaaata tagactagag ctgttttttt ttttatttcc atcagtctct tcagtgaaaa   3720
ctaacatttg agcatgattc ttttttttaaa tcattttgtg acagtttagc aaggcttgtg   3780
ataagcaagt tatggtatgg taatatttct agtgtccacg tttcttcaca tgtctggtgt   3840
atgggaacta ctaactccat caggaccttg cctatagtag gtactcaaca tttactgaat   3900
taaatcaata aacattttta atgaattaca gtacaagtca gacctctgta tctgtgggct   3960
ctgcatctgc aaattcagcc aaccatggat cagaaatatt agaaaaatgg aagaacagtc   4020
cagcaataca agtaatatga ataaaaacaa tacaacaact atgtacattg tatcaggtat   4080
tataagtaat ttagagatgc tttaagtata ctgaaggatt tgcgtaggtt atatgcagat   4140
actgtaccat tttatataag gaacttgagc atctgtggat tttggtattt gcatggttcc   4200
tggaaccaat cccccaggga tactgaggga ctatagttga tcataccacc tgattttaga   4260
gattttctga gtctcagaag ttaattaagt aaactacaat agtctgttct taacctcgga   4320
ggatacattc caagaacctc agtgaatatc tgaaaccaca gatagtattg aatccaatat   4380
atacacggta atattttttc ctatacatat gtatctataa agtttaaatt ctaaatcaga   4440
cacagtatta acgataataa taaattagtg caagactggg catagtggtt cacacctata   4500
atcttaacac tttaactatg acgttgtctt tgaaaagaaa tcagctagcc aaggtggctc   4560
atggctgtaa tcctagtgtt ttgagaagct aagtcaggaa gattgcttga gcccaggagt   4620
ctgagaccac cctaggcaac atggtgaaac cctgtttcta taaaaaatac caaaaaatag   4680
gctgggcgcg gtggctcacg cctgtaatct cagcactttg ggaggctgag gcgggtggat   4740
cacgaggtca ggagattgag accgtcctgg ctaacacggt gaaaccccgt ctctactaaa   4800
aatacaaaaa attagccggg agtagtgggc gcctgtagtc ccagctactc aggagactga   4860
ggcaggagaa tggcgtgaac ccgggaggtg gagcttgcag tgaaccgaga tcgcgccact   4920
gcatgccagc ctgggcaaca gagcgagact ccatctcaaa aaaaaaaaaa aaaaaaccaa   4980
aaaattagcc agacgtggtg gtgcttgcct gtagtaccag ctatccagaa ggctgaggtg   5040
ggaggattgc ttgaacttgg gaggtcaagt ctagaatgtt gacaatgttg ggtcctttat   5100
gtagttgcat aagtgagcca tgatcgtgcc actgcactac atccttgggc aacagcctga   5160
```

-continued

```
ccctgtctca aaattttaat ttaattaaaa aaataaaata gaacaattac aacaatacac   5220
tgtattactg gacaagaagg gcaaatttaa aaaaaattaa accaatatgc tataataagt   5280
tatatgaatg aggggaccct cccctacccc agaatatctg attgtactat atcataggta   5340
actgaaaccg tgaagagcaa aaactgaaga taaagagact actgtgtctt ttaagtttct   5400
tttcaactcc caaattcttg gatttctcac ctcttggctt cctcaataga ggtgagaaat   5460
gttaaagtag tgaaaacagg aaaaataact tactcattca agaagtagat aatggtccag   5520
atggaaagct tgaattattt ttgtaaaact aaaattaaat aaagtagcca ggcatggtgg   5580
cttacgcctg taatcccagc actttgggag gctgaggcgg gtggatcact tgcggtcagg   5640
agttcaagac cagcctggcc aacaaggtga aaccctgtct atactaaaaa tacaaaaatt   5700
agctgagcat ggtggcgggc gcctgtaatc ccagctactc gagaggctga ggcaggagaa   5760
tcgcttgaac ttgggggcg gacattgcag tgagcccaga tcacgccact gcactctagt   5820
ctgggtaaca tcttgagact ccatctcaaa taataataat aattaaataa agtaaaaagt   5880
ttcccacacc tcataaatgt ctaataaaaa ttgaatatgt tgagttcaag tactctgaaa   5940
aaggagttga atatagttgg aggttggttt ttaggaatta ctatttttct taaattaact   6000
atccttgtag tcacctagga attgtgtatt ttctatagat cttagaaaat tatcaaatct   6060
acagttcatt ttgtttttc agttttttt ttttttttaa gagatggagt cttgctgtat   6120
tagcgttgaa ctcctggcct cagccagttc tcccatctca gcttctgaag tagctggggc   6180
tgcaggtgcc actgagcctg gcttctttat tggtattttt attaaacact tttctctaat   6240
gtctttgtaa cagttctcag tttttgaaat gctgttactg tttctttagt gtgaactgtc   6300
aactttcatt ttttctttc ttttctttc ttttcttttt ttcttttttg agacagagtc   6360
tcgctctgtc acccagactg gagtgcagtg gtgcgatctt ggctcactgc gacctctgcc   6420
tcccgggttc aagtgattct cctgcctgag cctcccgagt agctggaatt acaggtgcgc   6480
accactgtgc ctggctaatt tttttttttt tttttgtat ttttagtaga ggtggtgttt   6540
caccatgtca gtcaggctgg tcttgaactc ctgaactcat gatcccccc gccctgcctc   6600
ggcctcccaa agtgctggga ttacaggcat gagccaccac gcctggcctc agctttcatt   6660
ttcatttggt tagtttttga actattcagt gggtaaagtt gtataaataa gtgtcttttc   6720
tctgtataga agtgtcttgg agttcaagga gtgctgcttt gcaaactcat agagtattta   6780
taaaagctaa ctgcagaagg tattcatagg ctaaaccgtt tcctattctt ggtagcacca   6840
ttttctctgg cctgaaatac tttccttcta ctattagtgc ctgtcgatac ccagcagtgt   6900
atttactttc ctgaggaaca attcaaatgc taagtgcttt aagacctaag ggtggaaaag   6960
cagtgttttc aggcattatt aggaaaataa gatttaaatt agacacccag aaacaaaaac   7020
aggtttgtaa ttggtaaagt gaaagatggt taaagaaggt tagattgacc aaagcgagaa   7080
tttacctttt tttttttttt tttttgaga cagagtctca tgccgttgcc caggctggag   7140
tgcagtggcg tgatcttggc tcaccgtaac ctccacttcc tgggttcaag cagttctccc   7200
acctgagcct cccgagtagc tgggtgacat gcgccaccac gctcagctaa tttctttgta   7260
tttttagtag agactgggtt tctccatgtt ggtcaggctg gtctcgaact cctgacctca   7320
gtgatctgcc cgccttggcc tcccaaaatg ctgggattac aggcatgagc cactgtgtcc   7380
ggctgagagt gtaccttttt ttttttttat caagcaatct agtacttgat cctaataatc   7440
tttgtggtag gtgtttgcat ttttagatga ggaaaaggga aatctatgag tcctaggaaa   7500
tacagttggt atatgggaac tgatatgtaa ttagacttaa gtgatccatg ttgaatttat   7560
```

-continued

```
gacttaagca cttaactata atcttaacct ctccagttgt ctgatgaagt tagtatatgg   7620
gaactgatac atagacttaa gtgatccatg ttgaatttat gacttcagca cttaactata   7680
attttaccct ctccagttgt ctgatgataa taaaaacttg aagcagttat ccatatgggg   7740
atctctttgg ggaatcccag tcaccaaaag ttaggttttc tttaatattt tttcatggaa   7800
gatttcaaat atactcaaaa ttgaaagaat tatataataa attctcatga gcccatcaca   7860
catcaataat gaatgtacag cattgcagtg tggagcttgg cctattgctg accactcagc   7920
aatgtggcag aaccactcca tgattcccca tggaaatggg aactacttcg gttgtccttt   7980
tatagaaaaa ttcagtaagt atctgctgat tgtgccctac ttgtgacttg aagccaggtt   8040
tttttttttg ttttttattt tttttgtttt gttttgtttg taacagtctt gctctgtcat   8100
ccaagagggg catgatattg gtgcactgca acctccacct cctgggttca agtgattctc   8160
gtgcctcagc ctcccgagta gctgggacta tgggcgtgca ccaccacacc tggctaattt   8220
ttgtatttag tagagatgga gtttcatcat gttgcccagg ctgctctcga actcctgagc   8280
tcaagcaatc tacccacctc cacctcccaa agtgctaaga ttacaggcat gagccaccat   8340
gacagcaaag ctgggtattt cttaaattgg ttcagtcagg tgcaataaat tatttgccct   8400
actctaaaat ttaaaaatct tctaagaatt atggttttgc agctgaggtt tttttaagac   8460
tcgagctccc tggactccta catatatcct tagaacaaca ttgtccaata gaagtacaat   8520
gtgagccaca tgttttgttt aacccagcat atccaaaata ttaccccctt tgcatgtgct   8580
taatataaaa atttaagatg atttatattc caggttttca atattcagtg agtaatttta   8640
cacttagagc aagtatcatt tcagactagt cacattttga gtactcaata accacatatg   8700
gctagtggct accttactag atagcatagc ctttgagtcc cacaaagtgt tcacattcta   8760
tgtgtttaca cacatctttt gaagtgtcat gacagagcca gataggatcc agattttctt   8820
taaatctggt ctctcttccg gattcctagt tgattacttc tttgttgctt cttataggga   8880
tgtatcagaa gtttaataat cttatgatta ttatgttaac tgcctgaagt attaatggta   8940
gcaataaatt gaactataat tttaattttt caagtaaatt ttcttatgtg atactaaata   9000
tttcacatat acatgtatca ggaagtaaat gggggtaatt tagtaatgaa tagtatataa   9060
tagtttatga tggtattttt cttttttttt tttagattgc agcaaaaatt ggaggtgatg   9120
cagggacatc actgaattca aatgactatg gttatggggg acaaaaaaga cctttagaag   9180
atggaggtaa gttatactct aagtatttta aattgttttt cagagtgttt agttgaagtg   9240
attctcggta tttttctgtt attttattga gatattaact tttattataa ggttgttaaa   9300
attgtaagct gtatattggc ctaaaagggg ggaaagaaaa ctagacaagg taagtaaaat   9360
ttgaaagaaa tttttttaaaa aatttttttaa aaaaggaagt tttgtcttaa tagaaaacaa   9420
tttattttcc ctcttttagg attgtgccag attgaaagtt tgcacagacg tcttgttaat   9480
aatattaaaa aacatataaa ttgcttagaa gacacttcac tggttttact catacgtgaa   9540
tggattttaa tatgctgtat tttcgtcatt tttctatttc caattgcacc ttaaaggttg   9600
aaattcctat agtttgctac tctagtgtgt tgcaggttat accatttttt ttttaatgtt   9660
ctttactttc agtactttttg tgtttcacgt ttagctttaa acctgtggat taaaacagtg   9720
gatttacagt gctatgtatt tttaaaaatc gtaatcgttg aagcttctga acttagaagt   9780
ctgcatgtat tttttgtttt aggtttgata tatgagtttt gatacatttt ctttttaccc   9840
ttttttttaa agggaggatt ctcactgagg ctatagaatg tatttgtagc ttttgaccag   9900
gagaacttgg tttcctttta tttaagtgtc tttcatattt atagtgaggt ttttaatgta   9960
```

-continued gaaaaaaaat gagctaatga tgcttcagat gttgtatgta atgtattctt tttattttat 10020
gtgtagatgg ctcttggaca agtccgagca gtacaacaca ctgggaggga atgccctctc 10080
cttttaaagg caggaatttt tatttattac ctgtgttcag tatgtaaacg tgaaataaac 10140
cagtggattc ttaaatggac acaaatattt cttggattat gtgtctgcgc atattttatt 10200
tttgctgcac aacattctga tgtttaatca tttaagtttg aagggggggag gagaatgtag 10260 tactttgagc tataggttgt ctgttccaag gtatgcattg tattcatctg tgtaatggat 10320
ttaggtgaag gtagtcatgt agttgctttg agattttatt tttttgctaa agttttatgc 10380
agtgaaatgt ttgtttataa ataatagaac agtttaggtt gagattgcct tgtaatgttg 10440
tggggggttt ttttgttttt ttttttttgg gcatagcttt gtggtcactg tcagatacac 10500
tttaatatgt cagatttttg tagtttgata ggcttttctc cccccagtct tcagttcctg 10560
aggtggaagc atcattagcc tttagcatgt gatattttgc tagtaatgga cctaaagtac 10620
gttgtcttgt gtcattctaa tgtgcttaac atacattaag gtcagtgatt tcttaagaat 10680
cagataacta ttttaatgtc tgtgcatctt ttgaacgtga agagaatgaa gtatcgtttc 10740 tttttagat tactgagttg gggttgaatt ttggcagttt tggttcaaat gataaaccat 10800
accttcagat atttcaataa atgtttatat tgttatttat tcttgtttgg gaggggagaa 10860
gctttgtact taattggcaa aaaattaaaa gacacttaat tttgcagatc aaccagatgc 10920
taagaaagtt gctcctcaaa atgactgtaa gtattccttt taaactgggt caaaagctaa 10980
agtaacaatt tcaatgttaa gattttgttc atattattgg gtatctttga agttagttgg 11040
tttatgagta ttttggatca gctagcctga atttctttgt aaatatatac ctttttctcc 11100
tattttacaa tctgtcccat taattgtggc cgggtatatg taaagattgg ttgctgaatt 11160
attttacata tttaacaact ccaattcttg atctatactt gtacaacttg aaaaaggaaa 11220
ttattttgtt ctgtgccatt gctaatataa tgtcttccct ttcattggct ctcttgcccc 11280
tgtcaatgcc aatataaata ttgtgtaaaa aatttgactc tcttcaaggt gttgtctgtg 11340
cattagggag agatttttga atgtttgatg tgattgtgtt gttaaatata taagtaaatt 11400
taaattttga atttttgttt tatttttatt taattttttg atagcttttg gaacacagtt 11460
accaccgatg catcagcagc aaaggtatag tcacaagatt ttcaaaaagt actctgcaag 11520
ttttggttga gctgtatgta aaaacacaac cacattggtg tatattgaat atgtgtctgt 11580 gtatttttttg gtgtacctag ttcatatcac tccccttggg aaggtaccat aaagtgatga 11640
tttttctttt gagtgagaaa aatttgtgat ttggagagat aggtggaatt aaccacattt 11700
tagaagaaca ggggtgaatt agagtaactg ttaagatgac attctctaaa ctccacttca 11760
acttctttac agttaatgcc ttcagactgt tccattcatc atcccttctt cacttgatgt 11820
gtcatcttaa atttcttaat ttaactactc aagtaataag atcatatttt ttgacatgag 11880
tctgagccta gaaccttagt ttaagccatt gggagacatt agacttccat ttttattaat 11940
agattatctt ttatttgtaa acaaagtatc tttcattgaa ggaaaatggt gctttctgtt 12000
atttcttagc agatctgtaa tgacagaaga atacaaagtt ccagatggaa tggttggatt 12060
cagtaagtaa cttgattttt aaagttttga aaacatgatc aaaacatact ttagaatctt 12120
tcaaccaaaa aaaaaatttt tttttttcta actagtaatt ggcagaggag gtgaacagat 12180
ctcacgcata caacaggaat ctggatgcaa aatacagata gctcctggta atgttacatt 12240
ctcatggtat tttcagtgtg actagaaaac tagctttttt ttttttttaa gccttctagt 12300
aacaataatg ctacttttaa tcttttgacc tgaagttatc tgtttgtttt aaattgtaga 12360

-continued

```
cagtggtggc cttccagaaa ggtcctgtat gttaactgga acacctgaat ctgtccagta  12420
agtttgaaaa atcttaaaaa tctacttaag taacaacagc agaactcttt gaattttgtc  12480
tcttctcttt gttactgctt tattttacac tgtggtttcg ctgccacctt ccctcaaagt  12540
cctccaactc ctttgaagtt tatgcctcat gcctttctca ggtggggttc atcatctgaa  12600
tcattaaaca cagaaaatgg ttaaaacaac tccatatcta ctccagtctc tacttgtaaa  12660
gccacgtgta gcctggagaa gaatgcacag tcaggtcgac tggtgacact taaaactcag  12720
acattaagct caagtggact gttgtgttgc ctgcatttcc ctagttccat tcacttttcc  12780
actcctctcc caggctcttt aatactgtat ttccccacct ccaaatcttc agcatctaac  12840
cccacgctct cccacttaag cttatttact gagaaaatgg aagcaaatga taagaagctt  12900
ttctttttcc ctaccactaa acctaccagc cttcattttt cctctgttca catagtactc  12960
aggtaattgc tttccttttg tgttcgagtg cctaaagcca gccctttctt cctactgaag  13020
gttcagcttg cagttgtact ttcttctgca ttgttagttc tccctcatta ctaggttttt  13080
tcttttcttt tttttgagac gaagtctcgc tctgttgcca ggctggagtg caggggcacg  13140
atctcggctc actgcaacct ccgcctcccg agtagctggg actaccggtg catgccacca  13200
cacccagcta atttttgtat ttttttagta gagacagggt ttcaccatgt tggccgggat  13260
ggtctcaatc tcttgacctc gtgatccacc cacctcggcc tcccaaagtc ctgggattac  13320
aggcgtgagc cacttccccc agcctgattt tctttatggc actttccaaa taatgtgtta  13380
ttcatttgac atgttatttt tacttattta atgaaatgaa gccactctag caggaaccct  13440
gtttctttga gtgctattac cccattacct agaatagcac ctgcacatag ttgatattta  13500
aatatttgtt gaatgaataa ttgtagcata tgagtaagca aaatggtagt ttaaaaatgt  13560
aaataaatca tttagttctt ggaagaatca gtttaattct gagataactt tagcattaga  13620
gttctttctt ggaaattttg gactattctt aaaaataaaa attgtatatc tagaaaattt  13680
ttttgcataa tctctcaatc tttgaccctt gatggcattt tctttcagtt aaaagtaaaa  13740
gcattgttaa agttagcatc aaggcaccta atcctgaact gggataggag gagtacttgg  13800
ttatattgtt ttatatttct ctatttgaat aagcttgggt atgctacagc ttactattta  13860
aatattaatt tgttaacagg tcagcaaaac ggttactgga ccagattgtt gaaaaaggaa  13920
gaccagctcc tggcttccat catggcgatg gaccgggaaa tgcagttcaa gaaatcatga  13980
ttccagctag caaggcagga ttagtcattg gaaaaggggg agaaactatt aaacagcttc  14040
aggtattgtt atttttgtga aatggctact tttgatctgt tttgatgccc atttttgtcc  14100
acttcctttt gttaatatat attatttcta tgattgtaac aggaacgggc tggagttaaa  14160
atggttatga ttcaagacgg gccgcagaac actggtgctg acaaacctct taggattaca  14220
ggagacccat ataaagttca agtaaactta actttatact ttataaagaa agagtgggtt  14280
gaatggggtt gggcaaaata tgcatgaata attaaaatgt tttgagacat gctttctaaa  14340
ttagctaact ttttctgctt tagcaagcca aggaaatggt gttagagtta attcgtgatc  14400
aaggcggttt cagagaagtt cggaatgagt atgggtcaag aataggagga aatgaaggga  14460
tagatgtaag taaaaatacc cattcagaaa tggttgtatg ctaattcata aatataatag  14520
tgttttctgt tttgtgttaa gtagctctaa cattgttatc cttttatttc acctttatac  14580
tttagaatac agaattctat atatcttgtt accctattta ctataaatat agaattatat  14640
gtacttttat gatttgaggc agattttcag gaaatggcgc ttttttaaaa tacttttttt  14700
tactttaaac cctgagaagc tagctttctt aatacttagt cttttttaca taaggtcccc  14760
```

```
attccaagat ttgctgttgg cattgtaata ggaagaaatg gagagatgat caaaaaaata  14820
caaaatgatg ctggtgttcg cattcagttt aagccaggtg agtacatata ataatcttgt  14880
aagtgttggc agcagtgagt tttgacatac atttattgtt taattaattt tgtttctttg  14940
ttttgaagat gatgggacaa cacccgaaag gatagcacaa ataacaggac ctccagaccg  15000
atgtcaacat gctgcagaaa ttattacaga ccttcttcga agtgttcagg tttgatagaa  15060
agttaacatt ttcatttttt gtttttatgg aaaagtattt tccttcatga aatctgaagt  15120
tacctctata tcagagtctg cttgatgatg ctttattaat ggagaaagtt taaattgctt  15180
taaggtaaag atcttggagc aggaagaact actaccttaa gtgctacctt atttactctt  15240
gtattttaaa aaatgttatt acttattagg gccagttcat ctctacattt ctgattcagg  15300
tatatgagag ctgggaaaaa taaacttaat aattttatca tgaaacaaaa gtatttctgt  15360
gctgactctt cgttcttgtc tttccctctc tataggctgg taatcctggt ggacctggac  15420
ctggtggtcg aggaagaggt agaggtcaag gcaactggaa catgggacca cctggtggac  15480
tacaggaatt taattttatt gtgccaactg ggaaaactgg attaataata ggaaaaggca  15540
atgtatttta aactcttaat gttttaacac attattcatt tttctggaca ctttctgttg  15600
ctgtcgtaaa caagtggcaa tgctttttct ctgaccgtat tttagtagaa aagaattctt  15660
atgttaatat gtaacaagta aaacataaat gagggatctc atgtatattt agagaaagag  15720
caggatttta atcttactag cttctagaga aagcgaacta agagataatt attagcataa  15780
gaaatgtctt ttgacccaaa aagtggtttg agtgtttttg tttgtgcatt ttggtttttc  15840
ccgactcata ttttaaaaat ttgaatgttt ataagtgtat tagtttatat ttacactgct  15900
tttaaaagca gttaattcaa atattttatt ataatcacat taagtttatg tttaaacata  15960
ctaagtaaat gtaaatgtat tttaagagaa gcatgaaatg cttcctaaaa tttgattttc  16020
agtgtagaat attaaatgaa aaatcttaat acaatattgt caattaggat actgaccaaa  16080
ccatattttt aatggcccat ttaattgtga ccattttctt ctaaatagct cctagtacac  16140
ccttgaaacc tttagagaaa ttactgtctt ttgattttag gaggtgaaac cataaaaagc  16200
ataagccagc agtctggtgc aagaatagaa cttcagagaa atcctccacc aaatgcagat  16260
cctaatatga agttatttac aattcgtggc actccacaac agatagacta tgctcggcaa  16320
ctcatagaag aaaagattgg tgtgagtata ctttaaactt ttaattttta gtgtagaccc  16380
ttagactgta gttaaattaa gacgtttatt caaatacatc aaaggaaaat gtatcattac  16440
tagtcagcat ttatagattt catgatatgt ataatagata caacgtgaag attttccagc  16500
aatgaaaata acctaattaa atgtgtagtt acaggttttg agaacaacct tacatttggg  16560
tgtggctaga taagaggagg gtagtgttac ctgtaggcat gatattagtg ttggtgtagg  16620
attgtggaac atacttgaag gacatagtta acgggaattc attatttatt aagattttac  16680
tctactgaac cccagcgagg caaacaagat aaatcagata catctgccac tctacagtag  16740
aaattcataa atcctaggtt ttggactggc tcacagatca tctgggggta ttaaaatgta  16800
gactatttgg gtgcttccca ctcctacaca taatatacag agacagacct gactcaaaat  16860
gtctgggata gggcccagca tctaatttta catagatgtt tgggtgattc tggtgcacag  16920
acaaatttgg aaatttttcc tccaggaaag ttttctgtta gaacaaaaaa gtatgaaacg  16980
ctttgactgc ttttttgtaa gtgaggcaga cagtgtctta ctggagtttt taacacaaag  17040
tgtgcagggg gcatcttaaa ttattagaat tgcctaggaa aaattatttt tggtgtttgc  17100
catgctgtga atggggtgcg tgcaaaacaa ggttgacact gtttctgtca acttgggaag  17160
```

-continued acaaaaatag atgtacaaaa gacgcttaag gaacgtctta caaaatgtac acaaacattg 17220
tgagttctgt tgtatggata gtttaatggt tcaaaaaatg aagaggatgt ttgtagagta 17280
atgatagagg ttgatgccat ggcaaaaaaa tgaatagcac tcatcttggt tttttatttt 17340
acagtattag cctaacatgc atgcgtcagg atttctgttg gattcatgga aaaacaagat 17400
agattgtttt ggagaagcaa tttggtgtgg tgattaagag catggactct gtagtcgggt 17460
tgcctcagtt cagaattctg tgaatcattt actggttctg tgaccttgga gaagttactc 17520
aggcttttct gtgccttggt ttcctcctgt aaaatgaaga taatggtatc tacttcatag 17580
agttgtaggg attaaatgaa tgttcatgtg tgtgtcactt aaaagaatgc ctgccacata 17640
accctaaaaa atgttgctac tttttcagta ttatttttac tacttggaaa gaataggtca 17700
tggatagtaa gtgagagatg acagcaattg gagatttaaa gagacaagtt aataaaaaga 17760
actttaaagg tcatgaagtt tagtttccct attttgcagt gagaaattta caacaaaatg 17820
tagtgttagc attttgtcca acatgtcgcc tggttgtgtt aactactcag aaggagcatt 17880
ttaggacagt taagtgtaat gtctttgttg gcttaaccaa acagaaatca gttaagcgtt 17940
attaatgatg tggcatgcat gcatgataag gatataaaat atcctgattt attgaaggaa 18000
ttaaaaaggg aatttttgtg ctattaaaca tcatgataca tgaaaggcca aaaaggatat 18060
aaattattga tctgaatggg attttagtga cagaaatagg ttgtgaggtg gattttagtt 18120
tcatagtgaa acaactagct attaacgtta tcagtgaaat gttcagaaga cgatgataca 18180
ggacccaagc ggtttgggaa tatattgtca agacggttgt ctcatgttag gcaagtagat 18240
atagagagaa gagctgaaga taaggacctg atttctgtga gtaagatgga aaaagatagt 18300
aaaagtaaga atgataaaag gaaagggaac tactgctgtc cgcaaacaag ctaaaggaaa 18360
tttaattgct aatttaaatt taatttaatt taaattgcat ttaattgcta ctgctattga 18420
ttttagtgaa ttttacatgt ctcattatta tggcagatga aatagttttt gcaaaatgaa 18480
tgaggaaagg aaggaaaacc taaaatttgt tatttgtgac tataagaggg tagaaatgga 18540
tgattatttg gccgtagagt tgtttaacca ttactgtgtt tttctgattt ttctatgtca 18600
tcctttttttt tgtagggccc agtaaatcct ttagggccac ctgtacccca tgggccccat 18660
ggtgtcccag gcccccatgg acctcctggg cctccagggc ctggaactcc aatgggacca 18720
tacaaccctg caccttataa tcctggacca ccaggcccgg ctcctcagta agtattgggt 18780
ttagttctgg gctttcccca aagattctag ttttgggact gttttttatg ctgatttttc 18840
ttttcagtgg tcctccagcc ccatatgctc cccagggatg gggaaatgca tatccacact 18900
ggcagcagca ggctcctcct gatccaggta gaagatgctt attatttgtg tgttatctgt 18960
attattttcc actcctgtta cattattaaa ttttctagtg ttgattctac atttgtatgc 19020
atcaccttca ctcactttac tctttcaaca gtgttaggca ctgcctctac cccagtgtat 19080
aggactgaca tgaatatgag ctctgctttt atggaatttc tttctacttg cctttggctt 19140
atgagttgat acagtagaat gataaaagct aaaagctgca ggaaagagca cagtgtcata 19200
ggttttggat accagtgctg tcaaatgtgt agtatgttca ttgtgacatt atctgtggaa 19260
aaatagtttt tacttattta gaaaagtatg tgataggggc tgggcactga ggctcacgtc 19320
tgtaatccca cctattcaga agtctgaggc tgaggcttga gaccagcctg ggcaatatgg 19380
caagacccat ctctaaaaaa atttgtttta aattagccgg gcagggtggt atgtgcctgt 19440
acttgaggct gaggtgggag gattgcttga gcctagaagt tctagattgt attgagctgt 19500
gggcacacca ttgcactccc ctgggcaaca gaatgggatc ccatctctta aaaaattatg 19560

-continued

```
tatatatgta acagtctata taaatatata tatataacag tccaacagag tgttaagtat  19620
tggggcatta aacttccaaa ttgtcaaata agatatctgt tctagtactc ctcatatgac  19680
aacttcatgt gagtaaaaat caggcctgta tttaataact gcatgctaaa gcccaaatac  19740
gtttaattat tttctatatt cagatttatt tttatcctat tatattctgg catctttcca  19800
taccctgtag tttgctttcc atcttggtca aagagtcatt ctttgaaacc aattaacatt  19860
tatttatgat cctttttttct cacctgctac ctacctttta ggcctctttc actcgtgtag  19920
tttcaaggaa aatatactca attatggaat actttctaca cataatacat ttatcccaaa  19980
aaaacttgaa gtaatttatg taaatgaaat tgcttgatta acttcatagg aagtgtgctg  20040
tttggaatat gatgacacag catgacagtt accaagcatg acttgagttg tgctaggata  20100
taggtgtgca aagttggggt tgtgttctat agcaaaagaa tgcactccca gcgtaagcaa  20160
cactgatgga aggggctcac agggtacagg atataatact cttaacaact aatttttgga  20220
gaatgaaagg gcttttcttt ccctcttgtt ggctgattgg gatggtataa ttaatgggat  20280
tgaagagttt gagtaggtta aaaggcagat tcatattggg taacttggat ctgccaggat  20340
tgtatttttg agcactactg ggtggttagc atgattgagg aaaaatgatg ggaataagaa  20400
gtggaagtgg tctttgtatc acaagttgaa tttctcactt ggagtagtag tgaagtcact  20460
actgtaagag ctggtcagtg aatgtggttg cagcatggcc tttgggcaag aagtaaccca  20520
tttaactaaa accagctggt tggccccact cagatttatc aaagggttac tgggtccctg  20580
ggggtggata ttgcttatat tagacttaga atagcatact gttttaatat tatatgaact  20640
aaaatgtttc tttaaaaaaa gagtggtctg ttaatggatt tatgtagtgg tcaagaattt  20700
agacttcaga gtcaaataaa cctatatcag tcctagtcct acagtttact aattgtgaga  20760
tgtcaagcaa gtttttgaac tcctctaagc ctctgttttc ttatctataa attaataaat  20820
gaatgaatcg ggttgagtga atatttagta aattcttagt acatactagt tatttgtaac  20880
tgtgagactg gtttttttggt atggttttca catttgggag tagaaatacc acttcctaaa  20940
gtctgtttta tctcaaattc tctatccagg catagtgtaa agtgaaatac ctagatttct  21000
tgattaatat acagataatg gccagacgcc atggctaaaa cctgtgacgc tagcacttcg  21060
gaaggctgag gcgggcggat cacttgaggt caggagttgg agaccagcct ggcaaacatg  21120
gcgaaaccct gtctctacta aaaatacaaa aattagctgg atgtggtggc aggtgtctgt  21180
aatcccagct acttaggagg ctgagacagg agaactcctt gagaattgct ccactgccct  21240
ccagcctggg caacagagtg agacacttca tctcaaaaaa aaaaaaaaaa tacagataat  21300
gacactattg agatatgtaa acatccaaca taaaaaagca gtacattggg caattgagaa  21360
aagtttggca ggtgtcctaa taacacctta caattatatt accttgcaat tttctttttc  21420
tagaaattct tgctcatttt tctcaaactt gactaacctt tattaagcag ctgagaattg  21480
ctactgttca gaatgaaggt ataatagaaa atttaaaagt tttaattgta tggtattcct  21540
agtataaaag acaatcaagt tttttctggt ttctagaaga ttgaaaggtc tcaaactgtt  21600
cgcacttcag ttgatgtggg agatgagtga gggtcagtca agtgtagagg agacaacata  21660
gctaaaagcc gagacacggg catagtgatt tctgaaaagt acaagcactg tgttgtggct  21720
ggagcttggg tgttgaagag atacaaccaa agggagagat gaggctgaaa tggaaaggat  21780
aagccagggg cttcaggctg ttaaagatgt tgaatgatag gctgtactta agctttgaac  21840
atcctgaaga ttgcagagaa tgaagaattt caagtaggat gacatcaagt ttataacatt  21900
caatgtgaaa taggatgaaa tgtggctaat ctttttttaag atttttatat tttctcttca  21960
```

ttgaaaataa ggacaaagtt cattgttcta aaataatttt ctttcttata caggttagtc 22020
cctagaaatg tttttcttta gtcatcttct agatagagct gtttgtgctt gaggcgaaac 22080
caatttagaa aaaaacaagg gcacaggatg gtttgagaca gagcattgga tttggagcca 22140
aaagaccttt attcatatcc cagttatgcc actcagtagt ttttaaccta ggaaagtcac 22200
ttagtctctg agacttggtt ttctttaata aaagctgatg gtgacaacaa aaataataga 22260
aaatttaagt tttcatatac ttttttaat gttctagtta attttgggggg ctgtatattt 22320
gccagagagc tgggcggggg ggtggtgtgt gtgtgtgtga gagagaatta cagacttcac 22380
atgcaaacct tgaactttca tttattttag ctaaggcagg aacggatcca aattcagcag 22440
cttgggctgc ttattacgct cactattatc aacagcaagc acagccacca ccagcagccc 22500
ctgcaggtgc accaactaca actcaaacta atggacaagg taactacaga acttattgta 22560
tgtgaaagcc aaaagttgtg cttggaatta tatatgaagt acatcactgt ataataccta 22620
aaatttctga cattatttaa ttataattta agcagacttt tcctttttta aattgttact 22680
ttgaaatagt ttcaaacttt cataaaagtt gtaagaagaa tacccggagc acccagatag 22740
cccagctgtt aatgttttat tcccttgttt actctgttac catctatatc atacatgtgt 22800
atctgtattt attttaaata tccattataa ttagttctga aggaagctaa ttatatccag 22860
cataattagt tctgaaagaa atcactgaag actaaactgt agacatgatg tcctgttggg 22920
tacttcttca aaaatacata accatcatac agccctccaa atcagtaagt caacattgat 22980
atattaagtt ctttatatca ttatggattt ctgatttttg cagtaggtta tatttttaaa 23040
gtatttttat aattttgata atcagattat cctggatttg gccagtcagg gagtatattc 23100
agggtggtgc ctatatcctt ttgaaatacc tgtcattctt ttaagcactt ccatactgtc 23160
tggcacagta agattgttat tttgtgcttt ctgggctcca gccctcgagt cagctatttc 23220
ttcaaggagc tcttattcct tttagtagag tatggtagtt agaaacgaga cttgagtatg 23280
cttgttgcta ctgaggtgta attgcttcta gcttctttca acaggcagaa ctaggaaata 23340
tatttacata catgcatacc tacatacaca caccaaaaaa cacataaaca tcgatatatg 23400
tatatatttt taaaaactat gttcatatca ccacatccgt ttcagcattt tggggttttc 23460
aagcctttc cttttttgta cttgtttaca aacgtgagaa acctggtgtc ctcagtgtat 23520
ttccttattt gacatgcatt tacttatatg ttcaacataa ccagtcttca aacaggttgg 23580
ttttctttc tgtccaccac ctctgtaccc ccagtacctt ctatctttgg cactgttagg 23640
gatgccacca ccacatagta cttccctcct accctcactg tcacattgca ggcccctgcc 23700
agctcctgca cccaaggaaa cggccaaaat tgccttttaa aaactttaat tctgtttttt 23760
gttttgtttt gcttgaacaa ggagatcagc agaatccagc cccagctgga caggttgatt 23820
ataccaaggc ttgggaagag tactacaaga aaatgggtat gttttataca tttcttgaaa 23880
atacatactt aattaaattg aaacaaatta ttctcttcag gaagagaata attgaataaa 23940
atcactggac ttgtaaacat atcaagacag ttgtaaatta tagtttttaa atttgtggtt 24000
atatggcaag gaaatttttt tttctaattg catttgtcaa ccagttatta attgaaacta 24060
gaaatgtcct tactggtaca tacaatatta acattactat acttttgaca atgacagtta 24120
tatatattat cagtctaaat gacataaggt taaattttaa tgtgtcaggc gaaaattgtg 24180
tgtgatacca ttatttttgc tgcaagataa gcaggtaaga agtaatctgc agtgacggaa 24240
agtaaccaag tgatggaacc agaatctggc ttccaagagg gtctgagtcc caagcttgtc 24300
tcccaaattt gtctctttag gaaccatttg gaacctgata ctatacttct ggacaaatca 24360

-continued

```
ctatatttca gctgcttttg ctcttagtca tttaaaatta ttacatacca cagctagatg  24420
tcacaaatga aagctaaatt ggtaagcttg gttatccttc actagcagaa aaagaaccta  24480
taggtggtag agttttgtca taagagaacg gtctacttgg gattttcaat gttttctttg  24540
ccaaagaatg tttctcattc tccacagaaa gaaaaatttc cagaaaggtg atgattttaa  24600
tcttctagat gtaaaattac atatacctga tgataaagtt gttttgcaca actggtttct  24660
ttttaaagaa aaattgtttt tcctcttaga atggcttcct aggagagtca tgttccgtct  24720
ctttctgagg ctttaacaga ttatgttttt gtgacctagc ttaggcagat ctacagtagc  24780
tacaattcgg caaaaagaaa cttttaactt aaaaacagca tactctgatt aaggttggtt  24840
acataattta ttttctgaac tgggatcctt tttagaatga atagggatgc tattaataat  24900
catgccctga cagcattgtg gtcaggacct gtaatcaact taactttaat taaatagcat  24960
caccatttta aaagacttga gcatgagcca cgtgcggtgg cacacacttg tagtcccagc  25020
tgcttgggag gctaaggtgg aaggattcct tgaacacagg agattgaggc cagccttggc  25080
atcatagtga gacctggtca cgtgtttggg ttaaaaatca ctaacttcaa cttctatttt  25140
ctcaatgggt aatgtcccct agatagggtc cctagttatt attaagtagg taaaaataaa  25200
ggcttgttaa tggatttagg taattatgga ggaatgagtt tggcttctgt gctttatttt  25260
accatattga ttatttgtaa tatggccatt aatacattta ctgtttagtc tttttttgttt  25320
tactttttat gttttactca aaatgagtgg gtgggtggaa ttctaatttt tattgttaag  25380
ggaagacatt ttaccttgtc tttaattttt tattttttttt taccatttcc ctgccagtta  25440
gagatactat actatactgt cttgaatcct ctgtaggaaa acatggcata gaaataatta  25500
aataataatt agatgttaaa taataatgct gtatgactaa agaacctcct taccccacct  25560
tttctgttgt tgttctgtag taccacaata atcacttgtt aattttattt atttatttat  25620
ttgagaggga gtctcactct cgcccaggct ggagtgcggt ggcgcaatct cagctcactg  25680
caacctccgc ctcccaggtt caagcgattc tccggcctca tactcccaag tagctgggat  25740
tacaggcgcc tgctaccaca tccggctgat tttttgtata tttagtagat acgggctttc  25800
atcatgttgg ccaagctggt ctcaaactcc tgacctcagg tgatccacct gcctcagcct  25860
tccaaagtgt tgggattatg ggtgtgagcc actgcaccca gcctcacctg ttaattttat  25920
gagcaaaaca gattagttgg gcaagtcctt cacatgcata tctcgttgtt gttgtttttt  25980
ttaagacgga gtcttggtct tactccccaa gcaatggtgc gatttcgtct cagtgcaacc  26040
tctgcttcct gggttcaagc tattctcctg cctcaacttc ccaagtagct gggattacag  26100
gcgcccaacc acacccagct aatttttgta tttttagtag agacagagtt tcaccatgtt  26160
ggccaggctg gtctcgaact cctgacctca ggtgatccac ccgcctcagc ctcgcaaagt  26220
gttgggatta caggtgtgag ccactgcgcc tggccacatg tgtatatctt aaaggaaata  26280
atgctaggta atttagtcag gtgcttgatg agcatttgtc atcatcatac ggagtcaatt  26340
tgtctttttc tataaaagtt ctttttgtaa atgattagtt gcttaactgc tttaatttct  26400
tctaggtacc ttacctgtca tcaggatctt tttaccacaa ataagaaacc ttaaagcata  26460
aaacttggtt cagtcttcac atttcttaaa tggaaggaga aagggaataa tagggagata  26520
tctttatctc aaagccaact gttgttgact tttccagtgg caggggtatg atgctaggac  26580
ttcagatttc ctgattcccc atcctagtgc cccttttgcc aaactaggca ggctttcaca  26640
gcttttggag cctaatttaa gtttttcttg ttaagaacag aaaactccat tcatagattt  26700
taatttgtca ttatttgctt atttactgaa aaaaaaaaaa aactattgaa aacaggtgtg  26760
```

ggttaagttt cccaaaatta ggtttatatt tcaaaacaat tctaagttcc caaggataac 26820
accaaactaa gaggataaat ttttatttta ttttttttta ttttattttt ttgagatgga 26880
gcctttccct gtcgcccagg ctgaagtgca gtggcatgat ctcggctcac ttgcagcatc 26940
cacctcccag gttgaagcaa ttcttctgcc tcagcctccc aagtagagaa aatcttgata 27000
agatttcaga ggcttataag gaacagcagt aaagatgggt gtttttaaag ctagaataca 27060
gggatttttt taagaccctt aagagaacaa acagggtttc aaaatagaaa ggagtaattc 27120
ttgtttggag aagtgaagac atttgggaaa agtttgactt gaggaaggcc attatgataa 27180
ggactgatgt ggtagactct gaaccctgaa gaatctggta ccttaagcct aaaggagggt 27240
agagtgagga cttgtgggaa aggtacagtt atatgggaag acaactgagt gtgaaaatct 27300
attcatgcaa ggctggctct taggctctaa tagaatcttg caagctaact ctagagcaag 27360
tcttttatct ttgggatgaa agaaatttaa ggctaaactt tatacattat aattataaaa 27420
ctataataaa tattagataa tgttctactg aagtataaac tcaactatct ggcatcaaac 27480
agtaactaag ccatgatcac accactgcca ctgtgttctg gcctaggtga cagagcaaga 27540
ccctgtctca aaacaaaatc cagtaactaa agagaggaat aaggggagcg caaggtaagg 27600
cagtacatgt ctgaaggggc agggaaagag ttctttctct acttccaact gggcaaaata 27660
aatcacattt gccctttaga ttggaagagt gaaataagct tttcttgaac atcttttaag 27720
attggagtgt caaatattac caacttattt accaagaatt tggtttttct taaagtctaa 27780
agtgtttact attagctttc cacagggata taggagtttg cagaggttgt agttttttaa 27840
gggaacatca atgaattttc ttgatgcata tgcctgtttc taccatttta cattgttaat 27900
ttgcctctaa aatgagtaac tcttacaatg gggtttaaaa cctgaagact attgattgct 27960
accttgatca ggtttggttt caagtgtgca ccctgtaaga gacaatgtgt ggttttattg 28020
ctattgtcac accagttttt tagatattga aacctgtttc agatttgctt gaattgtgtc 28080
ttgtaagagg aaaatgttaa acttacttcc tctttgagaa cagttattta tagaagacag 28140
gaaaatatga gaatttttaa tagtatatga gagttctctg ttacccaaga aaagagggtt 28200
tttttcaggc atttttaaag aatcataaat cttaaattct ttcactcagt tgctttgagt 28260
ctgtgacctg ttttacaatg gtgatagact gctttctgaa actatgaaat tggtcttgtt 28320
ggcagcatcc tacaaacata aaaagagctt cctgtgtgtc catgctccag tatttttgtc 28380
tatggtagtt atttcacaaa gccaagcgag ttacaaacga aataaaatag tgcttaagta 28440
aagaaactga ataggagaac atatactctc tcttctcaat tttttattta gaaaattata 28500
taccttcaga aattggggaa ataaggcatc agacactcag cttcatcatt ttttaaaagt 28560
ttgctgtatg cgctttatat gtatgttttt tgtgtatgaa ccatttcaaa gtaagttgca 28620
gacaagacag tttgctctaa ataaactcaa tgtctgggca cagtggttga cgcctgtaat 28680
cccaggactt tgggaggcca aggcaggtgg atcacttgag tccaggagtt caggaccagc 28740
ctggacaaca tggcaaaacc ccatctctac aaaaaaaagag aaaaatgtca gctaggcatg 28800
gtgggcctgt agtcccagct actctagagg ctgaggtggg aggatcacct gagccctggg 28860
aggttgaggc tgcagtgagc catgattgca ccgctgcact ccagcctggg tggcagagtg 28920
agaccctgtc tgaaaataaa taccctcaat attatcacaa acatacagac tatatttaaa 28980
tttccatagt tgtcaggaat atgtcttttg tcgtctgtgt gttttgttta attcagagta 29040
cattcaagat tcatgcgttg catttcattg ctatatttct ttaatctctt aattcagcaa 29100
agtcacctta tttggaaaaa gacctgattg tgaaagctga gttttatgtg ttttcattga 29160

-continued

```
tcttgttctt tattccttgt caggttactt ttaataacat tgtgttgtaa ttggaataaa  29220
ttattaatac ttttaacatc ttattatgtg tgtgtgtaca tacactttat aggttactaa  29280
tcaggaaaaa gtcttggcta ggtcttaata cagtctttaa atcattgcct ttaagtgggc  29340
ttaaagtttt tcaaaaatgt tctttttgta attctggaat cgaattaaga ttatgcctaa  29400
atctttacct tccttagcta aagcagtgtg gatttggggt tgattctgtt tttttactaa  29460
taatgacgct ctagaactaa aagttaacga ttaattataa ggcaaaaaga aaagagcgtt  29520
cttttttttt ttctaattgc agagtagttt cctgacacta ctaaatgaat attttaaata  29580
aaacaggagt aattctgacc ctctgtgctt ttgtcttata acctgtactt acagtggatg  29640
taattttata ttaaagttta ggggtttttt tttttggtca acaagggcaa acacaagatt  29700
attcaaaggc ttgggagaaa tattacaaga agcaaggtat tgtttttatt agaaatgaga  29760
tgttgggctt ataattgtgg ttacagcaac aaagttcttt tttttcaaag gtcaggcagt  29820
tcctgctccg actggggctc ctccaggtgg tcagccagat tatagtgcag cctgggctga  29880
gtattataga caacaagcag cctattatgc ccagacaagt ccccagggaa tgccacagca  29940
tcctccagca cctcaggtat aatgtaattg ctaatttgtt gatttctact ccagtctgtt  30000
ttctgcatgt ttactgtttg tctgtttggg agtgtttgcc ttttaaattt ttatctggca  30060
aagtataata actatttaaa tgaagtacta cggtgtattg tttgggtttt tttgtttttt  30120
ataatgcttt ccagcatctg agtggtgaat atttctgcaa tgcctttgat tttaaaaata  30180
aattttcttc ccccagggat ttgcaaatca tgcaagaagc caccaccatt tatattaacc  30240
actttttctt tcttaaagga ttcactcctg aattagctcc atttcaagga ttttctttaa  30300
ctttttgtgt atttcttatg tatctcttct gcacagggcc aataataaga agtggacaat  30360
acagtatttg cttcattgtg tgggggaaaa aaacctttgt taaatatatg gatgcagacg  30420
acttgatgaa gatcttaatt ttgtttttgg tttaaaatag tgtttccttt tttttttttt  30480
tttttgaaaa tgtacaaaat atctatcact actgatagga ggttaatatt tctgtgtaga  30540
aatgaaaatt ggtttgtttt tagtatttag tgtagatgta cacattccag caaatgtatt  30600
tgcaattatg tggttgatgc tttgtgatat aaatgtactt tttcaatgta tactttcact  30660
tttaaaatgc ctgttttgtg ctttacaata aatgatatga aacctcctgt gtcggtaagt  30720
tggatatgtg ggtatttaaa ggattcataa tttcttagca atgataaatt aagatacata  30780
tacacaaata tataagcttt ccccatgaaa tattgagttt ttaaacactg gcatgttttt  30840
ccccccttgc agtatagtgg tagattggag gatcttttcc atttattgta ttggctcttt  30900
cagcacaagt aatcctgata tcttcatttt ttttccttct gtttgattaa aaactgcatg  30960
tgtgtacaat gatcttttgg catacttcca ttgcattaac agtgaaattt ccttttatac  31020
atgaccactg tttcagacct gtactgctgc tataacagtt aacctttctg ttcttaattt  31080
gataatactt gatttccaag actgtttcgg cataactaat tttaaacagt tttcagatag  31140
tgaatatgag tagtctaata agaacagttt ttttccatgt gaagcaactc tttcaatgta  31200
tataatgtta gtgtgtttct ttctaaattt aggatagaaa agtgaatagt gtgcaaaaag  31260
tatagctaca ttgcatctgc cattgaaaca taaatggggt atggaaacgt tcaagctttt  31320
ttttttctt tatgcagtat agataagctt tgttttgtaa atgcacaagt ccaatcattg  31380
aatcaactta attttttat gtacttgaag tcattttatt actctttaac actcatgctg  31440
aagttctgat attttgttga aatccattgt tttactcttt gcatatttgt tggctctttg  31500
catattaata tattagacta catgcaaata cagtctgtct tgccattgtc tgttgaagtg  31560
```

-continued

```
caggtttgat ccagccagta tagaactagc tctgtagggg tgaggaggac tgtgctgtgt  31620
atcatccttg attgtgttcc ttcaaggagc attgcactgt aagtacatca gaatgacaaa  31680
ttgatgaact gcaacagtat ctttttgtca atgttccaca taatgcaaat gccatacgtt  31740
gtgtgaatat tatgttggaa tacagtgctg atatcttgga aaaccataac tgcctcttaa  31800
tttaacatag aataatacat agttctgtat tttttttaaa gtgagcttaa tgggtaagta  31860
ttttttatat gctttagcta tagctaaaga aaactgatac ttaacaaagt tgaatagtat  31920
tattcactgg tgctcctaaa atattgtttt tcagtgtaaa atatgcatat cttctatatt  31980
taatatgaaa gtcttgaaat gtatcagaca gaaggggatt tcagtttgca aataatgagc  32040
aatgtagcaa ttttaacaca tttcataaat atatattttg tcattggtgg agagcaccat  32100
ttgttgtttt gaatatactt taaaggaaga ggtacaagga cataaatgtt gagattacct  32160
acaggatgga aatagcagta cagttcattg tagatatttt gaaatgtttt tgattgtttt  32220
atataaccta gagtgacttc ccttaccctt atttagatct gcatatatag ttctagtatg  32280
aagtttaata gttaaggagt tagctatttg ttatctttaa gagtagggta ttgacgtgaa  32340
caattgcagt attttgcatg atactgtttt atagatgacc ttttaggaaa gtggtgcatt  32400
tattaattga actgaagaag tagttcagtt gaattcagta tcataattca caaattggag  32460
gctgttgatt ttgattcatt taaggtttaa aatctttatt aattgcaaac agtgcaatta  32520
tttatacttc acagtgcctt cccagacctt ccaccttagg ttctgctgca aaaagcacca  32580
ggtaagcaca acctaaggac atatataaat aaatatttca atacattaat gttgtccctg  32640
tgaggttttt gtggttgtgt attcaaaggc aatctgctac tgcttcccca aaatgtattt  32700
tgttatttta tgctaccatc ttagtggaaa gtctgtaagt tgttaaagca actgtttaca  32760
tttctgggta atgtttttta ttttactttt ttttttttat taagacaaga aaatgatgag  32820
tagattgctg cagtaattga actacatcca aatctttttg tattttttcc ccaaatatag  32880
aagtgttaat attaagaaag gacaattaca cagttttcaa gatttaggaa atcacttgtt  32940
tagaaacttc aacagccttc acaatctgtt ttatatgatg gacagaaaat ttctttgccc  33000
tccaaaatta taatttcttt attttttttct tattcttaaa ctataataat tcagtaagga  33060
tattatgggt tagaatttta ttatgatttt tttcttagac aaaagttata tgctgaagaa  33120
ggaaaaagtt ataaggcagt atgttttgat aaaaggcatg tgcatcagtg aaatgttaac  33180
tgtatagcaa ataacctttc ataatctgta gcaatcagta tttttctgat ttaataatat  33240
tttaataact gacgctgcat ttaatttttt tgccagttta aaatgtttgt gtgtttttat  33300
agatgatttt aactggtaca tattttgagt taagttgaat gtatgaaagc agcatcttat  33360
cagttttgtt tattcgattt ctaaaatgtg ctgatccttt taaaactcct gcttatctct  33420
gcaacaaaga aaaatattca aaaatactgc cttcattttc acacacagtg ctgaagatgc  33480
tgcaagcacc aaatcatagc tcataaaatc aggtcctgag atagttaccc ataaagagga  33540
atcctttgag tgtatgccat tggtgagccg atgagcatgg accatagaag ggctcaatgt  33600
agaaggtaaa attggcaaat cataattgag aaatatgaaa tgtattccca tacataatat  33660
ggtatagggt gtaatgtacc tgcttttgat cacttttcat tttaaagtgc tattcacttg  33720
atcttaaatg ttccatgaac tgttaaattt cttaagttac atagttacta caccacattt  33780
atgtgtatgt tatgttttaa tagtcaatga taggtatgta caattgataa tataaagggg  33840
ctcattgaaa cttgagagcc tgttgagttt tggttagttg tagattgcat ttttataaaa  33900
aaaaatacag atagattgat gataatagat attggggcat tgtttctgtc tcatgagaat  33960
```

```
tcttttattc attaccataa gccttcactg atactataag cattatttta aatgacgctg  34020
atcttaagtc tgaaataaat ggaaagcaga aaaggtgagc cagttgattt gaatgcattg  34080
gatattagtg ttagaaacaa tgtatagttt agattgaaac tgaactgact tatttagcac  34140
ttaaacaaaa atttgacaat gtttttagtt ttttttaaga cagcttagtg tggtgatact  34200
tagaattcta tggtttgatg tttcttttag aaatgagaag tatagtttta ttttttaata  34260
taaaaaatgg ttttaatact aaaactagta atttgatact agttgtttat aaacattgta  34320
aaatatatct tttaaacaaa ttatcttggt agttaattca taagggtggg tttgggtagg  34380
aatagcagag tactttcaga gggaaagggg agtcattcag aagtgatagc attttatttg  34440
tttgaatact ctgccagtaa aatcagctgt acttagaaag ttatctgttg tgtagaataa  34500
tgatgtagag tttactaatc agtgaggatg tcttgttttt attttctgca aactctgcct  34560
cactttaaaa tgcattataa caatacctaa ttaaagataa ttttggctct gaaagttacc  34620
ttattttttg ttgagttagt gacttcattt ttcttgccac aatataagct tttgagggat  34680
ttttttaaat tggtgctttt aataagcaaa taaatcccag ggttttattt tcttcagtga  34740
taccccctata gaaactctta aatgtatttg cgcatatata tatatatatt ttcttatgca  34800
tgctcgatgc attttcgtcc tgagaaaaat gttctctaca gaaactaccc gtgtgtaaaa  34860
agaagattgg cttaaaatgg ctactgtgat gggaacagtg tcttagggag atgcagcttg  34920
gacttgaggt aaattgaata ctttacaact gtggtttaga gtttgcttta atgacattgt  34980
atgtaaaagg tcacatgatt gctgtaatt tgtattcatt atggtttcct caataaatgt  35040
acattgatga ctatta                                                  35056
```

<210> SEQ ID NO 2
<211> LENGTH: 696
<212> TYPE: DNA
<213> ORGANISM: homo sapiens

<400> SEQUENCE: 2

```
atggcagact attcaacagt gcctccccc tcttctggct cagctggtgg cggtggtggc     60
ggcggtggtg gtggaggagt taacgacgct ttcaaagatg cactgcagag agcccggcag    120
attgcagcaa aaattggagg tgatgcaggg acatcactga attcaaatga ctatggttat    180
gggggacaaa aaagaccttt agaagatgga gatggctctt ggacaagtcc gagcagtaca    240
acacactggg agggaatgcc ctctcctttt aaagatcaac cagatgctaa gaaagttgct    300
cctcaaaatg actcttttgg aacacagtta ccaccgatgc atcagcagca aagatctgta    360
atgacagaag aatacaaagt tccagatgga atggttggat tcataattgg cagaggaggt    420
gaacagatct cacgcataca acaggaatct ggatgcaaaa tacagatagc tcctgacagt    480
ggtggccttc cagaaaggtc ctgtatgtta actggaacac ctgaatctgt ccagtcagca    540
aaacggttac tggaccagat tgttgaaaaa ggaagaccag ctcctggctt ccatcatggc    600
gatggaccgg gaaatgcagt tcaagaaatc atgattccag ctagcaaggc aggattagtc    660
attggaaaag ggggagaaac tattaaacag cttcag                              696
```

<210> SEQ ID NO 3
<211> LENGTH: 1968
<212> TYPE: DNA
<213> ORGANISM: homo sapiens

<400> SEQUENCE: 3

```
atggcagact attcaacagt gcctcccccc tcttctggct cagctggtgg cggtggtggc     60
ggcggtggtg gtggaggagt taacgacgct ttcaaagatg cactgcagag agcccggcag    120
attgcagcaa aaattggagg tgatgcaggg acatcactga attcaaatga ctatggttat    180
gggggacaaa aaagaccttt agaagatgga gatcaaccag atgctaagaa agttgctcct    240
caaaatgact cttttggaac acagttacca ccgatgcatc agcagcaaag cagatctgta    300
atgacagaag aatacaaagt tccagatgga atggttggat tcataattgg cagaggaggt    360
gaacagatct cacgcataca acaggaatct ggatgcaaaa tacagatagc tcctgacagt    420
ggtggccttc cagaaaggtc ctgtatgtta actggaacac ctgaatctgt ccagtcagca    480
aaacggttac tggaccagat tgttgaaaaa ggaagaccag ctcctggctt ccatcatggc    540
gatggaccgg gaaatgcagt tcaagaaatc atgattccag ctagcaaggc aggattagtc    600
attggaaaag gggagaaac tattaaacag cttcaggaac gggctggagt taaaatggtt     660
atgattcaag acgggccgca gaacactggt gctgacaaac ctcttaggat tacaggagac    720
ccatataaag ttcaacaagc caaggaaatg gtgttagagt taattcgtga tcaaggcggt    780
ttcagagaag ttcggaatga gtatgggtca agaataggag gaaatgaagg gatagatgtc    840
cccattccaa gatttgctgt tggcattgta ataggaagaa atggagagat gatcaaaaaa    900
atacaaaatg atgctggtgt tcgcattcag tttaagccag atgatgggac aacacccgaa    960
aggatagcac aaataacagg acctccagac cgatgtcaac atgctgcaga aattattaca   1020
gaccttcttc gaagtgttca ggctggtaat cctggtggac ctggacctgg tggtcgagga   1080
agaggtagag gtcaaggcaa ctggaacatg ggaccacctg gtggactaca ggaatttaat   1140
tttattgtgc caactgggaa aactggatta ataataggaa aaggaggtga aaccataaaa   1200
agcataagcc agcagtctgg tgcaagaata gaacttcaga gaaatcctcc accaaatgca   1260
gatcctaata tgaagttatt tacaattcgt ggcactccac aacagataga ctatgctcgg   1320
caactcatag aagaaaagat tggtggccca gtaaatcctt tagggccacc tgtaccccat   1380
gggccccatg gtgtcccagg cccccatgga cctcctgggc ctccagggcc tggaactcca   1440
atgggaccat acaaccctgc accttataat cctggaccac caggcccggc tcctcatggt   1500
cctccagccc catatgctcc ccagggatgg ggaaatgcat atccacactg gcagcagcag   1560
gctcctcctg atccagctaa ggcaggaacg gatccaaatt cagcagcttg ggctgcttat   1620
tacgctcact attatcaaca gcaagcacag ccaccaccag cagcccctgc aggtgcacca   1680
actacaactc aaactaatgg acaaggagat cagcagaatc cagccccagc tggacaggtt   1740
gattatacca aggcttggga agagtactac aagaaaatgg gtcaggcagt tcctgctccg   1800
actggggctc ctccaggtgg tcagccagat tatagtgcag cctgggctga gtattataga   1860
caacaagcag cctattatgc ccagacaagt ccccagggaa tgccacagca tcctccagca   1920
cctcagggat ttgcaaatca tgcaagaagc caccaccatt tatattaa                1968
```

<210> SEQ ID NO 4
<211> LENGTH: 1935
<212> TYPE: DNA
<213> ORGANISM: homo sapiens

<400> SEQUENCE: 4

```
atggcagact attcaacagt gcctcccccc tcttctggct cagctggtgg cggtggtggc     60
ggcggtggtg gtggaggagt taacgacgct ttcaaagatg cactgcagag agcccggcag    120
```

-continued

```
attgcagcaa aaattggagg tgatgcaggg acatcactga attcaaatga ctatggttat    180
gggggacaaa aaagaccttt agaagatgga gatcaaccag atgctaagaa agttgctcct    240
caaaatgact cttttggaac acagttacca ccgatgcatc agcagcaaag cagatctgta    300
atgacagaag aatacaaagt tccagatgga atggttggat tcataattgg cagaggaggt    360
gaacagatct cacgcataca acaggaatct ggatgcaaaa tacagatagc tcctgacagt    420
ggtggccttc cagaaaggtc ctgtatgtta actggaacac ctgaatctgt ccagtcagca    480
aaacggttac tggaccagat tgttgaaaaa ggaagaccag ctcctggctt ccatcatggc    540
gatggaccgg gaaatgcagt tcaagaaatc atgattccag ctagcaaggc aggattagtc    600
attggaaaag ggggagaaac tattaaacag cttcaggaac gggctggagt taaaatggtt    660
atgattcaag acgggccgca gaacactggt gctgacaaac ctcttaggat tacaggagac    720
ccatataaag ttcaacaagc caaggaaatg gtgttagagt taattcgtga tcaaggcggt    780
ttcagagaag ttcggaatga gtatgggtca agaataggag gaaatgaagg gatagatgtc    840
cccattccaa gatttgctgt tggcattgta ataggaagaa atggagagat gatcaaaaaa    900
atacaaaatg atgctggtgt tcgcattcag tttaagccag atgatgggac aacacccgaa    960
aggatagcac aaataacagg acctccagac cgatgtcaac atgctgcaga aattattaca   1020
gaccttcttc gaagtgttca ggctggtaat cctggtggac ctggacctgg tggtcgagga   1080
agaggtagag gtcaaggcaa ctggaacatg ggaccacctg gtggactaca ggaatttaat   1140
tttattgtgc caactgggaa aactggatta ataataggaa aaggaggtga aaccataaaa   1200
agcataagcc agcagtctgg tgcaagaata gaacttcaga gaaatcctcc accaaatgca   1260
gatcctaata tgaagttatt tacaattcgt ggcactccac aacagataga ctatgctcgg   1320
caactcatag aagaaaagat tggtggccca gtaaatcctt tagggccacc tgtaccccat   1380
gggccccatg gtgtcccagg cccccatgga cctcctgggc ctccagggcc tggaactcca   1440
atgggaccat acaaccctgc accttataat cctggaccac caggcccggc tcctcatggt   1500
cctccagccc catatgctcc ccagggatgg ggaaatgcat atccacactg gcagcagcag   1560
gctcctcctg atccagctaa ggcaggaacg gatccaaatt cagcagcttg ggctgcttat   1620
tacgctcact attatcaaca gcaagcacag ccaccaccag cagcccctgc aggtgcacca   1680
actacaactc aaactaatgg acaaggagat cagcagaatc cagccccagc tggacaggtt   1740
gattatacca aggcttggga agagtactac aagaaaatgg gtcaggcagt tcctgctccg   1800
actggggctc ctccaggtgg tcagccagat tatagtgcag cctgggctga gtattataga   1860
caacaagcag cctattatgc ccagacaagt ccccagggaa tgccacagca tcctccagca   1920
cctcagggcc aataa                                                    1935
```

<210> SEQ ID NO 5
<211> LENGTH: 39750
<212> TYPE: DNA
<213> ORGANISM: macaca fascicularis
<220> FEATURE:
<221> NAME/KEY: misc_feature
<222> LOCATION: (1246)..(1266)
<223> OTHER INFORMATION: n is a, c, g, or t
<220> FEATURE:
<221> NAME/KEY: misc_feature
<222> LOCATION: (2077)..(2131)
<223> OTHER INFORMATION: n is a, c, g, or t
<220> FEATURE:
<221> NAME/KEY: misc_feature
<222> LOCATION: (2666)..(2690)
<223> OTHER INFORMATION: n is a, c, g, or t
<220> FEATURE:
<221> NAME/KEY: misc_feature
<222> LOCATION: (3304)..(3345)
<223> OTHER INFORMATION: n is a, c, g, or t
<220> FEATURE:
<221> NAME/KEY: misc_feature
<222> LOCATION: (3869)..(3870)
<223> OTHER INFORMATION: n is a, c, g, or t
<220> FEATURE:
<221> NAME/KEY: misc_feature
<222> LOCATION: (6076)..(6076)
<223> OTHER INFORMATION: n is a, c, g, or t
<220> FEATURE:
<221> NAME/KEY: misc_feature
<222> LOCATION: (6091)..(6093)
<223> OTHER INFORMATION: n is a, c, g, or t
<220> FEATURE:
<221> NAME/KEY: misc_feature
<222> LOCATION: (6159)..(6183)
<223> OTHER INFORMATION: n is a, c, g, or t
<220> FEATURE:
<221> NAME/KEY: misc_feature
<222> LOCATION: (6259)..(6277)
<223> OTHER INFORMATION: n is a, c, g, or t
<220> FEATURE:
<221> NAME/KEY: misc_feature
<222> LOCATION: (6869)..(6906)
<223> OTHER INFORMATION: n is a, c, g, or t
<220> FEATURE:
<221> NAME/KEY: misc_feature
<222> LOCATION: (7072)..(7139)
<223> OTHER INFORMATION: n is a, c, g, or t
<220> FEATURE:
<221> NAME/KEY: misc_feature
<222> LOCATION: (7714)..(7714)
<223> OTHER INFORMATION: n is a, c, g, or t
<220> FEATURE:
<221> NAME/KEY: misc_feature
<222> LOCATION: (11374)..(11394)
<223> OTHER INFORMATION: n is a, c, g, or t
<220> FEATURE:
<221> NAME/KEY: misc_feature
<222> LOCATION: (11454)..(11491)
<223> OTHER INFORMATION: n is a, c, g, or t
<220> FEATURE:
<221> NAME/KEY: misc_feature
<222> LOCATION: (12562)..(12562)
<223> OTHER INFORMATION: n is a, c, g, or t
<220> FEATURE:
<221> NAME/KEY: misc_feature
<222> LOCATION: (12699)..(12742)
<223> OTHER INFORMATION: n is a, c, g, or t
<220> FEATURE:
<221> NAME/KEY: misc_feature
<222> LOCATION: (12793)..(12794)
<223> OTHER INFORMATION: n is a, c, g, or t
<220> FEATURE:
<221> NAME/KEY: misc_feature
<222> LOCATION: (13648)..(13656)
<223> OTHER INFORMATION: n is a, c, g, or t
<220> FEATURE:
<221> NAME/KEY: misc_feature
<222> LOCATION: (14247)..(14261)
<223> OTHER INFORMATION: n is a, c, g, or t
<220> FEATURE:
<221> NAME/KEY: misc_feature
<222> LOCATION: (14474)..(20234)
<223> OTHER INFORMATION: n is a, c, g, or t
<220> FEATURE:
<221> NAME/KEY: misc_feature
<222> LOCATION: (21758)..(21789)
<223> OTHER INFORMATION: n is a, c, g, or t
<220> FEATURE:
<221> NAME/KEY: misc_feature
<222> LOCATION: (23223)..(23225)
<223> OTHER INFORMATION: n is a, c, g, or t
<220> FEATURE:
<221> NAME/KEY: misc_feature
<222> LOCATION: (24454)..(24512)
<223> OTHER INFORMATION: n is a, c, g, or t
<220> FEATURE:
<221> NAME/KEY: misc_feature
<222> LOCATION: (24563)..(24589)
<223> OTHER INFORMATION: n is a, c, g, or t
<220> FEATURE:
<221> NAME/KEY: misc_feature
<222> LOCATION: (25270)..(25338)
<223> OTHER INFORMATION: n is a, c, g, or t
<220> FEATURE:
<221> NAME/KEY: misc_feature
<222> LOCATION: (25723)..(25734)
<223> OTHER INFORMATION: n is a, c, g, or t
<220> FEATURE:
<221> NAME/KEY: misc_feature
<222> LOCATION: (25857)..(25857)
<223> OTHER INFORMATION: n is a, c, g, or t
<220> FEATURE:
<221> NAME/KEY: misc_feature
<222> LOCATION: (26517)..(26523)
<223> OTHER INFORMATION: n is a, c, g, or t
<220> FEATURE:
<221> NAME/KEY: misc_feature
<222> LOCATION: (27589)..(27590)
<223> OTHER INFORMATION: n is a, c, g, or t
<220> FEATURE:
<221> NAME/KEY: misc_feature
<222> LOCATION: (27660)..(27688)
<223> OTHER INFORMATION: n is a, c, g, or t
<220> FEATURE:
<221> NAME/KEY: misc_feature
<222> LOCATION: (28733)..(28733)
<223> OTHER INFORMATION: n is a, c, g, or t
<220> FEATURE:
<221> NAME/KEY: misc_feature
<222> LOCATION: (30266)..(30266)
<223> OTHER INFORMATION: n is a, c, g, or t
<220> FEATURE:
<221> NAME/KEY: misc_feature
<222> LOCATION: (30317)..(30371)
<223> OTHER INFORMATION: n is a, c, g, or t
<220> FEATURE:
<221> NAME/KEY: misc_feature
<222> LOCATION: (30453)..(30768)
<223> OTHER INFORMATION: n is a, c, g, or t
<220> FEATURE:
<221> NAME/KEY: misc_feature
<222> LOCATION: (30833)..(30837)
<223> OTHER INFORMATION: n is a, c, g, or t
<220> FEATURE:
<221> NAME/KEY: misc_feature
<222> LOCATION: (30906)..(30912)
<223> OTHER INFORMATION: n is a, c, g, or t
<220> FEATURE:
<221> NAME/KEY: misc_feature
<222> LOCATION: (30997)..(30998)
<223> OTHER INFORMATION: n is a, c, g, or t
<220> FEATURE:
<221> NAME/KEY: misc_feature
<222> LOCATION: (31271)..(31562)
<223> OTHER INFORMATION: n is a, c, g, or t
<220> FEATURE:
<221> NAME/KEY: misc_feature
<222> LOCATION: (31697)..(31697)
<223> OTHER INFORMATION: n is a, c, g, or t
<220> FEATURE:
<221> NAME/KEY: misc_feature
<222> LOCATION: (31707)..(31782)
<223> OTHER INFORMATION: n is a, c, g, or t
<220> FEATURE:
<221> NAME/KEY: misc_feature
<222> LOCATION: (32257)..(32257)
<223> OTHER INFORMATION: n is a, c, g, or t
<220> FEATURE:
<221> NAME/KEY: misc_feature
<222> LOCATION: (33477)..(33478)
<223> OTHER INFORMATION: n is a, c, g, or t
<220> FEATURE:
<221> NAME/KEY: misc_feature
<222> LOCATION: (37353)..(37427)
<223> OTHER INFORMATION: n is a, c, g, or t

<400> SEQUENCE: 5
gagatttcgt tccttcagtc tccacccctt tacggcacga tggtcgcgca agaatgtgat 60
acagcttcga cggccgccat tttctttctt tcttagctgt tagctgagag gaagtctctg 120
aacgggcggc agcggctagc gtagtgtaac catggcagac tattcaacag tgcctccacc 180
gtcttctggc tcagctggtg gcggcggtgg cggcggtggt ggtggaggag ttaacgacgc 240
tttcaaagat gcactacaga gagcccggca ggtaagtgtg gaccgcgcgg cggaatcccg 300
aaagctcacg gtaattggcc gctgactgag taggccgcta ccctttagcg catgaggaag 360
aggaaagagg tgtccttccg ggctgaaatg tgaggagaca cgtttcccct tgttggtaat 420
aaagattaga gaccagaact cagttttgtg ttcttggtgt gtaatccact tagaaccccg 480
acgcgtgcta cgcaaaggcc tgaagtcttt ctcccgcttc tgcggcactc gtgtgtcgcc 540
agcgagctag cttagcctcc ccttttcctc gagatgaaga tcctcttcca ggggataaag 600
cgcaggtagt ttcacacaat ttaatggaag gttctggtaa tcagtttggg aaagaactag 660
ggtcggtctc ctggagccat agcaagggaa gggatttgtc gttaaagtag cctttacagc 720
tcatttccgt tccctctcgc aattaaaacc gctttccgta cctttcacct tctcacctct 780
acaaggaagg gacttgaaag ccgtcttttt ctgggcggga tttacgcgtc agtctgttct 840
aacagtcagt ccccccttatt tctcaaaatg gcctcaggcc cattatacca gaggtttcaa 900
tttgaatctg cctctctgtt aagagtcgta aactgaccag acctctttgt attacgtagt 960
gcgtacattt gccctgaaga caccactttc ccagacgaaa gctgttaaaa tagtgcgagt 1020
attccaggaa aatagaagat ttcttaattt gaactttaca tttttagata gtcccctaat 1080
atatttaaaa tttcaaaatg tatggtgttg gtatggattt gcatgtaagc aaaagaattc 1140
tattctctat gacactatgc atgttgtact aggtgctgga catttttact agtgttaagc 1200
taatggtagg tagaaaccag tgttgtgctg tgttttcatt gcattnnnnn nnnnnnnnnn 1260
nnnnnncggt acagttaaag gaacattgag tcaaaatcag aattcataaa atccgttgta 1320
acatacctaa tgtgaacaca ttatcaacat gtacctgtac ttgtttataa ccagagatat 1380
tagaggtagt caacaaaagg ttatcattaa tattagttct gcggtttttt cacataattt 1440
aagaaattct gaacatgttt agcagcaagc atttgtataa ctatgacaaa cactgttagc 1500
gcgttttatt agattgattt gtaaaactta actattgtat ttattggaac caactatttt 1560
attttactag aaccagcaca ttggattact tagtatcaaa cactgtaggt agatactgga 1620
gttttgtttt gttttgtttg agacggagtc tccctctgtc gcccaggctg gattggagta 1680
gcgtggtgcg atctcgtccc actgcaacct ccgcctccgg cttcaagcaa ttctcctgcc 1740
tcagcctccc gagtggctgg aattacaggc gcccgccacc gtgcccggct aattttttgt 1800
tttgtttttg ttttttaagt agagacaggg tttcaccatg ctggccaggc tggtctcgaa 1860
ctcctgacct cgtgatccgc ccgccttgac ctcccaaagt gctgcgatta cagcagtgag 1920
cccggccttt tttgttgttg ttgtttaaat gcatgaattg tttcctacta agaagctatg 1980
atatagttcc ttgaccaaat gcagatgaac aggattatct gataaattga ttaacgagag 2040

-continued cagacaaaat acgggtattt aattcatctg ctcattnnnn nnnnnnnnnn nnnnnnnnnn 2100
nnnnnnnnnn nnnnnnnnnn nnnnnnnnnn ngttgggagg ggatacccag cttcctaagt 2160
aaaggagtga tatttgagca aggcattata gaataaatga gagtttggcc agtagggaaa 2220
agaagcagca tgcggagagg tatgggacgt gggggaatga caagaaccca gaattgaagt 2280
cactagaaga tggtggtggg aggacgtgaa acaaggcaag gaaaggtaca agcggatcca 2340
gatactggaa gactttgtgt tgcaatgctt taatgaaaaa ttggatttcg ggccgggttc 2400
ggtggctcat gcctgtaatc ccagcacttt gggaggctga ggcagacaga tcacttgaag 2460
tcggggttta agaccagcct ggccaacatg gtgaaacccc atctctacaa aaaatacaaa 2520
aggtagccgg gcttggtggc ctgtgcctgt agttccagct acttgggagg ctgaggcaca 2580
agaattgcct gaacctggaa agtggaggta gcagtgagtg gagatcatgc tgctgcactc 2640
cagcctgggc atagagcgag accctnnnnn nnnnnnnnnn nnnnnnnnnn ggttttatta 2700
ttaggctaag ccataatttc tttctacttt ttaaaataca gaaattgcca tcaaactgaa 2760
atttattgtc ttatatgcta ataggtcagt tgttctgtct ttactgtaat gatttcttta 2820
tgaaaatgat cttaaatctg agattcctaa ctttggcttt taactagaat tacccattac 2880
atttgatgat gtctttaaat gtcagttgta gctattagtc tgataaatatg tgtggaatat 2940 acagaagggt atttagacag aagttaggtt aacatctgaa ctacttcctc cttgcgtatt 3000
taagagaata ttgagttagg tttctagaat cctcaactaa ctctaagttt attttctttg 3060
tctagaatac tatgctgttt ttgtttttgg aaggaagaga tataagaaca gtttgctgct 3120
ctcaaggagc ttcaaaggct gtaccagtgg ggatgccatt ggtatattta gctggatagt 3180
tgttattcag aaaagcagga caagtaattt tgattcctgg tccgtacttg gtaatgtcag 3240
taatgttaac tctagctggt tgttgacatc tggtcattta gttgccaatt cctttttttt 3300
tttnnnnnnn nnnnnnnnnn nnnnnnnnnn nnnnnnnnnn nnnnntattc tgagctcaat 3360
tcaacacagg gacaccaggt tgctgctttt gttcatggtt tccagcctgt gcacttaaga 3420
aatttatttt tatgtatttc aagctgtaac tccagagatt gggattgttt gattgcgtcc 3480
ttagcagtga tactaatagc aacttctgtc tctagaacat tggaaaatta aaatgtattt 3540
atctaccgtt ttttcccttg aggttatatg aaggtagaaa tgaatcagac tagatgatta 3600
gctaagcaaa actgttaacc ctcatccctt cccctctaga caactatgaa attagtcagt 3660
atgtattcga tccttcttgc aatctcttct ctgacaatta taaaagtgat tcaggctgca 3720
taatgttgtt tgaatgaaat gaaaatacag actagagctg tttttggttt tgtttttttt 3780
tttatttacc atcagtctgt tcagtgaaaa ctaacattta agcatgattc tttttaaaaa 3840
tcattttgtg acagtttagc agggcttgnn tgataagcaa actatggtat ggtaatattt 3900
ctagtgtgca cgtttcttca catgtctggt atatgggaac tctaactcca tcaggacttt 3960
gcctatagta ggtactcagc atttactgaa ttaaatcaat aaacattttt gatgaattaa 4020
agtacaagtc agacctctgt gtctgtgggc tctgcatctg caaattcagc caactgtgga 4080
tcaaaaatat tagaaaaatg gaatgacggt ccaacaatac aagtaatacg aatgaaaaca 4140
atacaactat gtacattgta tcaggtatta taagtaattt agagatgctt taagtatacc 4200
aaaggatttg cataggttgt atgcagatac tgtaccattt tgtgtaagga acttgagcat 4260
ctgtggattt tggtatttgc atggttcctg gaaccaatcc ctcagggaca ctgagggact 4320
atagttggtc ataccacctg attttagaga ttttctgatc ctcagaagtt aattaagtaa 4380
actacagtag tctgttctta acctcggagg atacattcca agaacctcag tgaatatctg 4440

-continued

```
aaaccacata tagtattgaa tccgatatat acacggtaat attttttcct atacatgtgt   4500
atctataaag tttaaattct aaattagaca tagtattaac aataataata aattagaaaa   4560
agactgggca tagtggttca cgcctataat cttaacactt taacttttaa ctatgacgtt   4620
gtcttgaaaa agaaatcagc cagccaaggt ggctcatgtc tgtaatccta gtgttttgag   4680
aagctcagtc aggaagtttg tttgaaccca ggaatccgag accaccctag gcaacatggt   4740
gaaaccttgt ttctataaaa aaaaaccaaa aaattagcca gacctggtgg tgcatgcctg   4800
tagtaccagc tacccaggag gctgaggtgg gaggagtgct tgaacttggg aggtcaagtt   4860
tacaatgttg acaatgttgg gtcctttacg tagttgtgta agtgagccat gatcatgcca   4920
ctgcactaca gccttgggca acagcctgac cctgtctcaa aattttaatt taattttaaa   4980
aatgaaatag aacaattaca acaatacgct gtattactga caagaagggc aaatttttaa   5040
aaaaccaata tgctgtaata agttatatga ataaggggat cctcccctac cccagaatat   5100
ctgattgtac tataccgtag gtaactgcaa ccgtggagag caaaaactga agatactgtg   5160
tcttaagttt ctttttcaac tcccaaattc ttggatttct cacgtcttgg cttcctcagt   5220
agaggtgaga aatgctaaaa cagtgaaaac aggaaaaata acttactcat tcaagaagtc   5280
gattatggtc cagatggaaa atttgaatta tttttgtaaa actaaactaa agtagccagg   5340
caccgtggct cacgcctgta atctcagcac tttgggaggc tgaggcgggt ggatcacttg   5400
aggtcaggaa ttcaagacca gcctggccaa caaggtgaaa ccctgtctct actaaaaata   5460
caaaaattag tcaggcatgg tggcgggcac ctgtagtccc ggctacttgg gaggctgagg   5520
tgggagaatc gcttgaacct ggggtgtgga cattgcagtg agcccagatc acgccactgc   5580
actccagcct gggcaacatt gtgagactac aaaaaaatata atagtaagta aagtaaaaag   5640
tttcccatac ttgataaatg tctaataaaa attgaatatg ttctaggact ctgaaaaagg   5700
agttgaatat agttggaggt tggtttttag gaattatttt tcttaaatta attatccttg   5760
tagtcaccta ggaattgtat attttctgtt gatcttagaa aattgatcaa atctatagtt   5820
cattttgttt tttcaatttt tttttaaaga gatggggtct tactgtatta atgttgaact   5880
cctggcctca accaggtctc ccacctcagc ttctgaagta actgggattg caggtgccac   5940
tgagccaggc tcctttattg gtatttttat taaaagcttt tctctaatgt ctttgtaaca   6000
gttctcaatt tttgaaatgg tgttactcat tctttagagt aaactgtcaa ctttcatttt   6060
cttttttttt tttttntttt ttctttcttt nnnttgagac ggaatctcgc tctgtcaccc   6120
aggctggagt gtagtggtgg gatctcggct cactgtgann nnnnnnnnnn nnnnnnnnnn   6180
nnntctcctg cctcagcctc cagagtagct ggaattaacg ggcacgtgac accgtgccca   6240
gctacttttt tttttttttnn nnnnnnnnnn nnnnnnngat gggggtttca ccatgttggt   6300
caggctggtc tcgaactcca gacgtcaggt gatccaccca cctcagcctc ccaaagtgct   6360
ggtattacag gcatgagcaa cagcgcccag cctcaacttt cattttcatt tggttagttt   6420
ttgaactatt cagtgggtaa ggttgtataa atgtcttttc tctgtataga agtttcttgg   6480
agttcaagga gtgctacttt gcaaactcat agagtattta taaaagctaa ctgcagaagg   6540
tgttcatagg ctaaaccgtt tcctattctt ggtagcacca ttttctctgg cctgaaatac   6600
tttccctcta ctattagtgt ctgtcagtgc ccagcagtgt atttactttc ctgaggaaca   6660
attcaaatgc taagtgcttt aagacctaag ggtggaaaag cagtgttttc aggcattatt   6720
aggaaaataa gattttaatt agacacccag aaacaaaaac aggtttgtaa ttggtaaagt   6780
gaaagatggt taaagaaggt tagattgacc aaagctagag tttttctttt tttcttttt   6840
```

-continued

```
tttttttttt tttttgagac agtgtctcnn nnnnnnnnnn nnnnnnnnnn nnnnnnnnnn   6900
nnnnnnggct agctgcaacc tccacttcct gggttcaaac agttctccca cctgagcctc   6960
ctgagtagct gcgaggcatg tgtcaccatg ctcagccatt ttttgtgtgt ttttagtaga   7020
gactgagttt ctccatgttg gtcaggctgg tctcgaactc ttgagctcag gnnnnnnnnn   7080
nnnnnnnnnn nnnnnnnnnn nnnnnnnnnn nnnnnnnnnn nnnnnnnnnn nnnnnnnnnt   7140
gtaccttttt ttaatcgagc aatctagttc ttgatcctaa tagtctttgt ggtgggtgtt   7200
tgcattttta gatgaggaaa agggaaatct aggagtccta ggaaatacag ttggtatatg   7260
ggaactgata cgtaattaga cttaagcaat ccatgttgaa tttgtgactt aagcacttaa   7320
ctataaattt accctctcca gttgtctgat gataatcaaa acttgaagca gttatccata   7380
ttgggatctc tttggggaat cccagtcacc aaaagttagg ttttctttaa tattttttca   7440
tggaagtttt caaatatact caaaattgaa agaattatgt aataaattct catgagccca   7500
tcacacatct tcaataatga atgtacagca ttgcagtgtg gagcttggcc tattgctgac   7560
cactcatcaa tgtggcagaa ccactccatg gttccccatg gaaatgggag ctacttcagt   7620
tctcttttta cagaaaaatt caataaatat ctactgattg tgccctactt gtgacttgaa   7680
gccaggtttg tttgttgttg tttttctttt tttnttttt tttttttttt actagtcttg   7740
ctctgtcacc cgagctacag tgcaatggca tgatatcagt gcactgcaac ctccagctcc   7800
tgggttcaag tgattctctt gcctcagcct cccgagtagc tgggactatg ggcgtgcacc   7860
acaataccta gctaattttt gtatatagta gagatagagc ttcatcatgt tgcccaggct   7920
gctctcgaac tcctgagctc aagcagtcta cccacctcca cctcccaaag tactaagatt   7980
acaggcatga gccaccatgc cagcaaagct gggtatttct taaatttgtt cagtcaggtg   8040
caagaaatta tttgccctac tctgaaagtt aaaaatattc taagagaatt atggtttcgc   8100
agctggggtt ttttaagact tgagctcctg ggctcctgc atatatcctt agaacaacat   8160
tgtccagtag aagtacaatg taagccatgt tttgtttaac ccagcatatc caaaatatta   8220
ccccttttgc atgtgcttaa tataaaaaat taagatgatt tctattccag gttttcaata   8280
ttcagtgagt aattttacac ttagagcaag tgtcatttca gactagtcac attttgagta   8340
ctcagtaacc acatatgggc tagtgctacc ttgctagata gcatagcctt tgggtcccac   8400
aaagtgttca cattctctgt ttacacacat cttttgaagt gtcatgagag agagccagat   8460
aggatccaga ttttctttat atctgtttgg tctgtcttac ggattcctag ttgattattt   8520
ctttgttgct tcttataggg atgtatcaga agcttaataa actcatgatt attatgttaa   8580
ctgcctgaag tattaatttt agcaacaaat tgaactataa ttttaatttt tcaagtaaat   8640
tttcttatgt gatactaagt atttcatata tacatgtatt agaagtaaat gggagtttag   8700
taatgaatag tatatagtag tttgtgatta tatttttctg tttttttttt ttagattgca   8760
gcaaaaattg gaggtgatgc tgggacatca ctgaattcaa atgactatgg ttacggggga   8820
caaaaaagac ctttagaaga tggaggtaag ttatactcat acgtatttta aattgttttt   8880
cagagtgttt agttgaagtg gttctcagta ttttttgtta ttctattgag acattacttt   8940
tattataaga ttgttaaaac tgtaaggtgt atattggcct aaaggggggg aagagaccta   9000
gagaaggtaa gtaaaatttc agtcaaccag aaagttttgt cttactagaa aacagtttat   9060
tttccctctt ttaggattgt gccagattga aagtttgcac agacgtcttg ttaataatat   9120
taaaaaaaca aaaatataaa ttgcttagaa gacacttcac tggttttact catacatgaa   9180
tggattttaa tatgctgtgt tttcgtcatt tttctatttg caattacact ttaaaggtcg   9240
```

-continued

```
aaattcgtat tgtttgctac tctagtgtgt tgcaggttat accgtttttt ttaatgttct   9300
ttgcttttag tacttttgtg tttcacgttt agctgtaaac ctatagatta aaacagtggg   9360
ttcacagtgc tttgtagttt taaaaatcat aatcattgaa gcttctgaac ttagaagtct   9420
gcatgtattt tttgttttag gtttgatgta tgagttttga tacattttct ttttaccctt   9480
ttttttaaag gaaggattct cactgaggct atagaatgta tttgtagctt ttgaccagga   9540
gaactttgtt tcctttattt aagtgtcttt catatttata gtgaggtttt taatataaaa   9600
aaaaaaaatg agctaatgat gcttcagatg ttgtatgtaa tgtattcttt ttattttatg   9660
tgtagatggc tcttggacaa gtccgagcag tacaacacac tgggagggaa tgccctctcc   9720
ttttaaaggc aggaattttt atttattacc tgtgttcagt atgtaaacgt gaaataaacc   9780
agtggattct taaatggaca caaatatttc ttggattatg tgtctgaatt tttgctgcac   9840
aacattctga tggttaatca tttaagtttg aaggggggag gagaatgtag tactttgagc   9900
tataggttgt ctgttccaag gtatgcattg tattcatctg tgtaatggat ttagatgaag   9960
gtagtcatgt agttgccttg agttttttttg tttttttgtgt ttttttttgct aaagttttat  10020
acagtgaaat gtttgtttat aaataataga acagtttaag ttgagattgc cttgtaatgt  10080
tgtggggttt gttttttttt ttaatttttt ggggcatagc tttgtggtca ctgtccgata  10140
tactcaactt ttaatatgtc agatttttgt agtttgatac gctttttttcc ccccagtctt  10200
cagttcctga ggtggaagca tcattagcct ttagcatgtg atattttgct agtaatggac  10260
ctaaagtact ttgtcttgta tcattctaat gtgcataaca tacattaagg tcagtgattt  10320
gttaagaatc agataactat tttaatgtct gtgcatcttt tgaatgtgaa gagaatgaag  10380
tatagtttct tttttagatt actgagtttg tgttgaattt tggcagtttt ggttcaaatg  10440
ataaaccgta ccttcagata tttcaataaa tgtttatatt tattcttgtt tgggagggga  10500
gaagctttgt acttaattgg taaaaaaatta aaagacactt aattttgcag atcaaccaga  10560
tgctaagaaa gttgctcctc aaaatgactg taagtattcc ttttaaactg ggtcaaaagc  10620
tatattaaga ttttgttcat attattgggt atctttgaag ttagttggtt tatgagtatt  10680
ttggatcagc tagcctgaac ttctttgtaa atatgtacct ttttctccta ttttacaatc  10740
tgtcccatta attgtggcca ggtatatgta aggattggtt gccgaattat tttacatatt  10800
taacaactcc aattcttgat ctacgcttgt acaacttgaa aaaggaaatt atattgttct  10860
gtgccattgc taatataatg tcttcccttt cattggctct cttacccctg tcagtgccaa  10920
tataaatatt ctgtataaaa tttgactctc ttcaaggtgt tgtctgtgca ttagggaaag  10980
gtttttgaat gtttgatgtg attttgttgt taaatacata agtaacttta aattttgaat  11040
tttcgtttta tttttattta attttttgat agcttttgga acacagttac caccgatgca  11100
tcagcagcaa aggtatagtc acaaactttt caaaaagtac tctgcaagtt ttggttgagc  11160
tgcatgtaaa aacacaacca cattggtata tattgaatat gtgtctgtat tttttggtgt  11220
acctagttca tatcactccc cttgggaagg taccataaag tgatgatttt tcttttgagt  11280
gagaaaaatt tgtgatttgg agagagagag ggaattagcc acagtttaga agaacagggg  11340
tgaattagag taactgttaa gatgacattc tctnnnnnnn nnnnnnnnnn nnnnacagtt  11400
catgccttca gactgttcca ttgatcatcc cttcttcact tgatgtatca tctnnnnnnn  11460
nnnnnnnnnn nnnnnnnnnn nnnnnnnnnn natttttga catgagtctg agcatagaac  11520
cttagtttaa gccattggga gacattagac ttccattttt attaatagat tatcttttat  11580
ttgtaaacaa agtatctttc actgaaggaa aaatggtact ttctgttact ttttagcaga  11640
```

-continued

```
tctgtaatga cagaagaata caaagttcca gatggaatgg ttggatttag taagtaactt  11700
gatttttaaa gttttgaaaa catgatcaaa acatacttta gaatctttca accaaaaaaa  11760
cttttttttt ctaactagta attggcagag gaggtgaaca gatctcacgc atacaacagg  11820
aatctggatg caaaatacag atagctcctg gtaatgttac attctcttgg tattttcaga  11880
gtgactagaa aagtagcttt tttttttct tttaggtttc tagtactaat aatgctgcct  11940
ttaatctttt gacctgaagt tctatttttg ttttaaattg tagacagtgg tggccttcca  12000
gaaaggtcct gtatgttaac tggaacacct gaatctgtcc agtaagtttg aaaatcttta  12060
aaatggactt aaagtaacaa cgggagaact ctttgaattt tctctctgct ctttgttact  12120
gctttatttt acactactct ttcgttgcct ccttccctcc caagtcctct gactcctttg  12180
aagtttatgc ctcatgcctt tctcaattag ggtttatcat taaacacaga aaatggttaa  12240
aacaacttca tatctactcc agtctctact tacaaagcga agtgtagcct ggaggagaat  12300
gcgcagtaat gttgactggt gacacctaaa actcagacat taagctcaag tggactgttg  12360
tgttgtctgc atttccctag ttccattcac ttttccattc ctctccaagg ctctttaata  12420
ctatatttcc ccatctccaa atcttcagca tctaacccca cctctctcct tcttaagctt  12480
atttacggag aaaatggaaa cgaatgataa gaagcttttc ttttccccta ccgctaaacc  12540
taccagcctt catttttttt cnctgttcac atagtactca ggtaattgct ttcctttgtg  12600
ttcatgtgcc taaagccagc cctttcttcc tattgaaggt tcagcctgca gttgtacttt  12660
cttctgcgtt attagttccc cccctttact agatttttnn nnnnnnnnnn nnnnnnnnnn  12720
nnnnnnnnnn nnnnnnnnnn nntgcaggtg catgccacca cacccagcta atttttgtat  12780
ttttttagta ganncagggt ttcaccatgt tggccaggat ggtgtcaatg tcttgacctc  12840
gttatccacc cgcctcggcc tccccaagtc ctgggattat aggcgtgagc cactgccccc  12900
agcctgattt tctttgtagc actttccaaa taatacgtta ttcatttgac atgttatttt  12960
tacttatttt aatgaaacga agccactcca gcaggaaccc tgtctctttg agtgttacca  13020
ccccattacc taaaatggca cttgcacatg gttgatattt aagtatttgt tgaatgaata  13080
attgtagcat atgagtaagt aaaatggtag tttaaaaatg taaataaata aatcttttag  13140
ttcttggaag aatcagttta attctgagat aactttagca ttagagttct tggaaattgt  13200
ggactattct taaaaataaa aattgtatat ctagaaaatt tattgcctaa tctctcaatc  13260
tttgaccctt gatggcattt tctttcagtt aaaagtaaaa acattgttaa agttagcatt  13320
aaggcaccta atcctgaatt ggggtaggag gagtacttgg ttacattgtt ttgtatttct  13380
ctatttgaat aaacttgggt atgctgcaac ttactattta aatattaatt tgttaacagg  13440
tcagcaaaac ggttactgga ccagattgtt gaaaaaggaa gaccagctcc tggcttccat  13500
catggcgatg gaccgggaaa tgcagttcaa gaaatcatga ttcctgctag caaggcagga  13560
ttagtcattg gaaagggggg agaaactatt aaacagcttc aggtattgtt atgtttgtga  13620
aatggctact tttggtctgt tttgatgnnn nnnnnngtct gctccctttt gttaatatgt  13680
attattttct atgattataa caggaacggg cgggagttaa aatggttatg attcaagacg  13740
ggccgcaaaa cactggtgct gacaaacctc ttaggattac aggagaccca tataaagttc  13800
aagtaaactt aactttatac tttataaaga aagagtttgg gttgaatggg gttgggcaaa  13860
atatgcatga ataattaaaa tgttttgaga cgtgctttct aaattagcta actttttcta  13920
ctttagcaag ccaaggaaat ggtgttagag ttaattcgtg atcaaggtgg tttcagagaa  13980
gttcggaatg agtatgggtc aagaatagga ggaaatgaag ggatagatgt aagtaaaaat  14040
```

-continued

```
acccattcag aaatggttgt atgctaattc gtaaatatag tagtgttttc tgttttgtgt  14100
taaatagctc taacattgtt atccttttat ttcaccttta tactttagaa tacagaatta  14160
agtattttat atcttgtcac cctatttgct ataaatataa aattatatgt actattatga  14220
tttgaggcag attttcagga aatggtnnnn nnnnnnnnnn nctttttttt actttaaacc  14280
ctgagaagct agttttctta atactcagtc ttttttacat aaggtcccca ttccaagatt  14340
tgctgttggc attgtaatag gaagaaacgg agagatgatc aaaaaaatac aaaatgatgc  14400
tggtgttcga attcagttta agccaggtga gtgcatataa taatcttgta agtgttggca  14460
gcaatgagtt ttgnnnnnnn nnnnnnnnnn nnnnnnnnnn nnnnnnnnnn nnnnnnnnnn  14520
nnnnnnnnnn nnnnnnnnnn nnnnnnnnnn nnnnnnnnnn nnnnnnnnnn nnnnnnnnnn  14580
nnnnnnnnnn nnnnnnnnnn nnnnnnnnnn nnnnnnnnnn nnnnnnnnnn nnnnnnnnnn  14640
nnnnnnnnnn nnnnnnnnnn nnnnnnnnnn nnnnnnnnnn nnnnnnnnnn nnnnnnnnnn  14700
nnnnnnnnnn nnnnnnnnnn nnnnnnnnnn nnnnnnnnnn nnnnnnnnnn nnnnnnnnnn  14760
nnnnnnnnnn nnnnnnnnnn nnnnnnnnnn nnnnnnnnnn nnnnnnnnnn nnnnnnnnnn  14820
nnnnnnnnnn nnnnnnnnnn nnnnnnnnnn nnnnnnnnnn nnnnnnnnnn nnnnnnnnnn  14880
nnnnnnnnnn nnnnnnnnnn nnnnnnnnnn nnnnnnnnnn nnnnnnnnnn nnnnnnnnnn  14940
nnnnnnnnnn nnnnnnnnnn nnnnnnnnnn nnnnnnnnnn nnnnnnnnnn nnnnnnnnnn  15000
nnnnnnnnnn nnnnnnnnnn nnnnnnnnnn nnnnnnnnnn nnnnnnnnnn nnnnnnnnnn  15060
nnnnnnnnnn nnnnnnnnnn nnnnnnnnnn nnnnnnnnnn nnnnnnnnnn nnnnnnnnnn  15120
nnnnnnnnnn nnnnnnnnnn nnnnnnnnnn nnnnnnnnnn nnnnnnnnnn nnnnnnnnnn  15180
nnnnnnnnnn nnnnnnnnnn nnnnnnnnnn nnnnnnnnnn nnnnnnnnnn nnnnnnnnnn  15240
nnnnnnnnnn nnnnnnnnnn nnnnnnnnnn nnnnnnnnnn nnnnnnnnnn nnnnnnnnnn  15300
nnnnnnnnnn nnnnnnnnnn nnnnnnnnnn nnnnnnnnnn nnnnnnnnnn nnnnnnnnnn  15360
nnnnnnnnnn nnnnnnnnnn nnnnnnnnnn nnnnnnnnnn nnnnnnnnnn nnnnnnnnnn  15420
nnnnnnnnnn nnnnnnnnnn nnnnnnnnnn nnnnnnnnnn nnnnnnnnnn nnnnnnnnnn  15480
nnnnnnnnnn nnnnnnnnnn nnnnnnnnnn nnnnnnnnnn nnnnnnnnnn nnnnnnnnnn  15540
nnnnnnnnnn nnnnnnnnnn nnnnnnnnnn nnnnnnnnnn nnnnnnnnnn nnnnnnnnnn  15600
nnnnnnnnnn nnnnnnnnnn nnnnnnnnnn nnnnnnnnnn nnnnnnnnnn nnnnnnnnnn  15660
nnnnnnnnnn nnnnnnnnnn nnnnnnnnnn nnnnnnnnnn nnnnnnnnnn nnnnnnnnnn  15720
nnnnnnnnnn nnnnnnnnnn nnnnnnnnnn nnnnnnnnnn nnnnnnnnnn nnnnnnnnnn  15780
nnnnnnnnnn nnnnnnnnnn nnnnnnnnnn nnnnnnnnnn nnnnnnnnnn nnnnnnnnnn  15840
nnnnnnnnnn nnnnnnnnnn nnnnnnnnnn nnnnnnnnnn nnnnnnnnnn nnnnnnnnnn  15900
nnnnnnnnnn nnnnnnnnnn nnnnnnnnnn nnnnnnnnnn nnnnnnnnnn nnnnnnnnnn  15960
nnnnnnnnnn nnnnnnnnnn nnnnnnnnnn nnnnnnnnnn nnnnnnnnnn nnnnnnnnnn  16020
nnnnnnnnnn nnnnnnnnnn nnnnnnnnnn nnnnnnnnnn nnnnnnnnnn nnnnnnnnnn  16080
nnnnnnnnnn nnnnnnnnnn nnnnnnnnnn nnnnnnnnnn nnnnnnnnnn nnnnnnnnnn  16140
nnnnnnnnnn nnnnnnnnnn nnnnnnnnnn nnnnnnnnnn nnnnnnnnnn nnnnnnnnnn  16200
nnnnnnnnnn nnnnnnnnnn nnnnnnnnnn nnnnnnnnnn nnnnnnnnnn nnnnnnnnnn  16260
nnnnnnnnnn nnnnnnnnnn nnnnnnnnnn nnnnnnnnnn nnnnnnnnnn nnnnnnnnnn  16320
nnnnnnnnnn nnnnnnnnnn nnnnnnnnnn nnnnnnnnnn nnnnnnnnnn nnnnnnnnnn  16380
nnnnnnnnnn nnnnnnnnnn nnnnnnnnnn nnnnnnnnnn nnnnnnnnnn nnnnnnnnnn  16440
```

-continued nnnnnnnnnn nnnnnnnnnn nnnnnnnnnn nnnnnnnnnn nnnnnnnnnn nnnnnnnnnn 16500
nnnnnnnnnn nnnnnnnnnn nnnnnnnnnn nnnnnnnnnn nnnnnnnnnn nnnnnnnnnn 16560
nnnnnnnnnn nnnnnnnnnn nnnnnnnnnn nnnnnnnnnn nnnnnnnnnn nnnnnnnnnn 16620
nnnnnnnnnn nnnnnnnnnn nnnnnnnnnn nnnnnnnnnn nnnnnnnnnn nnnnnnnnnn 16680
nnnnnnnnnn nnnnnnnnnn nnnnnnnnnn nnnnnnnnnn nnnnnnnnnn nnnnnnnnnn 16740
nnnnnnnnnn nnnnnnnnnn nnnnnnnnnn nnnnnnnnnn nnnnnnnnnn nnnnnnnnnn 16800
nnnnnnnnnn nnnnnnnnnn nnnnnnnnnn nnnnnnnnnn nnnnnnnnnn nnnnnnnnnn 16860
nnnnnnnnnn nnnnnnnnnn nnnnnnnnnn nnnnnnnnnn nnnnnnnnnn nnnnnnnnnn 16920
nnnnnnnnnn nnnnnnnnnn nnnnnnnnnn nnnnnnnnnn nnnnnnnnnn nnnnnnnnnn 16980
nnnnnnnnnn nnnnnnnnnn nnnnnnnnnn nnnnnnnnnn nnnnnnnnnn nnnnnnnnnn 17040
nnnnnnnnnn nnnnnnnnnn nnnnnnnnnn nnnnnnnnnn nnnnnnnnnn nnnnnnnnnn 17100
nnnnnnnnnn nnnnnnnnnn nnnnnnnnnn nnnnnnnnnn nnnnnnnnnn nnnnnnnnnn 17160
nnnnnnnnnn nnnnnnnnnn nnnnnnnnnn nnnnnnnnnn nnnnnnnnnn nnnnnnnnnn 17220
nnnnnnnnnn nnnnnnnnnn nnnnnnnnnn nnnnnnnnnn nnnnnnnnnn nnnnnnnnnn 17280
nnnnnnnnnn nnnnnnnnnn nnnnnnnnnn nnnnnnnnnn nnnnnnnnnn nnnnnnnnnn 17340
nnnnnnnnnn nnnnnnnnnn nnnnnnnnnn nnnnnnnnnn nnnnnnnnnn nnnnnnnnnn 17400
nnnnnnnnnn nnnnnnnnnn nnnnnnnnnn nnnnnnnnnn nnnnnnnnnn nnnnnnnnnn 17460
nnnnnnnnnn nnnnnnnnnn nnnnnnnnnn nnnnnnnnnn nnnnnnnnnn nnnnnnnnnn 17520
nnnnnnnnnn nnnnnnnnnn nnnnnnnnnn nnnnnnnnnn nnnnnnnnnn nnnnnnnnnn 17580
nnnnnnnnnn nnnnnnnnnn nnnnnnnnnn nnnnnnnnnn nnnnnnnnnn nnnnnnnnnn 17640
nnnnnnnnnn nnnnnnnnnn nnnnnnnnnn nnnnnnnnnn nnnnnnnnnn nnnnnnnnnn 17700
nnnnnnnnnn nnnnnnnnnn nnnnnnnnnn nnnnnnnnnn nnnnnnnnnn nnnnnnnnnn 17760
nnnnnnnnnn nnnnnnnnnn nnnnnnnnnn nnnnnnnnnn nnnnnnnnnn nnnnnnnnnn 17820
nnnnnnnnnn nnnnnnnnnn nnnnnnnnnn nnnnnnnnnn nnnnnnnnnn nnnnnnnnnn 17880
nnnnnnnnnn nnnnnnnnnn nnnnnnnnnn nnnnnnnnnn nnnnnnnnnn nnnnnnnnnn 17940
nnnnnnnnnn nnnnnnnnnn nnnnnnnnnn nnnnnnnnnn nnnnnnnnnn nnnnnnnnnn 18000
nnnnnnnnnn nnnnnnnnnn nnnnnnnnnn nnnnnnnnnn nnnnnnnnnn nnnnnnnnnn 18060
nnnnnnnnnn nnnnnnnnnn nnnnnnnnnn nnnnnnnnnn nnnnnnnnnn nnnnnnnnnn 18120
nnnnnnnnnn nnnnnnnnnn nnnnnnnnnn nnnnnnnnnn nnnnnnnnnn nnnnnnnnnn 18180
nnnnnnnnnn nnnnnnnnnn nnnnnnnnnn nnnnnnnnnn nnnnnnnnnn nnnnnnnnnn 18240
nnnnnnnnnn nnnnnnnnnn nnnnnnnnnn nnnnnnnnnn nnnnnnnnnn nnnnnnnnnn 18300
nnnnnnnnnn nnnnnnnnnn nnnnnnnnnn nnnnnnnnnn nnnnnnnnnn nnnnnnnnnn 18360
nnnnnnnnnn nnnnnnnnnn nnnnnnnnnn nnnnnnnnnn nnnnnnnnnn nnnnnnnnnn 18420
nnnnnnnnnn nnnnnnnnnn nnnnnnnnnn nnnnnnnnnn nnnnnnnnnn nnnnnnnnnn 18480
nnnnnnnnnn nnnnnnnnnn nnnnnnnnnn nnnnnnnnnn nnnnnnnnnn nnnnnnnnnn 18540
nnnnnnnnnn nnnnnnnnnn nnnnnnnnnn nnnnnnnnnn nnnnnnnnnn nnnnnnnnnn 18600
nnnnnnnnnn nnnnnnnnnn nnnnnnnnnn nnnnnnnnnn nnnnnnnnnn nnnnnnnnnn 18660
nnnnnnnnnn nnnnnnnnnn nnnnnnnnnn nnnnnnnnnn nnnnnnnnnn nnnnnnnnnn 18720
nnnnnnnnnn nnnnnnnnnn nnnnnnnnnn nnnnnnnnnn nnnnnnnnnn nnnnnnnnnn 18780
nnnnnnnnnn nnnnnnnnnn nnnnnnnnnn nnnnnnnnnn nnnnnnnnnn nnnnnnnnnn 18840

-continued nnnnnnnnnn nnnnnnnnnn nnnnnnnnnn nnnnnnnnnn nnnnnnnnnn nnnnnnnnnn 18900
nnnnnnnnnn nnnnnnnnnn nnnnnnnnnn nnnnnnnnnn nnnnnnnnnn nnnnnnnnnn 18960
nnnnnnnnnn nnnnnnnnnn nnnnnnnnnn nnnnnnnnnn nnnnnnnnnn nnnnnnnnnn 19020
nnnnnnnnnn nnnnnnnnnn nnnnnnnnnn nnnnnnnnnn nnnnnnnnnn nnnnnnnnnn 19080
nnnnnnnnnn nnnnnnnnnn nnnnnnnnnn nnnnnnnnnn nnnnnnnnnn nnnnnnnnnn 19140
nnnnnnnnnn nnnnnnnnnn nnnnnnnnnn nnnnnnnnnn nnnnnnnnnn nnnnnnnnnn 19200
nnnnnnnnnn nnnnnnnnnn nnnnnnnnnn nnnnnnnnnn nnnnnnnnnn nnnnnnnnnn 19260
nnnnnnnnnn nnnnnnnnnn nnnnnnnnnn nnnnnnnnnn nnnnnnnnnn nnnnnnnnnn 19320
nnnnnnnnnn nnnnnnnnnn nnnnnnnnnn nnnnnnnnnn nnnnnnnnnn nnnnnnnnnn 19380
nnnnnnnnnn nnnnnnnnnn nnnnnnnnnn nnnnnnnnnn nnnnnnnnnn nnnnnnnnnn 19440
nnnnnnnnnn nnnnnnnnnn nnnnnnnnnn nnnnnnnnnn nnnnnnnnnn nnnnnnnnnn 19500
nnnnnnnnnn nnnnnnnnnn nnnnnnnnnn nnnnnnnnnn nnnnnnnnnn nnnnnnnnnn 19560
nnnnnnnnnn nnnnnnnnnn nnnnnnnnnn nnnnnnnnnn nnnnnnnnnn nnnnnnnnnn 19620
nnnnnnnnnn nnnnnnnnnn nnnnnnnnnn nnnnnnnnnn nnnnnnnnnn nnnnnnnnnn 19680
nnnnnnnnnn nnnnnnnnnn nnnnnnnnnn nnnnnnnnnn nnnnnnnnnn nnnnnnnnnn 19740
nnnnnnnnnn nnnnnnnnnn nnnnnnnnnn nnnnnnnnnn nnnnnnnnnn nnnnnnnnnn 19800
nnnnnnnnnn nnnnnnnnnn nnnnnnnnnn nnnnnnnnnn nnnnnnnnnn nnnnnnnnnn 19860
nnnnnnnnnn nnnnnnnnnn nnnnnnnnnn nnnnnnnnnn nnnnnnnnnn nnnnnnnnnn 19920
nnnnnnnnnn nnnnnnnnnn nnnnnnnnnn nnnnnnnnnn nnnnnnnnnn nnnnnnnnnn 19980
nnnnnnnnnn nnnnnnnnnn nnnnnnnnnn nnnnnnnnnn nnnnnnnnnn nnnnnnnnnn 20040
nnnnnnnnnn nnnnnnnnnn nnnnnnnnnn nnnnnnnnnn nnnnnnnnnn nnnnnnnnnn 20100
nnnnnnnnnn nnnnnnnnnn nnnnnnnnnn nnnnnnnnnn nnnnnnnnnn nnnnnnnnnn 20160
nnnnnnnnnn nnnnnnnnnn nnnnnnnnnn nnnnnnnnnn nnnnnnnnnn nnnnnnnnnn 20220
nnnnnnnnnn nnnnacaccc atttactgtt taattaattt tgtttctttg ttttgaagat 20280
gatgggacaa cacctgagag gatagcacaa ataacaggac ctccagaccg atgtcaacat 20340
gctgcagaaa ttattacaga ccttcttcga agtgttcagg tttgatagaa agttaacatt 20400
ttcatttttt gtttttatgg aaaaatactt tccttcatga aatctgaagt ttcctctata 20460
tcagagtctg cttgatgatg ctttattaat ggagaaagtt taaattgttt taaggtaaag 20520
atcttggagc aggaagaact actaccttaa gtgctacctt atttactctt taatttaaaa 20580
aaatgttatt acttatgatt atttgggccg gttcatctct acatttatgg ttcaggtatt 20640
tgagagctgg gaaaaataga cataattaat tttatcatga aaaaaagtat ttctgtgctg 20700
attttttcct tcttgtctat tcctctctat aggctggtaa tcctggtgga cctggacctg 20760
gtggtcgagg aagaggtaga ggtcaaggca actggaacat gggaccacct ggtggactac 20820
aggaatttaa ttttattgtg ccaactggga aaactggatt aataatagga aaaggcaatg 20880
tattttaaac tcttaatgtt taacacatta ttcatttttc tggacactat ttctgttgct 20940
gttgtaaaca agtggcaatg ctttttctct ggctgtgttt tagtagaaaa gcattcttat 21000
gttaatacgt aacaagtaaa acataaatga aggatctaat gtatatttat aaaaagagca 21060
ggattttaat cttactagct tctagagaaa gtgaactaag ataattatta gcataagaaa 21120
ggtcttttga cccaaaaagt tgtttgagtg tttttgtttg tgcattttgg tttttcccga 21180
ctcatatttt aaaaatttga atgtttataa gtgtattagt ttatatttat ctgcttttaa 21240
aagcagttta ttcaaatatt ttattataat cacattaagg ttaagtttaa acataccaag 21300
taaatgtaaa tgtattttaa gagaagcatg aaatgcttcc taaaatttag atttaaagtg 21360
tagaatatta aatgaaaaat cttaatacaa tactgtcaag tagaatactg actgaccaaa 21420
ccatgttttt aatggcctat ttaattgtga ccattttctt ctaaatagct tctagtatac 21480
ccttgaaacc tttagagaaa ttactgtctt ttattttagg aggtgaaacc ataaaaagca 21540
taagccaaca gtctggtgca agaatagagc ttcagagaaa tcctccacca aatgcagatc 21600
ctaatatgaa gttatttaca attcgtggca ctccacaaca gatagattat gctcggcaac 21660
tcatagaaga aaagattggt gtgagtatac tttaaacttt taatttatag tgtagaccct 21720
tagattgtag ttaaattaag acgtttattc gaatacannn nnnnnnnnnn nnnnnnnnnn 21780
nnnnnnnnnt tatagatttc atgataccta taatagatac aatgtgaaga ttttccagca 21840
atgaaaataa cctaattaaa tgtgcagtta caggttttga gaacaacctt acgtttgagt 21900
gtggatagat aggagggtgc aggcatcata ttagtgttat tgtaggattg tggaacatac 21960
ttgaaggaca cagttaatgg gaattcatta tttattaaga ttttactata ctgaacccca 22020
gcaaggcaaa caagataaat cagatgcatc ttccgctctg cagtagaaat tcgtaaatcc 22080
tagcttttgg actggctcac aaatcatctg ggttttaaaa tgtagactat ttgggtgctt 22140
ccaactccta cacataatat acagagacag acctgactca aaatgtctgg gatagggccc 22200
agcatctgat tttacacaga tgtttgggtt tttttcttcc agaaaagttt tctgttagaa 22260
caaaaagtat aaaaagcttt gactgctttt ttgtaaatga ggcagatggt gtcttactgg 22320
agtttttaac acaaagtgtg cagggagcat cttaaattat taatcagaat ttcctaggaa 22380
aaattagttt tggtgtttgc catgctgtga atggagtgca tgcaaaacaa ggttgacgct 22440
gttttctgtg tacttgggaa gacaaaaata gatgtactaa agatgcttaa ggaacatctt 22500
ataaaatgta cacaaacatt gtaagttctg ttgtatggat agtttaattg ttcaaaaaat 22560
gaagatgttt gtggagtaat gataggaggt tgatgccata gcaaaaaaaa atgaatagca 22620
catcttggtt tttgatttta cagtattagc cttacatgca tggatcagga tttctgttgg 22680
attcatggta aaacaagata gattgtttta gagaagcaat ttggtgtggt gattaagagc 22740
acggactctt ttctctgaat catttactgg gtctgtgacc ttggagaagt tgctcaggct 22800
tttctgtgcc ttggtttcct cctataaaat gaggataatt gtatctattt catagagttg 22860
tagggattaa atgaacgttc acctgtgtgt cacttaaaag aatgcctggc acatagccct 22920
aaaaaatgtt gctacttttt cagtattatt tttactattt ggaaagaata gataatggat 22980
aataaagtga gagatgacag caattggaga cttaaagaga caagttaata aaaataactt 23040
taaaggtcat gaagtttagt ttccctattt tgcagtgaga aatttacaac aaaatatagt 23100
gttaccattt tgtccagcat gtcgcctggt tgtgttaact actcagaagg agcattttag 23160
gacagttaag tgtaatgtct ttgttggctt aacaaaacag aaatcagtta agcattatta 23220
atnnngatgt ggcatgcatg catgataagg atataaaata tcctgattta ttgaaggact 23280
taaaaaggga atgtttgtgc tgtttagaat tatgatacat gaaaggccaa aaaggatata 23340
aattattgat ctgaatgggg tttcagtgac agaaataggt tgtgaggtgg agtttggttt 23400
aatagtgaac caactagctg ttaacattat caatgaagtg ttcagaagac aattgatgat 23460
ataggaccca agcagtttgg gaatatattg tcaagatggt tgtcttatgt taggcaagta 23520
gatgtagaga gaagagctga agataaagac ctgatttctg tgattaagat gaaaaaagat 23580
agtaaaagaa agaattataa aaggaaaggg atctactgct gtcgcagaca agctaaagaa 23640

-continued

```
aatttaattg ctaattttaa tttaatttaa attgcattta attgctaccg ctattgattt  23700
tagtaaattt cacatgtctc cttattatgg cagataaaat agtttttgca aaatgaatga  23760
ggaaaggaag gaaaacctaa aatttgttgt ttgtgactat aagagggtag aaatggaaga  23820
ttatttgtcc atagagttgg tttgctgatt tttctatgtc ttcctttttt tttttgtagg  23880
gcccagtaaa tcctttaggg ccacctgtac cccatgggcc ccatggcgtc ccaggccccc  23940
atggacctcc tgggcctcca gggcctggaa ctccaatggg accatataac cctgcacctt  24000
ataatcctgg accaccaggc ccagctcctc agtaagtatt gggtttagtt ctgggctttc  24060
ccccaaagat tctagttttt ggactacatt tttatactga attttcttct cagtggtcct  24120
ccagccccat acgctcccca gggatgggga aatgcatatc cacactggca gcagcaggct  24180
cctcctgatc caggtaaaaa gatgcttatc atttgtgtgt tagctgtatt gtttttcact  24240
cgtgttacat tattaaattt tctagtgttg attctacatt tgtatgcctc accttcactc  24300
actctactct ttcaacagcg ttaggcactg cctctacccc agtgtatata gaactgacat  24360
gaatatgatc tctgctttta tgaaattcct ttcagcttgc atttggcttt cttatgagtc  24420
gatatagcag aatgataaaa actaaaagct gcannnnnnn nnnnnnnnnn nnnnnnnnnn  24480
nnnnnnnnnn nnnnnnnnnn nnnnnnnnnn nnaatatgta gtgtgttaat tgtgacatta  24540
tctatgaaaa aatagttttt acnnnnnnnn nnnnnnnnnn nnnnnnnnng ggcactgagg  24600
ctcacgtctg taatcccacc tgttcagaag tcgaggctga ggcttgagac cagcctaggc  24660
aacatggcaa gacccatctc taaaaaaatt tgttttaaat tagccagcca gggtggtatg  24720
tgtctgtatt tctagctgct cagaaggctg gaggggggc ggggattgct tgaggctaga  24780
agttctagat tgtattgagc tgtgggcgca ccactgcact cccctgggca acagaatggg  24840
accccatctc ttaaaaaata tatatatatg tatatataaa acagtcttac agagtgttaa  24900
gtatttgggc attaaactcc caaattgtca aataagatac cggttctagt actcctcata  24960
atgacaactt catgtgagta aaaatcaggc ctgtatttaa taactgcatg ctaaaaccca  25020
aatacattta attattttct atattcagat ctgtattttc gatatgtatc tattatatcc  25080
tgtactattc tggcgtcttt ccataccctg tagtttgctt tccatcttgg tcaaagagtc  25140
attctttgaa accagttaac atttatttat gatctttttt tttcacctgc tacctacctt  25200
ttaggcctct ttcaccagag tagtttcaag gaaaatatac tcaattatgg attactttct  25260
acacataatn nnnnnnnnnn nnnnnnnnnn nnnnnnnnnn nnnnnnnnnn nnnnnnnnnn  25320
nnnnnnnnnn nnnnnnnntg ctgtttggaa tatgatgaca cagcatgata gttaccaaat  25380
aatcacaact tccattaatt caaggaatga cttgagttgt gctaggatat aggtatgcaa  25440
agttggggtt gtattctata gcaaaagaat gcactcccag cataccaaca ctgatagaag  25500
ggctcacaag gtacagaata taatactgta aacacgaatt tttggagaat gaaagggctt  25560
tgcttttcct cttgttggct aattgggatg gtataattaa gtaatgagat tgaagagttt  25620
gagtaggtta agagacagat tcatactggg taacttggat ctgccaggat tgtatttttg  25680
agcactactg ggtggttagc atgattgaga aaaaatgatg ggnnnnnnnn nnnnaagtgg  25740
tctttgtatc acatgttgag tttcccactt ggagtagtag tgaagtcact actataaaag  25800
ctggtcagtg aatgtggttg cagcatggcc tttgggcaag aagtaaccca tttaaancca  25860
gctggttggc cccactcaga tttatcaaag ggttactggg tctctggggt ggatattgct  25920
tatattagac ttagaatgac gtaacgtttt aatgtatgaa ctaaaatatt tctttaaaaa  25980
aagagtggtc tgttacggat ttatgtagtg gtcaagaatt tagacttcag agtcaaatag  26040
```

-continued

```
acctagatca gtcctagtcc tacagtttac taatggtgag atgtcaggca agtttttgaa  26100
ctcctctaag cctgttttct tatctataaa ttgatcaatg aatgaatctt gggttgagtg  26160
aatatttagt aaattcttag tacatactag ttatttgtga gactggtact tcagtatggt  26220
ttacacgttt gggtgtagaa ataacacttc ctaaagtctg ttttatctca aattctctgt  26280
ccaggcatag tgtaaagtga aatacctaga tttcttgatt aatatacaga taatagccgg  26340
gcgccatggc taacacctgt aatcctagta ctttgggaga ctgaggcggg cggttcactt  26400
gaggtcagga gttggagacc agcctagcca acatggcgaa aacctgtctc tactaaaaat  26460
acaaaaatta gctgggtgtg gtggcgggtg cctgtaatgc cagctacttg ggaggcnnnn  26520
nnnggagaat tgcttgagaa tcgctccact gcattccagc ctgggcaaca gagtgagaca  26580
cttcatctca aaaaataata ataaataccg ataatgacac tattgagata tgtaaacatc  26640
caggatacaa aagcagtaca ttgggcaatt gagaaaagct tggagggtgt cctaaaaaca  26700
ccttacaatt atattacctt gtagttttct ttttctacaa attctcactc ctttttctca  26760
aacttgacta acctttgtta agcagctgag aattgctact gttcagaatg aaagcataat  26820
agaaaattta aaagttttaa ttgtatgata ttcctagtat aaaggacaga atcaagtttt  26880
tttgtggttt ctagaagatt gagaggtctc aaactgtttg cacttcagtt gatgtgggag  26940
atgagtgagg gtcagtcaag tgtagaggaa acatagctaa aagctgagac atgggcatag  27000
tgatttctga aaagtacaag cactgtgttg tggctggagc ttgggtgtta aagagataca  27060
aatgaaggga gaggtgaggc tgaaatggaa aggataagcc aggggattca gactgttaaa  27120
gatgttgaat gataggctgt acttaagctt tgaccatcct gaagattcta gagaatgaag  27180
aatttcaagt aggatgacat caagtttata acattcaatg tgaaatagga tgaaatgtgg  27240
ctaatctttt ttttaagatt tttatatttt ctcttcattg aaaataagga caaagttcat  27300
tgttctaaaa taattgtttc tttcttatgc aggttagccc ctagaaatgt ttttcttaag  27360
tcatcttcca gatagagctg tttgtgcttg aggcgaaacc aatttagaaa aaaacaaggg  27420
cacaggatgg tttgagacag agcattggat ttggagccaa aagaccttta ttcatatccc  27480
agttatgcaa ctcagtagtt tttaacctgg gaaagtcact tggtctctga gccttgtttt  27540
ctttaataaa agctgatggt aacaacaaaa ataatagaaa atataaaann tttcatgtac  27600
tttttttaa tgttctagtt aattttggga gctgtatatt tgccagagag ctgggggggn  27660
nnnnnnnnnn nnnnnnnnnn nnnnnnnngt gagaattaca gacttcaaca tgcaaacctt  27720
gaactttcat ttattctagc taaggcagga acggatccaa attcagcagc ttgggctgct  27780
tattatgctc actattatca acagcaagca cagccaccac cagcagcccc tgcaggtgca  27840
ccaactacaa ctcaaactaa tggacaaggt aactaaagaa cttatatgtg aaagtcaaaa  27900
cttgtgcttg gaattatata tgaagtacat cactgtataa tacctaaaat ttctaacatt  27960
atttaattat aatttaagca gacttttcct tttttaaatt gttacctgga aatagtttca  28020
aactttcata aaagttataa gaataccagg agccacccat ataaccagct gttaatgttt  28080
tatcccttgt ttactctaat accgtctata tcatacaagt gtatgggtgt gtatttattt  28140
taaatatcca ttataattag ttctgaagga aactaattat atccagtata attagttctg  28200
aaagaaatca tttaagacta aactatagac acaatgtcct gttgggtact tcttcaaaaa  28260
tatataacca tcatacagcc ctccaaatca gtaagtcaac attaatatat taagctcttt  28320
atatcattat ggatttctga tttttgcagt gggttatatt ttttgaatat ttttataatt  28380
ttgataatca gactatccta gatttggcca gtcagggagt atattcaggg tggtgcctat  28440
```

-continued

```
atccttttga aatatctgtc gttattttaa gcacttccat actgtctggc acagtgagat  28500
tgttattttg tgttttatgg gctccaaccc ttaagtcagc tatttcttca aggagctctg  28560
attcctttta gtagagtatg gtagttagaa acgaggcttg actatgcttg ttgctactga  28620
ggtgtaattg cttctaactt ctttcagcag acagaactag gaaatatatt tacatacatg  28680
catacctaca tacacatgcc aaaaaacaca taaacattga tatgtgtata tantttttaa  28740
aactatgttc atattacgac attcatttca gcattttggg gttttcaagc cttttccttt  28800
tctgtacttg tttacaaatg gtgagaaacc tggtatcctc agtgtatctc cttattttac  28860
atacatttac ttatatgttc gacataacca gtcttccaaa caggttggtt ttcttttctg  28920
tccaccacct ctgtaccccc agtaccttct atctttggca ccagtaggga tgccaccacc  28980
acatagtacc ttcctcctac ccctcactgt cacattgcag gcccctgcca gctcctgcac  29040
ccaaggaaac agctaaaatt gccttttaaa aactttaatt ctgtttttct gttttgtttt  29100
gttttgtttt gcttgatcaa ggagatcagc agaatccagc cccagctgga caggttgatt  29160
ataccaaggc ttgggaagag tactacaaga aaatgggtat gttttataca tttcttgaaa  29220
atacatactt aattaaattg aaacacaagg tattctcttc agaaagagaa taattgaata  29280
aaatcactgg actcgtaaac ataccaagac agttgcaaat tatagttttt aaatttgtgg  29340
ttatatagca aggaaatatt tttctttcta attgcatttg tcaaccagtt attaattgaa  29400
actagaaatt tcctcactgg cacatacagt attaacatta ctatactttt gacaatgaca  29460
gttatatata ttagtctgag tgacataagg ttaaatttta atgtgtcagg tgaaaatgga  29520
ttgtgtgtga taccattatt tttgctgcaa gataagcagg taagaagtaa tctgtagtga  29580
gggaaagtaa ctaagtgatg gaaccagaat ctggcttcca agagggtctg agtcccaagc  29640
ttgtctccca aatttgtctc tttagggacc atttggaacc tggtactata cttctggaca  29700
aatcactatg tttcaactgc ttttgctctt taaaaattat tacataccac agctagatgt  29760
cacaaacgaa aactaaattg gtaagcttgg ttatccttca ctagcagaaa aagaatctat  29820
aggtggtagt tttgtcataa gagatcggtc tacttgggat tctcagtgta agtttcaatg  29880
ttttctttgc caaagaatgt ttctcattct ccgcagaaag aaaaatttcc agaagggtga  29940
tgattttaat cttctaggtg taaaattata tatacttgat gataaagatg ttctgcacaa  30000
ctggtttctt tttaaagaaa gaaaaaattg tttttcctca tagagtggct tcctaggaga  30060
gtcatattcc atctatttct gagactataa cagattaata tatgtttttg tgacgtagct  30120
taggcagatc tacagtagct gaaattccgc aaaaagaaac ttttaactta aaaacagcat  30180
actctgatta aggttggtta cataatatat tttctgaaca gggatctttt ttagaatgaa  30240
tagggatgct attaatcatg tcctgncggg cgcggtggct cacgcctgta atcccagcac  30300
tttgggaggc cgaggcnnnn nnnnnnnnnn nnnnnnnnnn nnnnnnnnnn nnnnnnnnnn  30360
nnnnnnnnnn ncgtctctac taaaaataca aaaaattaac cgggcgcgat ggcgggcgcc  30420
tgtagtccca gctactcagg agcctgaggc agnnnnnnnn nnnnnnnnnn nnnnnnnnnn  30480
nnnnnnnnnn nnnnnnnnnn nnnnnnnnnn nnnnnnnnnn nnnnnnnnnn nnnnnnnnnn  30540
nnnnnnnnnn nnnnnnnnnn nnnnnnnnnn nnnnnnnnnn nnnnnnnnnn nnnnnnnnnn  30600
nnnnnnnnnn nnnnnnnnnn nnnnnnnnnn nnnnnnnnnn nnnnnnnnnn nnnnnnnnnn  30660
nnnnnnnnnn nnnnnnnnnn nnnnnnnnnn nnnnnnnnnn nnnnnnnnnn nnnnnnnnnn  30720
nnnnnnnnnn nnnnnnnnnn nnnnnnnnnn nnnnnnnnnn nnnnnnnnta aaaatcttca  30780
acttctattt tctcaatggg taatgttccc tagatatggt ccctagttat tannnnntta  30840
```

-continued

```
agtagataaa aataaaggct tgttaatgga tttagctaat tactgaggaa tgagtttgac  30900
ttctgnnnnn nnttttacct tattgattat ttgtaatatg gccgttaata catttactgt  30960
ttagtctttt atgttttact tttttatgtt ttactcnntg agtgggtggg ttgaattctg  31020
atttttattg ttaagggaag aaattctaat tttcattgtt aagggaagaa attgtcttta  31080
ttgtctttaa ttttttttt caccatttcc ctgccagtta gagatactgt gctatactgt  31140
cttaaatcct ctgtaggaaa acatggcata gaaataatta aataataata ctgcatgact  31200
aaagaacctc cttaccccac cttttctatc atttttctgt agtaccacaa taatcacctg  31260
ttaattttat nnnnnnnnnn nnnnnnnnnn nnnnnnnnnn nnnnnnnnnn nnnnnnnnnn  31320
nnnnnnnnnn nnnnnnnnnn nnnnnnnnnn nnnnnnnnnn nnnnnnnnnn nnnnnnnnnn  31380
nnnnnnnnnn nnnnnnnnnn nnnnnnnnnn nnnnnnnnnn nnnnnnnnnn nnnnnnnnnn  31440
nnnnnnnnnn nnnnnnnnnn nnnnnnnnnn nnnnnnnnnn nnnnnnnnnn nnnnnnnnnn  31500
nnnnnnnnnn nnnnnnnnnn nnnnnnnnnn nnnnnnnnnn nnnnnnnnnn nnnnnnnnnn  31560
nntcacctgt taattttatg agcaaaatag attagttgaa aacagatgta ggttaagttt  31620
tccaaaattg gctttatatt ttaaagacaa ttctaaattc cccaggataa caccaaacta  31680
agttattttt ttttttnttt tttttnnnn nnnnnnnnnn nnnnnnnnnn nnnnnnnnnn  31740
nnnnnnnnnn nnnnnnnnnn nnnnnnnnnn nnnnnnnnnn nnggttcaag caattcttct  31800
gcctcagcct cccaagtaga gaaaatcttg atgagatttc agagagttat aaggaatggc  31860
agcaatctaa agatgggtat ttttaaagct agaatagaag gatttttat aagagactct  31920
taagagaaca agcagggttt caaagtagaa aggagtaatt ctttttgga gaagtgaaga  31980
catttgagaa aagtttgact taaggaaggc ccttacaata aggactgatg tagtagactc  32040
tgaaccctta agaatctggt accttaagcc taaaggaggg tagagtgaga cttgtaggaa  32100
aggtacaagt atataggaag acaactgagt gtgaaaatct attcaagcaa ggctgactct  32160
taggctataa taaaatctta caggctaact gtagagcaag tcttttatct tttggatgaa  32220
agaaatgtaa ggctaaactt tatagattat aattatnaaa ctataataaa tattagataa  32280
tgttctactg aagtgtaaac tcaactgtct tgaatcaaac agtaactaag ccatgatcac  32340
accactacca ctgtgttcca gcctaggtga cagagcaaga ccctgtctca aaacaaaatc  32400
caataactaa agagaataat aaggggagca aggtaaggca gtacatgtct gaaagggcaa  32460
ggaaagagtt ctttaaagtc taaagtgttt actattagct ttccacaggg atataggagt  32520
ttgcagacgt tgtagttttt taagggaaca ttgatggaat tttcttgatg aatatgcctg  32580
tttctaccat cttacatcta aaatgagtaa ctctcacagt gggtttaaaa cctgaagaat  32640
attgattgct accttgatca ggtttggttt caagtgtgca gcttgtaaga gaaaacgtgt  32700
ggttttattg ctgttgttac acgagagtat ttggcagttt tttaaatatt gaaacctgtt  32760
tcagatttgc ttgaattgtg tcttgtaaga ggcaaatgtt cctgtttgat taacagttct  32820
ttatagaaga caggaaaata tgagaatttt taatagtcta tgagagttct ctgttaccca  32880
agaaaagagg gtttgtttca tgcattttta aagaatcata aatcttaaat tctttcactc  32940
agttgctttg attctgtcac ctattttaca atggtgatgg acaggtttct gaaactagga  33000
aattggcctt gttggcaaca tcatacaaac ataaaaacag cttcctatac gtccatgctc  33060
cagtactttt gtctgtggta attatttcac aaagccaagt gagttacaaa cgaaataaaa  33120
tagtgcttaa gtaaagcaac tgaataggaa aacacatctc tcttctcaat tttttattta  33180
gaaaattata taccttcaga aattggggaa attaggtacc actcagcttc attcatcatt  33240
```

```
tttttaaagt ttgctgtatg tgctttatat gtacgttttt ctgtatgaac catttcaatg  33300
taagttgcag acaagacagt tggctctaaa gaaactcaat gtctggacac agtgattcac  33360
gcctgtaatc ccaggacttt tgggagacca aggcaggtgg atcactttag cccaggagtt  33420
aaagaccagc ctggacaacg ctgcaaaacc ccatctctgc aaaaaaagag aaaaatnnca  33480
gctaggcatg gtgggcttgt agtcccagct actctagagg cagaagtggg aggatcatct  33540
gagccgtggg aggtcgaggc tgcagcgagc catgaatgca ccgctgcact ccagcctggg  33600
tggcatagtg agaccctgtc tgaaaataaa taccttcaat agtatcacaa aaatacagac  33660
tatatttaaa tttccatagt tgtcaggaat atgtctttcg tcgtctgtgt gtttgttaaa  33720
ttcagagtgc attcaaagat tcgtgcattg catttcattg ttatatttct ttagtctctt  33780
aattcagcaa agtcatctca tttggagaaa gacctgatcg tgaaagctga gttatgtgtt  33840
tcattgatct tgttctttat tccttgtcac gttactttta ataccattgt gttgtaattg  33900
gaataaatta ttgatacttt taacatctta ctactaatct ctgtgtgtgt gtacatgtac  33960
atgtacatac actttatagg ttactaatca ggaaaaagtc ttggctaggt cttaaaataa  34020
taaaatcttt aaatcattgc aattaagtgg gtttttgtt tttaattctg gaatccaatc  34080
aagattatgc ctaaatcttt accttcctta gctaaagcag tgtggatttg gggttgattt  34140
tgttttttta ctaataatga cgctctagaa ctaaacatta tgattaatta taaggcaaaa  34200
agaaaataaa gagcgttttt tttttatttt agagtagttt cctgacacta ctaatgaata  34260
ttttaaataa aacaggagta attctgaccc tctgtgcttt tgtcttatga ttgtaattta  34320
atattaaatt tagggggttt ttttaggtca acaagggcag acacaagatt attcaaaggc  34380
ttgggaggaa tattacaaga agcaaggtat tgtttttact ggaaatgagg tgttggactt  34440
ttaattgtgg ttacagcaac aaaattcttt tttttcaaag gtcaagcagt tcctgctccg  34500
actggggctc ctccaggtgg tcagccagat tatagtgcag cctgggctga gtattataga  34560
caacaagcag cctattatgc ccagacaagt ccccagggaa tgccacagca tcctccagca  34620
cctcaggtat aatgtaattg ctaatttgtt gatttctact ccagtctgtt ttctgcatgt  34680
ttactgtttg tctgtttggg agtgtttgcc ttttaaattt ttatctggca aagtataact  34740
tatttaaatg aagtactacg gtgtattgtt tgggtttttt tgtttgtttt ttataatgtt  34800
ttccggcatc tgagtgctga atatttctgc aatgcctttg attttaaaaa taaattttct  34860
tcccccaggg atttgcaaat catgcaagaa gctaccacca tttatattaa ccagtttttc  34920
tttcttaaag gattcactcc tgaattagct ccatttcaag gattttcttt aacttttttgt  34980
gtatttctta tgtatctctt ctgcacaggg ccaataataa gaagtggaca atacagtatt  35040
tgcttcattg tgtgggggaa aaaaaccttt gttaaatata tggatgcaga cgacttgatg  35100
aagatcttaa ttttgttttt ggtttaaaat agtgtttttt tttgtttttt tttgtttttt  35160
ttttttgcaa atgtacaaaa tatctatcac tactgatagg aggttaatat ttctgtgtag  35220
aaatgaaaat tggtttgttt ttagtattta gtgtagatgt acacattcca gcaaatgtat  35280
ttgcaattat gtggttgatg ctttgtgata taaatgtact ttttcaatgt atactttcac  35340
ttttaaaatg cctgttttgt gctttacaat aaatgatatg aaacctcctg tgtcggtaag  35400
ttggatatgt gggtatttaa aggattcata atttcttagc aatgataaat taagatacat  35460
atacacaaat atataagctt tccccatgaa atattgagtt tttaaacact ggcatgtttt  35520
tccccccttg cagtatagtg gtagattgga ggatcttttc catttattgt atttggctct  35580
ttcagcacaa gtaatcctgg tatcttcatt tttttccttc tgtttgatta aaaactgcat  35640
```

-continued

```
gtgtgtacaa tgatcttctg gcatacttcc attgcattaa cagtgaaatt tcctttttat  35700
acatgaccac tgtttcagac ctgtactgct gctataacag ttaacctttc tgttcttaat  35760
ttgataatac ttgatttcca agactgtttc ggcataacta attttaaaca gttttcagat  35820
agtgaatatg agtagtctaa taagaacagt ttttttccat gtaaagcaac tctttcaatg  35880
tatataatag tgtgtttctt tctaaattta ggatagaaaa gtgaatagtg tgcaaaaagt  35940
atagctacat tgcatctgcc attgaaacat aaatggggta tggaaacgtt caagcttttt  36000
ttttttcttt aagcagtata gataagcttt gttttgtaaa tgcacaagtc caatcattga  36060
atcaacttaa ttttttttatg tacttgaagt cattttatta ctctttaaca ctcatgctga  36120
agttctgata ttttgttgaa atccattgtt ttactctttg catatttgtt ggctctttgc  36180
atattaatat attagactac atgcaaatac agtctgtctt gccattgtct gttgaagtgc  36240
aggtttgatc cagccagtat agaactagct ctgtaggggt gaggaggact gtgctgtgta  36300
tcatccttga ttgtgttcct tcaaggagca ttgcactgta agtacatcag aatgacaaat  36360
tgatgaactg caacagtatc tttttgtcaa tgttccacat aatgcaaatg ccatactttg  36420
tgtgaatatt atgttggaat acagtgctga tatcttggaa aaccataact gcttcttaat  36480
ttaacataga ataatacata gttctgtatt tttttaaag tgagcttaat gggtaagtat  36540
tttttatatg ctttagctat agctaaagaa aactgatact taacaaagtt gaatagtatt  36600
attcactggt gctcctgaaa tattgttttt cagtgtaaaa tatgcatata ttctatattt  36660
aatatgaaag tcttgaaatg tatcagaagg gatttcagtt tgcaaataat gagcaatgta  36720
gcaattttaa cacatttcat aaatatatat tttgtcattt gtggggagca ccatttgttg  36780
ttttgaatat actttaaagg aagaggtaca aggacataaa tgttgagatt acctacagga  36840
tggaaatagc agtacagttc attatagata ttttgaaatg tttttgattg ttttatataa  36900
cctagagtga cttcccttac ccttatttag atctggatat atagttctag tttgaagttt  36960
aatagttaag gagttagcta tttgttatct ttaagagtag ggtattgacg tgagcaattg  37020
cagtattttg catgatactg ttttatagat gacctttttag gaaagtggtg catttattaa  37080
ttgaactgaa gaagtagttc agttgaattc agtatcataa ctcacaaatt ggaggctgtt  37140
gattttgatt catttaaggt ttaaaatctt tattaattgc aaacagtgca attatttata  37200
cttcacagtg ccttcccaga ccttccacct taggttctgc tgcaaaaagc accaggtaag  37260
cacaacctaa ggacatatat aaataaatat ttcagtacat taatgttgtc cctgtgaggt  37320
ttttgtggtt gtgtattcaa aggcaatctg ctnnnnnnnn nnnnnnnnnn nnnnnnnnnn  37380
nnnnnnnnnn nnnnnnnnnn nnnnnnnnnn nnnnnnnnnn nnnnnnncca tcttagtgga  37440
aagtctgtaa gttgttaaag caactgttta catttctggg taatgttttt atttacgttt  37500
ttttttttta tttaagacaa gaaaatgatg agtagattgc tgcagtaatt gatctacatc  37560
caaatctttt tgtatttttt ccccaaatat agaagtgtta agattaagaa aggacaatta  37620
cacagttttc aagatttagg aaatcacttg ttcagaaact tcaacagcct tcacaatctg  37680
ttttatatga tggacagaaa atttctttgc cctccaaaac tataatttct ttattttttt  37740
cttaaactat aataattcag taaggatatt atgggttaca attttattat gtttttctg  37800
agacaaaagt tatatgctag aaaaggaaaa agttaataag gcagtatgtt ttgataaaag  37860
gcatgtgcat cagtgaaatg ttaactgtac agcaaataac ctttcataat ctgtagcaat  37920
cagtattttt ctgatttaat attttaataa ctgacgctgc atttatataa tttttttgcc  37980
agtttaaaat gtttgtgtgt ttttatagat gattttaact ggtacatatt ttgagttaag  38040
```

```
atgaatgtat gaaagcagca tcttaccagt tttgtttatt caatttctaa aatgtgctga  38100
tccttttaaa actcctgctt atctctgcaa caaagaaaaa tattcaaaaa tactgccttc  38160
attttcacac acagtgctga agatgctgca agcaccaaat catagctcaa taaaatcagg  38220
tcctgagata gttacccata aagaggaatc ctttgagtgt atgccattgg tgagccgatg  38280
agcatggacc atagaagggc tcaatgtaga aggtaaaatt ggcaaatcat aattgagaaa  38340
tatgaaatgt attcccatac ataatatggt atagggtgta atgtacctgc ttttgatcac  38400
ttttcatttt aaagtgctat tcacttgatc ttaaatgttc catgaactgt taaatttctt  38460
aagttacata gttattacac cacatttatg tgtatgttat gttttaatag tcaatgatag  38520
gtatgtaaat ataaagggac tcattgaaac ttgagagcct gtcgagtttt ggttagttgt  38580
agattgcatt tttattaaaa aaatatagat agatgaatga taatagatat tggggcactg  38640
tttctgtctc atgagaattc ttttattcat taccataagc cttcactgat aatataagca  38700
ttattttaaa tgacgctggt cttaaatctg aaataaatgg aaagcagaaa aggtgagcca  38760
gttgatttga atgcattgga tattagtgtt agaaacaatg tatagtttag attgaaattg  38820
aactgacttt atttagcact taaacaaaaa tttgacaatg tttttggttt tttttaaga  38880
cagcttagtg tggtgatact tagaattcta tggtttgatg tttcttttag aaatgagaag  38940
tatagtttta ttttttaata tcaaaaatgg ttttaatact aaaactagta atttaatact  39000
agttgtttat aaacattgta aaatatatct tttaaacaaa ttatcttagt agttaattca  39060
taagggtggt tttgggtagg aatagcagag taccttcaga gggaaagggg agtaattcag  39120
aagtgatagc attttatttg tttgaatact ctgccagtaa aatcagctct acttagaaag  39180
ttatctgttg tgtagaataa tgatgtagag tttactaatc agtgaggatg tcttgttttt  39240
attttctgca aactctgcct cactttaaaa tgcattttaa caatacctaa ttaaaaataa  39300
ttttggttct gaaaataacc ttattttttg ttgagttagt gacttcattt ttcttgtcac  39360
aatataagct tttgagggat ttttttaaat tggtgctttt aataagcaaa tcccagggtt  39420
ttattttctt cagtgatacc cctcttaaat gtatttgcac atatatatat atttttttctt  39480
atgcatgctc gatgcatttt cgtcctgaga aaaatgttct ctacagaaac tacccgtgtg  39540
taaaaagaag attggcttaa aatggctact gtgatgggaa cagtgtctta gggagatgca  39600
gcttggactt gaggtaaatt gaatacttta caaactgtgg tttagagttt gctttaatga  39660
cattgtatgt aaaaggtcac atgatagctg taattttgta ttcattatgg tttcctcaat  39720
aaataaatgt acattgatga atattataag                                  39750
```

<210> SEQ ID NO 6
<211> LENGTH: 1968
<212> TYPE: DNA
<213> ORGANISM: macaca fascicularis

<400> SEQUENCE: 6

```
atggcagact attcaacagt gcctccaccg tcttctggct cagctggtgg cggcggtggc     60
ggcggtggtg gtggaggagt taacgacgct ttcaaagatg cactacagag agcccggcag    120
attgcagcaa aaattggagg tgatgctggg acatcactga attcaaatga ctatggttac    180
gggggacaaa aaagaccttt agaagatgga gatcaaccag atgctaagaa agttgctcct    240
caaaatgact cttttggaac acagttacca ccgatgcatc agcagcaaag cagatctgta    300
atgacagaag aatacaaagt tccagatgga atggttggat ttataattgg cagaggaggt    360
gaacagatct cacgcataca acaggaatct ggatgcaaaa tacagatagc tcctgacagt    420
```

-continued

```
ggtggccttc cagaaaggtc ctgtatgtta actggaacac ctgaatctgt ccagtcagca    480

aaacggttac tggaccagat tgttgaaaaa ggaagaccag ctcctggctt ccatcatggc    540

gatggaccgg gaaatgcagt tcaagaaatc atgattcctg ctagcaaggc aggattagtc    600

attggaaagg ggggagaaac tattaaacag cttcaggaac gggcgggagt taaaatggtt    660

atgattcaag acgggccgca aaacactggt gctgacaaac ctcttaggat tacaggagac    720

ccatataaag ttcaacaagc caaggaaatg gtgttagagt taattcgtga tcaaggtggt    780

ttcagagaag ttcggaatga gtatgggtca agaataggag gaaatgaagg gatagatgtc    840

cccattccaa gatttgctgt tggcattgta ataggaagaa acggagagat gatcaaaaaa    900

atacaaaatg atgctggtgt tcgaattcag tttaagccag atgatgggac aacacctgag    960

aggatagcac aaataacagg acctccagac cgatgtcaac atgctgcaga aattattaca   1020

gaccttcttc gaagtgttca ggctggtaat cctggtggac ctggacctgg tggtcgagga   1080

agaggtagag gtcaaggcaa ctggaacatg ggaccacctg gtggactaca ggaatttaat   1140

tttattgtgc caactgggaa aactggatta ataataggaa aaggaggtga aaccataaaa   1200

agcataagcc aacagtctgg tgcaagaata gagcttcaga gaaatcctcc accaaatgca   1260

gatcctaata tgaagttatt tacaattcgt ggcactccac aacagataga ttatgctcgg   1320

caactcatag aagaaaagat tggtggccca gtaaatcctt tagggccacc tgtaccccat   1380

gggccccatg gcgtcccagg cccccatgga cctcctgggc ctccagggcc tggaactcca   1440

atgggaccat ataaccctgc accttataat cctggaccac caggcccagc tcctcatggt   1500

cctccagccc catacgctcc ccagggatgg ggaaatgcat atccacactg gcagcagcag   1560

gctcctcctg atccagctaa ggcaggaacg gatccaaatt cagcagcttg ggctgcttat   1620

tatgctcact attatcaaca gcaagcacag ccaccaccag cagcccctgc aggtgcacca   1680

actacaactc aaactaatgg acaaggagat cagcagaatc cagccccagc tggacaggtt   1740

gattatacca aggcttggga agagtactac aagaaaatgg gtcaagcagt tcctgctccg   1800

actggggctc ctccaggtgg tcagccagat tatagtgcag cctgggctga gtattataga   1860

caacaagcag cctattatgc ccagacaagt ccccagggaa tgccacagca tcctccagca   1920

cctcagggat ttgcaaatca tgcaagaagc taccaccatt tatattaa                1968


<210> SEQ ID NO 7
<211> LENGTH: 6825
<212> TYPE: DNA
<213> ORGANISM: macaca fascicularis

<400> SEQUENCE: 7

ccttagcccc acactagcgc gttgcccgga aacatcgcga gatttcgttc cttcagtctc     60

cacccccttta cggcacgatg gtcgcgcaag aatgtgatac agcttcgacg gccgccattt   120

tctttctttc ttagctgtta gctgagagga agtctctgaa cgggcggcag cggctagcgt    180

agtgtaacca tggcagacta ttcaacagtg cctccaccgt cttctggctc agctggtggc    240

ggcggtggcg gcggtggtgg tggaggagtt aacgacgctt tcaaagatgc actacagaga    300

gcccggcaga ttgcagcaaa aattggaggt gatgctggga catcactgaa ttcaaatgac    360

tatggttacg ggggacaaaa aagacctta gaagatggag atcaaccaga tgctaagaaa     420

gttgctcctc aaaatgactc ttttggaaca cagttaccac cgatgcatca gcagcaaaga    480

tctgtaatga cagaagaata caaagttcca gatggaatgg ttggatttat aattggcaga    540

ggaggtgaac agatctcacg catacaacag gaatctggat gcaaaataca gatagctcct    600
```

-continued

```
gacagtggtg gccttccaga aaggtcctgt atgttaactg gaacacctga atctgtccag    660
tcagcaaaac ggttactgga ccagattgtt gaaaaaggaa gaccagctcc tggcttccat    720
catggcgatg gaccgggaaa tgcagttcaa gaaatcatga ttcctgctag caaggcagga    780
ttagtcattg gaaagggggg agaaactatt aaacagcttc aggaacgggc gggagttaaa    840
atggttatga ttcaagacgg gccgcaaaac actggtgctg acaaacctct taggattaca    900
ggagacccat ataaagttca acaagccaag gaaatggtgt tagagttaat tcgtgatcaa    960
ggtggtttca gagaagttcg gaatgagtat gggtcaagaa taggaggaaa tgaagggata   1020
gatgtcccca ttccaagatt tgctgttggc attgtaatag gaagaaacgg agagatgatc   1080
aaaaaaatac aaaatgatgc tggtgttcga attcagttta agccagatga tgggacaaca   1140
cctgagagga tagcacaaat aacaggacct ccagaccgat gtcaacatgc tgcagaaatt   1200
attacagacc ttcttcgaag tgttcaggct ggtaatcctg gtggacctgg acctggtggt   1260
cgaggaagag gtagaggtca aggcaactgg aacatgggac cacctggtgg actacaggaa   1320
tttaatttta ttgtgccaac tggaaaaact ggattaataa taggaaaagg aggtgaaacc   1380
ataaaaagca taagccaaca gtctggtgca agaatagagc ttcagagaaa tcctccacca   1440
aatgcagatc ctaatatgaa gttatttaca attcgtggca ctccacaaca gatagattat   1500
gctcggcaac tcatagaaga aaagattggt ggcccagtaa atcctttagg gccacctgta   1560
ccccatgggc cccatggcgt cccaggcccc catggacctc ctgggcctcc agggcctgga   1620
actccaatgg gaccatataa ccctgcacct tataatcctg gaccaccagg cccagctcct   1680
catggtcctc cagccccata cgctccccag ggatggggaa atgcatatcc acactggcag   1740
cagcaggctc ctcctgatcc agctaaggca ggaacggatc caaattcagc agcttgggct   1800
gcttattatg ctcactatta tcaacagcaa gcacagccac caccagcagc ccctgcaggt   1860
gcaccaacta caactcaaac taatggacaa ggagatcagc agaatccagc cccagctgga   1920
caggttgatt ataccaaggc ttgggaagag tactacaaga aaatgggtca agcagttcct   1980
gctccgactg ggggctcctcc aggtggtcag ccagattata gtgcagcctg ggctgagtat   2040
tatagacaac aagcagccta ttatgcccag acaagtcccc agggaatgcc acagcatcct   2100
ccagcacctc agggccaata ataagaagtg gacaatacag tatttgcttc attgtgtggg   2160
ggaaaaaaac ctttgttaaa tatatggatg cagacgactt gatgaagatc ttaattttgt   2220
ttttggttta aaatagtgtt tttttttgt ttttttttt tgttttttttt tttttgcaaa   2280
tgtacaaaat atctatcact actgatagga ggttaatatt tctgtgtaga aatgaaaatt   2340
ggtttgtttt tagtatttag tgtagatgta cacattccag caaatgtatt tgcaattatg   2400
tggttgatgc tttgtgatat aaatgtactt tttcaatgta tactttcact tttaaaatgc   2460
ctgttttgtg ctttacaata aatgatatga aacctcctgt gtcggtaagt tggatatgtg   2520
ggtatttaaa ggattcataa tttcttagca atgataaatt aagatacata tacacaaata   2580
tataagcttt ccccatgaaa tattgagttt ttaaacactg gcatgttttt ccccccttgc   2640
agtatagtgg tagattggag gatcttttcc atttattgta tttggctctt tcagcacaag   2700
taatcctggt atcttcattt tttttccttc tgtttgatta aaaactgcat gtgtgtacaa   2760
tgatcttctg gcatacttcc attgcattaa cagtgaaatt tcctttttat acatgaccac   2820
tgtttcagac ctgtactgct gctataacag ttaacctttc tgttcttaat ttgataatac   2880
ttgatttcca agactgtttc ggcataacta attttaaaca gttttcagat agtgaatatg   2940
agtagtctaa taagaacagt tttttttcca tgtaaagcaa ctctttcaat gtatataata   3000
```

-continued

```
gtgtgtttct ttctaaattt aggatagaaa agtgaatagt gtgcaaaaag tatagctaca   3060
ttgcatctgc cattgaaaca taaatggggt atggaaacgt tcaagctttt tttttttctt   3120
taagcagtat agataagctt tgttttgtaa atgcacaagt ccaatcattg aatcaactta   3180
atttttttat gtacttgaag tcattttatt actctttaac actcatgctg aagttctgat   3240
attttgttga aatccattgt tttactcttt gcatatttgt tggctctttg catattaata   3300
tattagacta catgcaaata cagtctgtct tgccattgtc tgttgaagtg caggtttgat   3360
ccagccagta tagaactagc tctgtagggg tgaggaggac tgtgctgtgt atcatccttg   3420
attgtgttcc ttcaaggagc attgcactgt aagtacatca gaatgacaaa ttgatgaact   3480
gcaacagtat ctttttgtca atgttccaca taatgcaaat gccatacttt gtgtgaatat   3540
tatgttggaa tacagtgctg atatcttgga aaaccataac tgcttcttaa tttaacatag   3600
aataatacat agttctgtat ttttttaaa gtgagcttaa tgggtaagta ttttttatat   3660
gctttagcta tagctaaaga aaactgatac ttaacaaagt tgaatagtat tattcactgg   3720
tgctcctgaa atattgtttt tcagtgtaaa atatgcatat attctatatt taatatgaaa   3780
gtcttgaaat gtatcagaag gggatttcag tttgcaaata atgagcaatg tagcaatttt   3840
aacacatttc ataaatatat attttgtcat ttgtggggag caccatttgt tgttttgaat   3900
atactttaaa ggaagaggta caaggacata aatgttgaga ttacctacag gatggaaata   3960
gcagtacagt tcattataga tattttgaaa tgtttttgat tgttttatat aacctagagt   4020
gacttccctt acccttattt agatctggat atatagttct agtttgaagt ttaatagtta   4080
aggagttagc tatttgttat ctttaagagt agggtattga cgtgagcaat tgcagtattt   4140
tgcatgatac tgttttatag atgacctttt aggaaagtgg tgcatttatt aattgaactg   4200
aagaagtagt tcagttgaat tcagtatcat aactcacaaa ttggaggctg ttgattttga   4260
ttcatttaag gtttaaaatc tttattaatt gcaaacagtg caattattta tacttcacag   4320
tgccttccca gaccttccac cttaggttct gctgcaaaaa gcaccaggta agcacaacct   4380
aaggacatat ataaataaat atttcagtac attaatgttg tccctgtgag gtttttgtgg   4440
ttgtgtattc aaaggcaatc tgctactgct tccccaaaat gtattttgtt attttatgct   4500
accatcttag tggaaagtct gtaagttgtt aaagcaactg tttacatttc tgggtaatgt   4560
tttttatttt acttttttt ttttttatta agacaagaaa atgatgagta gattgctgca   4620
gtaattgatc tacatccaaa tctttttgta ttttttcccc aaatatagaa gtgttaagat   4680
taagaaagga caattacaca gttttcaaga tttaggaaat cacttgttca gaaacttcaa   4740
cagccttcac aatctgtttt atatgatgga cagaaaattt ctttgccctc caaaactata   4800
atttctttat tttttctta aactataata attcagtaag gatattatgg gttacaattt   4860
tattatgttt ttttctgaga caaaagttat atgctgaaaa aggaaaaagt tataaggcag   4920
tatgttttga taaaaggcat gtgcatcagt gaaatgttaa ctgtacagca aataaccttt   4980
cataatctgt agcaatcagt atttttctga tttaataata ttttaataac tgacgctgca   5040
tttatataat ttttttgcca gtttaaaatg tttgtgtgtt tttatagatg attttaactg   5100
gtacatattt tgagttaaga tgaatgtatg aaagcagcat cttaccagtt ttgtttattc   5160
aatttctaaa atgtgctgat ccttttaaaa ctcctgctta tctctgcaac aaagaaaaat   5220
attcaaaaat actgccttca ttttcacaca cagtgctgaa gatgctgcaa gcaccaaatc   5280
atagctcata aaatcaggtc ctgagatagt tacccataaa gaggaatcct ttgagtgtat   5340
gccattggtg agccgatgag catggaccat agaagggctc aatgtagaag gtaaaattgg   5400
```

```
caaatcataa ttgagaaata tgaaatgtat tcccatacat aatatggtat agggtgtaat   5460
gtacctgctt ttgatcactt ttcattttaa agtgctattc acttgatctt aaatgttcca   5520
tgaactgtta aatttcttaa gttacatagt tattacacca catttatgtg tatgttatgt   5580
tttaatagtc aatgataggt atgtaaatat aaagggactc attgaaactt gagagcctgt   5640
cgagttttgg ttagttgtag attgcatttt tattaaaaaa atatagatag atgaatgata   5700
atagatattg gggcactgtt tctgtctcat gagaattctt ttattcatta ccataagcct   5760
tcactgataa tataagcatt attttaaatg acgctggtct taaatctgaa ataaatggaa   5820
agcagaaaag gtgagccagt tgatttgaat gcattggata ttagtgttag aaacaatgta   5880
tagtttagat tgaaattgaa ctgactttat ttagcactta aacaaaaatt tgacaatgtt   5940
tttggttttt tttttaagac agcttagtgt ggtgatactt agaattctat ggtttgatgt   6000
ttcttttaga aatgagaagt atagttttat tttttaatat caaaaatggt tttaatacta   6060
aaactagtaa tttaatacta gttgtttata aacattgtaa aatatatctt ttaaacaaat   6120
tatcttagta gttaattcat aagggtggtt ttgggtagga atagcagagt accttcagag   6180
ggaaagggga gtaattcaga agtgatagca ttttatttgt ttgaatactc tgccagtaaa   6240
atcagctcta cttagaaagt tatctgttgt gtagaataat gatgtagagt ttactaatca   6300
gtgaggatgt cttgttttta ttttctgcaa actctgcctc actttaaaat gcattttaac   6360
aatacctaat taaaaataat tttggttctg aaaataacct tattttttgt tgagttagtg   6420
acttcatttt tcttgtcaca atataagctt ttgagggatt ttttaaaatt ggtgctttta   6480
ataagcaaat cccagggttt tattttcttc agtgataccc ctcttaaatg tatttgcaca   6540
tatatatata ttttttctta tgcatgctcg atgcattttc gtcctgagaa aaatgttctc   6600
tacagaaact acccgtgtgt aaaaagaaga ttggcttaaa atggctactg tgatgggaac   6660
agtgtcttag ggagatgcag cttggacttg aggtaaattg aatactttac aaactgtggt   6720
ttagagtttg ctttaatgac attgtatgta aaaggtcaca tgatagctgt aattttgtat   6780
tcattatggt ttcctcaata aataaatgta cattgatgaa tatta                  6825
```

<210> SEQ ID NO 8
<211> LENGTH: 1959
<212> TYPE: DNA
<213> ORGANISM: macaca fascicularis

<400> SEQUENCE: 8

```
atggcagact attcaacagt gcctccaccg tcttctggct cagctggtgg cggcggtggc     60
ggcggtggtg gtggaggagt taacgacgct ttcaaagatg cactacagag agcccggcag    120
attgcagcaa aaattggagg tgatgctggg acatcactga attcaaatga ctatggttac    180
gggggacaaa aaagaccttt agaagatgga gatggctctt ggacaagtcc gagcagtaca    240
acacactggg agggaatgcc ctctcctttt aaagatcaac cagatgctaa gaaagttgct    300
cctcaaaatg actgtaacag atctgtaatg acagaagaat acaaagttcc agatggaatg    360
gttggattta taattggcag aggaggtgaa cagatctcac gcatacaaca ggaatctgga    420
tgcaaaatac agatagctcc tgacagtggt ggccttccag aaaggtcctg tatgttaact    480
ggaacacctg aatctgtcca gtcagcaaaa cggttactgg accagattgt tgaaaaagga    540
agaccagctc ctggcttcca tcatggcgat ggaccgggaa atgcagttca agaaatcatg    600
attcctgcta gcaaggcagg attagtcatt ggaaaggggg gagaaactat taaacagctt    660
caggaacggg cgggagttaa aatggttatg attcaagacg ggccgcaaaa cactggtgct    720
```

gacaaacctc ttaggattac aggagaccca tataaagttc aacaagccaa ggaaatggtg 780
ttagagttaa ttcgtgatca aggtggtttc agagaagttc ggaatgagta tgggtcaaga 840
ataggaggaa atgaagggat agatgtcccc attccaagat ttgctgttgg cattgtaata 900
ggaagaaacg gagagatgat caaaaaaata caaaatgatg ctggtgttcg aattcagttt 960
aagccagatg atgggacaac acctgagagg atagcacaaa taacaggacc tccagaccga 1020
tgtcaacatg ctgcagaaat tattacagac cttcttcgaa gtgttcaggc tggtaatcct 1080
ggtggacctg gacctggtgg tcgaggaaga ggtagaggtc aaggcaactg gaacatggga 1140
ccacctggtg gactacagga atttaatttt attgtgccaa ctgggaaaac tggattaata 1200
ataggaaaag gaggtgaaac cataaaaagc ataagccaac agtctggtgc aagaatagag 1260
cttcagagaa atcctccacc aaatgcagat cctaatatga agttatttac aattcgtggc 1320
actccacaac agatagatta tgctcggcaa ctcatagaag aaaagattgg tggcccagta 1380
aatcctttag ggccacctgt accccatggg ccccatggcg tcccaggccc ccatggacct 1440
cctgggcctc cagggcctgg aactccaatg ggaccatata accctgcacc ttataatcct 1500
ggaccaccag gcccagctcc tcatggtcct ccagccccat acgctcccca gggatgggga 1560
aatgcatatc cacactggca gcagcaggct cctcctgatc cagctaaggc aggaacggat 1620
ccaaattcag cagcttgggc tgcttattat gctcactatt atcaacagca agcacagcca 1680
ccaccagcag cccctgcagg tgcaccaact acaactcaaa ctaatggaca aggagatcag 1740
cagaatccag ccccagctgg acaggttgat tataccaagg cttgggaaga gtactacaag 1800
aaaatgggtc aagcagttcc tgctccgact ggggctcctc caggtggtca gccagattat 1860
agtgcagcct gggctgagta ttatagacaa caagcagcct attatgccca gacaagtccc 1920
cagggaatgc cacagcatcc tccagcacct caggtataa 1959

<210> SEQ ID NO 9
<211> LENGTH: 26405
<212> TYPE: DNA
<213> ORGANISM: mus musculus

<400> SEQUENCE: 9
gctgaaacat cgcgggattt ccgtctgcca gtctccgccc ctttacggca cgatggtcgt 60
gcaagaatgt gatagagcct cgacggccgc catcttcttc ctttcttagc agttaaccga 120
gagcggcgcc tccctccgcg aggaaacggc agcgtgtgct gtagcgtggg tatggccgac 180
tactccacag tgcctccgcc gtcgtctggc tcggctggcg gcggcggcgg cggagtcgtt 240
aacgacgctt tcaaagatgc cctgcagaga gcgcggcagg taagcgtgga ccgaccgcgc 300
ggcggcttcc cctccccgac ccccgagagc cgccggcggg gcaggtccgg ccctgctcgc 360
actcgcggct gccgcccgag gagatggcgt cttctcacga ggggtcccag cggctcgagg 420
ccgagcccgt tgtcgtggtc tgaagcgccc ccccctccca cgcgctctcc ccgagcgtgg 480
cctccacttc cgccccgcgc gcgcggcctc gccgccccgt gcgccctgcc tgccccggct 540
ccctcggctc cggttccgcc cgacccaggc gcgtggaagg ttctgggcgc tcaggtcacg 600
gcgagggcaa gccagggagg gccggctgcc tggctagcgg tccccgccgc ttcccgcgcc 660
gccgagctct ccaccctcgc cgtaattagc ctaacgttcc ccgcggcgtt caccagcgag 720
gctctccccg gggcgggatc tgcgtgcgat ccaccaatcc tttccccagc tccaaatggc 780
cccgggccct ttcttcccca gccttgagtt tgaatctgcc tctctcttcc caagtcgaag 840
cctccaacct ctttgtgcta cgtagggacg tactgttgcc tcgaatggca accattttcc 900

-continued

```
cagatgaaaa gggttggata gataagagtc cttgcatttg acaccccccc cccaataacc    960
tgaacgtcaa tgtcttcaag tagcccccgc ccccgacttc tttgtagctt aaaaatgtat   1020
aatgttgcct tgccgggtgg ggtggtgctc gactttagtc ccagcactcg agagacagag   1080
cctggcaggt ctcttgagtt tgaggccagt caaaacggcc aagagggacc tgtctcaaaa   1140
aaaaaagtat gttatggaat ttgcctgtaa ggtaaaataa acccttatgg ctctgttgta   1200
gttgctagac atgagcaggt ttttaaagcc agctttgact atactggaaa cttccttcag   1260
gaccgaaaga ttaccgactc aatcaaggtt tatcaagtct accataatac agcaagcaca   1320
cttatctagt gcatagatac tgaaaaaata tatttattca tacagaggga ttccatgagc   1380
aatgtggttg gtgtacatag aagtcagagg acaacttgtg ggagttgatt ctccttccat   1440
gtaggaccct ttggtcaggt gtaagttgtt aggctcaggg acaagtgtgt ctgcctgggc   1500
atctgaggaa actttttgat gcagggcctc taccgaaagc ctaggcaggc ctgaggttta   1560
aggcttcctg ctgaattgtc tctagtgtag gtgtactcca cctctcggct ttggaagctt   1620
tttaagtgtg tgatttctag tcttgtgaga taaaaatcga acacgagtga gcagacagct   1680
ttgatgataa agtaaaccac agcggttaca taaatagtca cactgtgagg caggcgctgt   1740
acaggacgct gctggaaagg gatgcctcac tgaaagatgg gtgacattca tatagtgcag   1800
tgaggagtgg gagtctggcc agcatagaca agaagctgct gcttgctcta caaagatcga   1860
gggtttctgg aaggacagct ctaagaggta gtcagctaat ataggataac ataggaggag   1920
gaaaaaggtg ggaatgtgag aaaaactatg gatagattcc attgttagca agcattggct   1980
gtgataatac aagtgtttat tatagatgat agtatctgtt acacctttgg acattctggg   2040
tatgtagaaa ttccatcagg accttgcctg tgtaagtaag ggactaaggt ctcactatgt   2100
agttctggct gtcctggaac tcactgccta cctctgcctt taggactaaa ggtgtgtgcc   2160
acccatgccc agatgagatt ttgttttcaa aatgagagtc tttctgcctc accctcctga   2220
atgctggagt gacaggtctg cctacactga tcctggcaca cttacttttt ctaaaaatta   2280
ttttctttat ttacattcct gcccactcac ccccagttcc tcacaccatt ccttcttcat   2340
ctccccacct cccttccctg gggcctcaag tctcaagggt taggtggatc ttctcccact   2400
gagaccagac caggcagtcc tctgctgtta cacacacaca cacacacaca cacacacaca   2460
cacatataca cacataagcc agggaacttg gaccagcccg agtgtgctgc taggcacact   2520
ttttataagt ttggtgcaac tgtgtctttg aggatgaatg tgcgcattgt taaattttcc   2580
aaaaggaaaa tttgaaagtt gctgtggacc ctgcctagga agcactagaa gtagatttgc   2640
acttccacct ttaaaactac taaagaaagt gtgggctaaa gtgtaggaga tagatgtttt   2700
cacgtcatta ccttcttaga attatcttta actccaaaat tggtgagggt gggtcagtga   2760
agaaagtggt aaatgctggt ttggtttgat ttttgtctga agtaaaaaag cacagaaata   2820
cagtagagca aaaatcaagt ggaaagcttg aattatttct gtgggttaaa ataaaaacat   2880
tacttacact taatgtgtgt ttaatagaaa cattgggttc ataattgtag catgtgagaa   2940
gttaggatta gactagctgg ggctataatc agaccatgtt cccatccacc caccacccac   3000
ccccaatgag gggagagttg aaagttttgc ttggtctttt gaatgaactg tgtaccaatt   3060
tttcttttgg atgcttgtag acctattaca tgaatggagt gtgaataagc atgctttctt   3120
atggatattc cttggtcttc aagtaaactc agaagtgttc ataaaagcta attgtagaac   3180
atagccatag tctaagccgt tttcctctcg ttcaattgta cgtaacactt ccctttttaac   3240
atcagttcct gtcagtccca tacagtgcac ttaaatacct aagatatagt ttacaaatgc   3300
```

-continued tatgatttga aatcaaaggg tggaaaagat tttgtttcca aatgtgtggg ttgttttaaa 3360
tggggatata acataagttt aatagatcat taactatttg ttagctccct gaagtattag 3420
tggtagtttt aattattctt aataagtgaa tctttctagt gtttttaaaa gtatatcttt 3480
tattgtagga aatttagtgc tgagtagtac ataaagtatt aataccctga ttagtattcc 3540
gatttttctt ttaagattgc agcaaaaatt gggggtgatg ctggtacatc attgaattca 3600
aatgactatg gttatggggg acaaaaaaga cccttagaag atggaggtaa gttatagcca 3660
acaagaataa ttatcttcca tggtattcat ttgataagat tttcagtatt gtttatcaag 3720
atgatttatc aaaatactac tatctattgg tctcagaaga ataggatttt gaaaaagaca 3780
gacctagaaa aggtaggtat aatttgaatc tattgggaag tattattgta atagaaaaca 3840
ggttttgtta tttttttttt tttttgtcct gttataggat tatgcttgct ttgagttgca 3900
cagactgtta atgatataaa taaagttatg ttatttggga aacactttac tgaattttct 3960
catttattga atgagtcttt gatactccct ttcattcagt cagaatccac gtctaggtta 4020
aggttggttg gttgcaggca tcccattttt atattgtttt agtgttttgt gtgtttcata 4080
tttatcttta aacattgatt aaaactgtgg attcatagtg ttttctcttt ttaaaaatca 4140
tcacttctgc acttagaagt gtgtactttt ttattttagt tttgatgtat gtataaattt 4200
tgatattgat atatttgccc ttttgtaaaa gattctgata gcatatagga ctgactgtat 4260
ttgtggccct ttctggtaat acttggtttc cttttgttta agtatgttta tatttgcaag 4320
tgaggttttt aatatgcaag aaaaaatgag ctaatgatgc ttcagatgtt gtgtgtaatg 4380
tactcttttt attttatgtg tagatggctc ttggacaaat ccgagcagta ccacacactg 4440
ggagggaatg ccctctcctt ttaaaggcag gaatttttat ttattacctg tgtttagtat 4500
gtaaatgtga aataagccag tggattctta aatggacaca atggtctctt ggtttatgtg 4560
tctgaatttt tgctatacaa aagccttgaa gttgggagaa taataatagt gttttgagct 4620
ataggctgtc tattcatatg ttgtatgcat tttgtttatt tgagaaaggc aatcgtgtgg 4680
ttgctttgag gttttggtgt tctgtagtga aatgcttcat ttgagaataa tagaacagtt 4740
tagattgaaa ttgtcttgta acgtgagctt tctttttttgg tatagtttta tgatcactgt 4800
cagattcact catcttttga tatgtctggt ttttatgtag tgctctctaa ttgtcagttc 4860
tagagtggat gaagcatcat taaccattag cataaggtat tcaccagcat tgaagctaaa 4920
cagtttgtgc tgtattattc caaactaaag tgtctgtgca ttgtttaaac acaagagaat 4980
gaaagaattt aggttttgtg ggtttttttt tttttttag atttttgagt ctaggttgaa 5040
ttgtgtcagt tttgattcaa ttggtaaacc aatatatcat gtattttaat aaatatcatt 5100
attcttgctt ggtgggggtg gggagctttg tttttaattg acaaaaagta aaagacactt 5160
aattttgcag atcagccaga tgctaagaaa gtacctcccc aaaatgactg taagtacttt 5220
aagctgaggt tttgttgctt ctttaaaaat tacgtgtgtg tgtgtgtgtg tgtgtatgtg 5280
tgtgtgtatg tatgtatgta tgtatgtatg tcaagatggc ataggaattc cctgaaagtg 5340
gactacatgt gggtgctgag aacttggttc tctacaagag catgtgtcct ctttatcatc 5400
taagtcttct ctccagactg ttgtttctac tttgggtggg ttgtgagttt ggggtttggg 5460
gaatttgctt ttgagccaaa gtctcaaata tgtaattctg actgcccttg acttcacaga 5520
gatctacctg tgtaaaagta ttttttattt tgcctgatgt aattgtcatc tctgagcctt 5580
actgcctcaa accttctagt tctttctgaa ctctggtgca aactcctctc caagctgatt 5640
caatatagct tctctcttga cctctgccgg aattgctctg cttggcctca aactatcctt 5700

-continued

```
ctcattttct ggcttattct gtttttacat gtgtctagct tgttccctct ctgcaaccta   5760
tatatctcta caactgttcc aataagactg tcctcccacc ccctgggcta tttatttatc   5820
tcttaagtcc tcctctctat tctcctgaga gctagacata attaatccca ttctttttgg   5880
ggtttttttt tggggggggg gggttagaca gggtttctct gtgtagccct ggctgtcctg   5940
gaactcactc tgtagaccag gctggcctcg aactcagaaa tccacctgcc tttgcctccc   6000
aagtgctggg attaaaggtg tgcgccacca acgcccggct gtttgttttt caaaacaggg   6060
tttctctgta gctctggctg tctagaactc accctggacc aggctgacct ctgcctccca   6120
agtgctggga ttaaaaggcg tgacccacca ctgcccggct tttttccctt ttcttttcct   6180
caaagatttg ttactttata tatgagtgca ctgtagctgc cttcaggcac actagaatcg   6240
gatcctatcc cattacagat ggttgtgagc caccctgtgg ttgctgggaa ttgatctcag   6300
gacctctgga agaacagtca gtgctcttaa ccactgagcc attttcccag ccctaatttt   6360
attcttttga ctccttctct gattgatcac tttgtctgct actctaaatt aaacatcact   6420
ttcaaacatg agtgcttcct tctacaaact aacttcatct ttactgtttg ggattaaagg   6480
tcattaaagg attaaagagc aaagccacac cacaactata agcacataca cccccacccc   6540
cgtaaataac acaatcttgg ggctcaccct ataatctaag tgatcaaata gcctacaaca   6600
gacttgcttt tgttttctcc tgtgcttgga ctaaggatgt gtgtgccttg ccatactcaa   6660
cagggttggt attacaaatg tctagctgga atttccttac aaatgtatat aggtttttac   6720
tatattttta aaaaagaatg attctctttt acttgggagc cacgtatata caaacactga   6780
tggctgagct gtgactataa gttaactact ctagttgtta atctgtgtgt ccctttcctg   6840
actttcttgc tactctcagt gatgattcaa atatgaatgg tccgaatttt tttcctatgt   6900
atacatcagg gaaagagttt ggagtacgtg gtatgtttgt ctcaaataaa ctcgaactta   6960
agcttgtttt tgttcatttt ttcgtagctt ttggagcaca gttacctcca atgcatcagc   7020
agcaaaggta tagtcaaaac ttttaaagct actttgcaag tcttagttgg attgtatgta   7080
cagccaagtt agtctataat gcaaatgtct gcataccatt ttgtatgtgt ggtttacttc   7140
tgtaaaccac attgggaaaa tggtatagaa acattgttaa tttgggaaaa caggttgaaa   7200
ttgacgcatt tcagaagagg taaaataaat gttaaagtgg cattcgcttt gacaggtgtt   7260
cagtttcctg ccctgctcac acatgctgcc tcatttaaga acctggctgg gctactggga   7320
gactttaaga ttgggtttat tagactgctt ttatgtgtat atgtacatta tttttctgtg   7380
aggaaaatgt tagtttctgt tctttcttag cagatctgta atgacagaag aatacaaagt   7440
cccagatggg atggtcggat ttagtaagta ccattaatac taaggtttta agacaaagca   7500
tactttcaaa aatagtatga atgataactt ctccccttc tctaccttaa ctagtaattg   7560
gcagaggagg tgaacagatc tcacgaatac agcaggaatc tggatgcaag atacagatag   7620
cacctggtaa cattccgtgt gtgtgtgtgt gtgtgtacga attacttgtt gttttgtcca   7680
gttcttacag ttttttgaga gtggctagga aactcaagta ttttaagttt ctaaatatct   7740
gatattttta ttgtattttt tacttaaact tttcttttta tttaattgta gatagtggtg   7800
gcctaccaga aaggtcttgt atgctaactg gaacacctga atctgtccag taagtttgaa   7860
aatgttaagt ctacttacag ttaagactga agactataag cttcgttttc ataccatttc   7920
gctttaaaag tttacatatt atgcctttct taaaataggg ttcatcatct gaacctaaga   7980
cagagaaatt gttaaagcca gagactaagc cgtaactcag gcatttaggt gcttgccttc   8040
catgtaggaa gaactgagtt tgatcctaaa actaaaaaaa aaaaaactgg cgtggtaata   8100
```

-continued

```
tcatggctca ggagttggac acaggcagat tttggggact tggtaaccaa ccagctaaca   8160
ctatttgatg ggttcaaagt cattgagaga ccttgcctca aggtacttat cacaaaaaag   8220
gtactgatgg ttgtaatttg acctatacac cttccatacg tgtctataca gactcagaaa   8280
ttattaaaac ctgccttgca caaatatgtt aataacgtca cctaaaactc atgaccaatc   8340
tagtcatgaa aattttatat tcctgttttt ctcttccact caattctaag gctctgataa   8400
aactacccaa tctttacctc taattgtctt ctccccactg ccatctcccc tccagacagg   8460
gtttcattgt atatccatag ctgactgtct ctgaactcac tcgctctgta gtccaggctg   8520
gcctaaaact taaaagatct gcctgccgaa ggcatgtacc accattgccc accacactca   8580
ctgtcttgac tgacttgtgt tgctgtgacc aagaaagtgt tatcatccta cactgaaatc   8640
ttaacaccgt tccttgcata cttttttttt tttgtctagt attgagatac tgttttacgt   8700
tcatttgcct gactttctac ttcaagaaat tcctgactaa actgattttt tacttcattc   8760
ctaaaatttt aggagtaatt tctaagagtt tatagacaga tttggaaatt acatatcata   8820
aaaatatctt tgaacctcat gttgtatttt gttaacacag tgctttaaaa ggtttgtacc   8880
attgaagttt cccctttaaa agtttatcta gtgtgtgtgc ctctcagttt ccttcaagct   8940
ctgcttctaa cagctgcatc gacagttctc tttccaaggc agaggctgag tcgtgcacta   9000
gttaaccccg ttgctgtgtg acaggatgga tggaagatgt ttaatgactg tgttcacttg   9060
gagcatacag acttcagtac ttactgccca tttgacttga cactcactcc tttggtttag   9120
gttcttgcct ccgaccatga aatgccatat gaccaattta gagtatgttt gaaacctgac   9180
taagataaaa ctgctgactt ttattatttt gggataagtt gggttatgct acgtattttt   9240
atcaagatta atttgttaac agatcagcaa aaagattatt ggaccagatt gttgaaaagg   9300
gaagaccagc ccctggcttt catcatggtg atggacctgg aaatgcagtt caggaaatca   9360
tgattccagc cagcaaagca ggactagtta ttggaaaggg gggcgagact attaaacaac   9420
ttcaggtatt attatattgt aaagaatatt attaagtctt ttgaggccac tttttattgt   9480
ttttactaac atattttcat gatattaata ggaacgggct ggtgttaaaa tggtaatgat   9540
tcaagatggg cctcaaaaca ctggtgctga taaacctctt aggattacgg gtgacccata   9600
caaagttcag gtaagcttca ctttgtctct tatatataaa ggctgagggg gtggacaaaa   9660
tacgtattaa atttttttga caaatattct gaattggata actttctatt atagcaagcc   9720
aaggaaatgg tattagagtt aattcgtgat caaggtggtt tcagagaagt gcggaatgag   9780
tatggctcaa gaataggagg caatgaaggg atagatgtaa gtaagaattc tgagtcagca   9840
gtggttgtat cctaatccat gggcactagt gttttcctgc tttgaattaa atggacttgg   9900
cttaacatca tgtccctttt cttgttttct tccttggggt ttttttatct tgttattttt   9960
atgatcattt agtatattta cttttatgat taagtgggga tgagtttttg agaaatgtct  10020
tttaaaatat acttttactt aaggtcccaa ttccaagatt tgctgttggc attgtaatag  10080
gaagaaatgg agaaatgatt aaaaaaatac aaaatgatgc tggtgttcga attcagttta  10140
agccaggtaa gtttaaggta tatttaatgt tctaagaatt gatagctttt aatcttgaca  10200
tttataattg gtttgtcaca acttactctg tttttttttg ttgttgttgt tgttattgtt  10260
ttagatgatg gaacaacacc tgataggata gcacagataa caggacctcc agacaggtgt  10320
cagcacgctg cagaaataat cacagacctt ctacgaagtg ttcaggtgtg ataggaaatt  10380
aacattttca gtttgctttc tttggaaaag tttttatcat acctgaatga aaaaaatgcc  10440
cctccaggtt atattagaat ctgttggcag tgttaaaatg actaacgtta aattgcttta  10500
```

-continued

```
aggtaaacat tttagggtag atttgcataa atgttctgcc ttatttcccc cagtgcatgt  10560
gaacttttat ttctatgggt atatgtgcct tggcaattgt gcctatggaa gccaaaggaa  10620
atttttctga agttggttct ctattatgtg ggtcctagaa attaaaccca ggtcattttg  10680
catgtatggg tagtctccca atatatttta aaagtggaag ttattactta gttgactatt  10740
tttgtttgac gtcatctctt aatttcattg tttagaaata cgagagttgg ggataataag  10800
ctaatagttt tattacagag tttattttgt tctctccttt cttaggctgg caatcctggt  10860
ggaccgggac ctggtggtcg aggacgaggt agaggtcaag gaaactggaa tatggggccc  10920
ccgggtggac tccaggagtt taatttcatt gtgccaactg ggaaaactgg actgatcatt  10980
ggaaaaggca atgtatttta aactctttgt tttgatatac tggatatttg taaacaaaag  11040
atgctattta tattttttta ggaaaggggt cttaacatgg cagctaaaat aagaatactc  11100
tttaatgtat gctaaaaatg ggattgtgtc tcaactgctt ctagggaaag gggaccaaaa  11160
gtctgtcagt tacaaaactt gatcctaatt caaatgggtt ttgttggtgt tttttgtttt  11220
gttttgcatt taacttcttt gttacttaca aaacctgttg attgaaatat ttttctgttc  11280
tgacccatat cagggtgtat gtttagtaag gtgtgtataa aatagacttt agtgtgtttt  11340
gcattagttc tagatggaag aacaggctaa atagaaaatc ctaacattat tgtccagtgg  11400
aatgctacaa aactgtttaa tgggcaaagt aataggtgtt tggggttttt tttggttttt  11460
tttaaatagt atttctgcca gacatggtga cagacacctt taatcccagc acttagtagg  11520
cagatgcagg tgtttctctt gtgagtttga agccagcatg gtctacaggg tgagttatag  11580
gacaaccagg gccacacaga gacccttgtc ttaggaaaga gtattgcttg cattctgtga  11640
acttagtgtc ttgcggtttt aggaggtgaa accataaaaa gcataagcca acagtctggt  11700
gcaagaatag aactgcagag aagccctcca cctaatgcag atcccaatat gaagttattt  11760
acaattcggg gcactccaca gcaaatagac tatgctcgac aactcataga agagaagatt  11820
ggggtaagtg tactctcatt tatagcatag ttcctggtaa ctttaaaatg tactgtggga  11880
aaatacatcg tttctaatat gaaattgcag gtattgtgat atagtgtata tacatatatt  11940
gacataggaa agatatccaa aatacaagaa ccatgaactc agaaatccgc ctgcctctgc  12000
ctgtcaagtg ctgggattaa aggcgtgcgc caccacaccc ggctgagaat accatgtgtt  12060
aagttttccc ttgatgtgca atttgcagaa tatactctca gcagttgtca cattagggaa  12120
gtaaagggaa ctaggcagtc ttgtttttaa aagaaaatca taaaaagagt aagaaacaca  12180
gaagactaag ctgaaagaac tctgctggag ctgaggattt cagtgaattt tacatggcag  12240
atgatgacat tttatttttt gcaccaaaat tcaaagaggg taaatttaaa tttgttattt  12300
aagcgtagaa atggaagagt agttggactt tgaattactc aaccattaca ttgtttgagt  12360
gtctagttat tgtttatgtt ttcttttcct tttttttttt ataatagggc ccagtaaatc  12420
ctttagggcc acctgtaccc catgggcccc atggggttcc aggtcctcat gggcctcctg  12480
gacctccagg gccgggaact ccaatgggac catacaaccc tgcaccttac aatccaggac  12540
cacctggccc agctcctcag taagtaccac atttgcttgg ttctgggctt tccctaaaga  12600
cctaggaatt gggggctgga gagatgacga tggctcagca gtgcagagca cttgttcctg  12660
ttgcagaggg acctgagctc acttcccagc accacacggg ggttcgcaac cattcgtgac  12720
aggttccagg gtatctttac agcgacacta ggcatacata gctgcatata catacatgca  12780
atacatgcag aggcaaaacc tacacataaa ataaataaag ctggctttta ttaatggtat  12840
ttgtgttttg ttccccaccc ctagcggtcc tccagcccca tatgctcccc agggatgggg  12900
```

-continued aaatgcgtat ccacattggc agcaacaggc tcctcctgac ccaggtaaag ggtaatctac 12960
tattaatatg ttagcttcat tgtatactgc tggtcacagt cctaaactac ctactgcatg 13020
tgcgatcttt taaggcactt cccctgcagt ataggatgac actgctgtct agtatgttgt 13080
gactttattc atagtagttc atatttataa aataatgtgt ttaacactac tatgttctca 13140
aataataagt ataaattatt ttgttgctga taaaattaag gtcccttaat taccaaaaca 13200
ggagagtaca tttattttc tctcttataa tctggatttt ctatagcatg gtgttctcat 13260
tatatcttcc catactggtt ttgtttctac tccatcatga tcaggaatca acttggaaat 13320
aggacttttt tctttgtttt tcttttgttt tttcactttg cagcccctgt agtttgattc 13380
atttgaaaag tttgagagaa cgtgttctga gttatagatt tctacatagt gtattttta 13440
caaatcaaag ttgatttaga tgtaattgct ttgttggatt tgttaaatgt tttaatattt 13500
taatgtatgt taaattcata ggaacttttc tcagtcacca aataaccaca acttctattc 13560
atttaagaaa caacttgagc cgggcggcag tggtgaacgc cattagtccc agcacacagg 13620
agacagaagc aggcagatct ctgagttcga ggacagcctg atctacagag catgttcaag 13680
gatagccagg gacacacagg aaaaatccta tctcaaaaaa gagagagaga gaaaaaaaaa 13740
gaaaaagaaa taacttgaat tgtgatggca tctgaatatg aaagatgagt gtcgattagc 13800
aaaagagtgc attcccaggg cagacaagaa gcatcagtta tgacttcctt tgtaagggtt 13860
ttaaaagtga atcttctcct tctaacaagc atttagacgt ggcatgatca aatagagttg 13920
gaacaggtta tattgaaggt tttatatggc taattcaatt tcataggatt gctcaaatga 13980
gtgatgtttg atattagcac tgtaaggtct ggtcagtgaa tatgacttcc agcattacct 14040
ggaagactga ctcggcaata tgttgcttaa atttgacttg gaagtataca gtattttatt 14100
gtctgcattt tcaagaaact gctgctgtga ggttgagatt tatatagatg tcaagaattt 14160
aatcttcaat cttaaatgga taatatgcga attcatccta tgtaaaagaa tagtgagctc 14220
ttagtacctg ctagttgcaa gtcacaaaaa aaaagtttgg gttttggttt ggtttttgag 14280
ttacaaaggt gagcttagtg cagaggatgc tggttgtggt gacttgggaa tagggcagca 14340
gctaaaactt gagtattggg ggatgctaaa agaattaata gaaaggataa gccacagtgc 14400
tggggataag cattagaacc tgagttctat ccctccccacc tgttgtaaag aaaaataaat 14460
aaagcgcttt aataaagttc gtaaaaagga tccgtaaagt ttcctggcct gctcttgtaa 14520
ccaaatctag gagctctggg ttcagagaga aatcctatct caaaaaaaat taggaaggaa 14580
ggctggagag agggctcagt ggataagaaa agcaataact gctcttccag aggtctgagt 14640
tcaattccca gcaaccacat ggtagttcac aaccatctgc aatgggatct gatgccctct 14700
gctggtgttt ctgaagagag cttcaagtgt actcatatac aaaataataa taattctttt 14760
aaaaaatgag gaagggtgtc agagaggtag cttagtgatt attataaagg tcttcctgct 14820
ctttgagagg atgcaagttg agatccagtt actctcacac cttctggttc tctttagtaa 14880
cccacatttg tgtagataca cacaggttca cagatacaca taactagaag tgggacttta 14940
aagtctagat aaaacaaggt gagcatgtct agggagatca cccagaatca gtacacacaa 15000
acagacacgc cacgacacga tggctaagct ggggagggcg gccagaccac agcatgtagc 15060
ccggaaacag gaaaagtgga ggaagaaaag gtaacggctt ggaaatccaa cggcctgtgt 15120
taaatggggc atggtcttaa aactgtacag gagctttcaa atgataagct atgcttgaag 15180
tatcctaaag gtgttagaaa aggatagagc aggactttca ggattgtgac tgaaataaat 15240
ataaactgca tgtatctaac ctttgtttct ttcttgtaca aattagtcca taactgcctg 15300
ctatacagaa ctgttgcact tggcagctta acttgttggg ggaaaaaaag caaagacacg 15360
ggattgagct gagacaaacc attggattgg aagccaaaag atcatccatt tatataccag 15420
ttccaccgat cactagtaaa ttacttaata cctgtaacct aggaaattac ttaattcccg 15480
aggctgaagt ttctgaacta aaagccaagt gatgatgata atactagaac attttgaaag 15540
tttccattcg ctattggtaa cttttgagcc tatttgtcag gaatcaccaa aaaggtaagg 15600
gttggtttct agagtttaca tattaacctt gaaaccgctc tttgttttta cattgtagcc 15660
aaggcaggag cagatccaaa ctcggcagct tgggctgctt attatgctca ctattaccag 15720
cagcaggcac aaccccccacc tgcagctcct gccggtgcac cagctacaac ccaaacgaac 15780
ggacaaggta actacggtaa tgaaagattt tatttcctat tttaaagcta tagtttgtgt 15840
ttggattcat gtatgaagtc ataacaaaac tctctttcag tcctgagaat tgttgggcct 15900
tgtgcatgat ggtatcatta ggttagatcc tcgggcctaa ggttttgaag actcagttgt 15960
gactttgtgt aagcaaacta agtcaaataa tagttggaag aataatgcct taagtagtga 16020
gactgttaac tgtcctcccc ccacccccat ttacttcact accctgattt atgtctgtta 16080
taatagttct gaagagagct actgaaaact gtacttagag acataaaatc atatcacctt 16140
tctacagacc cttattcatt ccaaaataaa tgaccaccat ggactttaaa gtcagttact 16200
catcattgat ataccactgt tatacacagc ccttgcttag atcaccaact gaccccgtgt 16260
tttcattagg ttcattaagt ctcatcaagc tagagcactt tcttggtctt cttttatgcc 16320
tctaataaga ggataactca acagttagat agctgccaag ctatagagtt actaaccatg 16380
gttgtttaaa tggtcttgct actaccagcc tggtttttgc actatactac aactatgtac 16440
tgtaaagaat tacctagggg ctggtgagat ggctcagtgg ataagagcac ccgactgctc 16500
ttccaaaggt ccggagttca aatcccagca accacatggt ggctcacaac catctgtaat 16560
gggatacgat ccgattctag tgtgcctgaa ggcagctaca gtgtacttac atataataaa 16620
taaataaatc ttttaaaaaa aaaaagaatt acctagtatt ttctgctact ttttactgga 16680
gtaatgtcac tatcctatac attgaacttc tgcctcagcc ttagtctgta ttattaataa 16740
accttgcctt ggtaccctac tattacagca gctgttaact gttagtttct gtcattgtat 16800
attagttgct attttactac aaggaataga ttgccctttt ttaactactt tcattatatt 16860
gtcctagatt tggggtggtt ggggttatct tcaaggtggc tctggtgcct ctgacgttcg 16920
ttcttcaggt gcttccttag tacctgacac agtaagataa ctttgtcttc tgagctccaa 16980
tcggtgattc atttcctttt ctctctctct ttctctctct ctctctctct ctctctctcc 17040
ctctctctct ctctctctct ctctctctct ctcaggatag aatttagaga tcagtctaag 17100
tatactaatt gctatctaaa tgtcactaat tataatcctg tccaaattag aactaaaaag 17160
tatgtttggg gctggcattc agtcaatagt acttgttcct gcagaaaacc caggtttgat 17220
tgctagtacc cacatggtaa ctcacactga aactgattcc aggggaccca gtgccctctt 17280
ctgatctgtg gagcaccaga tacccagggt gcacagatta tacatgtgga caaaatgctc 17340
acacataaaa ttaaacagta tctttaaaaa catgcaggac aacacgtgtc tactaaaaat 17400
cacatgatta tatactactt tttcatttaa tctttaaaat tagtgcttca aagctatttg 17460
tggcttttct aaaaatgtgt gcaggagata tcaagggatg aaccatgctt gaactgtcct 17520
taaaaatgga tagaaaccat gttctatatt tcttttgtgt gcatttactt actattccca 17580
gtttctgtgt ccacccccttc tatacccact tgtcatgtat tcccaacaaa cacttgcaca 17640
actccgtggt gtagacagtg ctaattacag tactgatggt gtagaagcaa aagtgcataa 17700

-continued caaccttcag aaacttaaat cttgttttgt ttgtttgttt tttaaaaagg agatcagcag 17760
gctccagctc cagctggaca ggttgattat acaaaggctt gggaagaata ctacaagaaa 17820
atgggtatgc tctacagttt acgtcttatc ctttatctta gtaactaaac ggaagtaaat 17880
acacattaca aagctagaga tgagtaacaa aacatttgct tgtttttaaa aaagaatact 17940
tgaggtaact catccgtatg tttttataat gttaaagttt atattaaaca agctaggcag 18000
tggtgatacc tgcctttaat cccagtactt ggaaggtaga ggaaggtaga tctccgagtt 18060
tgaggccagc cttgtctaca aagcaagttc caggacactt gggactctta gacagagaaa 18120
ccccatcttg aaaaacaaaa ataataataa acaggaaagg tgacatcctg aaattgactg 18180
gaagttaaga catattaaga gcaattcaag aaattcttat aattgtgctt atggcagaga 18240
aatacaattg tcagcaagtt aataattaaa acctggcatt tccttactag gtaataatat 18300
atggctttat tactgtactt ttgtgtagtg gtctaaatgg aatgagatta aattttaggc 18360
cagcaaagta gttgtatcac tggctttact gcaaaataag cataaaatta gcccacagtg 18420
acattgcttt acatttctaa acatttgcat gcattgaaaa ggaaaaaagg gtgacctttt 18480
aaaaagattt tgacaactat tgaacgtaat tcttaacata accatagtga ttgtgttaat 18540
gtatttcttg tcggtgatac agctttcgac aaagttcctt tcagaacaac tgtttgggga 18600
aatgtgataa caaacttctg cagtgaacag atgggctgat aacttttctt aacctcactg 18660
atcgcaggca ggttctaaca gatggacctt agcactagaa acttgaaacc tgccgggcgt 18720
ggtggcacac acctttaatc ccagcacttg gtgggcagag gcaggcagat ttctgagttc 18780
gaggacagcc tggtctacag agtgagttcc atccaggaca gccagggcta cacagagaaa 18840
ccctgtttgg ggcctggggg gaagaaactt gaaaccttaa aacaatattg tgtgtaatta 18900
gaatgcttac ataatttctt ctctgaactg tgatattttt gagagtagat ggaaatgtat 18960
taatcattcc gtggtagccg tgctgaaata gtgctacttg tttataagaa gctgagcatg 19020
ccaaggtgaa agtgcgctaa ctccattgtt tgtttttact gtgtgagtgt tgattgggta 19080
gaaacctggt aactggacta cgtaattaag acagagtaag gtatttgtct gtgctcgatt 19140
atgtcatgtt atttgtttac atgacttcaa ataagtttta tagatatttt gcattctgta 19200
ttcttaaaaa gtatattgac taggactttt gagagtaggt attttaactc aattaggttt 19260
tagtttttaa tattctagca ctttccagca cacagttctg tgaattcctc ttcttctaat 19320
tattattatt attattagag atttatttat tttatgtata tgaatgcact gtagctgtac 19380
agatggttgt gagccttcat atggttgttg gaaattgaat tttaagaact ctgctcaatc 19440
cgacccaaag atttatttac tgtcataaat aagtacaccg ttgctgactt cagacatacc 19500
agaagagggc atcatatctc actatgggtg gttgtgagct accatgtggt tgctaggatt 19560
tgaactcagg accttgagaa gagtagtact cttactcgct gagccgtctc ccagcccgaa 19620
ttcctgttct tggttgttat gtctaccgat caatcagttg gcatacatag agacagacac 19680
acacagacag cagcatcgtg caggataact atttggagac tcatttttctt catttgtgct 19740 tttttgtaat tatgttgaag atcttaatcc tgtgagcaaa aaaagactaa ctgaacaatt 19800
ccctgtcata tagatcttga aagatactgt tttaggtaat ttaattaatc attgaattag 19860
tatttttaat tatatgatag ttataaaaat catttttccc tgtaaaacat ttaactacaa 19920
tttttttctg aaagtatggt ccttgatata ttttttagta taatcatgaa ttaagagacc 19980
ttaaagcaaa aggttcagaa tagaagctca ggagatagat gggtaagagt gcttaatgac 20040
ctgggttcaa atcccactac ctatcttaaa agccaatcat gactgttgca tgttgggaag 20100

-continued

```
cagttgcagg agcttgctag ccaactgtgg attcagtaaa aggagcaggg gaataaggta  20160
cagagggata gaagaaggca aaggcaggca gatttctgag ttcgaggcca gcctggtctg  20220
caaagtgagt tccaggacag ccagggctat acagagaaac cctgtctcga aaaaaaagaa  20280
aaagaaactc atttgcagtt aacttgcttg tttacaaaat tcattaagta tttctagaat  20340
tcgattttta tcatttgata actcagaatg gtcacttaaa acaaaattac taataaacgc  20400
tgagttttgg gctggtgaga tcgctcagtg ggtaagagca ccctactgct cgtccgaagg  20460
tccggagttc aaatcccagc aaccacatgg tggctcacaa caaccatctg taacaagatc  20520
tgacaccctc ttctggagtg tctgaagaca gctacagtgt acttacatat aataaataaa  20580
taaatcttta aaaaaaaaaa gctgagtttt acatctttca ttgaacttta tttcagctgc  20640
caggttattt ttagtaaagc tgtgatataa actcagtatg tcttttgctt cattgtgtgt  20700
gtcataaata tctttcagta cttctctgta gtttaagact agtaatatag tgacccaaat  20760
ggatagaaga gtggtgagct aggtatggtg gcacatatac gcatttagtc ctagtgctca  20820
ggaggcagaa gcaggtagat ctccaaggat gaggtcagcc ctggatagtg agaccctttc  20880
tcagttagca aaaaaaaaaa acaaagcgtt tcttctttcc ttgtcaaaga ttatatctga  20940
attttcccct ttgtttaaag gtatgtgagt ttgggtcatt ttgtctttta ctaatcaagc  21000
tgaactaaga gactgaaact tgtgattgaa gtgaaaagag tatctttgcc gtttcttgtg  21060
tgctgcactt tcccccctca tcctccctcc cttgtctaag gcatatttaa gataaacaga  21120
aactgaaggg gcaatgaggc acagataatc ctagcacgtg ggaagttgcc aagaggataa  21180
caagttttga gccacctgtg ctacataagt gaaaccctgt gttgagataa aaacaagagc  21240
tattgcccct ctgtgccttg cattataagc tgtacttaat ggtacataca tttttgtatt  21300
aaagttgagg gggtgtttta ggtcacaagg gcagacacga ggttattaaa aggcttggaa  21360
gaagtattaa aaaggcaaga tgctgtgttt actagagaag agttactgtg agatttgtaa  21420
ttatagcagc aataaagttc tctgttttcc tgaaggtcaa gcagttcctg ctcctgctgg  21480
ggccccacca ggtggtcagc cggattatag tgcagcctgg gctgagtact atagacagca  21540
agcagcgtat tatgcccaga caagtcccca ggggatgccg cagcatcctc cagcacctca  21600
ggtagaaaac atttgctatt ttttttgttt tgtttttgtt tttgttttcc actccaacca  21660
tgttttctgc atgtttgtct gtttgggaat gaatatgttt tacttggtaa agtataacta  21720
catgaaatat cgtgttgtgt ttggggactc agtttttcta ataatgtttt ctggcatctg  21780
agtgctattt ttgtaatgcc tttgatttta aaaataaatt ttcttccccc cagggatttg  21840
caaatcatgc aagaagccac catcatttat attaaccagt ttttctttct taaaggattc  21900
actcctgaat tagctccatt taaaggattt tctttaactt tttgtgtatc tcttatgtat  21960
ctcttctgca cagggccaat aataagaagt ggacaataca gtatttgctt cattgtgtgg  22020
gggaaaaaac ctttgttaaa tatatggatg cagacgactt gatgaagatc ttaattttgt  22080
ttttggttta aagtagtgtt tttttccccc cctttttttt tattttgaaa atgtacaaaa  22140
taactatcac tactgatagg aggttaatat ttctgtgtag aaatgaaaat tggtttgttt  22200
ttagtcttta gtgtagatgt acacattcca gcaaatgtat ttgcaactat tatgtggtcg  22260
atgctttgtg atataaatgt actttttcaa tgtatacttt cacttttaaa atgcctgttt  22320
tgtgctttac aataaatgat atgaaacctc ctgtgtcggt aagttggata tgtgggtaaa  22380
ggattcatag tttcttagca gtgataaatt aagatacatg tacacgaata tataagcttt  22440
ccccatgaat tactgagttt ttaaacactg gcatgttttt tcccctgttg gagtatagtg  22500
```

-continued

```
gtagattgga ggttcttttc tgttgtattt ggctatttca gcacaagtaa tcctgatatt  22560
ttcatgtttt tccttctatt tgattaaaaa ctgcatgtgt atacaatgat ctttagtata  22620
cttccattgc attaacagtg acatttcctt ttatacatga gcactatttc agacctgtac  22680
cgctgctaca acagttaacc ttcctgttct tcacttattt ccgagactgt ttcagcataa  22740
ctaattttga acagtttgca gacagtgatt tgaggagttt ataagaaaca ttgttttttt  22800
catgtaaagc aactctttcc atgtatatat atatattata atagtgtgtt tctctctaaa  22860
ttcaggatag aaaagtaata gaatgtgaaa gtatagctac attgcatctg ccattgaaac  22920
atttggggta tgaaaatgtt caagcttttt ttttcttttt gcagtataga taagctttgt  22980
cttgtaattg cacaagtcca gtcattgaat caaattaatt tttttatgta ctgaatcatt  23040
ttattaatct ttaacattca tgctgaagtt ctgatatttt gttgaaaacc attgttttac  23100
tctgcatatt tgttggctct ttgcatatta atatattaga ctacatgcaa atacagtctg  23160
tcttgccatt gtctgttgaa gtgcaggttt gatccagcca gtatagaact agctctgtag  23220
gggtgaggag gactgtgctg tgtatcatcc ttgattgtgt tccttcaagg agcattgcac  23280
tgtaagtaca tcagagtgac aaattgatga actgcaacag tgtctttttg tcgatgttcc  23340
acataatgca attgctatat tttgtgtgac tattatgttg gaatacagtg ctgtcatggg  23400
aaaccataac tgcttcttaa catagaataa tacatagttc tgtatttttt ttaagtgagc  23460
ttaatgggta agtatttttg atatgcttta gctaatagct aaagaaaatt gatcagtaac  23520
aaagttgaat agtattatca gtgctcctaa aatgctgttt ttcagtgtaa aatatgccta  23580
tcttttatag tgatatgaaa aacttgaaat gtttaagaca gaagtgcttt tcagtttgca  23640
aagtttaagg acttaacgcc ttttcattaa atgttagttc tatcatctgt ggggagcacc  23700
atttgtatga ggacaaaaat gttgaggtta tagggcagaa aatagtacag ctcattgtgg  23760
atgttttgaa atgtttttttg attgttttat gtaacttagt gacttccctt ccccttattt  23820
agatctggat gcatagctct agtatgaagt ttaatagtaa tagttaaggc cttacctgtt  23880
aagatcttaa gtgtagggta ttgacatgaa cagtttcagt attttgcatg atattgttgc  23940
atagatgacc taggaaagtg ttgtggtgca tttagtaatt aaactgaagg aaatagttgg  24000
attcagtatc ataattcaca aattggaggc tgttgatttt gattcgttta aaatttaaaa  24060
tctttattaa ttgcaaacag tgcaattatt tatacttcac agtgccttcc cagaccttcc  24120
accttaggtt ctgctgcaaa aagcaacagg taagcacaac ctaaggccat ctctatataa  24180
atatatcagt acatacatgt tgtccctgtg aggtttgtgg ttgtgtactc actcaagcaa  24240
tctgctgctg ccgctgcccc aaatgtactt tgttatttat ggtaccattc tagtggaaag  24300
tctgttaagt tgttcaagca actgtttaca attttgggtg atgttttgtt tttggttttt  24360
ttgggttttt tttttcccca ttaaaatgag tagattgctg caataactga aaaacatcca  24420
aatctttttg tgcacccctc ctctcccaga gttatagaaa tgtttaagaa cacttcagta  24480
gttgagacat aggaaatcat ttggtcagaa atttcaacag ccttcacagc ccgtttgtat  24540
gagtaacagg aaattctctt tgccctccaa atctgatctt tttatagttt tatttttatt  24600
atttttcccc tgtattagta ctgctttaaa gtacagtaat tcagtgagat cgttttggtt  24660
cagtttcata gacagttcta ttttcatgac ttgtatttgc tgacaaggaa gaataaagaa  24720
tactggcagt aagttttggg aaaggcatgt gcatcagtga aatgttactt gtataacaaa  24780
taacctttca taatctgcat aaccagtagt ttctgattta taatatttta ataactgact  24840
gcatttattt ttgccagttt aaaatgtttt gtgttcttag gattgatgtt tagtgcatat  24900
```

```
tttgagttaa atgactatct taaagcagca ccatatcagt tgtttttatt cattttctaa  24960

aatgtgctga tcctattaaa aactcctgct tatcttttac aacaaagaaa aatattcaaa  25020

aatactgcct tcattttcac acacagtgct gaagatgctg caagcaccaa atcatagctc  25080

ataaaatcag gtcctgagat agttacccat aaagaggaat cctttgagtg tatgccattg  25140

gtgagccgat gagcatggac catagaaggg ctcaatgtag aaggtaaaat tggcaaatca  25200

taattgagaa atatgactgt gttcccatac ataatatggt atagggtgta atgtacctgc  25260

tcttgatcac tttcatttta aagtgctatt cacttaaatg ttccatgaat tgtttattgc  25320

accacagttt gtgtgtgtgt gtgtgtgtga gagagagaga gagagagaga gaaataggtc  25380

agatcagtat gttgcaagca gatctttaga gcctgtcaag ttttggttag ttgtagtttc  25440

catttggaaa tgtagatgaa tgcttgtaga tattggagat tgtttctatc ttgtaagaac  25500

ttttcactgg tgctgtaagc atttcaaata gcaccagtct taacctttaa atgggaagta  25560

gaaaaggtga gcccaaagtt tacagatgat tttaatgcta tacatgttag tgtagtgata  25620

cttagaatgc tttgtttgat gtttatttca gaaatgcgta tactagaaaa tcattttaat  25680

attaaaactg gtgacttaat actagttgta aagtgttttc ttaaagaagg atcttggtac  25740

ttaattgata aagtgggttt agataggagt agcaagtgct ctcgatagag aaagtttttg  25800

ttcacttcaa tactttgtca ttacaaccag ttcttcctga aaatagttac atgtctagta  25860

aattgatgta gaattaactc gctggagata atctcatttt agttctgcaa attctgcctg  25920

gctttaaaat gcattttcat aatacttaga aataatttga ctgaaaataa ctgctttttt  25980

atttaatcag tcaatcaact tttactacaa atttaattga gggatttttt aatttaattg  26040

gtgctttaaa gaagcaaata aatccctggg ttttgttttc ttcagtaaat atcctaaaga  26100

aactctttaa tgtatttgcg agtatatata tattttctta tgcatgctcg atgcattttc  26160

gtcctgagaa aagtgttctc tacagaaact acccgtgtgt taaaagaaga ttggcttaaa  26220

atggctactg tgatgggaac agtgtcttag ggagatgcag cttggacttg aggtaaattg  26280

aatactttac aaactggctt agagttttgc tttaatgtca ttatatgtaa aagggcacat  26340

gattattgta attttgtatt ctttatggtt tccttaatta aaataataaa tgtacagtga  26400

ttact                                                              26405
```

<210> SEQ ID NO 10
<211> LENGTH: 4525
<212> TYPE: DNA
<213> ORGANISM: mus musculus

<400> SEQUENCE: 10

```
cctttcttag cagttaaccg agagcggcgc ctccctccgc gaggaaacgg cagcgtgtgc     60

tgtagcgtgg gtatggccga ctactccaca gtgcctccgc cgtcgtctgg ctcggctggc    120

ggcggcggcg gcggagtcgt taacgacgct ttcaaagatg ccctgcagag agcgcggcag    180

attgcagcaa aaattggggg tgatgctggt acatcattga attcaaatga ctatggttat    240

gggggacaaa aaagaccctt agaagatgga gatcagccag atgctaagaa agtacctccc    300

caaaatgact cttttggagc acagttacct ccaatgcatc agcagcaaag atctgtaatg    360

acagaagaat acaaagtccc agatgggatg gtcggattta taattggcag aggaggtgaa    420

cagatctcac gaatacagca ggaatctgga tgcaagatac agatagcacc tgatagtggt    480

ggcctaccag aaaggtcttg tatgctaact ggaacacctg aatctgtcca atcagcaaaa    540

agattattgg accagattgt tgaaaaggga agaccagccc ctggctttca tcatggtgat    600
```

-continued

```
ggacctggaa atgcagttca ggaaatcatg attccagcca gcaaagcagg actagttatt    660
ggaaaggggg gcgagactat taaacaactt caggaacggg ctggtgttaa aatggtaatg    720
attcaagatg ggcctcaaaa cactggtgct gataaacctc ttaggattac gggtgaccca    780
tacaaagttc agcaagccaa ggaaatggta ttagagttaa ttcgtgatca aggtggtttc    840
agagaagtgc ggaatgagta tggctcaaga ataggaggca atgaagggat agatgtccca    900
attccaagat ttgctgttgg cattgtaata ggaagaaatg gagaaatgat taaaaaaata    960
caaaatgatg ctggtgttcg aattcagttt aagccagatg atggaacaac acctgatagg   1020
atagcacaga taacaggacc tccagacagg tgtcagcacg ctgcagaaat aatcacagac   1080
cttctacgaa gtgttcaggc tggcaatcct ggtggaccgg gacctggtgg tcgaggacga   1140
ggtagaggtc aaggaaactg gaatatgggg cccccgggtg gactccagga gtttaatttc   1200
attgtgccaa ctgggaaaac tggactgatc attggaaaag gaggtgaaac cataaaaagc   1260
ataagccaac agtctggtgc aagaatagaa ctgcagagaa gccctccacc taatgcagat   1320
cccaatatga agttatttac aattcggggc actccacagc aaatagacta tgctcgacaa   1380
ctcatagaag agaagattgg gggcccagta aatcctttag ggccacctgt accccatggg   1440
ccccatgggg ttccaggtcc tcatgggcct cctggacctc cagggccggg aactccaatg   1500
ggaccataca accctgcacc ttacaatcca ggaccacctg gcccagctcc tcacggtcct   1560
ccagccccat atgctcccca gggatgggga aatgcgtatc cacattggca gcaacaggct   1620
cctcctgacc cagccaaggc aggagcagat ccaaactcgg cagcttgggc tgcttattat   1680
gctcactatt accagcagca ggcacaaccc ccacctgcag ctcctgccgg tgcaccagct   1740
acaacccaaa cgaacggaca aggtaactac ggagatcagc aggctccagc tccagctgga   1800
caggttgatt atacaaaggc ttgggaagaa tactacaaga aaatgggtca agcagttcct   1860
gctcctgctg gggccccacc aggtggtcag ccggattata gtgcagcctg ggctgagtac   1920
tatagacagc aagcagcgta ttatgcccag acaagtcccc aggggatgcc gcagcatcct   1980
ccagcacctc agggccaata ataagaagtg gacaatacag tatttgcttc attgtgtggg   2040
ggaaaaaacc tttgttaaat atatggatgc agacgacttg atgaagatct taattttgtt   2100
tttggtttaa agtagtgttt ttttcccccc ctttttttt atttgaaaa tgtacaaaat   2160
aactatcact actgatagga ggttaatatt tctgtgtaga aatgaaaatt ggtttgtttt   2220
tagtctttag tgtagatgta cacattccag caaatgtatt tgcaactatt atgtggtcga   2280
tgctttgtga tataaatgta ctttttcaat gtatactttc acttttaaaa tgcctgtttt   2340
gtgctttaca ataaatgata tgaaacctcc tgtgtcggta agttggatat gtgggtaaag   2400
gattcatagt ttcttagcag tgataaatta agatacatgt acacgaatat ataagctttc   2460
cccatgaatt actgagtttt taaacactgg catgtttttt cccctgttgg agtatagtgg   2520
tagattggag gttcttttct gttgtatttg gctatttcag cacaagtaat cctgatattt   2580
tcatgttttt ccttctattt gattaaaaac tgcatgtgta tacaatgatc tttagtatac   2640
ttccattgca ttaacagtga catttccttt tatacatgag cactatttca gacctgtacc   2700
gctgctacaa cagttaacct tcctgttctt cacttatttc cgagactgtt tcagcataac   2760
taattttgaa cagtttgcag acagtgattt gaggagttta taagaaacat tgttttttttc   2820
atgtaaagca actctttcca tgtatatata tatattataa tagtgtgttt ctctctaaat   2880
tcaggataga aaagtaatag aatgtgaaag tatagctaca ttgcatctgc cattgaaaca   2940
tttggggtat gaaaatgttc aagctttttt tttcttttg cagtatagat aagctttgtc   3000
```

-continued

```
ttgtaattgc acaagtccag tcattgaatc aaattaattt ttttatgtac tgaatcattt   3060

tattaatctt taacattcat gctgaagttc tgatattttg ttgaaaacca ttgttttact   3120

ctgcatattt gttggctctt tgcatattaa tatattagac tacatgcaaa tacagtctgt   3180

cttgccattg tctgttgaag tgcaggtttg atccagccag tatagaacta gctctgtagg   3240

ggtgaggagg actgtgctgt gtatcatcct tgattgtgtt ccttcaagga gcattgcact   3300

gtaagtacat cagagtgaca aattgatgaa ctgcaacagt gtctttttgt cgatgttcca   3360

cataatgcaa ttgctatatt ttgtgtgact attatgttgg aatacagtgc tgtcatggga   3420

aaccataact gcttcttaac atagaatat acatagttct gtattttttt taagtgagct   3480

taatgggtaa gtatttttga tatgctttag ctaatagcta aagaaaattg atcagtaaca   3540

aagttgaata gtattatcag tgctcctaaa atgctgtttt tcagtgtaaa atatgcctat   3600

cttttatagt gatatgaaaa acttgaaatg tttaagacag aagtgctttt cagtttgcaa   3660

agtttaagga cttaacgcct tttcattaaa tgttagttct atcatctgtg gggagcacca   3720

tttgtatgag gacaaaaatg ttgaggttat agggcagaaa atagtacagc tcattgtgga   3780

tgttttgaaa tgtttttga ttgttttatg taacttagtg acttcccttc cccttattta   3840

gatctggatg catagctcta gtatgaagtt taatagtaat agttaaggcc ttacctgtta   3900

agatcttaag tgtagggtat tgacatgaac agtttcagta ttttgcatga tattgttgca   3960

tagatgacct aggaaagtgt tgtggtgcat ttagtaatta aactgaagga aatagttgga   4020

ttcagtatca taattcacaa attggaggct gttgattttg attcgtttaa aatttaaaat   4080

ctttattaat tgcaaacagt gcaattattt atacttcaca gtgccttccc agaccttcca   4140

ccttaggttc tgctgcaaaa agcaacagtg ctgaagatgc tgcaagcacc aaatcatagc   4200

tcataaaatc aggtcctgag atagttaccc ataaagagga atcctttgag tgtatgccat   4260

tggtgagccg atgagcatgg accatagaag ggctcaatgt agaagaaact acccgtgtgt   4320

taaaagaaga ttggcttaaa atggctactg tgatgggaac agtgtcttag ggagatgcag   4380

cttggacttg aggtaaattg aatactttac aaactggctt agagttttgc tttaatgtca   4440

ttatatgtaa aagggcacat gattattgta attttgtatt ctttatggtt tccttaatta   4500

aaataataaa tgtacagtga ttact                                         4525
```

<210> SEQ ID NO 11
<211> LENGTH: 800
<212> TYPE: DNA
<213> ORGANISM: mus musculus

<400> SEQUENCE: 11

```
cagggatggg gaaatgcgta tccacattgg cagcaacagg ctcctcctga cccagccaag     60

gcaggagcag atccaaactc ggcagcttgg gctgcttatt atgctcacta ttaccagcag    120

caggcacaac ccccacctgc agctcctgcc ggtgcaccag ctacaaccca aacgaacgga    180

caaggagatc agcaggctcc agctccagct ggacaggttg attatacaaa ggcttgggaa    240

gaatactaca agaaaatggg tcaagcagtt cctgctcctg ctggggcccc accaggtggt    300

cagccggatt atagtgcagc ctgggctgag tactatagac agcaagcagc gtattatgcc    360

cagacaagtc cccaggggat gccgcagcat cctccagcac ctcagggcca ataataagaa    420

gtggacaata cagtatttgc ttcattgtgt gggggaaaaa acctttgtta aatatatgga    480

tgcagacgac ttgatgaaga tcttaatttt gtttttggtt taaagtagtg ttttttttccc   540

cccctttttt tttattttga aaatgtacaa aataactatc actactgata ggaggttaat    600
```

```
atttctgtgt agaaatgaaa attggtttgt ttttagtctt tagtgtagat gtacacattc    660

cagcaaatgt atttgcaact attatgtggt cgatgctttg tgatataaat gtactttttc    720

aatgtatact ttcactttta aaatgcctgt tttgtgcttt acaataaatg atatgaaacc    780

tcctgtgtcg gtaagttgga                                                800


<210> SEQ ID NO 12
<211> LENGTH: 2526
<212> TYPE: DNA
<213> ORGANISM: mus musculus

<400> SEQUENCE: 12

gcctcgacgg ccgccatctt cttcctttct tagcagttaa ccgagagcgg cgcctccctc     60

cgcgaggaaa cggcagcgtg tgctgtagcg tgggtatggc cgactactcc acagtgcctc    120

cgccgtcgtc tggctcggct ggcggcggcg gcggcggagt cgttaacgac gctttcaaag    180

atgccctgca gagagcgcgg cagattgcag caaaaattgg gggtgatgct ggtacatcat    240

tgaattcaaa tgactatggt tatgggggac aaaaaagacc cttagaagat ggagatcagc    300

cagatgctaa gaaagtacct ccccaaaatg actcttttgg agcacagtta cctccaatgc    360

atcagcagca aagcagatct gtaatgacag aagaatacaa agtcccagat gggatggtcg    420

gatttataat tggcagagga ggtgaacaga tctcacgaat acagcaggaa tctggatgca    480

agatacagat agcacctgat agtggtggcc taccagaaag gtcttgtatg ctaactggaa    540

cacctgaatc tgtccaatca gcaaaaagat tattggacca gattgttgaa aagggaagac    600

cagcccctgg ctttcatcat ggtgatggac ctggaaatgc agttcaggaa atcatgattc    660

cagccagcaa agcaggacta gttattggaa agggggggcga gactattaaa caacttcagg    720

aacgggctgg tgttaaaatg gtaatgattc aagatgggcc tcaaaacact ggtgctgata    780

aacctcttag gattacgggt gacccataca aagttcagca agccaaggaa atggtattag    840

agttaattcg tgatcaaggt ggtttcagag aagtgcggaa tgagtatggc tcaagaatag    900

gaggcaatga agggatagat gtcccaattc caagatttgc tgttggcatt gtaataggaa    960

gaaatggaga aatgattaaa aaaatacaaa atgatgctgg tgttcgaatt cagtttaagc   1020

cagatgatgg aacaacacct gataggatag cacagataac aggacctcca gacaggtgtc   1080

agcacgctgc agaaataatc acagaccttc tacgaagtgt tcaggctggc aatcctggtg   1140

gaccgggacc tggtggtcga ggacgaggta gaggtcaagg aaactggaat atggggcccc   1200

cgggtggact ccaggagttt aatttcattg tgccaactgg gaaaactgga ctgatcattg   1260

gaaaaggagg tgaaaccata aaaagcataa gccaacagtc tggtgcaaga atagaactgc   1320

agagaagccc tccacctaat gcagatccca atatgaagtt atttacaatt cggggcactc   1380

cacagcaaat agactatgct cgacaactca tagaagagaa gattgggggc ccagtaaatc   1440

ctttagggcc acctgtaccc catgggcccc atggggttcc aggtcctcat gggcctcctg   1500

gacctccagg gccgggaact ccaatgggac catacaaccc tgcaccttac aatccaggac   1560

cacctggccc agctcctcac ggtcctccag ccccatatgc tccccaggga tggggaaatg   1620

cgtatccaca ttggcagcaa caggctcctc ctgacccagc caaggcagga gcagatccaa   1680

actcggcagc ttgggctgct tattatgctc actattacca gcagcaggca caaccccccac   1740

ctgcagctcc tgccggtgca ccagctacaa ccccaaacga cggacaagga gatcagcagg   1800

ctccagctcc agctggacag gttgattata caaaggcttg ggaagaatac tacaagaaaa   1860

tgggtcaagc agttcctgct cctgctgggg ccccaccagg tggtcagccg gattatagtg   1920
```

```
cagcctgggc tgagtactat agacagcaag cagcgtatta tgcccagaca agtccccagg   1980

ggatgccgca gcatcctcca gcacctcagg gatttgcaaa tcatgcaaga agccaccatc   2040

atttatatta accagttttt ctttcttaaa ggattcactc ctgaattagc tccatttaaa   2100

ggattttctt taactttttg tgtatctctt atgtatctct tctgcacagg gccaataata   2160

agaagtggac aatacagtat ttgcttcatt gtgtggggga aaaaaccttt gttaaatata   2220

tggatgcaga cgacttgatg aagatcttaa ttttgttttt ggtttaaagt agtgtttttt   2280

tcccccccctt ttttttattt ttgaaaatgt acaaaataac tatcactact gataggaggt   2340

taatatttct gtgtagaaat gaaaattggt ttgtttttag tctttagtgt agatgtacac   2400

attccagcaa atgtatttgc aactattatg tggtcgatgc tttgtgatat aaatgtactt   2460

tttcaatgta tactttcact tttaaaatgc ctgttttgtg ctttacaata aatgatatga   2520

aacctc                                                              2526
```

<210> SEQ ID NO 13
<211> LENGTH: 809
<212> TYPE: DNA
<213> ORGANISM: mus musculus

<400> SEQUENCE: 13

```
gaaatgcgta tccacattgg cagcaacagg ctcctcctga cccagccaag gcaggagcag     60

atccaaactc ggcagcttgg gctgcttatt atgctcacta ttaccagcag caggcacaac    120

ccccacctgc agctcctgcc ggtgcaccag ctacaaccca aacgaacgga caaggagatc    180

agcaggctcc agctccagct ggacaggttg attatacaaa ggcttgggaa gaatactaca    240

agaaaatggg tcaagcagtt cctgctcctg ctggggcccc accaggtggt cagccggatt    300

atagtgcagc ctgggctgag tactatagac agcaagcagc gtattatgcc cagacaagtc    360

cccaggggat gccgcagcat cctccagcac ctcagtgcct tcccagacct tccaccttag    420

gttctgctgc aaaaagcaac agtgctgaag atgctgcaag caccaaatca tagctcataa    480

aatcaggtcc tgagatagtt acccataaag aggaatcctt tgagtgtatg ccattggtga    540

gccgatgagc atggaccata gaagggctca atgtagaagg taaaattggc aaatcataat    600

tgagaaatat gactgtgttc ccatacataa tatggtatag ggtgtaatgt acctgctctt    660

gatcactttc attttaaagt gctattcact taaatgttcc atgaattgtt tattgcacca    720

cagtttgtgt gtgtgtgtgt gtgtgagaga gagagagaga gagagagaaa taggtcagat    780

cagtatgttg caagcagatc tttagagcc                                      809
```

<210> SEQ ID NO 14
<211> LENGTH: 1040
<212> TYPE: DNA
<213> ORGANISM: mus musculus

<400> SEQUENCE: 14

```
gatggtcgtg caagaatgtg atagagcctc gacggccgcc atcttcttcc tttcttagca     60

gttaaccgag agcggcgcct ccctccgcga ggaaacggca gcgtgtgctg tagcgtgggt    120

atggccgact actccacagt gcctccgccg tcgtctggct cggctggcgg cggcggcggc    180

ggagtcgtta acgacgcttt caaagatgcc ctgcagagag cgcggcagat tgcagcaaaa    240

attgggggtg atgctggtac atcattgaat tcaaatgact atggttatgg gggacaaaaa    300

agacccttag aagatggaga tggctcttgg acaaatccga gcagtaccac acactgggag    360

ggaatgccct ctccttttaa agatcagcca gatgctaaga aagtacctcc ccaaaatgac    420
```

-continued

```
tcttttggag cacagttacc tccaatgcat cagcagcaaa gatctgtaat gacagaagaa    480

tacaaagtcc cagatgggat ggtcggattt ataattggca gaggaggtga acagatctca    540

cgaatacagc aggaatctgg atgcaagata cagatagcac ctgatagtgg tggcctacca    600

gaaaggtctt gtatgctaac tggaacacct gaatctgtcc aatcagcaaa aagattattg    660

gaccagattg ttgaaaaggg aagaccagcc cctggctttc atcatggtga tggacctgga    720

aatgcagttc aggaaatcat gattccagcc agcaaagcag gactagttat tggaaagggg    780

ggcgagacta ttaaacaact tcaggaacgg gctggtgtta aaatggtaat gattcaagat    840

gggcctcaaa acactggtgc tgataaacct cttaggatta cgggtgaccc atacaaagtt    900

cagcaagcca aggaaatggt attagagtta attcgtgatc aaggtggttt cagagaagtg    960

cggaatgagt atggctcaag aataggaggc aatgaaggga tagatgtccc aattccaaga   1020

tttgctgttg gcattgtaat                                               1040
```

<210> SEQ ID NO 15
<211> LENGTH: 796
<212> TYPE: DNA
<213> ORGANISM: mus musculus

<400> SEQUENCE: 15

```
cccatatgct ccccagggat ggggaaatgc gtatccacat tggcagcaac aggctcctcc     60

tgacccagcc aaggcaggag cagatccaaa ctcggcagct tgggctgctt attatgctca    120

ctattaccag cagcaggcac aaccccccacc tgcagctcct gccggtgcac cagctacaac    180

ccaaacgaac ggacaaggag atcagcaggc tccagctcca gctggacagg ttgattatac    240

aaaggcttgg gaagaatact acaagaaaat gggtcaagca gttcctgctc ctgctggggc    300

cccaccaggt ggtcagccgg attatagtgc agcctgggct gagtactata gacagcaagc    360

agcgtattat gcccagacaa gtccccaggg gatgccgcag catcctccag cacctcaggg    420

ccaataataa gaagtggaca atacagtatt tgcttcattg tgtgggggaa aaaacctttg    480

ttaaatatat ggatgcagac gacttgatga agatcttaat tttgtttttg gtttaaagta    540

gtgttttttt cccccccttt ttttttattt tgaaaatgta caaaataact atcactactg    600

ataggaggtt aatatttctg tgtagaaatg aaaattggtt tgtttttagt ctttagtgta    660

gatgtacaca ttccagcaaa tgtatttgca actattatgt ggtcgatgct ttgtgatata    720

aatgtacttt ttcaatgtat actttcactt ttaaaatgcc tgttttgtgc tttacaataa    780

atgatatgaa acctcc                                                    796
```

<210> SEQ ID NO 16
<211> LENGTH: 585
<212> TYPE: DNA
<213> ORGANISM: mus musculus

<400> SEQUENCE: 16

```
aatttcattg tgccaactgg gaaaactgga ctgatcattg gaaaaggagg tgaaaccata     60

aaaagcataa gccaacagtc tggtgcaaga atagaactgc agagaagccc tccacctaat    120

gcagatccca atatgaagtt atttacaatt cggggcactc cacagcaaat agactatgct    180

cgacaactca tagaagagaa gattgggggc ccagtaaatc ctttagggcc acctgtaccc    240

catgggcccc atggggttcc aggtcctcat gggcctcctg gacctccagg gccgggaact    300

ccaatgggac catacaaccc tgcaccttac aatccaggac cacctggccc agctcctcac    360

ggtcctccag ccccatatgc tccccaggga tggggaaatg cgtatccaca ttggcagcaa    420
```

-continued

```
caggctcctc ctgacccaga aacaacttga gccgggcggc agtggtgaac gccattagtc    480
ccagcacaca ggagacagaa gcaggcagat ctctgagttc gaggacagcc tgatctacag    540
agcatgttca aggatagcca gggacacaca ggaaaaatcc tatct                    585
```

<210> SEQ ID NO 17
<211> LENGTH: 2374
<212> TYPE: DNA
<213> ORGANISM: mus musculus

<400> SEQUENCE: 17

```
ttcctttctt agcagttaac cgagagcggc gcctccctcc gcgaggaaac ggcagcgtgt     60
gctgtagcgt gggtatggcc gactactcca cagtgcctcc gccgtcgtct ggctcggctg    120
gcggcggcgg cggcggagtc gttaacgacg ctttcaaaga tgccctgcag agagcgcggc    180
agattgcagc aaaaattggg ggtgatgctg gtacatcatt gaattcaaat gactatggtt    240
atgggggaca aaaaagaccc ttagaagatg gagatcagcc agatgctaag aaagtacctc    300
cccaaaatga ctcttttgga gcacagttac ctccaatgca tcagcagcaa agcagatctg    360
taatgacaga agaatacaaa gtcccagatg ggatggtcgg atttataatt ggcagaggag    420
gtgaacagat ctcacgaata cagcaggaat ctggatgcaa gatacagata gcacctgata    480
gtggtggcct accagaaagg tcttgtatgc taactggaac acctgaatct gtccaatcag    540
caaaaagatt attggaccag attgttgaaa agggaagacc agcccctggc tttcatcatg    600
gtgatggacc tggaaatgca gttcaggaaa tcatgattcc agccagcaaa gcaggactag    660
ttattggaaa ggggggcgag actattaaac aacttcagga acgggctggt gttaaaatgg    720
taatgattca agatgggcct caaaacactg gtgctgataa acctcttagg attacgggtg    780
acccatacaa agttcagcaa gccaaggaaa tggtattaga gttaattcgt gatcaaggtg    840
gtttcagaga agtgcggaat gagtatggct caagaatagg aggcaatgaa gggatagatg    900
tcccaattcc aagatttgct gttggcattg taataggaag aaatggagaa atgattaaaa    960
aaatacaaaa tgatgctggt gttcgaattc agtttaagcc agatgatgga acaacacctg   1020
ataggatagc acagataaca ggacctccag acaggtgtca gcacgctgca gaaataatca   1080
cagaccttct acgaagtgtt caggctggca atcctggtgg accgggacct ggtggtcgag   1140
gacgaggtag aggtcaagga aactggaata tggggccccc gggtggactc caggagttta   1200
atttcattgt gccaactggg aaaactggac tgatcattgg aaaaggaggt gaaaccataa   1260
aaagcataag ccaacagtct ggtgcaagaa tagaactgca gagaagccct ccacctaatg   1320
cagatcccaa tatgaagtta tttacaattc ggggcactcc acagcaaata gactatgctc   1380
gacaactcat agaagagaag attgggggcc cagtaaatcc tttagggcca cctgtacccc   1440
atgggcccca tggggttcca ggtcctcatg ggcctcctgg acctccaggg ccgggaactc   1500
caatgggacc atacaaccct gcaccttaca atccaggacc acctggccca gctcctcacg   1560
gtcctccagc ccccatatgct ccccagggat ggggaaatgc gtatccacat tggcagcaac   1620
aggctcctcc tgacccagcc aaggcaggag cagatccaaa ctcggcagct tgggctgctt   1680
attatgctca ctattaccag cagcaggcac aacccccacc tgcagctcct gccggtgcac   1740
cagctacaac ccaaacgaac ggacaaggta actacggaga tcagcaggct ccagctccag   1800
ctggacaggt tgattataca aaggcttggg aagaatacta caagaaaatg ggtcaagcag   1860
ttcctgctcc tgctggggcc ccaccaggtg gtcagccgga ttatagtgca gcctgggctg   1920
agtactatag acagcaagca gcgtattatg cccagacaag tccccagggg atgccgcagc   1980
```

-continued

```
atcctccagc acctcagggc caataataag aagtggacaa tacagtattt gcttcattgt   2040

gtgggggaaa aaacctttgt taaatatatg gatgcagacg acttgatgaa gatcttaatt   2100

ttgtttttgg tttaaagtag tgtttttttc cccccctttt tttttatttt gaaaatgtac   2160

aaaataacta tcactactga taggaggtta atatttctgt gtagaaatga aaattggttt   2220

gtttttagtc tttagtgtag atgtacacat tccagcaaat gtatttgcaa ctattatgtg   2280

gtcgatgctt tgtgatataa atgtactttt tcaatgtata ctttcacttt taaaatgcct   2340

gttttgtgct ttacaataaa tgatatgaaa cctc                                2374
```

<210> SEQ ID NO 18
<211> LENGTH: 3163
<212> TYPE: DNA
<213> ORGANISM: mus musculus

<400> SEQUENCE: 18

```
gatagagcct cgacggccgc catcttcttc ctttcttagc agttaaccga gagcggcgcc     60

tccctccgcg aggaaacggc agcgtgtgct gtagcgtggg tatggccgac tactccacag    120

tgcctccgcc gtcgtctggc tcggctggcg gcggcggcgg cggagtcgtt aacgacgctt    180

tcaaagatgc cctgcagaga gcgcggcaga ttgcagcaaa aattgggggt gatgctggta    240

catcattgaa ttcaaatgac tatggttatg gggacaaaa aagacccctta gaagatggag    300

atcagccaga tgctaagaaa gtacctcccc aaaatgactc ttttggagca cagttacctc    360

caatgcatca gcagcaaaga tctgtaatga cagaagaata caaagtccca gatgggatgg    420

tcggatttat aattggcaga ggaggtgaac agatctcacg aatacagcag gaatctggat    480

gcaagataca gatagcacct gatagtggtg gcctaccaga aaggtcttgt atgctaactg    540

gaacacctga atctgtccaa tcagcaaaaa gattattgga ccagattgtt gaaaagggaa    600

gaccagcccc tggctttcat catggtgatg gacctggaaa tgcagttcag gaaatcatga    660

ttccagccag caaagcagga ctagttattg gaaagggggg cgagactatt aaacaacttc    720

aggaacgggc tggtgttaaa atggtaatga ttcaagatgg gcctcaaaac actggtgctg    780

ataaacctct taggattacg ggtgacccat acaaagttca gcaagccaag gaaatggtat    840

tagagttaat tcgtgatcaa ggtggtttca gagaagtgcg gaatgagtat ggctcaagaa    900

taggaggcaa tgaagggata gatgtcccaa ttccaagatt tgctgttggc attgtaatag    960

gaagaaatgg agaaatgatt aaaaaaatac aaaatgatgc tggtgttcga attcagttta   1020

agccagatga tggaacaaca cctgatagga tagcacagat aacaggacct ccagacaggt   1080

gtcagcacgc tgcagaaata atcacagacc ttctacgaag tgttcaggct ggcaatcctg   1140

gtggaccggg acctggtggt cgaggacgag gtagaggtca aggaaactgg aatatggggc   1200

ccccgggtgg actccaggag tttaatttca ttgtgccaac tgggaaaact ggactgatca   1260

ttggaaaagg aggtgaaacc ataaaaagca taagccaaca gtctggtgca agaatagaac   1320

tgcagagaag ccctccacct aatgcagatc ccaatatgaa gttatttaca attcggggca   1380

ctccacagca aatagactat gctcgacaac tcatagaaga gaagattggg ggcccagtaa   1440

atcctttagg gccacctgta ccccatgggc cccatggggt tccaggtcct catgggcctc   1500

ctggacctcc agggccggga actccaatgg gaccatacaa ccctgcacct tacaatccag   1560

gaccacctgg cccagctcct cacggtcctc cagccccata tgctccccag ggatggggaa   1620

atgcgtatcc acattggcag caacaggctc ctcctgaccc aggtaaaggg taatctacta   1680

ttaatatgtt agcttcattg tatactgctg gtcacagtcc taaactacct actgcatgtg   1740
```

-continued

```
cgatctttta aggcacttcc cctgcagtat aggatgacac tgctgtctag tatgttgtga   1800

ctttattcat agtagttcat atttataaaa taatgtgttt aacactacta tgttctcaaa   1860

taataagtat aaattatttt gttgctgata aaattaaggt cccttaatta ccaaaacagg   1920

agagtacatt tatttttctc tcttataatc tggattttct atagcatggt gttctcatta   1980

tatcttccca tactggtttt gtttctactc catcatgatc aggaatcaac ttggaaatag   2040

gactttttc tttgttttc ttttgtttt tcactttgca gcccctgtag tttgattcat   2100

ttgaaaagtt tgagagaacg tgttctgagt tatagatttc tacatagtgt attttttaca   2160

aatcaaagtt gatttagatg taattgcttt gttggatttg ttaaatgttt taatatttta   2220

atgtatgtta aattcatagg aacttttctc agtcaccaaa taaccacaac ttctattcat   2280

ttaagaaaca acttgagccg ggcggcagtg gtgaacgcca ttagtcccag cacacaggag   2340

acagaagcag gcagatctct gagttcgagg acagcctgat ctacagagca tgttcaagga   2400

tagccaggga cacacaggaa aaatcctatc tcaaaaaaga gagagagaga aaaaaaaaga   2460

aaaagaaata acttgaattg tgatggcatc tgaatatgaa agatgagtgt cgattagcaa   2520

aagagtgcat tcccagggca gacaagaagc atcagttatg acttcctttg taagggtttt   2580

aaaagtgaat cttctccttc taacaagcat ttagacgtgg catgatcaaa tagagttgga   2640

acaggttata ttgaaggttt tatatggcta attcaatttc ataggattgc tcaaatgagt   2700

gatgtttgat attagcactg taaggtctgg tcagtgaata tgacttccag cattacctgg   2760

aagactgact cggcaatatg ttgcttaaat ttgacttgga agtatacagt attttattgt   2820

ctgcattttc aagaaactgc tgctgtgagg ttgagattta tatagatgtc aagaatttaa   2880

tcttcaatct taaatggata atatgcgaat tcatcctatg taaaagaata gtgagctctt   2940

agtacctgct agttgcaagt cacaaaaaaa aagtttgggt tttggtttgg tttttgagtt   3000

acaaaggtga gcttagtgca gaggatgctg gttgtggtga cttgggaata gggcagcagc   3060

taaaacttga gtattggggg atgctaaaag aattaataga aaggataagc cacagtgctg   3120

gggataagca ttagaacctg agttctatcc ctcccacctg ttg                     3163
```

<210> SEQ ID NO 19
<211> LENGTH: 6523
<212> TYPE: DNA
<213> ORGANISM: mus musculus

<400> SEQUENCE: 19

```
gctgaaacat cgcgggattt ccgtctgcca gtctccgccc ctttacggca cgatggtcgt     60

gcaagaatgt gatagagcct cgacggccgc catcttcttc ctttcttagc agttaaccga    120

gagcggcgcc tccctccgcg aggaaacggc agcgtgtgct gtagcgtggg tatggccgac    180

tactccacag tgcctccgcc gtcgtctggc tcggctggcg gcggcggcgg cggagtcgtt    240

aacgacgctt tcaaagatgc cctgcagaga gcgcggcaga ttgcagcaaa aattgggggt    300

gatgctggta catcattgaa ttcaaatgac tatggttatg gggggacaaaa aagaccctta    360

gaagatggag atcagccaga tgctaagaaa gtacctcccc aaaatgactc ttttggagca    420

cagttacctc caatgcatca gcagcaaaga tctgtaatga cagaagaata caaagtccca    480

gatgggatgg tcggatttat aattggcaga ggaggtgaac agatctcacg aatacagcag    540

gaatctggat gcaagataca gatagcacct gatagtggtg gcctaccaga aaggtcttgt    600

atgctaactg gaacacctga atctgtccaa tcagcaaaaa gattattgga ccagattgtt    660

gaaaagggaa gaccagcccc tggctttcat catggtgatg gacctggaaa tgcagttcag    720
```

-continued

```
gaaatcatga ttccagccag caaagcagga ctagttattg gaaagggggg cgagactatt    780
aaacaacttc aggaacgggc tggtgttaaa atggtaatga ttcaagatgg gcctcaaaac    840
actggtgctg ataaacctct taggattacg ggtgacccat acaaagttca gcaagccaag    900
gaaatggtat tagagttaat tcgtgatcaa ggtggtttca gagaagtgcg gaatgagtat    960
ggctcaagaa taggaggcaa tgaagggata gatgtcccaa ttccaagatt tgctgttggc   1020
attgtaatag gaagaaatgg agaaatgatt aaaaaaatac aaaatgatgc tggtgttcga   1080
attcagttta agccagatga tggaacaaca cctgatagga tagcacagat aacaggacct   1140
ccagacaggt gtcagcacgc tgcagaaata atcacagacc ttctacgaag tgttcaggct   1200
ggcaatcctg gtggaccggg acctggtggt cgaggacgag gtagaggtca aggaaactgg   1260
aatatggggc ccccgggtgg actccaggag tttaatttca ttgtgccaac tgggaaaact   1320
ggactgatca ttggaaaagg aggtgaaacc ataaaaagca taagccaaca gtctggtgca   1380
agaatagaac tgcagagaag ccctccacct aatgcagatc ccaatatgaa gttatttaca   1440
attcggggca ctccacagca aatagactat gctcgacaac tcatagaaga gaagattggg   1500
ggcccagtaa atcctttagg gccacctgta ccccatgggc cccatggggt tccaggtcct   1560
catgggcctc ctggacctcc agggccggga actccaatgg gaccatacaa ccctgcacct   1620
tacaatccag gaccacctgg cccagctcct cacggtcctc cagccccata tgctccccag   1680
ggatggggaa atgcgtatcc acattggcag caacaggctc ctcctgaccc agccaaggca   1740
ggagcagatc caaactcggc agcttgggct gcttattatg ctcactatta ccagcagcag   1800
gcacaacccc cacctgcagc tcctgccggt gcaccagcta caacccaaac gaacggacaa   1860
ggtaactacg gagatcagca ggctccagct ccagctggac aggttgatta tacaaaggct   1920
tgggaagaat actacaagaa aatgggtcaa gcagttcctg ctcctgctgg ggccccacca   1980
ggtggtcagc cggattatag tgcagcctgg gctgagtact atagacagca agcagcgtat   2040
tatgcccaga caagtcccca ggggatgccg cagcatcctc cagcacctca gggccaataa   2100
taagaagtgg acaatacagt atttgcttca ttgtgtgggg gaaaaaacct ttgttaaata   2160
tatggatgca gacgacttga tgaagatctt aattttgttt ttggtttaaa gtagtgtttt   2220
tttccccccc ttttttttta ttttgaaaat gtacaaaata actatcacta ctgataggag   2280
gttaatattt ctgtgtagaa atgaaaattg gtttgttttt agtctttagt gtagatgtac   2340
acattccagc aaatgtattt gcaactatta tgtggtcgat gctttgtgat ataaatgtac   2400
tttttcaatg tatactttca cttttaaaat gcctgttttg tgctttacaa taaatgatat   2460
gaaacctcct gtgtcggtaa gttggatatg tgggtaaagg attcatagtt tcttagcagt   2520
gataaattaa gatacatgta cacgaatata taagctttcc ccatgaatta ctgagttttt   2580
aaacactggc atgtttttc ccctgttgga gtatagtggt agattggagg ttcttttctg    2640
ttgtatttgg ctatttcagc acaagtaatc ctgatatttt catgtttttc cttctatttg   2700
attaaaaact gcatgtgtat acaatgatct ttagtatact tccattgcat taacagtgac   2760
atttcctttt atacatgagc actatttcag acctgtaccg ctgctacaac agttaacctt   2820
cctgttcttc acttatttcc gagactgttt cagcataact aattttgaac agtttgcaga   2880
cagtgatttg aggagtttat aagaaacatt gtttttttca tgtaaagcaa ctctttccat   2940
gtatatatat atattataat agtgtgtttc tctctaaatt caggatagaa aagtaataga   3000
atgtgaaagt atagctacat tgcatctgcc attgaaacat ttggggtatg aaaatgttca   3060
agcttttttt ttctttttgc agtatagata agctttgtct tgtaattgca caagtccagt   3120
```

-continued

```
cattgaatca aattaatttt tttatgtact gaatcatttt attaatcttt aacattcatg   3180
ctgaagttct gatattttgt tgaaaaccat tgttttactc tgcatatttg ttggctcttt   3240
gcatattaat atattagact acatgcaaat acagtctgtc ttgccattgt ctgttgaagt   3300
gcaggtttga tccagccagt atagaactag ctctgtaggg gtgaggagga ctgtgctgtg   3360
tatcatcctt gattgtgttc cttcaaggag cattgcactg taagtacatc agagtgacaa   3420
attgatgaac tgcaacagtg tctttttgtc gatgttccac ataatgcaat tgctatattt   3480
tgtgtgacta ttatgttgga atacagtgct gtcatgggaa accataactg cttcttaaca   3540
tagaataata catagttctg tatttttttt aagtgagctt aatgggtaag tatttttgat   3600
atgctttagc taatagctaa agaaaattga tcagtaacaa agttgaatag tattatcagt   3660
gctcctaaaa tgctgttttt cagtgtaaaa tatgcctatc ttttatagtg atatgaaaaa   3720
cttgaaatgt ttaagacaga agtgcttttc agtttgcaaa gtttaaggac ttaacgcctt   3780
ttcattaaat gttagttcta tcatctgtgg ggagcaccat ttgtatgagg acaaaaaatgt  3840
tgaggttata gggcagaaaa tagtacagct cattgtggat gttttgaaat gtttttttgat  3900
tgttttatgt aacttagtga cttcccttcc ccttatttag atctggatgc atagctctag   3960
tatgaagttt aatagtaata gttaaggcct tacctgttaa gatcttaagt gtagggtatt   4020
gacatgaaca gtttcagtat tttgcatgat attgttgcat agatgaccta ggaaagtgtt   4080
gtggtgcatt tagtaattaa actgaaggaa atagttggat tcagtatcat aattcacaaa   4140
ttggaggctg ttgattttga ttcgtttaaa atttaaaatc tttattaatt gcaaacagtg   4200
caattattta tacttcacag tgccttccca gaccttccac cttaggttct gctgcaaaaa   4260
gcaacaggta agcacaacct aaggccatct ctatataaat atatcagtac atacatgttg   4320
tccctgtgag gtttgtggtt gtgtactcac tcaagcaatc tgctgctgcc gctgccccaa   4380
atgtactttg ttatttatgg taccattcta gtggaaagtc tgttaagttg ttcaagcaac   4440
tgtttacaat tttgggtgat gttttgtttt tggttttttt gggttttttt tttccccatt   4500
aaaatgagta gattgctgca ataactgaaa aacatccaaa tctttttgtg cacccctcct   4560
ctcccagagt tatagaaatg tttaagaaca cttcagtagt tgagacatag gaaatcattt   4620
ggtcagaaat ttcaacagcc ttcacagccc gtttgtatga gtaacaggaa attctctttg   4680
ccctccaaat ctgatctttt tatagtttta tttttattat ttttcccctg tattagtact   4740
gctttaaagt acagtaattc agtgagatcg ttttggttca gtttcataga cagttctatt   4800
ttcatgactt gtatttgctg acaaggaaga ataaagaata ctggcagtaa gttttgggaa   4860
aggcatgtgc atcagtgaaa tgttacttgt ataacaaata acctttcata atctgcataa   4920
ccagtagttt ctgatttata atattttaat aactgactgc atttattttt gccagtttaa   4980
aatgttttgt gttcttagga ttgatgttta gtgcatattt tgagttaaat gactatctta   5040
aagcagcacc atatcagttg tttttattca ttttctaaaa tgtgctgatc ctattaaaaa   5100
ctcctgctta tcttttacaa caaagaaaaa tattcaaaaa tactgccttc attttcacac   5160
acagtgctga agatgctgca agcaccaaat catagctcat aaaatcaggt cctgagatag   5220
ttacccataa agaggaatcc tttgagtgta tgccattggt gagccgatga gcatggacca   5280
tagaagggct caatgtagaa ggtaaaattg gcaaatcata attgagaaat atgactgtgt   5340
tcccatacat aatatggtat agggtgtaat gtacctgctc ttgatcactt tcattttaaa   5400
gtgctattca cttaaatgtt ccatgaattg tttattgcac cacagtttgt gtgtgtgtgt   5460
gtgtgtgaga gagagagaga gagagagaga aataggtcag atcagtatgt tgcaagcaga   5520
```

```
tctttagagc ctgtcaagtt ttggttagtt gtagtttcca tttggaaatg tagatgaatg   5580
cttgtagata ttggagattg tttctatctt gtaagaactt ttcactggtg ctgtaagcat   5640
ttcaaatagc accagtctta acctttaaat gggaagtaga aaaggtgagc ccaaagttta   5700
cagatgattt taatgctata catgttagtg tagtgatact tagaatgctt tgtttgatgt   5760
ttatttcaga aatgcgtata ctagaaaatc attttaatat taaaactggt gacttaatac   5820
tagttgtaaa gtgttttctt aaagaaggat cttggtactt aattgataaa gtgggtttag   5880
ataggagtag caagtgctct cgatagagaa agtttttgtt cacttcaata ctttgtcatt   5940
acaaccagtt cttcctgaaa atagttacat gtctagtaaa ttgatgtaga attaactcgc   6000
tggagataat ctcattttag ttctgcaaat tctgcctggc tttaaaatgc attttcataa   6060
tacttagaaa taatttgact gaaaataact gctttttat ttaatcagtc aatcaacttt   6120
tactacaaat ttaattgagg gattttttaa tttaattggt gctttaaaga agcaaataaa   6180
tccctgggtt ttgttttctt cagtaaatat cctaaagaaa ctctttaatg tatttgcgag   6240
tatatatata ttttcttatg catgctcgat gcattttcgt cctgagaaaa gtgttctcta   6300
cagaaactac ccgtgtgtta aaagaagatt ggcttaaaat ggctactgtg atgggaacag   6360
tgtcttaggg agatgcagct tggacttgag gtaaattgaa tactttacaa actggcttag   6420
agttttgctt taatgtcatt atatgtaaaa gggcacatga ttattgtaat tttgtattct   6480
ttatggtttc cttaattaaa ataataaatg tacagtgatt act                     6523
```

<210> SEQ ID NO 20
<211> LENGTH: 2552
<212> TYPE: DNA
<213> ORGANISM: mus musculus

<400> SEQUENCE: 20

```
gcaagaatgt gatagagcct cgacggccgc catcttcttc ctttcttagc agttaaccga     60
gagcggcgcc tccctccgcg aggaaacggc agcgtgtgct gtagcgtggg tatggccgac    120
tactccacag tgcctccgcc gtcgtctggc tcggctggcg gcggcggcgg cggagtcgtt    180
aacgacgctt tcaaagatgc cctgcagaga gcgcggcaga ttgcagcaaa aattgggggt    240
gatgctggta catcattgaa ttcaaatgac tatggttatg ggggacaaaa aagaccctta    300
gaagatggag atcagccaga tgctaagaaa gtacctcccc aaaatgactc ttttggagca    360
cagttacctc caatgcatca gcagcaaagc agatctgtaa tgacagaaga atacaaagtc    420
ccagatggga tggtcggatt tataattggc agaggaggtg aacagatctc acgaatacag    480
caggaatctg gatgcaagat acagatagca cctgatagtg gtggcctacc agaaaggtct    540
tgtatgctaa ctggaacacc tgaatctgtc caatcagcaa aaagattatt ggaccagatt    600
gttgaaaagg gaagaccagc ccctggcttt catcatggtg atggacctgg aaatgcagtt    660
caggaaatca tgattccagc cagcaaagca ggactagtta ttggaaaggg gggcgagact    720
attaaacaac ttcaggaacg ggctggtgtt aaaatggtaa tgattcaaga tgggcctcaa    780
aacactggtg ctgataaacc tcttaggatt acgggtgacc catacaaagt tcagcaagcc    840
aaggaaatgg tattagagtt aattcgtgat caaggtggtt tcagagaagt gcggaatgag    900
tatggctcaa gaataggagg caatgaaggg atagatgtcc caattccaag atttgctgtt    960
ggcattgtaa taggaagaaa tggagaaatg attaaaaaaa tacaaaatga tgctggtgtt   1020
cgaattcagt ttaagccaga tgatggaaca acacctgata ggatagcaca gataacagga   1080
cctccagaca ggtgtcagca cgctgcagaa ataatcacag accttctacg aagtgttcag   1140
```

```
gctggcaatc ctggtggacc gggacctggt ggtcgaggac gaggtagagg tcaaggaaac   1200

tggaatatgg ggcccccggg tggactccag gagtttaatt tcattgtgcc aactgggaaa   1260

actggactga tcattggaaa aggaggtgaa accataaaaa gcataagcca acagtctggt   1320

gcaagaatag aactgcagag aagccctcca cctaatgcag atcccaatat gaagttattt   1380

acaattcggg gcactccaca gcaaatagac tatgctcgac aactcataga agagaagatt   1440

gggggcccag taaatccttt agggccacct gtaccccatg ggccccatgg ggttccaggt   1500

cctcatgggc ctcctggacc tccagggccg ggaactccaa tgggaccata caaccctgca   1560

ccttacaatc caggaccacc tggcccagct cctcacggtc ctccagcccc atatgctccc   1620

cagggatggg gaaatgcgta tccacattgg cagcaacagg ctcctcctga cccagccaag   1680

gcaggagcag atccaaactc ggcagcttgg gctgcttatt atgctcacta ttaccagcag   1740

caggcacaac ccccacctgc agctcctgcc ggtgcaccag ctacaaccca aacgaacgga   1800

caaggtaact acggagatca gcaggctcca gctccagctg gacaggttga ttatacaaag   1860

gcttgggaag aatactacaa gaaaatgggt caagcagttc ctgctcctgc tggggcccca   1920

ccaggtggtc agccggatta tagtgcagcc tgggctgagt actatagaca gcaagcagcg   1980

tattatgccc agacaagtcc ccaggggatg ccgcagcatc ctccagcacc tcagggattt   2040

gcaaatcatg caagaagcca ccatcattta tattaaccag tttttctttc ttaaaggatt   2100

cactcctgaa ttagctccat ttaaaggatt ttctttaact ttttgtgtat ctcttatgta   2160

tctcttctgc acagggccaa taataagaag tggacaatac agtatttgct tcattgtgtg   2220

ggggaaaaaa cctttgttaa atatatggat gcagacgact tgatgaagat cttaattttg   2280

tttttggttt aaagtagtgt ttttttcccc cccttttttt ttattttgaa aatgtacaaa   2340

ataactatca ctactgatag gaggttaata tttctgtgta gaaatgaaaa ttggtttgtt   2400

tttagtcttt agtgtagatg tacacattcc agcaaatgta tttgcaacta ttatgtggtc   2460

gatgctttgt gatataaatg tactttttca atgtatactt tcacttttaa aatgcctgtt   2520

ttgtgcttta caataaatga tatgaaacct cc                                 2552
```

<210> SEQ ID NO 21
<211> LENGTH: 19
<212> TYPE: RNA
<213> ORGANISM: homo sapiens

<400> SEQUENCE: 21

```
gacaaaccuc uuaggauua                                                  19
```

<210> SEQ ID NO 22
<211> LENGTH: 19
<212> TYPE: RNA
<213> ORGANISM: homo sapiens

<400> SEQUENCE: 22

```
gagaaguucg gaaugagua                                                  19
```

<210> SEQ ID NO 23
<211> LENGTH: 19
<212> TYPE: RNA
<213> ORGANISM: homo sapiens

<400> SEQUENCE: 23

```
gaaaggauag cacaaauaa                                                  19
```

-continued

<210> SEQ ID NO 24
<211> LENGTH: 19
<212> TYPE: RNA
<213> ORGANISM: homo sapiens

<400> SEQUENCE: 24
aauaagaagu ggacaauac 19

<210> SEQ ID NO 25
<211> LENGTH: 21
<212> TYPE: DNA
<213> ORGANISM: artificial
<220> FEATURE:
<223> OTHER INFORMATION: primer

<400> SEQUENCE: 25
tgtccagtca gcaaaacggt t 21

<210> SEQ ID NO 26
<211> LENGTH: 21
<212> TYPE: DNA
<213> ORGANISM: artificial
<220> FEATURE:
<223> OTHER INFORMATION: primer

<400> SEQUENCE: 26
gaactgcatt tcccggtcca t 21

<210> SEQ ID NO 27
<211> LENGTH: 21
<212> TYPE: DNA
<213> ORGANISM: artificial
<220> FEATURE:
<223> OTHER INFORMATION: primer

<400> SEQUENCE: 27
ggagtgtgga ttcgcactcc t 21

<210> SEQ ID NO 28
<211> LENGTH: 20
<212> TYPE: DNA
<213> ORGANISM: artificial
<220> FEATURE:
<223> OTHER INFORMATION: primer

<400> SEQUENCE: 28
agattgagat cttctgcgac 20

<210> SEQ ID NO 29
<211> LENGTH: 27
<212> TYPE: DNA
<213> ORGANISM: Artificial Sequence
<220> FEATURE:
<223> OTHER INFORMATION: Probe

<400> SEQUENCE: 29
aggcaggtcc cctagaagaa gaactcc 27

<210> SEQ ID NO 30
<211> LENGTH: 19
<212> TYPE: DNA
<213> ORGANISM: artificial
<220> FEATURE:
<223> OTHER INFORMATION: primer

<400> SEQUENCE: 30
ccgtgtgcac ttcgcttca 19

<210> SEQ ID NO 31
<211> LENGTH: 19
<212> TYPE: DNA
<213> ORGANISM: artificial
<220> FEATURE:
<223> OTHER INFORMATION: primer

<400> SEQUENCE: 31
gcacagcttg gaggcttga 19

<210> SEQ ID NO 32
<211> LENGTH: 23
<212> TYPE: DNA
<213> ORGANISM: artificial
<220> FEATURE:
<223> OTHER INFORMATION: Probe

<400> SEQUENCE: 32
catggagacc accgtgaacg ccc 23

<210> SEQ ID NO 33
<211> LENGTH: 15
<212> TYPE: DNA
<213> ORGANISM: artificial
<220> FEATURE:
<223> OTHER INFORMATION: oligonucleotide motif

<400> SEQUENCE: 33
ctcattccga acttc 15

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
ataaccatag tcatttga 18

<210> SEQ ID NO 35
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 35
cccataacca tagtcat 17

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
gagccatcta cacataaa 18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
caagagccat ctacacat 18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
tgtccattta agaatcca 18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
ttgtgtccat ttaagaat 18

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
tacctttgct gctgat 16

<210> SEQ ID NO 41
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 41
gactatacct ttgctgc 17

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
actttgtatt cttctgtcat 20

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
actttgtatt cttctgtc 18

<210> SEQ ID NO 44
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 44
gattcaggtg ttccagtta 19

<210> SEQ ID NO 45
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 45
ttcaaactta ctggaca 17

<210> SEQ ID NO 46
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 46
tacatctatc ccttcat 17

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
ttacatctat cccttc 16

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
cttcctatta caatgccaac 20

<210> SEQ ID NO 49
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 49
atttcttcct attacaatg 19

<210> SEQ ID NO 50
<211> LENGTH: 19
<212> TYPE: DNA
<213> ORGANISM: artificial sequence
<220> FEATURE:
<223> OTHER INFORMATION: Synthetic oligonucleotide

<400> SEQUENCE: 50
ccatttcttc ctattacaa 19

<210> SEQ ID NO 51
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 51
gtttaaaata cattgcc 17

<210> SEQ ID NO 52
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 52
gagtttaaaa tacattgcc 19

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
gctttttatg gtttcacc 18

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
atgcttttta tggtttcacc 20

<210> SEQ ID NO 55
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 55
ataatcaacc tgtccagct 19

<210> SEQ ID NO 56
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 56
ataatcaacc tgtccagc 18

<210> SEQ ID NO 57
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 57
ataatcaacc tgtccag 17

<210> SEQ ID NO 58
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 58
tataatcaac ctgtccag 18

<210> SEQ ID NO 59
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 59
gtataatcaa cctgtccag 19

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
ataatcaacc tgtcca 16

<210> SEQ ID NO 61
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 61
tataatcaac ctgtcca 17

<210> SEQ ID NO 62
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 62
gtataatcaa cctgtcca 18

<210> SEQ ID NO 63
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 63
gtataatcaa cctgtcc 17

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
tataatcaac ctgtcc 16

<210> SEQ ID NO 65
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 65
cccattttct tgtagta 17

<210> SEQ ID NO 66
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 66
acccattttc ttgtagta 18

<210> SEQ ID NO 67
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 67
tacccatttt cttgtagta 19

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
atacccattt tcttgtagta 20

<210> SEQ ID NO 69
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 69

atacccattt tcttgtag                                                      18

<210> SEQ ID NO 70
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 70

catacccatt ttcttgtag                                                     19

<210> SEQ ID NO 71
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 71

catacccatt ttcttgta                                                      18

<210> SEQ ID NO 72
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 72

tggagctaat tcaggagt                                                      18

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73

aaatggagct aattcaggag                                                    20

<210> SEQ ID NO 74
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 74

ttgtccactt cttattatt                                                     19

<210> SEQ ID NO 75
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 75

ccccacacaa tgaagcaa                                                      18
```

<210> SEQ ID NO 76
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 76
ttcatcaagt cgtctgcat 19

<210> SEQ ID NO 77
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 77
gatcttcatc aagtcgtc 18

<210> SEQ ID NO 78
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 78
atattaacct cctatcagt 19

<210> SEQ ID NO 79
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 79
aatattaacc tcctatcag 19

<210> SEQ ID NO 80
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 80
atttatatca caaagcatc 19

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
aagtacattt atatcaca 18

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
catttattgt aaagcacaaa 20

<210> SEQ ID NO 83
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 83
atcatttatt gtaaagca 18

<210> SEQ ID NO 84
<211> LENGTH: 18
<212> TYPE: RNA
<213> ORGANISM: Artificial seqyuence
<220> FEATURE:
<223> OTHER INFORMATION: siRNA sense

<400> SEQUENCE: 84
gcacuucgcu ucaccucu 18

<210> SEQ ID NO 85
<211> LENGTH: 21
<212> TYPE: DNA
<213> ORGANISM: artificial
<220> FEATURE:
<223> OTHER INFORMATION: Primer

<400> SEQUENCE: 85
cgtctgtgcc ttctcatctg c 21

<210> SEQ ID NO 86
<211> LENGTH: 20
<212> TYPE: DNA
<213> ORGANISM: artificial
<220> FEATURE:
<223> OTHER INFORMATION: primer

<400> SEQUENCE: 86
gcacagcttg gaggcttgaa 20

<210> SEQ ID NO 87
<211> LENGTH: 20
<212> TYPE: DNA
<213> ORGANISM: artificial
<220> FEATURE:
<223> OTHER INFORMATION: primer

<400> SEQUENCE: 87
ccgtctgaac tatcctgccc 20

<210> SEQ ID NO 88
<211> LENGTH: 20
<212> TYPE: DNA
<213> ORGANISM: artificial
<220> FEATURE:
<223> OTHER INFORMATION: primer

<400> SEQUENCE: 88
gccgtagtcg gtgtactcgt 20

-continued

```
<210> SEQ ID NO 89
<211> LENGTH: 43
<212> TYPE: DNA
<213> ORGANISM: artificial
<220> FEATURE:
<223> OTHER INFORMATION: primer

<400> SEQUENCE: 89

taatacgact cactataggg tttttcacct ctgcctaatc atc                      43


<210> SEQ ID NO 90
<211> LENGTH: 43
<212> TYPE: DNA
<213> ORGANISM: artificial
<220> FEATURE:
<223> OTHER INFORMATION: primer

<400> SEQUENCE: 90

taatacgact cactataggg tttttcacct ctgcctaatc atc                      43
```

USE OF FUBP1 INHIBITORS FOR TREATING HEPATITIS B VIRUS INFECTION

CROSS REFERENCE TO RELATED APPLICATIONS

This application is a continuation of PCT International Patent Application No. PCT/EP2019/058664, filed Apr. 5, 2019, and entitled "USE OF FUBP1 INHIBITORS FOR TREATING HEPATITIS B VIRUS INFECTION", which claims priority to European Patent Application No. 18165897.2 filed Apr. 5, 2018, the entire disclosures of which are incorporated herein by this reference.

REFERENCE TO A SEQUENCE LISTING SUBMITTED VIA EFS-WEB

The content of the ASCII text file of the sequence listing named "Sequence-Listing.txt" which was created on Oct. 5, 2020 and is 204,800 bytes in size submitted electronically via EFS-Web with this U.S. National Phase application is incorporated by reference in its entirety.

FIELD OF THE INVENTION

The present invention relates to Far Upstream Element-Binding Protein 1 (FUBP1) inhibitors for use in treating and/or preventing a hepatitis B virus (HBV) infection, in particular a chronic HBV infection. The invention in particular relates to the use of FUBP1 inhibitors for destabilizing cccDNA, such as HBV cccDNA. The invention also relates to nucleic acid molecules, such as oligonucleotides including siRNA, shRNA and antisense oligonucleotides, which are complementary to FUBP1 and capable of reducing a FUBP1 target nucleic acid, such as mRNA. Also comprised in the present invention is a pharmaceutical composition and its use in the treatment and/or prevention of a HBV infection.

BACKGROUND

Far Upstream Element-Binding Protein 1 (FUBP1 or FBP1) is a single stranded DNA-binding protein that binds to multiple DNA elements. This protein is also thought to bind RNA and contains 3'-5' helicase activity with in vitro activity on both DNA-DNA and RNA-RNA duplexes. FUBP1 is known to activate the transcription of the proto-oncogene c-myc by binding to far upstream element (FUSE) located upstream of c-myc in undifferentiated cells. The protein is primarily present in the nucleus of the cell. Upregulation of FUBP1 has been observed in many types of cancers. Furthermore, FUBP1 can bind to and mediate replication of RNA from Hepatitis C virus and Enterovirus (Zhang and Chen 2013 Oncogene vol 32 p. 2907-2916).

FUBP1 has also been identified in Hepatocellular carcinoma (HCC) where it has been suggested to be involved in HCC tumorigenesis (Ramdzan et al 2008 Proteomics Vol 8 p. 5086-5096) and that FUBP1 is required for HCC tumour growth as illustrated using lentivirus expressed shRNA targeting FUBP1 (Rabenhorst et al 2009 Hepatology vol 50 p 1121-1129).

It has been demonstrated that knock down of FUBP1 with lentivirus expressed shRNA's enhances treatment response in ovarian cancer (Zhang et al 2017 Oncology Letters Vol 14 p. 5819-5824).

WO 2004/027061 disclose a screening method which involves the step of analyzing whether or not a test substance inhibits FBP and a medicinal composition for treating a proliferative disease which contains as the active ingredient(s) a substance inhibiting FBP.

Some small molecules inhibiting FUBP1 have been identified, all with the purpose of treating cancer (Huth et al 2004 J Med. Chen Vol 47 p. 4851-4857; Hauck et al 2016 Bioorganic & Medicinal Chemistry Vol 24 p. 5717-5729 Hosseini et al 2017 Biochemical Pharmacology Vol 146 p. 53-62 and Xiong et al 2016 Int J Onc vol 49 p 623). WO2004/017940 describes lipid based formulations of SN-38, it claims treatment of viral infection, in particular HIV, there is however no example supporting this.

Poly(U) Binding Splicing Factor 60 (PUF60) is a potentially regulator of both transcriptional and post-transcriptional steps of HBV pregenome expression. PUF60 is known to form a complex with FUBP1 in relation to c-myc repression. FUBP1 does, however, not participate in the PUF60 dependent regulation of HBV pregenome expression (Sun et al 2017 Scientific Reports 7:12874).

To our knowledge FUBP1 has never been shown to bind cccDNA or associated with cccDNA stability, nor has molecules inhibiting FUBP1 ever been suggested as cccDNA destabilizers or for the treatment of HBV infection.

HBV infection remains a major health problem worldwide which concerns an estimated 350 million chronic carriers. Approximately 25% of carriers die from chronic hepatitis, cirrhosis, or liver cancer. Hepatitis B virus is the second most significant carcinogen behind tobacco, causing from 60% to 80% of all primary liver cancer. HBV is 100 times more contagious than HIV.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORE. The lifecycle of HBV has two main events: 1) generation of closed circular DNA (cccDNA) from relaxed circular (RC DNA), and 2) reverse transcription of pregenomic RNA (pgRNA) to produce RC DNA.

HBsAg quantification is a significant biomarker for prognosis and treatment response in chronic hepatitis B. However the achievement of HBsAg loss and seroconversion (functional cure) is rarely observed in chronically infected patients. Hepatitis B e-antigen (also called HBV envelope antigen or HBeAg) is a viral protein that is secreted by hepatitis B infected cells. HBeAg is associated with chronic hepatitis B infections and is used as a marker of active viral disease and a patient's degree of infectiousness.

Accordingly, reducing secretion of HBeAg in addition to secretion of HBsAg would lead to an improved inhibition of development of a chronic HBV infection as compared to the inhibition of secretion of HBsAg alone.

Current therapy such as Nucleos(t)ide analogues are molecules that inhibit HBV DNA synthesis but are not directed at reducing HBsAg level. Most therapies currently under development aim to reach a functional cure, with a durable HBsAg loss±anti-HBs seroconversion, undetectable serum DNA, and cccDNA in a transcriptionally inactive state, but do not address cccDNA persistence. These approaches do not therefore lead to a complete cure of HBV infection which is defined as durable HBV DNA and HBsAg loss with cccDNA elimination. The persistence of cccDNA in infected hepatocytes is the main barrier for eradicating the virus in CHB patients, and there is an urgent need to develop new therapies for the HBV complete cure that eliminates cccDNA.

Objective of the Invention

The present invention shows that there is a correlation between the inhibition of FUBP1 and reduction of cccDNA in an HBV infected cell, which is relevant in the treatment of HBV infected individuals. An objective of the present invention is to identify FUBP1 inhibitors which reduce cccDNA in an HBV infected cell. Such FUBP1 inhibitors can be used in the treatment of HBV infection.

The present invention further identifies novel nucleic acid molecules, which are capable of inhibiting the expression of FUBP1 in vivo and in vitro.

SUMMARY OF THE INVENTION

Figure 1A:
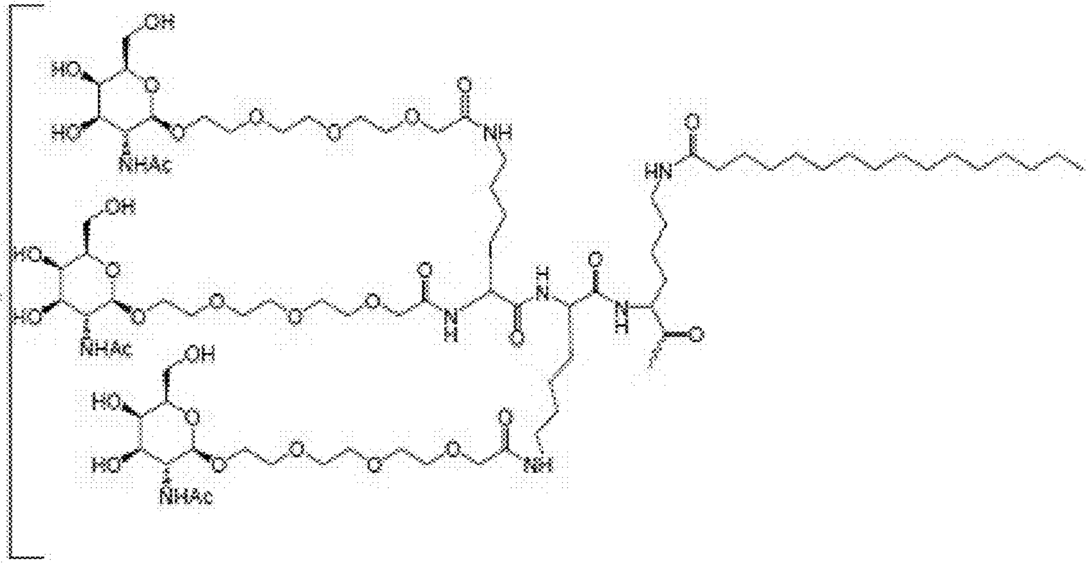
FIG. 1: Illustrates exemplary antisense oligonucleotide conjugates, where the oligonucleotide either is represented as a wavy line (A-D) or as "oligonucleotide" (E-H) or as $T_2$ (I) and the asialoglycoprotein receptor targeting conjugate moieties are trivalent N-acetylgalactosamine moieties. Compounds A to D comprise a di-lysine brancher molecule, a PEG3 spacer and three terminal GalNAc carbohydrate moieties. In compound A and B the oligonucleotide is attached directly to the asialoglycoprotein receptor targeting conjugate moiety without a linker. In compound C and D the oligonucleotide is attached to the asialoglycoprotein receptor targeting conjugate moiety via a C6 linker. Compounds E-I comprise a commercially available trebler brancher molecule and spacers of varying length and structure and three terminal GalNAc carbohydrate moieties.
Figure 1B:
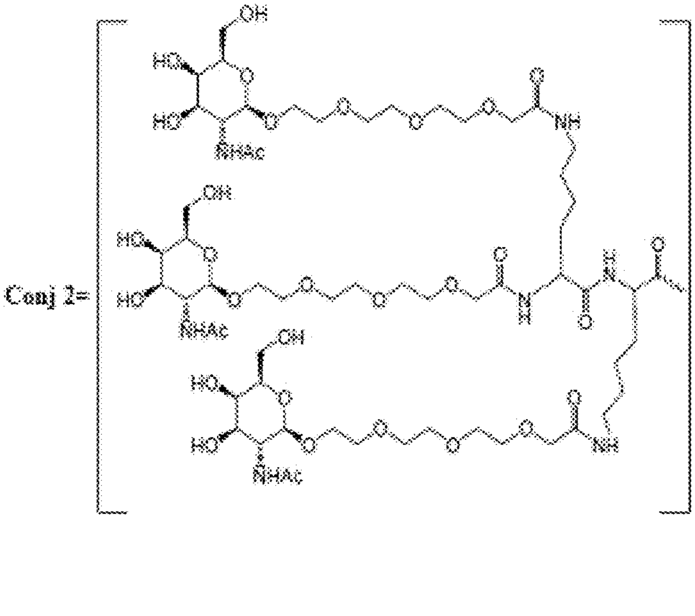
Figure 1C:
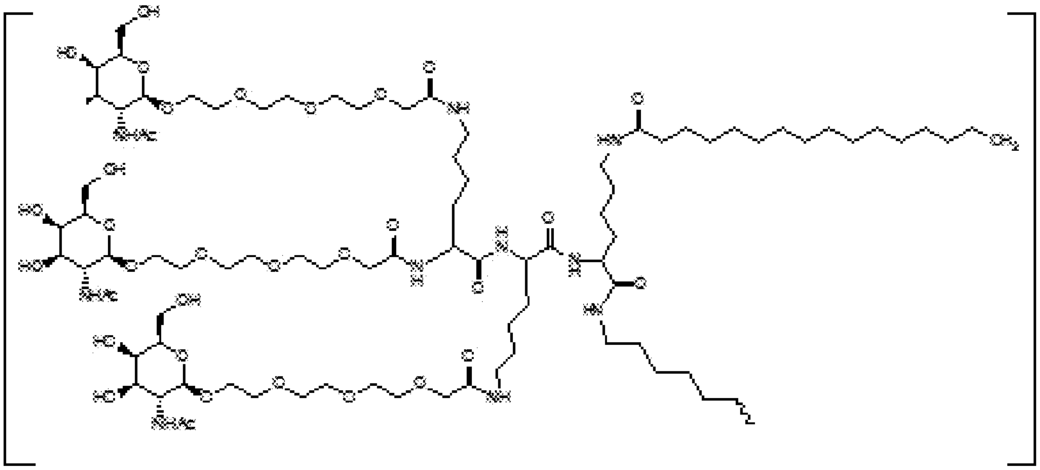

One aspect of the present invention relates to a FUBP1 inhibitor for use in the treatment and/or prevention of Hepatitis B virus infection. In particular, a FUBP1 inhibitor capable of reducing cccDNA and/or pre-genomic RNA (pgRNA) is useful. In the event that the FUBP1 inhibitor is a small molecule it is advantageous if it interacts with the DNA binding domain of FUBP1 protein, and prevents or reduces FUBP1 binding to cccDNA. The FUBP1 inhibitor can also be a nucleic acid molecule of 12 to 60 nucleotides in length which is capable of reducing FUBP1 mRNA.

A further aspect of the present invention relates to nucleic acid molecules that inhibit expression and/or activity of FUBP1. In particular, a nucleic acid molecule of 12 to 60 nucleotides in length which comprises or consists of a contiguous nucleotide sequence of 12 to 30 nucleotides in length wherein the contiguous nucleotide sequence is at least 95% complementary to a mammalian FUBP1 target nucleic acid. Such nucleic acid molecules can be selected from single stranded antisense, siRNA and chemically produced shRNA molecules (not relying on cell based expression from plasmids or viruses).

A further aspect of the present invention relates to single stranded antisense oligonucleotides or siRNA that inhibit expression and/or activity of FUBP1. In particular, modified antisense oligonucleotides or modified siRNA comprising one or more 2' sugar modified nucleoside and one or more phosphorthioate linkage that reduce FUBP1 mRNA are of advantageous.

Further aspects of the invention are conjugates of nucleic acid molecules of the invention and pharmaceutical compositions comprising the molecules of the invention. In particular conjugates targeting the liver are of interest, such as GalNAc clusters.

Definitions

Nucleic Acid Molecule

The term "nucleic acid molecule" or "therapeutic nucleic acid molecule" as used herein is defined as it is generally understood by the skilled person, as a molecule comprising two or more covalently linked nucleosides (i.e. a nucleotide sequence). The nucleic acid molecule(s) referred to in the method of the invention are generally therapeutic oligonucleotides below 50 nucleotides in length. The nucleic acid molecules may be or comprise an antisense oligonucleotide, or may be another oligomeric nucleic acid molecule, such as a CRISPR RNA, a siRNA, shRNA, an aptamer, or a ribozyme. Therapeutic nucleic acid molecules are commonly made in the laboratory by solid-phase chemical synthesis followed by purification and isolation. shRNA's are however often delivered to cells using lentiviral vectors (see for example Soan and Yang 2010 N Am J Med Sci 2(12): 598) which are then transcribed to produce the single stranded RNA that will form a stem loop (hairpin) RNA structure that is capable of interacting with the RNA interference machinery (including the RNA-induced silencing complex (RISC)). When referring to a sequence of the nucleic acid molecule, reference is made to the sequence or order of nucleobase moieties, or modifications thereof, of the covalently linked nucleotides or nucleosides. The nucleic acid molecule of the invention is man-made, and is chemically synthesized, and is typically purified or isolated. In some embodiments the nucleic acid molecule of the invention is not a shRNA transcribed from a vector upon entry into the target cell. The nucleic acid molecule of the invention may comprise one or more modified nucleosides or nucleotides.

In some embodiments, the nucleic acid molecule of the invention comprises or consists of 12 to 60 nucleotides in length, such as from 13 to 50, such as from 14 to 40, such as from 15 to 30, such as from 16 to 22, such as from 16 to 18 or 15 to 17 contiguous nucleotides in length. In some embodiments, the nucleic acid molecule or contiguous nucleotide sequence thereof comprises or consists of 24 or less nucleotides, such as 22, such as 20 or less nucleotides, such as 18 or less nucleotides, such as 14, 15, 16 or 17 nucleotides. It is to be understood that any range given herein includes the range endpoints. Accordingly, if a nucleic acid molecule is said to include from 12 to 30 nucleotides, both 12 and 30 nucleotides are included.

In some embodiments, the contiguous nucleotide sequence comprises or consists of 12, 13, 14, 15, 16, 17, 18, 19, 20, 21 or 22 contiguous nucleotides in length The nucleic acid molecule(s) are for modulating the expression of a target nucleic acid in a mammal. In some embodiments the nucleic acid molecules, such as for siRNAs, shRNAs and antisense oligonucleotides, are typically for inhibiting the expression of a target nucleic acid(s).

In one embodiment of the invention the nucleic acid molecule is selected from a RNAi agent, such as a siRNA or shRNA. In another embodiment the nucleic acid molecule is a single stranded antisense oligonucleotide, such as a high affinity modified antisense oligonucleotide interacting with RNaseH.

In some embodiments the nucleic acid molecule comprises phosphorothioate internucleoside linkages.

In some embodiments the nucleic acid molecule may be conjugated to non-nucleosidic moieties (conjugate moieties).

A library of nucleic acid molecules is to be understood as a collection of variant nucleic acid molecules. The purpose of the library of nucleic acid molecules can vary. In some embodiments, the library of nucleic acid molecules is composed of oligonucleotides with overlapping nucleobase sequence targeting one or more mammalian FUBP1 target nucleic acids with the purpose of identifying the most potent sequence within the library of nucleic acid molecules. In some embodiments, the library of nucleic acid molecules is a library of nucleic acid molecule design variants (child nucleic acid molecules) of a parent or ancestral nucleic acid molecule, wherein the nucleic acid molecule design variants retaining the core nucleobase sequence of the parent nucleic acid molecule.

Oligonucleotide

The term “oligonucleotide” as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides, such as 2' sugar modified nucleosides.

Antisense Oligonucleotides

The term “Antisense oligonucleotide” as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self complementarity is less than 50% across of the full length of the oligonucleotide Advantageously, the single stranded antisense oligonucleotide of the invention does not contain RNA nucleosides, since this will decrease nuclease resistance.

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides.

RNAi

Herein, the term “RNA interference (RNAi) molecule” refers to short double-stranded RNA molecule capable of inducing RNA-dependent gene silencing via the RNA-induced silencing complex (RISC) in a cell’s cytoplasm, where they interact with the catalytic RISC component argonaute. One type of RNAi molecule is a small interfering RNA (siRNA), which is a double-stranded RNA molecule composed of two complementary oligonucleotides, where the binding of one strand to complementary mRNA after transcription, leads to its degradation and loss of translation. A small hairpin RNA (shRNA) is a single stranded RNA molecule that forms a stem loop (hairpin) structure which upon expression is able to reduce mRNA via the DICER and RNA reducing silencing complex (RISC). RNAi molecules can be designed based on the sequence of the gene of interest (target nucleic acid). Corresponding RNAi can then be synthesized chemically or by in vitro transcription, or expressed from a vector or PCR product.

shRNA molecules are generally between 40 and 70 nucleotides in length, such as between 45 and 65 nucleotides in length, such as 50 and 60 nucleotides in length, and interacts with the endonuclease known as Dicer which is believed to processes dsRNA into 19-23 base pair short interfering RNAs with characteristic two base 3' overhangs which are then incorporated into an RNA-induced silencing complex (RISC). siRNA molecules are double stranded, with each strand being between 18 and 35 nucleotides in length, such as 20 to 30 nucleotides in length, such as 22 to 27 nucleotides in length. siRNA’s are often designed with a two base 3' overhang to resemble the product produced by Dicer, which forms the RISC substrate. Effective extended forms of Dicer substrates have been described in U.S. Pat. Nos. 8,349,809 and 8,513,207, hereby incorporated by reference. Upon binding to the appropriate target mRNA, one or more endonucleases within the RISC cleave the target to induce silencing. RNAi olignucleotides may be chemically modified using modified internucleotide linkages and 2' sugar modified nucleosides, such as 2'-4' bicyclic ribose modified nucleosides, including LNA and cET or 2' substituted modifications like of 2'-O-alkyl-RNA, 2'-O-methyl-RNA, 2'-alkoxy-RNA, 2'-O-methoxyethyl-RNA (MOE), 2'-amino-DNA, 2'-fluoro-DNA, arabino nucleic acid (ANA), 2'-fluoro-ANA.

In some embodiments RNAi nucleic acid molecules comprise one or more phosphorothioate internucleoside linkages. In RNAi molecules phosphorothioate internucleoside linkages may reduce or the nuclease cleavage in RICS it is therefore advantageous that not al internucleoside linkages are modified. Phosphorothioate internucleoside linkages can advantageously be place in the 3' and/or 5' end of the RNAi nucleic acid molecule, in particular in the of the part of the molecule that is not complementary to the target nucleic acid (e.g. the sense stand or passenger strand in an siRNA molecule). The region of the RNAi molecule that is complementary to the target nucleic acid (e.g. the antisense or guide strand in an siRNA molecule) may however also be modified in the first 2 to 3 internucleoside linkages in the 3' and/or 5' terminal.

Contiguous Nucleotide Sequence

The term “contiguous nucleotide sequence” refers to the region of the oligonucleotide which is complementary to the target nucleic acid. The term is used interchangeably herein with the term “contiguous nucleobase sequence” and the term “oligonucleotide motif sequence”. In some embodiments all the nucleotides of the oligonucleotide constitute the contiguous nucleotide sequence. In some embodiments the oligonucleotide comprises the contiguous nucleotide sequence and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as “units” or “monomers”.

Modified Nucleoside

The term “modified nucleoside” or “nucleoside modification” as used herein refers to nucleosides modified as compared to the equivalent DNA or RNA nucleoside by the introduction of one or more modifications of the sugar moiety or the (nucleo)base moiety. In a preferred embodiment the modified nucleoside comprises a modified sugar moiety. The term modified nucleoside may also be used herein interchangeably with the term “nucleoside analogue” or modified “units” or modified “monomers”. Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term “modified internucleoside linkage” is defined as generally understood by the skilled person as linkages other than phosphodiester (PO) linkages, that covalently couples two nucleosides together. The nucleic acid molecules of the invention may therefore comprise modified internucleoside linkages. In some embodiments, the modified internucleoside linkage increases the nuclease resistance of the nucleic acid molecules of the invention compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing nucleic acid molecules, single stranded antisense as well as double stranded siRNA and shRNA molecules for in vivo use, and may serve to protect against nuclease cleavage at regions of DNA or RNA nucleosides in nucleic acid molecules of the invention, for example within the gap region of a gapmer oligonucleotide, as well as in regions of modified nucleosides.

In an embodiment, the nucleic acid molecule, e.g. antisense oligonucleotide, shRNA or siRNA, comprises one or more internucleoside linkages modified from the natural phosphodiester, such as one or more modified internucleoside linkages, that is for example more resistant to nuclease attack. Nuclease resistance may be determined by incubating the oligonucleotide in blood serum or by using a nuclease resistance assay (e.g. snake venom phosphodiesterase (SVPD), both are well known in the art. Internucleoside linkages which are capable of enhancing the nuclease resistance of an oligonucleotide are referred to as nuclease resistant internucleoside linkages. In some embodiments at least 50% of the internucleoside linkages in the antisense oligonucleotide, or contiguous nucleotide sequence thereof, are modified, such as at least 60%, such as at least 70%, such as at least 75%, such as at least 80% or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

In some embodiments the internucleoside linkage comprises sulphur (S), such as a phosphorothioate internucleoside linkage. With the nucleic acid molecules of the invention it is advantageous to use phosphorothioate internucleoside linkages, in particular with single stranded antisense oligonucleotides.

Phosphorothioate internucleoside linkages are particularly useful due to nuclease resistance, beneficial pharmacokinetics and ease of manufacture. In some embodiments at least 20% of the internucleoside linkages in the nucleic acid molecule, or contiguous nucleotide sequence thereof, are phosphorothioate, such as at least 30%. For single stranded antisense oligonucleotides it is advantageous id at least 60% of the internucleoside linkages, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the antisense oligonucleotide, or contiguous nucleotide sequence thereof, are phosphorothioate. Nuclease resistant linkages, such as phosphorthioate linkages, are particularly useful in antisense oligonucleotide regions capable of recruiting nuclease when forming a duplex with the target nucleic acid, such as region G for gapmers. In an antisense gapmer oligonucleotide it is advantageous if the phosphodiester linkages, if present, are not located between contiguous DNA nucleosides in the gap region G. Advantageously, all the internucleoside linkages of the contiguous nucleotide sequence of the antisense oligonucleotide are phosphorothioate.

It is recognized that, as disclosed in EP 2 742 135, antisense oligonucleotides may comprise other internucleoside linkages (other than phosphodiester and phosphorothioate), for example alkyl phosphonate/methyl phosphonate internucleoside, which according to EP 2 742 135 may for example be tolerated in an otherwise DNA phosphorothioate the gap region.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context “nucleobase” refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide or modified nucleic acid molecule describes an oligonucleotide or nucleic acid molecule comprising one or more sugar-modified nucleosides and/or modified internucleoside linkages. The term "chimeric" is a term that has been used in the literature to describe oligonucleotides or nucleic acid molecules with modified nucleosides, in particular gapmer oligonucleotides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pair) between the two sequences (when aligned with the target sequence 5'-3' and the oligonucleotide sequence from 3'-5'), dividing that number by the total number of nucleotides in the oligonucleotide and multiplying by 100. In such a comparison, a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

The term "fully complementary", refers to 100% complementarity.

The following is an example of an oligonucleotide that is fully complementary to the target nucleic acid.

The following is an example of an oligonucleotide motif (SEQ ID NO: 33) that is fully complementary to the target nucleic acid SEQ ID NO: 22).

```
                                    (SEQ ID NO: 22)
5' gagaaguucggaaugagua 3'
                                    (SEQ ID NO: 33)
3' cttcaagccttactc 5'
```

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an antisense oligonucleotide or siRNA guide strand and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RT\ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for $\Delta G°$ measurements. $\Delta G°$ can also be estimated numerically by using the nearest neighbor model as described by SantaLucia, 1998, *Proc Nat/Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Nucleic Acid

According to the present invention, the target nucleic acid is a nucleic acid which encodes mammalian FUBP1 and may for example be a gene, a RNA, a mRNA, and pre-mRNA, a mature mRNA or a cDNA sequence. The target may therefore be referred to as a FUBP1 target nucleic acid.

The therapeutic nucleic acid molecules of the invention may for example target exon regions of a mammalian FUBP1 (in particular siRNA and shRNA, but also antisense oligonucleotides), or may for example target any intron region in the FUBP1 pre-mRNA (in particular antisense oligonucleotides). Table 1 lists predicted exon and intron regions of SEQ ID NO: 1.

TABLE 1

Exon and intron regions in the human FUBP1 pre-mRNA.

| Exonic regions in the human FUBP1 premRNA (SEQ ID NO 1) | | | Intronic regions in the human FUBP1 premRNA (SEQ ID NO 1) | | |
|---|---|---|---|---|---|
| ID | start | end | ID | start | end |
| E1 | 19 | 226 | I1 | 227 | 9095 |
| E2 | 9096 | 9186 | I2 | 9187 | 10907 |
| E3 | 10908 | 10946 | I3 | 10947 | 11444 |
| E4 | 11445 | 11484 | I4 | 11485 | 12009 |
| E5 | 12010 | 12062 | I5 | 12063 | 12155 |
| E6 | 12156 | 12227 | I6 | 12228 | 12359 |
| E7 | 12360 | 12417 | I7 | 12418 | 13879 |
| E8 | 13880 | 14042 | I8 | 14043 | 14142 |
| E9 | 14143 | 14241 | I9 | 14242 | 14363 |
| E10 | 14364 | 14465 | I10 | 14466 | 14754 |
| E11 | 14755 | 14857 | I11 | 14858 | 14948 |
| E12 | 14949 | 15049 | I12 | 15050 | 15395 |
| E13 | 15396 | 15537 | I13 | 15538 | 16180 |
| E14 | 16181 | 16341 | I14 | 16342 | 18615 |
| E15 | 18616 | 18767 | I15 | 18768 | 18847 |
| E16 | 18848 | 18927 | I16 | 18928 | 22410 |
| E17 | 22411 | 22539 | I17 | 22540 | 23781 |
| E18 | 23782 | 23856 | I18 | 23857 | 29810 |
| E19 | 29811 | 29956 | I19 | 29957 | 30196 |
| E20 | 30197 | 30706 | | | |

Suitably, the target nucleic acid encodes a FUBP1 protein, in particular mammalian FUBP1, such as human FUBP1 (See for example Tables 2 and 3) which provides the genomic sequence, the mature mRNA and pre-mRNA sequences for human, monkey and mouse FUBP1).

In some embodiments, the target nucleic acid is selected from the group consisting of SEQ ID NO: 2, 3, 4, 6, 7, 8, 10, 11, 12, 13, 14, 15, 16, 17, 18, 19 and/or 20, or naturally occurring variants thereof (e.g. sequences encoding a mammalian FUBP1).

In some embodiments, the target nucleic acid is selected from the group consisting of SEQ ID NO: 1, 5 and/or 9, or naturally occurring variants thereof (e.g. sequences encoding a mammalian FUBP1).

In some embodiments, the target nucleic acid is selected from the group consisting of SEQ ID NO: 1 and 5, or naturally occurring variants thereof (e.g. sequences encoding a mammalian FUBP1).

In some embodiments, the target nucleic acid is selected from the group consisting of SEQ ID NO: 1, to 8, or naturally occurring variants thereof (e.g. sequences encoding a mammalian FUBP1).

TABLE 2

Genome and assembly information for FUBP1 across species.

| Species | Chr. | Strand | Genomic coordinates Start | End | Assembly | ensembl gene_id |
|---|---|---|---|---|---|---|
| Human | 1 | Rv | 77944055 | 77979110 | GRCh38.p10 | ENSG 00000162613 |
| Cyno monkey | 1 | Fwd | 149243675 | 149283374 | Macaca_fascicularis_5.0 | ENSMFAG 00000031825 |
| Mouse | 3 | Fwd | 152210422 | 152236826 | GRCm38.p5 | ENSMUSG 00000028034 |

Fwd = forward strand.
Rv = reverse strand.
The genome coordinates provide the pre-mRNA sequence (genomic sequence).

If employing the nucleic acid molecule of the invention in research or diagnostics the target nucleic acid may be a cDNA or a synthetic nucleic acid derived from DNA or RNA.

For in vivo or in vitro application, the therapeutic nucleic acid molecule of the invention is typically capable of inhibiting the expression of the FUBP1 target nucleic acid in a cell which is expressing the FUBP1 target nucleic acid. The contiguous sequence of nucleobases of the nucleic acid molecule of the invention is typically complementary to a conserved region of the FUBP1 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides. Further information on exemplary target nucleic acids is provided in table 3.

TABLE 3

Sequence details for FUBP1 across species.

| Species | RNA type | Length (nt) | SEQ ID NO |
|---|---|---|---|
| Human | Pre-mRNA | 305056 | 1 |
| Human | Mature mRNA | 696 | 2 |
| Human | Mature mRNA | 1968 | 3 |
| Human | Mature mRNA | 1935 | 3 |
| Cyno monkey | Pre-mRNA | 39750 | 5 |
| Cyno monkey | Mature mRNA | 1968 | 6 |
| Cyno monkey | Mature mRNA | 6825 | 7 |

TABLE 3-continued

Sequence details for FUBP1 across species.

| Species | RNA type | Length (nt) | SEQ ID NO |
|---|---|---|---|
| Cyno monkey | Mature mRNA | 1959 | 8 |
| Mouse | Pre-mRNA | 26405 | 9 |
| Mouse | Mature mRNA | 4525 | 10 |
| Mouse | Mature mRNA | 800 | 11 |
| Mouse | Mature mRNA | 2526 | 12 |
| Mouse | Mature mRNA | 809 | 13 |
| Mouse | Mature mRNA | 1040 | 14 |
| Mouse | Mature mRNA | 796 | 15 |
| Mouse | Mature mRNA | 585 | 16 |
| Mouse | Mature mRNA | 2374 | 17 |
| Mouse | Mature mRNA | 3163 | 18 |
| Mouse | Mature mRNA | 6523 | 19 |
| Mouse | Mature mRNA | 2552 | 20 |

Note SEQ ID NO 5 comprises regions of multiple NNNNs, where the sequencing has been unable to accurately refine the sequence, and a degenerate sequence is therefore included. For the avoidance of doubt the compounds of the invention are complementary to the actual target sequence and are not therefore degenerate compounds.

Target Sequence

The term "target sequence" as used herein refers to a sequence of nucleotides present in the target nucleic acid which comprises the nucleobase sequence which is complementary to the oligonucleotide or nucleic acid molecule of the invention. In some embodiments, the target sequence consists of a region on the target nucleic acid with a nucleobase sequence that is complementary to the contiguous nucleotide sequence of the oligonucleotide of the invention (i.e. a sub-sequence). This region of the target nucleic acid may interchangeably be referred to as the target nucleotide sequence, target sequence or target region. In some embodiments the target sequence is longer than the complementary sequence of a single nucleic acid molecule, and may, for example represent a preferred region of the target nucleic acid which may be targeted by several nucleic acid molecules of the invention.

In some embodiments the target sequence is a sequence selected from the group consisting of a human FUBP1 mRNA exon, such as a FUBP1 human mRNA exon selected from the group consisting of e1, e2, e3, e4, e5, e6, e7, e8, e9, e10, e11, e12, 13, e14, e15, e16, e17, e18, e19 and e20 (see for example table 1 above).

In one embodiment the target sequence is a sequence selected from the group consisting of one or more of human FUBP1 mRNA exons selected from the group consisting of exon 9, 10, 12 and 20.

In some embodiments the target sequence is a sequence selected from the group consisting of a human FUBP1 mRNA intron, such as a FUBP1 human mRNA intron selected from the group consisting of i1, i2, i3, i4, i5, i6, i7, i9, 10, i11, i12, 13, i14, i15, i16, i17, i18 and i19 (see for example table 1 above).

The nucleic acid molecule of the invention comprises a contiguous nucleotide sequence which is complementary to or hybridizes to a region on the target nucleic acid, such as a target sequence described herein.

The target nucleic acid sequence to which the therapeutic nucleic acid molecule is complementary or hybridizes to generally comprises a stretch of contiguous nucleobases of at least 10 nucleotides. The contiguous nucleotide sequence is between 12 to 70 nucleotides, such as 12-50, such as 13 to 30, such as 14 to 25, such as 15 to 20, such as 16 to 18 contiguous nucleotides.

Target Cell

The term a "target cell" as used herein refers to a cell which is expressing the target nucleic acid. For the therapeutic use of the present invention it is advantageous if the target cell is infected with HBV. In some embodiments the target cell may be in vivo or in vitro. In some embodiments the target cell is a mammalian cell such as a rodent cell, such as a mouse cell or a rat cell, or a primate cell such as a monkey cell or a human cell.

In preferred embodiments the target cell expresses FUBP1 mRNA, such as the FUBP1pre-mRNA or FUBP1 mature mRNA. The poly A tail of FUBP1 mRNA is typically disregarded for nucleic acid molecule targeting.

Naturally Occurring Variant

The term "naturally occurring variant" refers to variants of the FUBP1 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms, and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian FUBP1 target nucleic acid, such as a target nucleic acid selected form the group consisting of SEQ ID NO: 1, 5 or 9. In some embodiments the naturally occurring variants have at least 99% homology to the human FUBP1 target nucleic acid of SEQ ID NO: 1. In some embodiments the naturally occurring variants are known polymorphisms.

Modulation of Expression

The term "modulation of expression" as used herein is to be understood as an overall term for a nucleic acid molecules ability to alter the amount of FUBP1 when compared to the amount of FUBP1 before administration of the nucleic acid molecule. Alternatively, modulation of expression may be determined by reference to a control experiment. It is generally understood that the control is an individual or target cell treated with a saline composition or an individual or target cell treated with a non-targeting or nucleic acid molecule (mock). It may however also be an individual treated with the standard of care.

One type of modulation is the ability of a nucleic acid molecule to inhibit, down-regulate, reduce, remove, stop, prevent, lessen, lower, avoid or terminate expression of FUBP1, e.g. by degradation of mRNA or blockage of transcription.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' sugar modified nucleosides, such as 2' substituted nucleosides like Ome and MOE as well as 2' to 4' bridged nucleic acids such as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The nucleic acid molecule of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of nucleic acid molecules, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the —OH groups naturally found in RNA or DNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

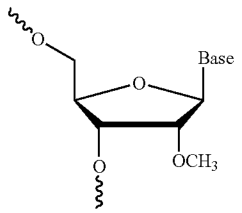

2'-O-Me

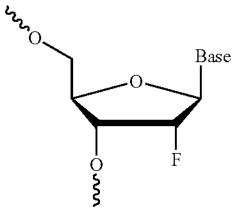

2'F-RNA

-continued

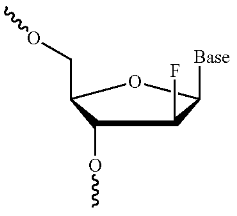

2'F-ANA

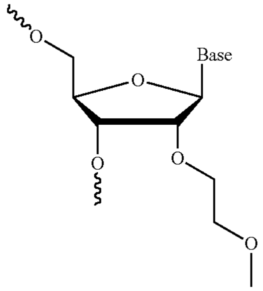

2'-O-MOE

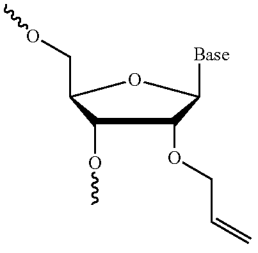

2'-O-Allyl

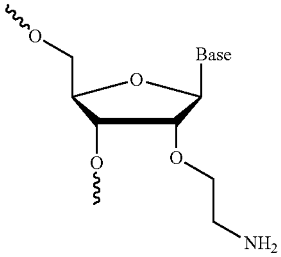

2'-O-Ethylamine

In relation to the present invention 2' substituted does not include 2' bridged molecules like LNA.

Locked Nucleic Acid Nucleosides (LNA).

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

Scheme 1

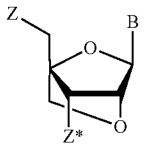

β-D-oxy LNA

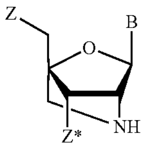

β-D-amino LNA

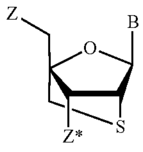

β-D-thio LNA

-continued

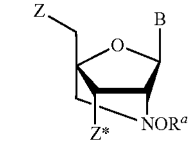
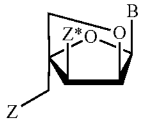

β-D-amino substituted LNA α-L-oxy LNA

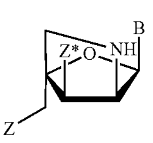
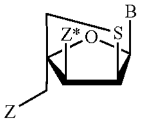
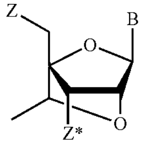

α-L-amino LNA α-L-thio LNA 6′-methyl-β-D-oxy LNA

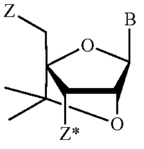
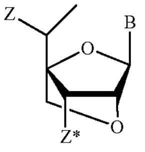

6′-dimethyl-β-D-oxy LNA 5′-methyl-β-D-oxy LNA

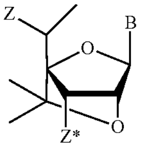

5′-methyl-6′-dimethyl-β-D-oxy LNA

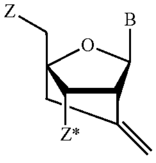
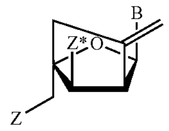

carbocyclic(vinyl)-β-D-oxy-LNA carbocyclic(vinyl)-α-L-oxy LNA

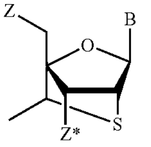
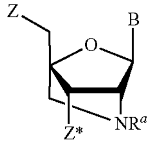

6′-methyl-β-D-thio LNA β-D-amino substituted LNA

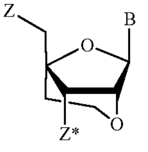
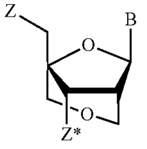
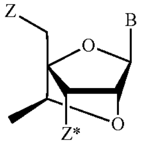

ENA COC (S)-cET

Particular LNA nucleosides are beta-D-oxy-LNA, 6'-methyl-beta-D-oxy LNA such as (S)-6'-methyl-beta-D-oxy-LNA (ScET) and ENA. A particularly advantageous LNA is beta-D-oxy-LNA.

Nuclease Mediated Degradation

Nuclease mediated degradation refers to nucleic acid molecule capable of mediating degradation of a complementary nucleotide sequence when forming a duplex with such a sequence.

In some embodiments, the nucleic acid molecule may function via nuclease mediated degradation of the target nucleic acid. In particular, antisense oligonucleotides are capable of recruiting an endoribonuclease (RNase) which recognizes RNA/DNA hybridization and effects cleavage of the RNA nucleic acid. RNase H has proven to be an advantageous endoribonuclease. Examples of antisense oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland Gapmer The nucleic acid molecule of the invention, or contiguous nucleotide sequence thereof may be a gapmer antisense oligonucleotide. The antisense gapmers are commonly used to inhibit a target nucleic acid via RNase H mediated degradation. In an embodiment of the invention the oligonucleotide of the invention is capable of recruiting RNase H.

A gapmer antisense oligonucleotide comprises at least three distinct structural regions a 5'-flank, a gap and a 3'-flank, F-G-F' in the '5→3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further be defined by having at least one sugar modified nucleoside at the end most distant from the gap region, i.e. at the 5' end of the 5' flank and at the 3' end of the 3' flank. Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides.

By way of example, the gapmer oligonucleotide of the present invention can be represented by the following formulae:

$$F_{1\text{-}8}\text{-}G_{5\text{-}16}\text{-}F'_{1\text{-}8}, \text{such as}$$

$$F_{1\text{-}8}\text{-}G_{7\text{-}16}\text{-}F'_{2\text{-}8}$$

with the proviso that the overall length of the gapmer regions F-G-F' is at least 12, such as at least 14 nucleotides in length.

In an aspect of the invention the antisense oligonucleotide or contiguous nucleotide sequence thereof consists of or comprises a gapmer of formula 5'-F-G-F'-3', where region F and F' independently comprise or consist of 1-8 nucleosides, of which 1-4 are 2' sugar modified and defines the 5' and 3' end of the F and F' region, and G is a region between 6 and 16 nucleosides which are capable of recruiting RNaseH.

In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, all the nucleosides of region F or F', or F and F' are LNA nucleosides, such as independently selected from beta-D-oxy LNA, ENA or ScET nucleosides. In some embodiments region F consists of 1-5, such as 2-4, such as 3-4 such as 1, 2, 3, 4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F', or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

Further gapmer designs are disclosed in WO2004/046160, WO2007/146511 and WO2008/113832, hereby incorporated by reference.

Conjugate

The term conjugate as used herein refers to an oligonucleotide which is covalently linked to a non-nucleotide moiety (conjugate moiety or region C or third region).

Conjugation of the therapeutic nucleic acid molecule of the invention to one or more non-nucleotide moieties may improve the pharmacology of the nucleic acid molecule, e.g. by affecting the activity, cellular distribution, cellular uptake or stability of the nucleic acid molecule. In some embodiments the conjugate moiety, modify or enhance the pharmacokinetic properties of the nucleic acid molecule by improving cellular distribution, bioavailability, metabolism, excretion, permeability, and/or cellular uptake of the oligonucleotide. In particular, the conjugate may target the nucleic acid molecule to a specific organ, tissue or cell type and thereby enhance the effectiveness of the oligonucleotide in that organ, tissue or cell type. At the same time the conjugate may serve to reduce activity of the nucleic acid molecule in non-target cell types, tissues or organs, e.g. off target activity or activity in non-target cell types, tissues or organs. For siRNA nucleic acid molecules the conjugate moiety is most commonly covalently linked to the passenger strand of the siRNA, and for shRNA molecules the conjugate moiety would most commonly be linked to the end of the molecule which is furthest away from the contiguous nucleotide sequence of the shRNA. For antisense oligonucleotides the conjugate moiety can be covalently linked to any of the terminal ends, advantageously using a biocleavable linker such as a 2 to 5 phosphodiester linked DNA nucleosides.

WO 93/07883 and WO2013/033230 provides suitable conjugate moieties, which are hereby incorporated by reference. Further suitable conjugate moieties are those capable of binding to the asialoglycoprotein receptor (ASGPR). In particular tri-valent N-acetylgalactosamine conjugate moieties are suitable for binding to the ASGPR, see for example US 2009/02398, WO 2014/076196, WO 2014/207232 and WO 2014/179620 (hereby incorporated by reference). Such conjugates serve to enhance uptake of the therapeutic nucleic acid molecule to the liver while reducing its presence in the kidney, thereby increasing the liver/kidney ratio of a conjugated nucleic acid molecule compared to the unconjugated version of the same nucleic acid molecule.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Conjugate Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect one region, e.g. a conjugate moiety to another region, e.g. an oligonucleotide (e.g. the termini of region A or C).

In some embodiments of the invention the conjugate or therapeutic nucleic acid molecule conjugate of the invention may optionally, comprise a linker region which is positioned between the oligonucleotide and the conjugate moiety. In some embodiments, the linker between the conjugate and oligonucleotide is physiologically labile linker, interchangeably termed biocleavable linker. The linker and the oligonucleotide is often attached via a phosphodiester linkage.

Biocleavable linkers (Region B) comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In some embodiments the physiologically labile linker (biocleavable) comprises between 1 and 10 linked nucleosides, such as 1, 2, 3, 4, 5, 6, 7, 8, 9 or 10 linked nucleosides, such as between 2 and 6 linked nucleosides, such as between 2 and 5 linked nucleosides, such as between 2 and 4 linked nucleosides, where at least two consecutive linkages are biocleavable, such as phosphodiester linkages, such as at least 3 or 4 or 5 consecutive phosphodiester linkages. Preferably the nucleosides are DNA or RNA.

In one embodiment the linker between the oligonucleotide and the conjugate moiety is a physiologically labile linker composed of 2 to 5 consecutive phosphodiester linked nucleosides comprising at least two consecutive phosphodiester linkages at the 5' or 3' terminal of the contiguous nucleotide sequence of the antisense oligonucleotide or siRNA guide strand.

In another embodiment the linker between the oligonucleotide and the conjugate moiety is a physiologically labile linker composed of 2 to 5 consecutive phosphodiester linked nucleosides comprising at least two consecutive phosphodiester linkages at the 5' or 3' terminal of the passenger strand of the siRNA, In another embodiment the linker between the oligonucleotide and the conjugate moiety is a physiologically labile linker composed of 2 to 5 consecutive phosphodiester linked nucleosides comprising at least two consecutive phosphodiester linkages at the terminal end of the shRNA molecule furthest away from the contiguous nucleotide sequence of the shRNA.

In some embodiments the physiologically labile linker comprises or consist of a DNA dinucleotide with a sequence selected from the group consisting of AA, AT, AC, AG, TA, TT, TC, TG, CA, CT, CC, CG, GA, GT, GC, or GG, where there is a phosphodiester linkage between the two DNA nucleosides and at least one further phosphodiester at the 5' or 3' end of the dinucleotide linking either the oligonucleotide of the nucleic acid molecule to the dinucleotide or the conjugate moiety to the dinucleotide. In some embodiments the physiologically labile linker comprises or consist of a DNA trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, or GGG, where there is phosphodiester linkages between the DNA nucleosides and potentially a further phosphodiester at the 5' or 3' end of the trinucleotide. Phosphodiester containing biocleavable linkers are described in more detail in WO 2014/076195 (hereby incorporated by reference). In a conjugate compound with a biocleavable linker at least about 50% of the conjugate moiety is cleaved from the oligonucleotide, such as at least about 60% cleaved, such as at least about 70% cleaved, such as at least about 80% cleaved, such as at least about 85% cleaved, such as at least about 90% cleaved, such as at least about 95% of the conjugate moiety is cleaved from the oligonucleotide cleaved when compared against a standard.

Conjugates may also be linked to the oligonucleotide via non-biocleavable linkers, or in some embodiments the conjugate may comprise a non-cleavable linker which is covalently attached to the biocleavable linker. Linkers that are not necessarily biocleavable primarily serve to covalently connect a conjugate moiety to the oligonucleotide or biocleavable linker, and potentially generate some distance between the conjugate moiety and the oligonucleotide.

Some example linkers (region Y) include 8-amino-3,6-dioxaoctanoic acid (ADO), succinimidyl 4-(N-maleimidomethyl)cyclohexane-I-carboxylate (SMCC), 6-aminohexanoic acid (AHEX or AHA), 6-aminohexyloxy, 4-aminobutyric acid, 4-aminocyclohexylcarboxylic acid, succinimidyl 4-(N-maleimidomethyl)cyclohexane-1-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like. Non-cleavable linkers may also comprise a chain structure or an oligomer of repeating units such as ethylene glycol, amino acid units or amino alkyl groups. In some embodiments the linker (region Y) is an amino alkyl, such as a $C_2$-$C_{36}$ amino alkyl group, including, for example $C_6$ to $C_{12}$ amino alkyl groups. In some embodiments the linker (region Y) is a C amino alkyl group (also termed a C6 linker). Conjugate linker groups may be routinely attached to an oligonucleotide via use of an amino modified oligonucleotide, and an activated ester group on the conjugate group. The linkage group between the amino alkyl and the oligonucleotide may for example be a phosphorothioate or a phosphodiester, or one of the other nucleoside linkage groups referred to herein. A conjugate compound of the present invention may be composed of the following regions C-B-A (Conjugate moiety-biocleavable linker-oligonucleotide/contiguous nucleotide sequence) or C-Y-B-A (conjugate moiety-non-cleavable linker-biocleavable linker-oligonucleotide/contiguous nucleotide sequence).

Treatment

The terms “treatment”, “treating”, “treats” or the like as used herein generally means obtaining a desired pharmacological and/or physiological effect. This effect is therapeutic in terms of partially or completely curing a disease and/or adverse effect attributed to the disease. The term “treatment” as used herein covers any treatment of a disease in a subject and includes: (a) inhibiting the disease, i.e. arresting its development like the inhibition of increase of HBsAg and/or HBeAg; or (b) ameliorating (i.e. relieving) the disease, i.e. causing regression of the disease, like the repression of HBsAg and/or HBeAg production. Thus, a compound that ameliorates and/or inhibits a HBV infection is a compound that treats a HBV invention. Preferably, the term “treatment” as used herein relates to medical intervention of an already manifested disorder, like the treatment of an already defined and manifested HBV infection.

Prevention

Herein the term “preventing”, “prevention” or “prevents” relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein “preventing a HBV infection” includes preventing a HBV infection from occurring in a subject, and preventing the occurrence of symptoms of a HBV infection. In the present invention in particular the prevention of HBV infection in children from HBV infected mothers are contemplated. Also contemplated is the prevention of an acute HBV infection turning into a chronic HBV infection.

Patient

For the purposes of the present invention the "subject" (or "patient") may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, guinea pig, ferret, cat, dog, chicken, sheep, bovine species, horse, camel, or primate. Preferably, the subject is a mammal. More preferably the subject is human.

HBV Infection

The term "hepatitis B virus infection" or "HBV infection" is commonly known in the art and refers to an infectious disease that is caused by the hepatitis B virus (HBV) and affects the liver. A HBV infection can be an acute or a chronic infection. Some infected persons have no symptoms during the initial infection and some develop a rapid onset of sickness with vomiting, yellowish skin, tiredness, dark urine and abdominal pain ("Hepatitis B Fact sheet No. 204*". *who.int*. July 2014. Retrieved 4 Nov. 2014). Often these symptoms last a few weeks and can result in death. It may take 30 to 180 days for symptoms to begin. In those who get infected around the time of birth 90% develop a chronic hepatitis B infection while less than 10% of those infected after the age of five do ("Hepatitis B FAQs for the Public-Transmission", U.S. Centers for Disease Control and Prevention (CDC), retrieved 2011-11-29). Most of those with chronic disease have no symptoms; however, cirrhosis and liver cancer may eventually develop (Chang, 2007, Semin Fetal Neonatal Med, 12: 160-167). These complications result in the death of 15 to 25% of those with chronic disease ("Hepatitis B Fact sheet No. 204*". *who.int*. July 2014, retrieved 4 Nov. 2014). Herein, the term "HBV infection" includes the acute and chronic hepatitis B infection. The term "HBV infection" also includes the asymptotic stage of the initial infection, the symptomatic stages, as well as the asymptotic chronic stage of the HBV infection.

cccDNA cccDNA (covalently closed circular DNA) is a special DNA structure that arises during the propagation of some DNA viruses (Polyomaviridae) in the cell nucleus. cccDNA is a double-stranded DNA that originates in a linear form that is ligated by means of DNA ligase to a covalently closed ring. In most cases, transcription of viral DNA can occur from the circular form only. The cccDNA of viruses is also known as episomal DNA or occasionally as a minichromosome.

cccDNA is typical of Caulimoviridae and Hepadnaviridae, including the hepatitis B virus (HBV). The HBV genome forms a stable minichromosome, the covalently closed circular DNA (cccDNA), in the hepatocyte nucleus. The cccDNA is formed by conversion of capsid-associated relaxed circular DNA (rcDNA). HBV cccDNA formation involves a multi-step process that requires the cellular DNA repair machinery and relies on specific interactions with distinct cellular components that contribute to the completion of the positive strand DNA in rcDNA (Alweiss et al. 2017, Viruses, 9 (6): 156).

Pharmaceutically Acceptable Salts

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition, these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

Inhibitor

The term "inhibitor" is known in the art and relates to a compound/substance or composition capable of fully or partially preventing or reducing the physiologic function (i.e. the activity) of (a) specific protein(s) (e.g. of FUBP1). In the context of the present invention, an "inhibitor" of FUBP1 is capable of preventing or reducing the activity/function of FUBP1, respectively, by preventing or reducing the expression of the FUBP1 gene products. Thus, an inhibitor of FUBP1 may lead to a decreased expression level of FUBP1 (e.g. decreased level of FUBP1 mRNA, or of FUBP1protein) which is reflected in a decreased functionality (i.e. activity) of FUBP1, wherein said function comprises the poly-A polymerase function. An inhibitor of FUBP1, in the context of the present invention, accordingly, may also encompass transcriptional repressors of FUBP1 expression that are capable of reducing the level of FUBP1. Preferred inhibitors are nucleic acid molecules of the invention.

Compound

Herein, the term "compound" means any molecule capable of inhibition FUBP1 expression or activity. Particular compounds of the invention are nucleic acid molecules, such as RNAi molecules or antisense oligonucleotides according to the invention or any conjugate comprising such a nucleic acid molecule. For example, herein the compound may be a nucleic acid molecule targeting FUBP1, in particular an antisense oligonucleotide or a siRNA.

Composition

The term "composition" may also be used to describe a nucleic acid molecule compound or another FUBP1 inhibitor. A nucleic acid molecule composition has less than 20% impurities, preferably less than 15% or 10% impurities, more preferably less than 9, 8, 7 or 6% impurities, most preferably less than 5% impurities. The impurities are typically nucleic acid molecules which are one or two nucleotides shorter (n-1 or n-2) than the primary nucleic acid molecule component.

The present invention is further described by reference to the non-limiting figures and examples.

DETAILED DESCRIPTION OF THE INVENTION

Overexpression of and mutations in FUBP1 has been known to be associated with cancers for many years. In particular, strong overexpression of FUBP1 in human hepatocellular carcinoma (HCC) supports tumour growth and correlates with poor patient prognosis. HBV cccDNA in infected hepatocytes is responsible for persistent chronic infection and reactivation, being the template for all viral subgenomic transcripts and pre-genomic RNA (pgRNA) to ensure both newly synthesized viral progeny and cccDNA pool replenishment via intracellular nucleocapsid recycling. In the context of the present invention it was for the first time shown that FUBP1 is associated with cccDNA stability. This knowledge allows for the opportunity to destabilize cccDNA in HBV infected subjects which in turn opens the opportunity for a complete cure of chronically infected HBV patients. The role of FUBP1 in HCC and cccDNA stability is expected to be different and independent of each other.

One aspect of the present invention is a FUBP1 inhibitor for use in the treatment and/or prevention of Hepatitis B virus (HBV) infection, in particular a chronic HBV infection.

An embodiment of the invention is a FUBP1 inhibitor which is capable of reducing cccDNA and pgRNA in an infected cell, such as an HBV infected cell.

In a further embodiment, the FUBP1 inhibitor is capable of reducing HBsAg and/or HBeAg in vivo in an HBV infected individual.

FUBP1 Inhibitors for Use in Treatment of HBV

Without being bound by theory, it is believed that FUBP1 is involved in the stabilization of the cccDNA in the cell nucleus, and by preventing the binding of FUBP1 to DNA, in particular cccDNA, the cccDNA is destabilised and becomes prone to degradation. One embodiment of the invention is therefore a FUBP1 inhibitor which interacts with the DNA binding domain of FUBP1 protein, and prevents or reduces binding to cccDNA.

Small molecules inhibiting FUBP1 have been identified in relation to FUBP1's role in cancer, where the small molecule inhibits the DNA binding activity of FUBP1, in particular the binding to the FUSE element on a single stranded DNA. In the present invention FUBP1 inhibitors are envisioned as useful in treating HBV. In particular targeting of such small molecule compounds, e.g. via conjugation or formulation, to the liver may be beneficial in the treatment of HBV.

Huth et al 2004 J Med. Chem Vol 47 p. 4851-4857 discloses a series of benzoyl anthranilic acid compounds capable of binding to a four tandem K homology (KH) repeat of FUBP1. All the compounds disclosed in Huth et al 2004 are hereby incorporated by reference. In particular the compounds of formula I, II or III shown below were found to be efficient in inhibiting FUBP1 DNA binding activity.

I

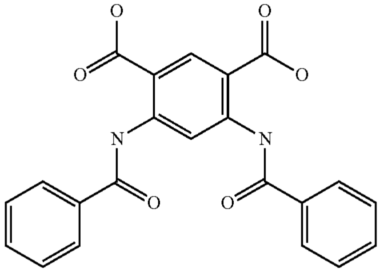

-continued

II

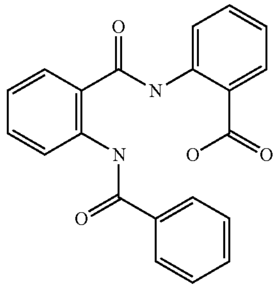

and

III

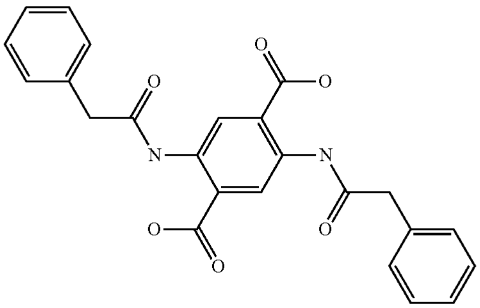

One embodiment of the present invention is a compound of formula I, II or III for use in treatment and/or prevention of Hepatitis B virus (HBV) infection.

Hauck et al 2016 Bioorganic & Medicinal Chemistry Vol 24 p. 5717-5729 describes an additional series of compounds with high FUBP1 inhibitory potential (see table 2, hereby incorporated by reference). In particular, the following compounds of formula IV were effective in inhibiting FUBP1 activity

IV

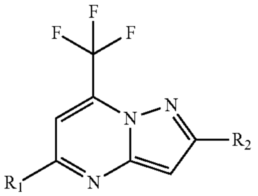

wherein R1 is selected from

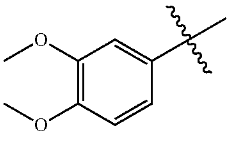

and

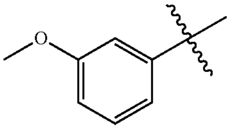

and

R2 is selected from

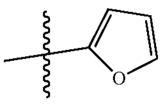

,

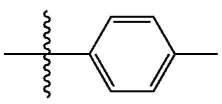

,

-continued

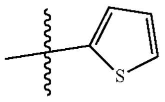

,

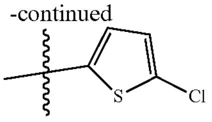

or

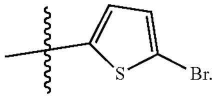

Specifically the compounds of formula V, VI and VII were shown to have IC50 values below 15 μM.

V

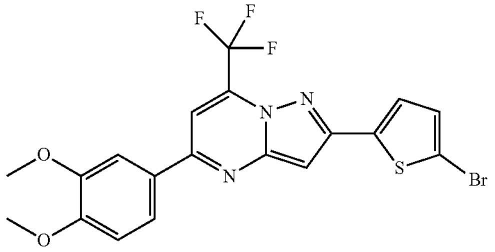

2-(5-Bromothiophen-2-yl)-5-(3,4-dimethoxyphenyl)-7-(trifluoromethyl)pyrazolo[1,5-a]pyrimidine

VI

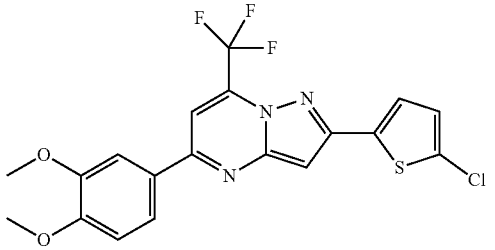

2-(5-Chlorothiophen-2-yl)-5-(3,4-dimethoxyphenyl)-7-(trifluoromethyl)pyrazolo[1,5-a]pyrimidine

VII

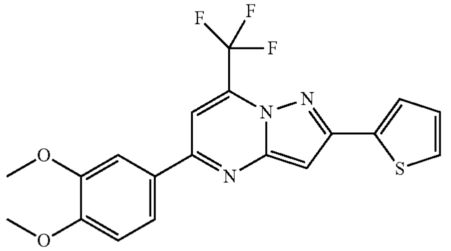

5-(3,4-Dimethoxyphenyl)-2-(thiophen-2-yl)-7-(trifluoromethyl)pyrazolo[1,5-a]pyrimidine One embodiment of the present invention is a compound of formula IV for use in treatment and/or prevention of Hepatitis B virus (HBV) infection.

One embodiment of the present invention is a compound of formula V, VI or VI for use in treatment and/or prevention of Hepatitis B virus (HBV) infection.

The S-adenosyl-L-methionine (SAM) competitive inhibitor, GSK343 (formula VIII), is currently in preclinical development for osteosarcoma. It has been shown that GSK343 inhibits FUBP1 expression in osteosarcoma cells (Xiong et al 2016 Int J Onc vol 49 p 623).

VIII

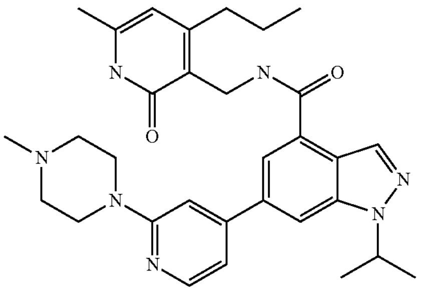

One embodiment of the present invention is a compound of formula VII for use in treatment and/or prevention of Hepatitis B virus (HBV) infection.

The FDA-approved cancer drugs camptothecin (CPT, formula IX) and its derivative SN-38 (7-ethyl-10-hydroxy-camptothecin, formula X), which are Topoisomerase I (TOP1) inhibitors, were recently shown to inhibit FUBP1 activity as well by preventing the FUBP1/FUSE interaction (Hosseini et al 2017 Biochemical Pharmacology Vol 146 p. 53-62).

IX

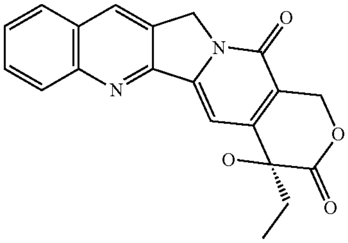

Camptothecin ((+)-4(S)-Ethyl-4-hydroxy-3,4,12,14-tetrahydro-1H-pyrano[3',4':6,7]indolizino[1,2-b]quinoline-3,14-dione).

X

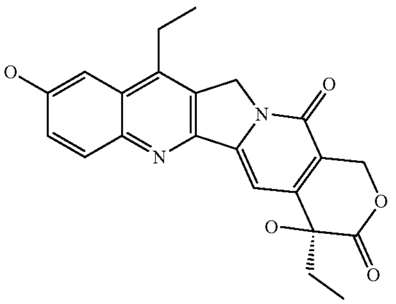

SN-38 (4(S),11-Diethyl-4,9-dihydroxy-3,4,12,14-tetrahydro-1H-pyrano[3',4':6,7]indolizino[1,2-b]quinoline-3,14-dione 7-Ethyl-10-hydroxycamptothecin).

One embodiment of the present invention is a compound of formula IX or X for use in treatment and/or prevention of Hepatitis B virus (HBV) infection.

Tringali et al 2012 Journal of Pharmacy and Pharmacology Vol 64, p. 360-365 describes the pharmacokinetic profile SN-38 conjugated to hyaluronic acid (HA-SN-38, formula XI) and shows an increased distribution to the liver.

XI

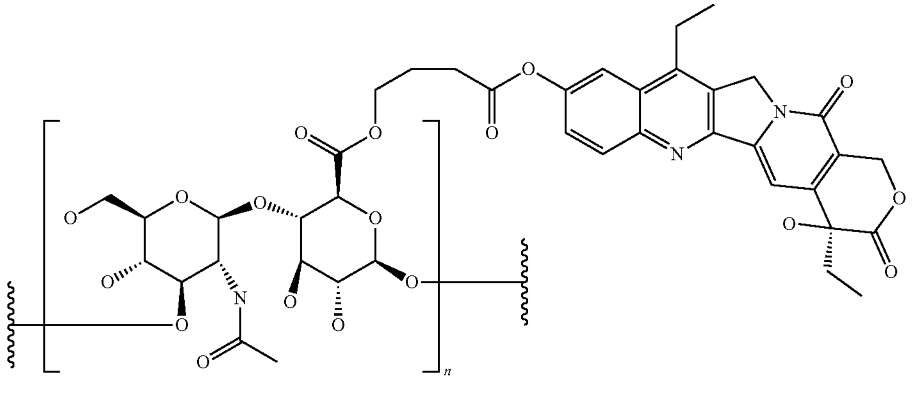

One embodiment of the present invention is a compound of formula XI for use in treatment and/or prevention of Hepatitis B virus (HBV) infection.

Various lipid conjugates of SN-38 also exist in the literature. WO2006/082053 for example describes the molecule of formula XII

XII

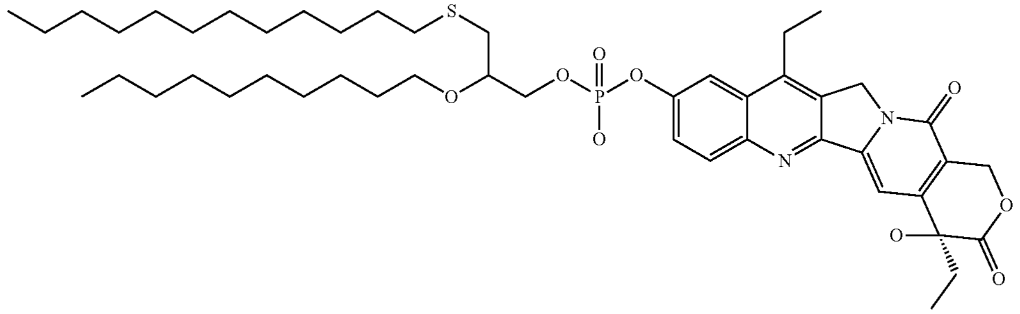

CN105777770 describes a palmitate conjugated SN-38 shown in formula XIII below.

XIII

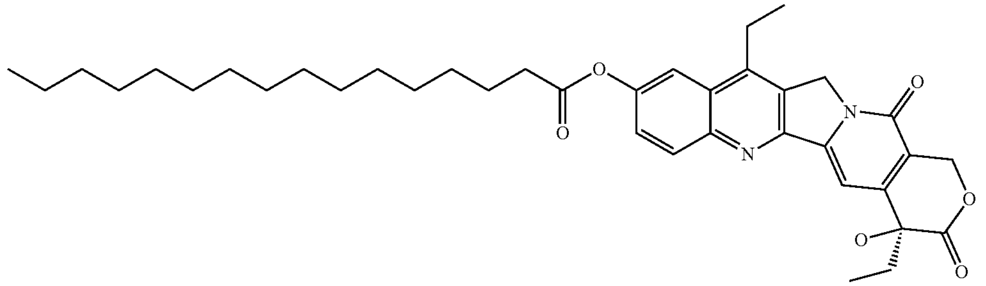

One embodiment of the present invention is a compound of formula XII or XIII for use in treatment and/or prevention of Hepatitis B virus (HBV) infection.

In a further aspect of the invention the FUBP1 inhibitors for use in treatment and/or prevention of Hepatitis B virus (HBV) infection can be targeted directly to the liver by covalently attaching them to a conjugate moiety capable of binding to the asialoglycoprotein receptor (ASGPr), such as divalent or trivalent GalNAc cluster.

Nucleic Acid Molecules of the Invention

Nucleic acid molecules are potentially excellent FUBP1 inhibitors since they can target the FUBP1 transcript and promote its degradation either via the RNA interference pathway or via RNaseH cleavage. Alternatively, nucleic acid molecules such as aptamers can also act as inhibitors of the DNA binding site of FUBP1 in line with the small molecules described above.

One aspect of the present invention is a nucleic acid molecule for use in treatment and/or prevention of Hepatitis B virus (HBV) infection. Such nucleic acid molecules can be selected from the group consisting of single stranded antisense, oligonucleotide; siRNA molecule; or shRNA molecule.

The present section describes novel nucleic acid molecules suitable for use in treatment and/or prevention of Hepatitis B virus (HBV) infection.

The nucleic acid molecules of the present invention are capable of inhibiting the expression of FUBP1 in vitro and in vivo. The inhibition is achieved by hybridizing an oligonucleotide to a target nucleic acid encoding FUBP1.

The target nucleic acid may be a mammalian FUBP1 sequence, such as a sequence selected from the group consisting of SEQ ID NO: 1 to 20. It is advantageous if the mammalian FUBP1 sequence is selected from the group consisting of SEQ ID NO: 1, 2, 3, 4, 5, 6, 7 and 8.

In some embodiments, the nucleic acid molecule of the invention is capable of modulating the expression of FUBP1 by inhibiting or down-regulating it. Preferably, such modulation produces an inhibition of expression of at least 40% compared to the normal expression level of the target, more preferably at least 50%, 60%, 70%, 80%, 90%, 95% or 98% inhibition compared to the normal expression level of the target. In some embodiments, the nucleic acid molecule of the invention is capable of inhibiting expression levels of FUBP1 mRNA by at least 65%-98%, such as 70% to 95%, in vitro using HepG2-NTCP cells or HBV infected primary human hepatocytes, this range of target reduction is advantageous in terms of selecting nucleic acid molecules with good correlation to the cccDNA reduction. In some embodiments compounds of the invention may be capable of inhibiting expression levels of FUBP1 protein by at least 50% in vitro using HepG2-NTCP cells or HBV infected primary human hepatocytes. The materials and Method section and the Examples herein provide assays which may be used to measure target RNA inhibition in HepG2-NTCP cells or HBV infected primary human hepatocytes as well as cccDNA. The target modulation is triggered by the hybridization between a contiguous nucleotide sequence of the oligonucleotide, such as the guide strand of a siRNA or gapmer region of an antisense oligonucleotide, and the target nucleic acids. In some embodiments, the oligonucleotide of the invention comprises mismatches between the oligonucleotide or the contiguous nucleotide sequence and one or both of the target nucleic acids. Despite mismatches hybridization to the target nucleic acid may still be sufficient to show a desired modulation of FUBP1 expression. Reduced binding affinity resulting from mismatches may advantageously be compensated by increased length of the oligonucleotide and/or an increased number of modified nucleosides capable of increasing the binding affinity to the target within the oligonucleotide sequence. Advantageously, the oligonucleotides of the present invention contain modified nucleosides capable of increasing the binding affinity, such as 2' sugar modified nucleosides, including LNA.

An aspect of the present invention relates to nucleic acid molecule of 12 to 60 nucleotides in length, which comprises a contiguous nucleotide sequence of 12 to 30 nucleotides in length which is capable of inhibiting the expression of FUBP1.

In some embodiments, the nucleic acid molecule comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid or a target sequence.

In one embodiment the nucleic acid molecule of the invention, or contiguous nucleotide sequence thereof is fully complementary (100% complementary) to a region of the target nucleic acids, or in some embodiments may comprise one or two mismatches between the oligonucleotide and the target nucleic acids.

In some embodiments, the nucleic acid molecule comprises a contiguous nucleotide sequence of 12 to 30 nucleotides in length with at least 95% complementary, such as fully (or 100%) complementary, to a target nucleic acid region present in SEQ ID NO: 1, SEQ ID NO: 2, SEQ ID NO: 3 and/or SEQ ID NO:4.

In some embodiments, the nucleic acid molecule or the contiguous nucleotide sequence of the invention is at least 93% complementarity, such as fully (or 100%) complementary, to the target nucleic acid of SEQ ID NO: 1, SEQ ID NO: 2, SEQ ID NO: 3, SEQ ID NO: 4, SEQ ID NO: 5, SEQ ID NO: 6, SEQ ID NO; 7 and/or SEQ ID NO; 8.

In some embodiments the nucleic acid molecule or the contiguous nucleotide sequence of the invention is at least 95% complementarity, such as fully (or 100%) complementary, to the target nucleic acid of SEQ ID NO: 1 and SEQ ID NO: 5.

In some embodiments the nucleic acid molecule or the contiguous nucleotide sequence of the invention is at least 95% complementarity, such as fully (or 100%) complementary, to the target nucleic acid of SEQ ID NO: 1, SEQ ID NO: 5 and SEQ ID NO: 9.

In some embodiments the nucleic acid molecule or the contiguous nucleotide sequence is 100% complementary to position 14200-14218 on SEQ ID NO: 1.

In some embodiments the nucleic acid molecule or the contiguous nucleotide sequence is 100% complementary to position 14413-14431 on SEQ ID NO: 1.

In some embodiments the nucleic acid molecule or the contiguous nucleotide sequence is 100% complementary to position 14966-14984 on SEQ ID NO: 1.

In some embodiments the nucleic acid molecule or the contiguous nucleotide sequence is 100% complementary to position 30344-30362 on SEQ ID NO: 1 In some embodiments, the nucleic acid molecule of the invention comprises or consists of 12 to 60 nucleotides in length, such as from 13 to 50, such as 14 to 35, such as from 15 to 30 such as from 16 to 22 nucleotides in length.

In some embodiments, the contiguous nucleotide sequence of the acid molecule which is complementary to the target nucleic acids comprises or consists of 12 to 30, such as from 14 to 25, such as from 16 to 23, such as from 18 to 22, contiguous nucleotides in length.

In some embodiments, the contiguous nucleotide sequence of the siRNA or shRNA which is complementary to the target nucleic acids comprises or consists of 18 to 28, such as from 19 to 26, such as from 20 to 24, such as from 21 to 23, contiguous nucleotides in length.

In some embodiments, the contiguous nucleotide sequence of the antisense oligonucleotide which is complementary to the target nucleic acids comprises or consists of 12 to 22, such as from 14 to 20, such as from 16 to 20, such as from 15 to 18, such as from 16 to 18, such as from 16 to 17 contiguous nucleotides in length.

It is understood that the contiguous nucleobase sequences (motif sequence) can be modified to for example increase nuclease resistance and/or binding affinity to the target nucleic acid.

The pattern in which the modified nucleosides (such as high affinity modified nucleosides) are incorporated into the oligonucleotide sequence is generally termed oligonucleotide design. The oligonucleotides of the invention are designed with modified nucleosides and RNA nucleosides (in particular for siRNA and shRNA molecules) or DNA nucleosides (in particular for single stranded antisense oligonucleotides). Advantageously, high affinity modified nucleosides are used.

In an embodiment, the oligonucleotide comprises at least 1 modified nucleoside, such as at least 2, at least 3, at least 4, at least 5, at least 6, at least 7, at least 8 modified nucleosides. In an embodiment the oligonucleotide comprises from 1 to 8 modified nucleosides, such as from 2 to 7 modified nucleosides, such as from 3 to 6 modified nucleosides, such as from 4 to 6 modified nucleosides, such as 4 or 5 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprise one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA). Often used LNA nucleosides are oxy-LNA or cET.

In a further embodiment the oligonucleotide comprises at least one modified internucleoside linkage. Suitable internucleoside modifications are described in the "Definitions" section under "Modified internucleoside linkage". It is advantageous if at least 2 to 3 internucleoside linkages at the 5' or 3' end of the oligonucleotide are phosphorothioate internucleoside linkages. For single stranded antisense oligonucleotides it is advantageous if at least 75%, such as, such as all, the internucleoside linkages within the contiguous nucleotide sequence are phosphorothioate internucleoside linkages.

In a further aspect of the invention the nucleic acid molecules, such as the antisense oligonucleotide, siRNA or shRNA, of the invention can be targeted directly to the liver by covalently attaching them to a conjugate moiety capable of binding to the asialoglycoprotein receptor (ASGPr), such as divalent or trivalent GalNAc cluster.

Conjugates

Since HBV infection primarily affects the hepatocytes in the liver it is advantageous to conjugate the FUBP1 inhibitor to a conjugate moiety that will increase the delivery of the inhibitor to the liver compared to the unconjugated inhibitor. In one embodiment liver targeting moieties are selected from moieties comprising cholesterol or other lipids or conjugate moieties capable of binding to the asialoglycoprotein receptor (ASGPR).

In some embodiments, the invention provides a conjugate comprising a nucleic acid molecule of the invention covalently attached to a conjugate moiety.

The asialoglycoprotein receptor (ASGPR) conjugate moiety comprises one or more carbohydrate moieties capable of binding to the asialoglycoprotein receptor (ASPGR targeting moieties) with affinity equal to or greater than that of galactose. The affinities of numerous galactose derivatives for the asialoglycoprotein receptor have been studied (see for example: Jobst, S. T. and Drickamer, K. JB. C. 1996, 271, 6686) or are readily determined using methods typical in the art.

In one embodiment the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine. Advantageously the asialoglycoprotein receptor targeting moiety is N-acetylgalactosamine (GalNAc).

To generate the ASGPR conjugate moiety the ASPGR targeting moieties (preferably GalNAc) can be attached to a conjugate scaffold. Generally, the ASPGR targeting moieties can be at the same end of the scaffold. In one embodiment, the conjugate moiety consists of two to four terminal GalNAc moieties linked to a spacer which links each GalNAc moiety to a brancher molecule that can be conjugated to the antisense oligonucleotide.

In a further embodiment, the conjugate moiety is monovalent, di-valent, tri-valent or tetra-valent with respect to asialoglycoprotein receptor targeting moieties. Advantageously the asialoglycoprotein receptor targeting moiety comprises N-acetylgalactosamine (GalNAc) moieties.

GalNAc conjugate moieties can include, for example, those described in WO 2014/179620 and WO 2016/055601 and PCT/EP2017/059080 (hereby incorporated by reference), as well as small peptides with GalNAc moieties attached such as Tyr-Glu-Glu-(aminohexyl GalNAc)3 (YEE (ahGalNAc)3; a glycotripeptide that binds to asialoglycoprotein receptor on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor).

The ASGPR conjugate moiety, in particular a trivalent GalNAc conjugate moiety, may be attached to the 3'- or 5'-end of the oligonucleotide using methods known in the art. In one embodiment the ASGPR conjugate moiety is linked to the 5'-end of the oligonucleotide.

Figure 1D:
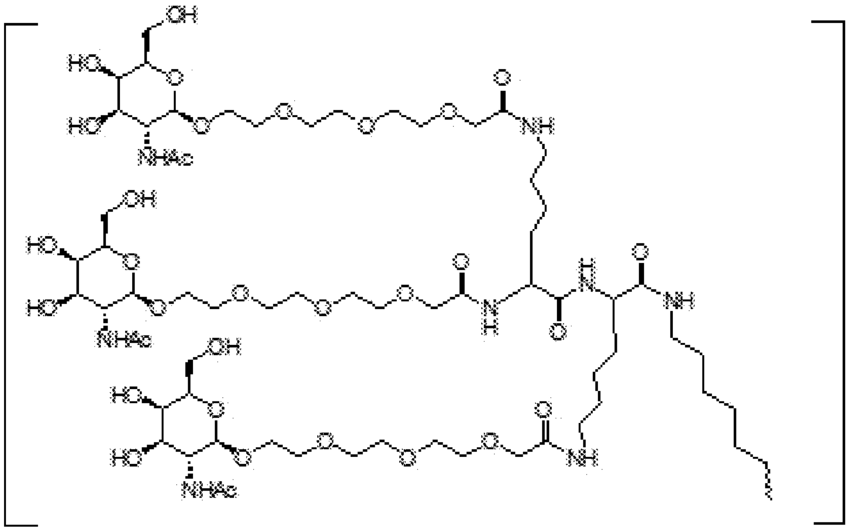
Figure 1E:
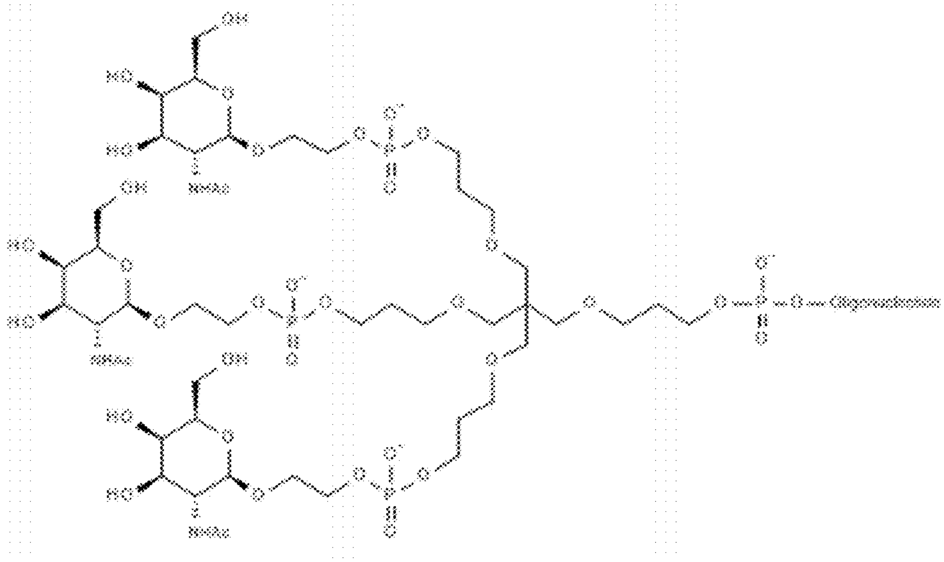
Figure 1F:
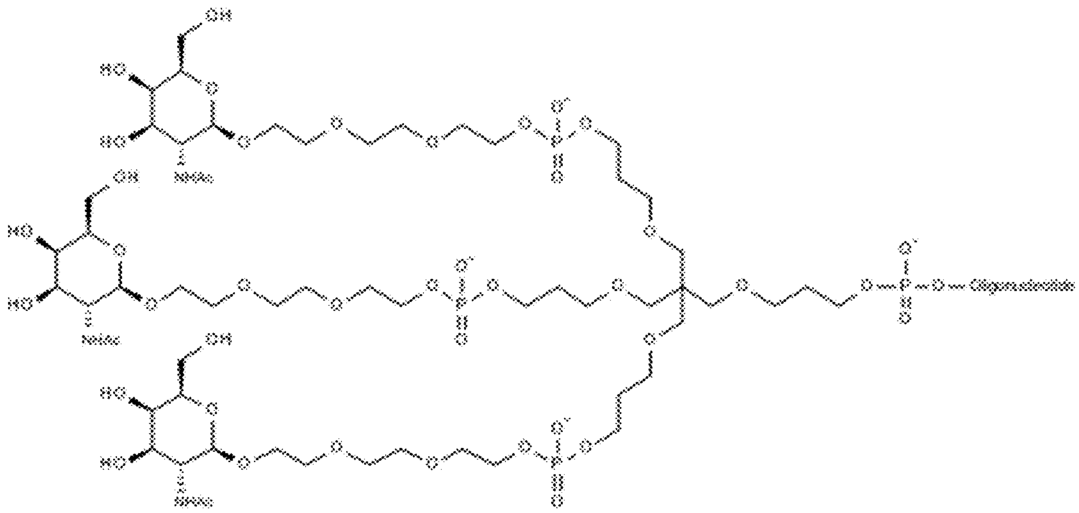
Figure 1G:
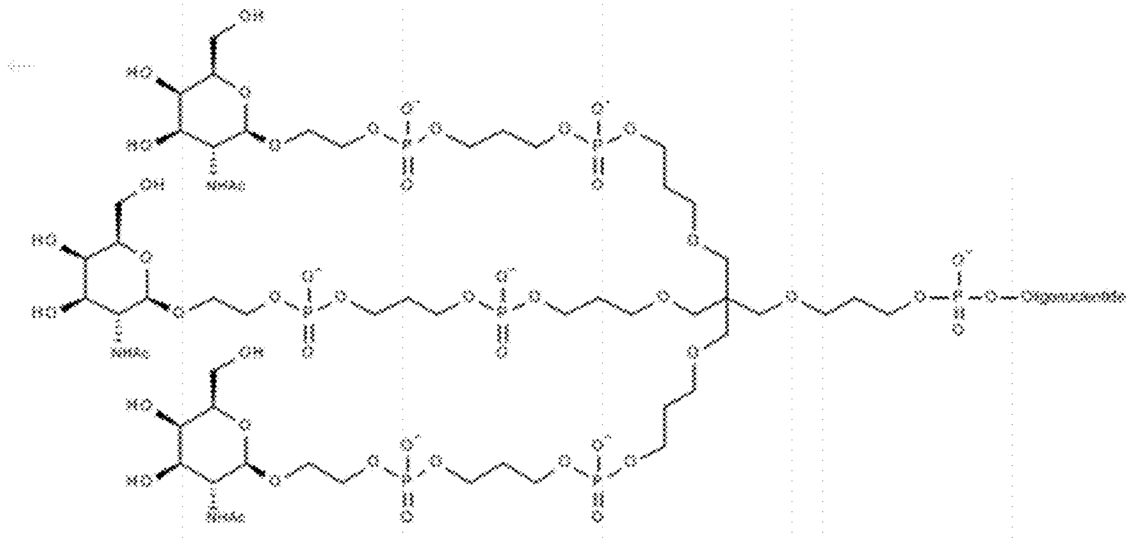
Figure 1H:
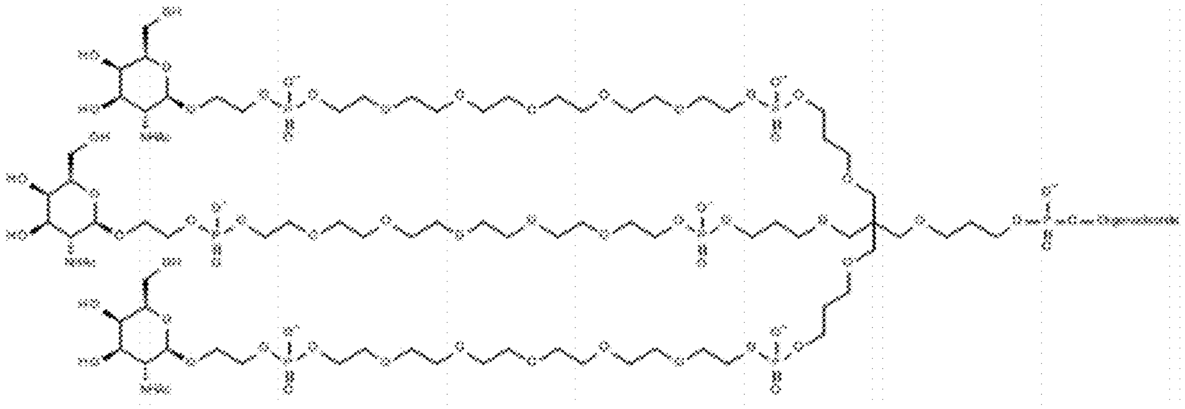
Figure 1I:
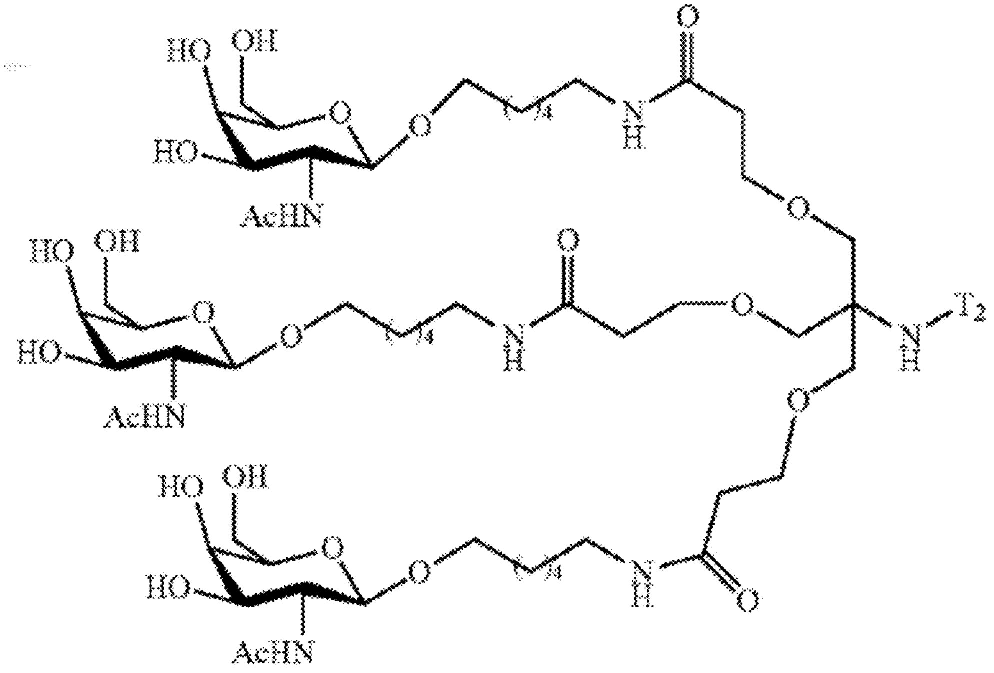
Figure 2:
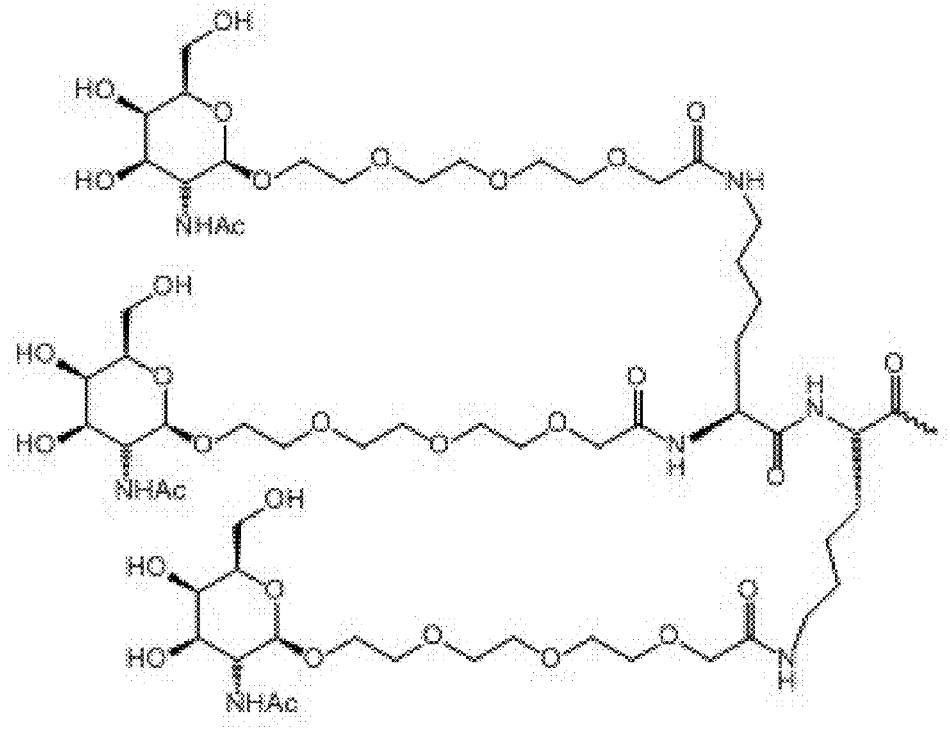
FIG. 2: Structural formula of the trivalent GalNAc cluster (GN2). GN2 is useful as conjugation moiety in the present invention. The wavy line illustrates the site of conjugation of the cluster to e.g. a C6 amino linker or directly to the oligonucleotide.

In one embodiment the conjugate moiety is a tri-valent N-acetylgalactosamine (GalNAc), such as those shown in FIG. 1, in particular as shown in FIG. 1D.

Method of Manufacture

In a further aspect, the invention provides methods for manufacturing the nucleic acid molecule of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the oligonucleotide with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant. Where the nucleic acid molecule is a siRNA the oligonucleotides are paired and allowed to form double stranded structures.

Pharmaceutical Salt

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect the invention provides a pharmaceutically acceptable salt of the antisense oligonucleotide or a conjugate thereof. In a preferred embodiment, the pharmaceutically acceptable salt is a sodium or a potassium salt.

Pharmaceutical Compositions

In a further aspect, the invention provides pharmaceutical compositions comprising a nucleic acid molecule and/or conjugate compounds of the invention or salts thereof and a pharmaceutically acceptable diluent, carrier, salt and/or adjuvant. A pharmaceutically acceptable diluent includes phosphate-buffered saline (PBS). In some embodiments the pharmaceutically acceptable diluent is sterile phosphate buffered saline. In some embodiments the oligonucleotide is used in the pharmaceutically acceptable diluent at a concentration of 50-300 μM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Nucleic acid molecules or conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the nucleic acid molecule or conjugate of the invention is a prodrug. In particular, with respect to oligonucleotide conjugates the conjugate moiety is cleaved off the oligonucleotide once the prodrug is delivered to the site of action, e.g. the target cell.

Applications

The nucleic acid molecules of the invention may be utilized as research reagents for, for example, diagnostics, therapeutics and prophylaxis.

In research, such nucleic acid molecules may be used to specifically modulate the synthesis of FUBP1 protein in cells (e.g. in vitro cell cultures) and experimental animals thereby facilitating functional analysis of the target or an appraisal of its usefulness as a target for therapeutic intervention. Typically, the target modulation is achieved by degrading or inhibiting the mRNA producing the protein, thereby prevent protein formation or by degrading or inhibiting a modulator of the gene or mRNA producing the protein.

If employing the nucleic acid molecules of the invention in research or diagnostics the target nucleic acid may be a cDNA or a synthetic nucleic acid derived from DNA or RNA.

Also encompassed by the present invention is an in vivo or in vitro method for modulating FUBP1 expression in a target cell which is expressing FUBP1, said method comprising administering a nucleic acid molecule, conjugate compound or pharmaceutical composition of the invention in an effective amount to said cell.

In some embodiments, the target cell, is a mammalian cell in particular a human cell. The target cell may be an in vitro cell culture or an in vivo cell forming part of a tissue in a mammal. In preferred embodiments the target cell is present in in the liver. The target cell may be a hepatocyte.

One aspect of the present invention is related the nucleic acid molecules, conjugate compounds or pharmaceutical compositions of the invention for use as a medicament.

In an aspect of the invention the nucleic acid molecules, conjugate compound or pharmaceutical composition of the invention is capable of reducing the cccDNA level in the infected cells and therefore inhibiting HBV infection. In particular, the antisense oligonucleotide is capable of affecting one or more of the following parameters i) reducing cccDNA and/or ii) reducing pgRNA and/or iii) reducing HBV DNA and/or iv) reducing HBV viral antigens in an infected cell.

For example, nucleic acid molecule that inhibits HBV infection may reduce i) the cccDNA levels in an infected cell by at least 40% such as 50%, 60%, 70%, 80%, or 90% reduction compared to controls; or ii) the level of pgRNA by at least 40% such as 50%, 60%, 70%, 80%, or 90% reduction compared to controls. The controls may be untreated cells or animals, or cells or animals treated with an appropriate control.

Inhibition of HBV infection may be measured in vitro using HBV infected primary human hepatocytes or in vivo for nucleic acid molecules complementary to mouse FUBP1 using HBV minicircle mouse (available at Covance Shanghai, see also Guo et al 2016 Sci Rep 6: 2552 and Yan et al 2017 J Hepatology 66(6):1149-1157) or humanized hepatocytes PXB mouse model (available at PhoenixBio, see also Kakuni et al 2014 Int. J. Mol. Sci. 15:58-74). Inhibition of secretion of HBsAg and/or HBeAg may be measured by ELISA, e.g. by using the CLIA ELISA Kit (Autobio Diagnostic) according to the manufacturers' instructions. Reduction of intracellular cccDNA or HBV mRNA and pgRNA may be measured by qPCR, e.g. as described in the Materials and Methods section. Further methods for evaluating whether a test compound inhibits HBV infection are measuring secretion of HBV DNA by qPCR e.g. as described in WO 2015/173208 or using Northern Blot; in-situ hybridization, or immuno-fluorescence.

Due to the reduction of FUBP1 levels the nucleic acid molecules, conjugate compounds or pharmaceutical compositions of the present invention can be used to inhibit development of or in the treatment of HBV infection. In particular, the destabilization and reduction of the cccDNA, the nucleic acid molecules, conjugate compounds or pharmaceutical compositions of the present invention more efficiently inhibits development of or treats a chronic HBV infection as compared to a compound that only reduces secretion of HBsAg.

Accordingly, one aspect of the present invention is related to use of the nucleic acid molecule, conjugate compounds or pharmaceutical compositions of the invention to reduce cccDNA and/or pgRNA in an HBV infected individual.

A further aspect of the invention relates to the use of the nucleic acid molecules, conjugate compounds or pharmaceutical compositions of the invention to inhibit development of or treat a chronic HBV infection.

A further aspect of the invention relates to the use of the nucleic acid molecules, conjugate compounds or pharmaceutical compositions of the invention to reduce the infectiousness of a HBV infected person. In a particular aspect of the invention, the nucleic acid molecules, conjugate compounds or pharmaceutical compositions of the invention inhibits development of a chronic HBV infection.

The subject to be treated with the nucleic acid molecules, conjugate compounds or pharmaceutical compositions of the invention (or which prophylactically receives antisense oligonucleotides, conjugate compounds or pharmaceutical compositions of the present invention) is preferably a human, more preferably a human patient who is HBsAg positive and/or HBeAg positive, even more preferably a human patient that is HBsAg positive and HBeAg positive.

Accordingly, the present invention relates to a method of treating and/or preventing a HBV infection, wherein the method comprises administering an effective amount of the nucleic acid molecules, conjugate compounds or pharmaceutical compositions of the invention.

The invention also provides for the use of a nucleic acid molecule, a conjugate compound or a pharmaceutical composition of the invention for the manufacture of a medicament, in particular a medicament for use in the treatment or prevention of HBV infection or chronic HBV infection or reduction of the infectiousness of a HBV infected person. In preferred embodiments the medicament is manufactured in a dosage form for subcutaneous administration.

The invention also provides for the use of a nucleic acid molecule, a conjugate compound, the pharmaceutical composition of the invention for the manufacture of a medicament wherein the medicament is in a dosage form for intravenous administration.

The nucleic acid molecule, conjugate or the pharmaceutical composition of the invention may be used in a combination therapy. For example, nucleic acid molecule, conjugate or the pharmaceutical composition of the invention may be combined with other anti-HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti-HBV agents such as a HBV RNA replication inhibitor, a HBsAg secretion inhibitor, a HBV capsid inhibitor, an antisense oligomer (e.g. as described in WO2012/145697, WO 2014/179629 and WO2017/216390), a siRNA (e.g. described in WO 2005/014806, WO 2012/024170, WO 2012/2055362, WO 2013/003520, WO 2013/159109, WO 2017/027350 and WO2017/015175), a HBV therapeutic vaccine, a HBV prophylactic vaccine, a HBV antibody therapy (monoclonal or polyclonal), or TLR 2, 3, 7, 8 or 9 agonists for the treatment and/or prophylaxis of HBV.

Administration

The nucleic acid molecule, conjugate compounds or pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of an nucleic acid molecule, conjugate compound or pharmaceutical composition of the invention, will be governed by such considerations, and is the minimum amount necessary to inhibit HBsAg and/or HBeAg. For example, such amount may be below the amount that is toxic to the cells of the recipient, or to the mammal as a whole.

In some embodiments, the nucleic acid molecule, conjugate or pharmaceutical composition of the invention is administered at a dose of 0.1-15 mg/kg, such as from 0.2-10 mg/kg, such as from 0.25-5 mg/kg. The administration can be once a week, every $2^{nd}$ week, every third week or even once a month.

The nucleic acid molecules, conjugates or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal).

In a preferred embodiment the nucleic acid molecule, conjugate compounds or pharmaceutical compositions of the present invention are administered by a parenteral route including intravenous, intraarterial, subcutaneous, intraperitoneal or intramuscular injection or infusion. In one embodiment the active oligonucleotide or oligonucleotide conjugate is administered intravenously. With GalNAc conjugated compounds it may be advantageous to administer subcutaneously in order to delay saturation of the ASGP receptor.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

By way of example, the oligomer or the oligomer conjugate of the present invention may be used in combination with other actives, such as oligonucleotide-based antivirals—such as sequence specific oligonucleotide-based antivirals—acting either through antisense (including LNA antisense oligonucleotides as described in WO 2011/047312 or WO2015/173208 or MOE antisense oligonucleotides such as GSK3389404 or those described in WO 2012/145697 or WO 2014/79629), siRNAs (such as ARC-520, ARC-521, ARB-1467 or those described in WO2 013/003520, WO2016/077321, US 2017/0016000 or WO 2017/027350), aptamers, morpholinos or any other antiviral, nucleotide sequence-dependent mode of action.

By way of further example, the oligomer or the oligomer conjugate of the present invention may be used in combination with other actives, such as immune stimulatory antiviral compounds, such as interferon (e.g. pegylated interferon alpha), TLR7 agonists (e.g. GS-9620), TLR8 agonists (e.g. GS-9688) or therapeutic vaccines.

By way of further example, the oligomer or the oligomer conjugate of the present invention may be used in combination with other actives, such as small molecules, with antiviral activity. These other actives could be, for example, nucleoside/nucleotide inhibitors (eg entecavir or tenofovir disoproxil fumarate), encapsidation inhibitors, entry inhibitors (eg Myrcludex B).

In certain embodiments, the additional therapeutic agent may be an HBV agent, an Hepatitis C virus (HCV) agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In particular related embodiments, the additional HBV agent may be interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; pegasys; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

Embodiments of the Invention

The following embodiments of the present invention may be used in combination with any other embodiments described herein.

1. A FUBP1 inhibitor for use in the in the treatment and/or prevention of Hepatitis B virus (HBV) infection.
2. The FUBP1 inhibitor for the use of embodiment 1, wherein the FUBP1 inhibitor is administered in an effective amount.
3. The FUBP1 inhibitor for the use of embodiment 1 or 2, wherein the HBV infection is a chronic infection.
4. The FUBP1 inhibitor for the use of embodiments 1 to 3, wherein the FUBP1 inhibitor is capable of reducing cccDNA and/or pgRNA in an infected cell.
5. The FUBP1 inhibitor for the use of any one of embodiments 1 to 4, wherein the FUBP1 inhibitor prevents or reduces the binding of FUBP1 to DNA, such as cccDNA.
6. The FUBP1 inhibitor for the use of any one of embodiments 1 to 5, wherein the inhibitor prevents or reduces the FUBP1/FUSE interaction.
7. The FUBP1 inhibitor for the use of any one of embodiments 1 to 6, wherein the inhibitor interacts with the DNA binding domain of FUBP1 protein.
8. The FUBP1 inhibitor for the use of any one of embodiments 1 to 6, wherein the inhibitor interacts with a FUSE element on cccDNA.
9. FUBP1 inhibitor for the use of embodiment 6 to 8, wherein said inhibitor is a small molecule that specifically prevents or reduces binding of FUBP1 protein to cccDNA.
10. The FUBP1 inhibitor for the use of any one of embodiments 1 to 9, wherein the inhibitor is selected from the compounds of Formula VII, IX or X

VIII

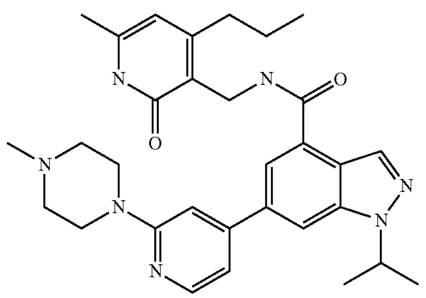

IX

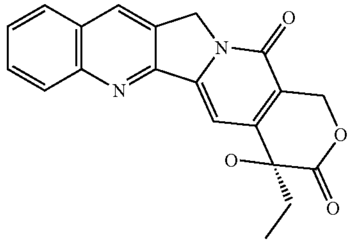

X

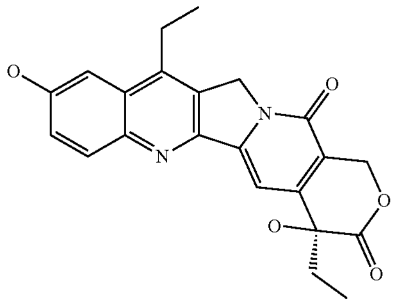

11. The FUBP1 inhibitor for the use of any one of embodiments 1 to 5, wherein said inhibitor is a genome editing machinery, comprising:
    a. a site-specific DNA nuclease or a polynucleotide encoding a site-specific DNA nuclease; and
    b. a guide RNA or a polynucleotide encoding a guide RNA.
12. The FUBP1 inhibitor for the use of any one of embodiments 1 to 5, wherein said inhibitor is a nucleic acid molecule comprising or consisting of a contiguous nucleotide sequence of 12 to 30 nucleotides in length which is at least 90% complementary to a mammalian FUBP1 target nucleic acid and capable of reducing the level of the target nucleic acid.
13. The FUBP1 inhibitor for the use of embodiment 12, wherein the target nucleic acid is RNA.
14. The FUBP1 inhibitor for the use of embodiment 13, wherein the RNA is pre-mRNA.
15. The FUBP1 inhibitor for the use of any one of embodiments 11 to 14, wherein the nucleic acid molecule is selected from a antisense oligonucleotide, siRNA or shRNA.

16. The FUBP1 inhibitor for the use of embodiments 15, wherein the nucleic acid molecule is a single stranded antisense oligonucleotide or a double stranded siRNA.
17. The nucleic acid molecule for the use of any one of embodiments 12 to 16, wherein the mammalian FUBP1 target nucleic acid is selected from SEQ ID NO: 1 to 20.
18. The nucleic acid molecule for the use of embodiment 12 to 16, wherein the mammalian FUBP1 target nucleic acid is selected from SEQ ID NO: 1 to 8.
19. The nucleic acid molecule for the use of embodiment 12 to 16, wherein the mammalian FUBP1 target nucleic acid is selected from SEQ ID NO: 1 to 4.
20. The nucleic acid molecule for the use of any one of embodiments 12 to 16, wherein the contiguous nucleotide sequence is at least 98% complementarity to the target nucleic acid of SEQ ID NO: 1 and SEQ ID NO: 5 and SEQ ID NO: 9.
21. The nucleic acid molecule for the use of any one of embodiments 12 to 16, wherein the contiguous nucleotide sequence is at least 98% complementarity to the target nucleic acid of SEQ ID NO:1 and SEQ ID NO:5.
22. The FUBP1 inhibitor for the use of any one of embodiments 1 to 21, wherein the cccDNA in an HBV infected cell is reduced by at least 50%, such as 60%, such as 70%, such as 80%, such 90%, such as 95%, such as 100%, when compared to a control.
23. The nucleic acid molecule for the use of any one of embodiments 12 to 22, wherein the FUBP1 mRNA is reduced by at least 50%, such as 60%, such as 70%, such as 80%, such as 90%, such as 95%, such as 100%, when compared to a control.
24. A nucleic acid molecule of 12 to 60 nucleotides in length which comprises or consists of a contiguous nucleotide sequence of 12 to 30 nucleotides in length wherein the contiguous nucleotide sequence is at least 90% complementary, such as 95%, such as 98%, such as fully complementarity, to a mammalian FUBP1 target nucleic acid.
25. The nucleic acid molecule of embodiment 24, wherein the nucleic acid molecule is chemically produced
26. The nucleic acid molecule of embodiment 24 or 25, wherein the mammalian FUBP1 target nucleic acid is selected from SEQ ID NO: 1 to 20.
27. The nucleic acid molecule of embodiment 24 or 25, wherein the mammalian FUBP1 target nucleic acid is selected from SEQ ID NO: 1 to 8.
28. The nucleic acid molecule of embodiment 24 or 25, wherein the mammalian FUBP1 target nucleic acid is selected from SEQ ID NO: 1 to 4.
29. The nucleic acid molecule embodiment 24 or 25, wherein the contiguous nucleotide sequence is at least 98% complementarity to the target nucleic acid of SEQ ID NO: 1 and SEQ ID NO:5 and SEQ ID NO:9.
30. The nucleic acid molecule of embodiment 24 or 25, wherein the contiguous nucleotide sequence is at least 98% complementarity to the target nucleic acid of SEQ ID NO: 1 and SEQ ID NO: 5.
31. The nucleic acid molecule of any one of embodiments 24 to 30, wherein the nucleic acid molecule is 12 to 30 nucleotides in length.
32. The nucleic acid molecule of any one of embodiments 24 to 31, wherein the nucleic acid molecule is a double stranded siRNA or a single stranded antisense oligonucleotide.
33. The nucleic acid molecule of any one of embodiments 24 to 31, wherein contiguous nucleotide sequence is complementary to a target sequence selected from the group consisting of position 14200-14218, 14413-14431, 14966-14984 and 30344-30362 on SEQ ID NO:1.
34. The nucleic acid molecule of embodiment 24 to 33, which is capable of hybridizing to a target nucleic acid of SEQ ID NO: 1 and SEQ ID NO: 5 with a $\Delta G°$ below −15 kcal.
35. The nucleic acid molecule of any one of embodiments 24 to 34, wherein the contiguous nucleotide sequence comprises or consists of at least 14 contiguous nucleotides, particularly 15, 16, 17, 18, 19, 20, 21 or 22 contiguous nucleotides.
36. The nucleic acid molecule of any one of embodiments 24 to 34, wherein the contiguous nucleotide sequence comprises or consists of from 14 to 22 nucleotides.
37. The nucleic acid molecule of embodiment 36, wherein the contiguous nucleotide sequence comprises or consists of from 16 to 18 nucleotides.
38. The nucleic acid molecule of embodiment 24 to 37, wherein the nucleic acid molecule comprises or consists of 14 to 25 nucleotides in length.
39. The nucleic acid molecule of embodiment 38, wherein the nucleic acid molecule comprises or consists of 16 to 22 nucleotides in length.
40. The nucleic acid molecule of any one of embodiments 24 to 39, wherein the contiguous nucleotide sequence has zero to three mismatches compared to the target nucleic acids it is complementary to.
41. The nucleic acid molecule of embodiment 40, wherein the contiguous nucleotide sequence has one mismatch compared to the target nucleic acids.
42. The nucleic acid molecule of embodiment 40, wherein the contiguous nucleotide sequence has two mismatches compared to the target nucleic acids.
43. The nucleic acid molecule of embodiment 40, wherein the contiguous nucleotide sequence is fully complementary to both target nucleic acid sequences.
44. The nucleic acid molecule of embodiment 24 to 43, comprising one or more modified nucleosides.
45. The nucleic acid molecule of embodiment 44, wherein the one or more modified nucleoside is a high-affinity modified nucleosides.
46. The nucleic acid molecule of embodiment 44 or 45, wherein the one or more modified nucleoside is a 2' sugar modified nucleoside.
47. The nucleic acid molecule of embodiment 46, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.
48. The nucleic acid molecule of embodiment 44-47, wherein the one or more modified nucleoside is a LNA nucleoside.
49. The nucleic acid molecule of embodiment 48, wherein the modified LNA nucleoside is selected from oxy-LNA, amino-LNA, thio-LNA, cET, and ENA.
50. The nucleic acid molecule of embodiment 48 or 49, wherein the modified LNA nucleoside is oxy-LNA with the following 2'-4' bridge $—O—CH_2—$.
51. The nucleic acid molecule of embodiment 50, wherein the oxy-LNA is beta-D-oxy-LNA.
52. The nucleic acid molecule of embodiment 48 or 49, wherein the modified LNA nucleoside is cET with the following 2'-4' bridge $—O—CH(CH_3)—$.
53. The nucleic acid molecule of embodiment 52, wherein the cET is (S)cET, i.e. 6'(S)methyl-beta-D-oxy-LNA.

54. The nucleic acid molecule of embodiment 48 or 49, wherein the LNA is ENA, with the following 2'-4' bridge —O—$CH_2$—$CH_2$—.
55. The nucleic acid molecule of any one of embodiments 24 to 54, wherein the nucleic acid molecule comprises at least one modified internucleoside linkage.
56. The nucleic acid molecule of embodiment 55, wherein the modified internucleoside linkage is nuclease resistant.
57. The nucleic acid molecule of embodiment 55 or 56, wherein the modified internucleoside linkages is a phosphorothioate internucleoside linkages.
58. The nucleic acid molecule any one of embodiments 24 to 57, wherein the nucleic acid molecule is a double stranded siRNA oligonucleotide capable of interacting with the RISC complex.
59. The nucleic acid molecule any one of embodiments 24 to 57, wherein the nucleic acid molecule is an antisense oligonucleotide capable of recruiting RNase H.
60. The antisense oligonucleotide of embodiment 59, wherein the antisense oligonucleotide or the contiguous nucleotide sequence is a gapmer.
61. The antisense oligonucleotide of embodiment 60, wherein the antisense oligonucleotide or contiguous nucleotide sequence thereof consists of or comprises a gapmer of formula 5'-F-G-F'-3', where region F and F' independently comprise or consist of 1-8 nucleosides, of which 1-4 are 2' sugar modified and defines the 5' and 3' end of the F and F' region, and G is a region between 6 and 16 nucleosides which are capable of recruiting RNaseH.
62. The antisense oligonucleotide of embodiment 61, wherein the 2' sugar modified nucleoside independently is selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
63. The antisense oligonucleotide of embodiment 61 or 62, wherein one or more of the 2' sugar modified nucleosides in region F and F' is a LNA nucleoside
64. The antisense oligonucleotide of embodiment 63, wherein all the 2' sugar modified nucleosides in region F and F' are LNA nucleosides.
65. The oligonucleotide of embodiment 62 to 64, wherein the LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET beta-D-ENA and alpha-L-ENA.
66. The antisense oligonucleotide of embodiment 62 to 65, wherein region F and F' consist of identical LNA nucleosides.
67. The antisense oligonucleotide of embodiment 62 to 66, wherein all the 2' sugar modified nucleosides in region F and F' are oxy-LNA nucleosides.
68. The antisense oligonucleotide of any one of embodiments 61 to 67, wherein the nucleosides in region G is DNA and/or alpha-L-LNA nucleosides.
69. The antisense oligonucleotide of embodiment 68, wherein region G consists of at least 75% DNA nucleosides.
70. The antisense oligonucleotide of embodiment 69, where all the nucleosides in region G are DNA nucleosides.
71. A conjugate compound comprising a nucleic acid molecule according to any one of embodiments 24 to 59 or an antisense oligonucleotide according to any one of embodiments 60 to 70, and at least one conjugate moiety covalently attached to said antisense oligonucleotide.
72. The conjugate compound of embodiment 71, wherein the nucleic acid molecule is a double stranded siRNA and the conjugate moiety is covalently attached to the sense strand of the siRNA.
73. The conjugate compound of embodiment 71 or 72, wherein the conjugate moiety is selected from carbohydrates, cell surface receptor ligands, drug substances, hormones, lipophilic substances, polymers, proteins, peptides, toxins, vitamins, viral proteins or combinations thereof.
74. The conjugate compound of any one of embodiments 71 to 73, wherein the conjugate moiety is capable of binding to the asialoglycoprotein receptor.
75. The conjugate compound of embodiment 74, wherein the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine.
76. The conjugate compound of embodiment 75, wherein the asialoglycoprotein receptor targeting moiety is N-acetylgalactosamine (GalNAc).
77. The conjugate compound of embodiment 75 or 76, wherein the conjugate moiety is mono-valent, di-valent, tri-valent or tetra-valent with respect to asialoglycoprotein receptor targeting moieties.
78. The conjugate compound of embodiment 77, wherein the conjugate moiety consists of two to four terminal GalNAc moieties and a spacer linking each GalNAc moiety to a brancher molecule that can be conjugated to the antisense compound.
79. The conjugate compound of embodiment 78, wherein the spacer is a PEG spacer.
80. The conjugate compound of embodiment 74 to 79, wherein the conjugate moiety is a tri-valent N-acetylgalactosamine (GalNAc) moiety.
81. The conjugate compound of embodiment 74 to 80, wherein the conjugate moiety is selected from one of the trivalent GalNAc moieties in FIG. 1.
82. The conjugate compound of embodiment 81, wherein the conjugate moiety is the trivalent GalNAc moiety in FIG. 1D.
83. The conjugate compound of embodiment 71-82, comprising a linker which is positioned between the nucleic acid molecule or the antisense oligonucleotide and the conjugate moiety.
84. The conjugate compound of embodiment 83, wherein the linker is a physiologically labile linker.
85. The conjugate compound of embodiment 84, wherein the physiologically labile linker is nuclease susceptible linker.
86. The oligonucleotide conjugate of embodiment 84 or 85, wherein the physiologically labile linker is composed of 2 to 5 consecutive phosphodiester linkages.
87. The conjugate compound of embodiment 74-86, which display improved cellular distribution between liver vs. kidney or improved cellular uptake into the liver of the conjugate compound as compared to an unconjugated nucleic acid molecule or antisense oligonucleotide.
88. A pharmaceutical composition comprising a nucleic acid molecule according to any one of embodiments 24 to 59 or an antisense oligonucleotide according to any one of embodiments 60 to 70, a conjugate compound of embodiment 71 to 87 or acceptable salts thereof and a pharmaceutically acceptable diluent, carrier, salt and/or adjuvant.

89. A method for identifying a compound that prevents, ameliorates and/or inhibits a hepatitis B virus (HBV) infection, comprising:
   a. contacting a test compound with
   b. FUBP1 polypeptide; or
   c. a cell expressing FUBP1;
   d. measuring the expression and/or activity of FUBP1 in the presence and absence of said test compound; and
   e. identifying a compound that reduces the expression and/or activity FUBP1 and reduces cccDNA.
90. An in vivo or in vitro method for modulating FUBP1 expression in a target cell which is expressing FUBP1, said method comprising administering the nucleic acid molecule of any one of embodiments 24 to 59 or an antisense oligonucleotide according to any one of embodiments 60 to 70, a conjugate compound of embodiment 71 to 87 or the pharmaceutical composition of embodiment 88 in an effective amount to said cell.
91. The method of embodiments 90, wherein the FUBP1 expression is reduced by at least 50%, or at least 60%, or at least 70%, or at least 80%, or at least 90%, or at least 95% in the target cell compared to the level without any treatment or treated with a control.
92. The method of embodiments 90, wherein the target cell is infected with HBV and the cccDNA in an HBV infected cell is reduced by at least 50%, or at least 60%, or at least 70%, or at least 80%, or at least 90%, or at least 95% in the HBV infected target cell compared to the level without any treatment or treated with a control.
93. A method for treating or preventing a disease comprising administering a therapeutically or prophylactically effective amount of the nucleic acid molecule any one of embodiments 24 to 59 or an antisense oligonucleotide according to any one of embodiments 60 to 70, a conjugate compound of embodiment 71 to 87 or the pharmaceutical composition of embodiment 88 to a subject suffering from or susceptible to the disease.
94. The nucleic acid molecule of any one of embodiments 24 to 59 or the antisense oligonucleotide according to any one of embodiments 60 to 70, or the conjugate compound of any one of embodiments 71 to 87 or the pharmaceutical composition of embodiment 88, for use as a medicament for treatment or prevention of a disease in a subject.
95. Use of the nucleic acid molecule any one of embodiments 24 to 59 or the antisense oligonucleotide according to any one of embodiments 60 to 70, or the conjugate compound of any one of embodiments 71 to 87 for the preparation of a medicament for treatment or prevention of a disease in a subject.
96. The method, the nucleic acid molecule, the antisense oligonucleotide, the conjugate or the use of embodiments 93-95 wherein the subject is a mammal.
97. The method, the nucleic acid molecule, the antisense oligonucleotide, the conjugate, or the use of embodiment 96, wherein the mammal is human.

EXAMPLES

The examples illustrate the invention.

Material and Methods

HepG2-NTCP Cell Line and HBV Infection

HepG2-NTCP cells (Urban et al. gastroenterology 2014, DOI:10.1053/j.gastro.2013.12.024) were cultured at 37° C. in a humidified atmosphere with 5% C02 in complete proliferation medium consisting of DMEM+GlutaMAX-1 (Gibco #31966-021), 5% HI FCII (Gibco), 1× Pen/Strep (Gibco, #15140), for 2 weeks. For HBV infection HepG2-NTCP cells were trypsinized and resuspended in Infection Medium (complete proliferation medium supplemented with 2.5% DMSO) and seeded into a 12 well plate at 400 000 cells/well. After 3 to 4 days, cells were then inoculated with HBV once they reached between 80% to 90% confluency (referred to as day 0) using 500 ul Infection Medium plus 4% PEG 8000 and HBV (MOI100) per well. After 16 h the cells were washed 3 times with phosphate-buffered saline and the medium was replaced every 3-4 days with 1 ml Modified Infection Medium (complete proliferation medium supplemented with 3.5% DMSO) per well. HBV genotype D was derived from HepAD38 cell culture supernatant and concentrated using PEG precipitation (Ladner et al 1997 Antimicrobial Agents and Chemotherapy 41(8) 171-1720).

HeLa Cell Lines

HeLa cell line was purchased from European Collection of Authenticated Cell Cultures (ECACC, #93021013) and maintained as recommended by the supplier in a humidified incubator at 37° C. with 5% C02. For assays, 2,500 cells/well were seeded in a 96 multi well plate in Eagle's Minimum Essential Medium (Sigma, M2279) with 10% fetal bovine serum (FBS), 2 mM Glutamin AQ, 1% NEAA, 25 μg/ml Gentamicin.

Primary Mouse Hepatocytes (PMH)

Primary mouse hepatocytes were isolated from livers of C57BL/6J mice anesthetized with Pentobarbital after a 2 step perfusion protocol according to the literature (Berry and Friend, 1969, J. Cell Biol; Paterna et al., 1998, Toxicol. Appl. Pharmacol.). The first step was 5 min with HBSS+15 mM HEPES+0.4 mM EGTA followed by 12 min HBSS+20 mM $NaHCO_3$+0.04% BSA (Sigma #A7979)+4 mM CaCL2 (Sigma #21115)+0.2 mg/ml Collagenase Type 2 (Worthington #4176). The Hepatocytes were captured in 5 ml cold Williams medium E (WME) (Sigma #W1878, complemented with 1× Pen/Strep/Glutamine, 10% (v/v) FBS (ATCC #30-2030)) on ice.

The crude cell suspension was filtered through a 70 μm followed by a 40 μm cell strainer (Falcon #352350 and #352340), filled up to 25 ml with WME and centrifuged at room temperature for 5 min at 50× g to pellet the hepatocytes. The supernatant was removed and the hepatocytes were resuspended in 25 ml WME. After adding 25 ml 90% Percoll solution (Sigma #P4937; pH=8.5-9.5) and centrifugation for 10 min at 25° C., 50× g the supernatant and floating cells were removed. To remove the remaining Percoll the pellet was resuspended again in 50 mL WME medium, centrifuged 3 min, 25° C. at 50× g and the supernatant discarded. The cell pellet was resuspended in 20 mL WME and cell number and viability determined (Invitrogen, Cellcount) and diluted to 250,000 cells/ml. 25,000 cells/well were seeded on collagen-coated 96-well plates (PD Biocoat Collagen I #356407) and incubated at 37° C., 5% CO2. 24 h after seeding the oligonucleotides were added in the desired concentration and the cells were incubated at 37° C., 5% C02 for 72 hours.

HBV Infected PHH Cells

Fresh primary human hepatocytes (PHH) were provided by PhoenixBio, Higashi-Hiroshima City, Japan (Cat #PXB-cells) in 24-well plate format. Upon arrival the PHH were infected with an MOI of 25GE using HepG2 2.2.15-derived HBV by incubating the PHH cells with HBV in 4% (v/v) PEG in PHH medium for 16 hours. The cells were then washed thrice with PBS and cultured in a humidified atmosphere with 5% C02 in fresh PHH medium consisting of DMEM (GIBCO, Cat #21885) supplemented with 10% (v/v) heat-inactivated fetal bovine serum (GIBCO, Cat #10082), 2% (v/v) DMSO, 1% (v/v) Penicillin/Streptomycin (GIBCO, Cat #15140-148), 20 mM HEPES (GIBCO, Cat #15630-080), 44 mM $NaHCO_3$(Wako, Cat #195-14515), 15 ug/ml L-proline (MP-Biomedicals, Cat #0219472825), 0.25 ug/ml Insulin (Sigma, Cat #11882), 50 nM Dexamethasone (Sigma, Cat #D8893), 5 ng/ml EGF (Sigma, Cat #E9644), and 0.1 mM L-Ascorbic acid 2-phosphate (Wako, Cat #013-12061).

siRNA Sequences and Compounds

TABLE 4

Human FUBP1 sequences targeted by individual FUBP1 siRNA molecules

| SEQ ID NO: | FUBP1 target sequence | Position on SEQ ID NO: 1 | Exon | Individual siRNA | Dharmacon catalog No. |
|---|---|---|---|---|---|
| 21 | GACAAACCUCUUAGGAUUA | 14200-14218 | 9 | FU2 | J-011548-06 |
| 22 | GAGAAGUUCGGAAUGAGUA | 14413-14431 | 10 | FU4 | J-011548-08 |
| 23 | GAAAGGAUAGCACAAAUAA | 14966-14984 | 12 | FU1 | J-011548-05 |
| 24 | AAUAAGAAGUGGACAAUAC | 30344-30362 | 20 | FU3 | J-011548-07 |

The pool of siRNA (ON-TARGET plus SMART pool siRNA Cat. No. L-011548-00-0005, Dharmacon) contains the four individual siRNA molecules listed in table 4 and are available.

Single Stranded Antisense Oligonucleotides

TABLE 4A

List of oligonucleotide motif sequences (indicated by SEQ ID NO), designs of these, as well as specific oligonucleotide compounds (indicated by CMP ID NO) designed based on the motif sequence.

| SEQ ID NO | Motif sequence | Design | Oligonucleotide compound | CMP ID NO | Start position on SEQ ID NO: 1 |
|---|---|---|---|---|---|
| 34 | ataaccatagtcatttga | 3-12-3 | ATAaccatagtcattTGA | 34_1 | 9138 |
| 35 | cccataaccatagtcat | 3-12-2 | CCCataaccatagtcAT | 35_1 | 9142 |
| 36 | gagccatctacacataaa | 2-12-4 | GAgccatctacacaTAAA | 36_1 | 10016 |
| 37 | caagagccatctacacat | 3-13-2 | CAAgagccatctacacAT | 37_1 | 10019 |
| 38 | tgtccatttaagaatcca | 4-12-2 | TGTCcatttaagaatcCA | 38_1 | 10144 |
| 39 | ttgtgtccatttaagaat | 4-12-2 | TTGTgtccatttaagaAT | 39_1 | 10147 |
| 40 | tacctttgctgctgat | 3-11-2 | TACctttgctgctgAT | 40_1 | 11472 |
| 41 | gactatacctttgctgc | 2-13-2 | GActatacctttgctGC | 41_1 | 11476 |
| 42 | actttgtattcttctgtcat | 1-16-3 | ActttgtattcttctgtCAT | 42_1 | 12020 |
| 43 | actttgtattcttctgtc | 2-14-2 | ACtttgtattcttctgTC | 43_1 | 12022 |
| 44 | gattcaggtgttccagtta | 1-16-2 | GattcaggtgttccagtTA | 44_1 | 12393 |
| 45 | ttcaaacttactggaca | 3-11-3 | TTCaaacttactggACA | 45_1 | 12412 |
| 46 | tacatctatcccttcat | 2-12-3 | TAcatctatcccttCAT | 46_1 | 14452 |
| 47 | ttacatctatcccttc | 2-10-4 | TTacatctatccCTTC | 47_1 | 14454 |
| 48 | cttcctattacaatgccaac | 1-17-2 | CttcctattacaatgccaAC | 48_1 | 14776 |
| 49 | atttcttcctattacaatg | 2-14-3 | ATttcttcctattacaATG | 49_1 | 14781 |
| 50 | ccatttcttcctattacaa | 3-14-2 | CCAtttcttcctattacAA | 50_1 | 14783 |
| 51 | gtttaaaatacattgcc | 2-11-4 | GTttaaaatacatTGCC | 51_1 | 15537 |
| 52 | gagtttaaaatacattgcc | 2-14-3 | GAgtttaaaatacattGCC | 52_1 | 15537 |
| 53 | gctttttatggtttcacc | 1-15-2 | GctttttatggtttcaCC | 53_1 | 16183 |
| 54 | atgctttttatggtttcacc | 1-17-2 | AtgctttttatggtttcaCC | 54_1 | 16183 |

TABLE 4A-continued

List of oligonucleotide motif sequences (indicated by SEQ ID NO), designs of these, as well as specific oligonucleotide compounds (indicated by CMP ID NO) designed based on the motif sequence.

| SEQ ID NO | Motif sequence | Design | Oligonucleotide compound | CMP ID NO | Start position on SEQ ID NO: 1 |
|---|---|---|---|---|---|
| 55 | ataatcaacctgtccagct | 1-16-2 | AtaatcaacctgtccagCT | 55_1 | 23804 |
| 56 | ataatcaacctgtccagc | 1-15-2 | AtaatcaacctgtccaGC | 56_1 | 23805 |
| 57 | ataatcaacctgtccag | 1-12-4 | AtaatcaacctgtCCAG | 57_1 | 23806 |
| 58 | tataatcaacctgtccag | 2-13-3 | TAtaatcaacctgtcCAG | 58_1 | 23806 |
| 59 | gtataatcaacctgtccag | 1-15-3 | GtataatcaacctgtcCAG | 59_1 | 23806 |
| 60 | ataatcaacctgtcca | 1-11-4 | AtaatcaacctgTCCA | 60_1 | 23807 |
| 61 | tataatcaacctgtcca | 1-12-4 | TataatcaacctgTCCA | 61_1 | 23807 |
| 62 | gtataatcaacctgtcca | 1-14-3 | GtataatcaacctgtCCA | 62_1 | 23807 |
| 63 | gtataatcaacctgtcc | 3-12-2 | GTAtaatcaacctgtCC | 63_1 | 23808 |
| 64 | tataatcaacctgtcc | 2-10-4 | TAtaatcaacctGTCC | 64_1 | 23808 |
| 65 | cccattttcttgtagta | 2-13-2 | CCcattttcttgtagTA | 65_1 | 23841 |
| 66 | acccattttcttgtagta | 1-15-2 | AcccattttcttgtagTA | 66_1 | 23841 |
| 67 | tacccattttcttgtagta | 1-16-2 | TacccattttcttgtagTA | 67_1 | 23841 |
| 68 | atacccattttcttgtagta | 1-17-2 | AtacccattttcttgtagTA | 68_1 | 23841 |
| 69 | atacccattttcttgtag | 1-14-3 | AtacccattttcttgTAG | 69_1 | 23843 |
| 70 | catacccattttcttgtag | 2-15-2 | CAtacccattttcttgtAG | 70_1 | 23843 |
| 71 | catacccattttcttgta | 2-14-2 | CAtacccattttcttgTA | 71_1 | 23844 |
| 72 | tggagctaattcaggagt | 2-14-2 | TGgagctaattcaggaGT | 72_1 | 30264 |
| 73 | aaatggagctaattcaggag | 3-14-3 | AAAtggagctaattcagGAG | 73_1 | 30265 |
| 74 | ttgtccacttcttattatt | 1-14-4 | TtgtccacttcttatTATT | 74_1 | 30341 |
| 75 | ccccacacaatgaagcaa | 2-14-2 | CCccacacaatgaagcAA | 75_1 | 30368 |
| 76 | ttcatcaagtcgtctgcat | 1-16-2 | TtcatcaagtcgtctgcAT | 76_1 | 30412 |
| 77 | gatcttcatcaagtcgtc | 1-15-2 | GatcttcatcaagtcgTC | 77_1 | 30417 |
| 78 | atattaacctcctatcagt | 1-15-3 | AtattaacctcctatcAGT | 78_1 | 30511 |
| 79 | aatattaacctcctatcag | 3-13-3 | AATattaacctcctatCAG | 79_1 | 30512 |
| 80 | atttatatcacaaagcatc | 2-13-4 | ATttatatcacaaagCATC | 80_1 | 30616 |
| 81 | aagtacatttatatcaca | 4-12-2 | AAGTacatttatatcaCA | 81_1 | 30623 |
| 82 | catttattgtaaagcacaaa | 2-14-4 | CAtttattgtaaagcaCAAA | 82_1 | 30675 |
| 83 | atcatttattgtaaagca | 2-12-4 | ATcatttattgtaaAGCA | 83_1 | 30679 |

Motif sequences represent the contiguous sequence of nucleobases present in the oligonucleotide.

Designs refer to the gapmer design, F-G-F', where each number represents the number of consecutive modified nucleosides, e.g. 2' modified nucleosides (first number=5' flank), followed by the number of DNA nucleosides (second number=gap region), followed by the number of modified nucleosides, e.g. 2' modified nucleosides (third number=3' flank), optionally preceded by or followed by further repeated regions of DNA and LNA, which are not necessarily part of the contiguous sequence that is complementary to the target nucleic acid.

Oligonucleotide compounds represent specific designs of a motif sequence. Capital letters represent beta-D-oxy LNA nucleosides, lowercase letters represent DNA nucleosides, all LNA C are 5-methyl cytosine, and 5-methyl DNA cytosines are presented by "e", all internucleoside linkages are phosphorothioate internucleoside linkages.

siRNA Transfection and Treatment Protocol for HBV Infected Cells siRNA treatments were performed in HepG2-NTCP or PHH. Cells were transfected at day 4 and day 6 post infection with 100 ul/well transfection mixture containing 25 nM of either scramble siRNA (ON-TARGETpus Non-targeting siRNA, D-001810-01, Dharmacon, CO, USA), FUBP1 pool or single siRNA (SMARTpool: ON-TARGETplus human FUBP1 siRNA, L-011548-00, Dharmacon, CO, USA) or no siRNA (OptiMEM) (0.5 ul/well) diluted in OptiMEM (50 ul/well, Thermo Fisher Scientific Reduced Serum media), and mixed for 5 minutes prior to transfection with Lipofectamine® RNAiMAX Transfection Reagent (3 ul/well) (Thermofisher Scientific catalog No. 13778) diluted in OptiMEM (50 ul/well).

For PHH southern blot, cells were also treated with an HBV-specific siRNA (HBx siRNA) used as negative control (2 pmol). The HBV-specific siRNA was custom made (GE Life science) (Sense: 5'-GCACUUCGCUUCACCUCUG-3' SEQ ID NO: 84) in addition to a second negative control (sicontrol) the Silencer® Negative Control #1 siRNA (Thermo Fisher Scientific). The transfection mixture was added to the cells with 1 ml of DMEM without DMSO and Pen/Strep for 24 h, then medium was replaced with HepG2 NTCP and PHH cell culture medium respectively. The cells were harvested at day 8 post infection (after 4 days of siRNA treatment) and stored at −80° C. for analysis of FUBP1 mRNA knockdown and the quantification of viral parameters.

Southern Blot Protocol

For Southern blot, cccDNA purification from HBV infected PHH was conducted using an adapted Hirt extraction protocol previously described in Hirt B 1967 J Mol Biol 26:365-369; and Cai D 2013 Methods Mol Biol. 1030:151-61. Briefly, cells were lysed with HIRT lysis buffer (10 mM Tris pH8, 10 mM EDTA, 0.7% SDS, 2 ul Ambion RNase Mix/ml buffer) to disrupt lipid membranes and viral capsids in order to release all the viral nucleic acids. RNA was removed by RNAse treatment before precipitating down with NaCl (5M, overnight at 4° C.) the high-molecular-weight cellular chromatin, proteins and protein-associated DNA including the HBV DNA replicative intermediates with viral polymerase covalently attached. After the overnight high-salt protein precipitation, viral DNA (enriched cccDNA) was extracted from the clarified lysates by direct phenol extraction.

DNA was then quantified and adjusted to load on an agarose gel (1.8% in TAE buffer) 15 μg of each samples in 15 μl per well. DNA ladder (NEB Quick-Load 1 kb), and recombinant HBV were also loaded and the gel was run at 50V for 3 h30 min.

For the Southern Blot, the gel was submerged in denaturing buffer (0.5 M NaOH (50 ml), 1.5 M NaCl (150 ml)) and rocked for 30 minutes at room temperature to separate the double-stranded DNA into single DNA strands for later hybridization to the probe. The transfer of DNA from the agarose gel to Hybond-XL membrane (Cat. No: RPN2020S, GE Healthcare) was done using Whatman Nytran SuPerCharge (SPC) TurboBlotter Kit (Cat. No: WHA10416328, Sigma). After transfer, the membrane was cross linked in a UV crosslinker chamber with UV energy dosage at 1800 J. A DIG-labelled RNA probe was generated using HBV plasmid DNA (HBV Genotype D cloned into a pGEM3Z plasmid) and the following primers:

```
Forward Primer HBVT7 + Fwd
                                        (SEQ ID NO: 89)
5'-taatacgactcactatagggthttcacctctgcctaatcatc-3'

Reverse Primer HBVRev
                                        (SEQ ID NO: 90)
5'-cctctagagcggccgcaaaaagttgcatggtgctggt-3'
```

with the DIG RNA Labeling Kit ((SP6/T7) Cat no 11175025910, Roche).

The membrane was then hybridized with the DIG-labelled probe in DIG Easy Hyb buffer (Cat. No: 11603558001, Roche) at 50° C. overnight while rotating in the hybridization oven. The membrane was then washed and incubated with CDP-Star with NitroBlock minutes before exposing to film. Detection of the signal was done with Fusion Fx (VILBER).

HBV Antigen Measurements

To evaluate the impact on HBV antigen expression and secretion, supernatants from the cell cultures can be collected. The HBV propagation parameters, HBsAg and HBeAg levels, are measured using CLIA ELISA Kits (Autobio Diagnostic #CL0310-2, #CL0312-2), according to the manufacturer's protocol. Briefly, 25 μL of supernatant per well is transferred to the respective antibody coated microtiter plate and 25 μL of enzyme conjugate reagent is added. The plate is incubated for 60 min on a shaker at room temperature before the wells are washed five times with washing buffer using an automatic washer. 25 μL of substrate A and B were added to each well. The plates are incubated on a shaker for 10 min at room temperature before luminescence is measured using an Envision luminescence reader (Perkin Elmer).

Real-Time PCR for Intracellular HBV pgRNA and FUBP1 RNA

FUBP1 RNA and HBV pgRNA were quantified by RTqPCR using SYBR green. Results were normalized over the human Gus B endogenous control. The mRNA expression was analysed using the comparative cycle threshold 2-ΔΔCt method normalized to the reference gene Gus B and to non-treated cells. Primers used for FUBP1 RNA and HBV pgRNA quantification are listed in table 5. RTqPCR conditions were as follow: 48° C., 15 min (RT step); 95° C., 10 min; 40 cycles at 95° C., 15 sec and 60° C., 1 min.

TABLE 5

FUBP1 and HBV pgRNA qPCR primers

| Parameter | | Primer Sequence | SEQ ID |
|---|---|---|---|
| FUBP1: | Fwd | TGTCCAGTCAGCAAAACGGTT | 25 |
| | Rev | GAACTGCATTTCCCGGTCCAT | 26 |
| HBV pgRNA (modified from Volz et al. Gastroenterology 2007) | Fwd | GGAGTGTGGATTCGCACTCCT | 27 |
| | Rev | AGATTGAGATCTTCTGCGAC | 28 |
| | probe | [6FAM]-AGGCAGGTCCCCTA GAAGAAGAACTCC-[BHQ1] | 29 |

Housekeeping gene primers Gus B: Hs99999908_m1 (Thermo Fisher Scientific)

HBV DNA and cccDNA Taqman qPCR

DNA was extracted from HBV infected cells (HepG2 NTCP or PHH) using the MasterPure™ DNA Purification Kit (Epicentre, Madison, Wis. USA) protocol. cccDNA levels were determined after digestion with T5 exonuclease (New England Biolabs, MA, USA) using 10 U of T5 for 500 ng of DNA, 1 hour at 37° C. in 20 ul total volume. After digestion, the samples were diluted to 50 ul of which 4 ul were used for the qPCR reaction. Quantitative real-time polymerase chain reaction measurements were performed on the ViiA7 Real-Time PCR System (Life Technologies). qPCR was performed with the Taqman® Fast Advanced Master Mix (Life Technologies, Cat. No 4444557). qPCR conditions were as follow: 50° C., 2 min; 95° C., 10 min; 40 cycles at 95° C., 15 sec and 60° C., 1 min. cccDNA Primers and probe are shown in table 6.

TABLE 6 cccDNA qPCR primers and probe.

| Parameter | | Primer Sequence | SEQ ID NO |
|---|---|---|---|
| cccDNA | Fwd | 5'-CCGTGTGCACTTCGCTTCA-3' | 30 |
| | Rev | 5'-GCACAGCTTGGAGGCTTGA-3' | 31 |
| | Probe | 5'-[6FAM]CATGGAGACCACCG TGAACGCCC[BHQ1]-3' | 32 |

The cccDNA primer and probes are described in Malmström et al. 2012 PLoS ONE 7(7): e36349.

b-globin was quantified using the HBB TaqMan® Gene Expression assay (ID Hs00758889_s1, Thermofischer scientific) and total HBV DNA with Taqman primers (Pa03453406_s1, Thermofischer).

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 μmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle, a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THE/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10p 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2× $T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Example 1: Chromatin Immunoprecipitation (ChiP) of FUBP1 in HBV Infected HepG2-NTCP In this experiment, it was investigated whether FUBP1 binds to cccDNA. In brief, chromatin fragments from HBV infected cells were immunoprecipitated with a FUBP1-specific antibody and it was analysed whether cccDNA was pulled down together with the FUBP1 Ab.

HBV infected HepG2-NTCP cells (see materials and method section) were crossed link with 1% formaldehyde in Williams medium without serum or antibiotics for 10 minutes and the reaction was stopped by adding 0.125 M glycine in PBS 1×, 5 min at room temperature. Cells were washed 2 times with cold PBS and harvested with a cell scraper. The pelleted cells were collected after centrifugation at 4500 rpm for 10 min at 4° C. in the presence of 1 ml of PBS 1× with PIC 1× and PMSF 1 mM and stored at −80° C. before proceeding to the chromatin immunoprecipitation. Nuclear extraction was performed using a dounce (tight pestle) after 30 minutes of incubation on ice in Nuclei Lysis buffer (PIPES 5 mM, KCl 85 mM, NP-40 0.5%, PMSF 1 mM and PIC 1×)

Isolated cross-linked nuclei were sheared by sonication in a 1% SDS sonication buffer to generate cellular chromatin fragments of 200-500 bp. Chromatin amounts from $2\times10^6$ cells was separated, 1/10 of this was saved to serve as reference input sample and the reminder was subjected to immunoprecipitation with antibody for 14-16 hours at 4° C. (ChIP is further described in Pollicino et al 2006 Gastroenterology 130:823-837). The antibody used for the immunoprecipitation was 5 ug FUBP1-specific Ab (C15410233 Diagenode). After the reverse cross-linking step, the precipitated chromatin sample and the input sample were subjected to Phenol: Chlorophorm: Isoamyl Alcohol (25:24:1) DNA extraction and cccDNA was then quantified by qPCR (see materials and method section on HBV cccDNA quantification starting with T5 exonuclease treatment and with the change that the cccDNA is not normalized to b-globulin (not precipitated by the antibody), but is expressed as the percentage of cccDNA in the input sample).

cccDNA amount in the samples precipitated with and without FUBP Ab is expressed as % of cccDNA in the input sample (non-ChIP treated sample). The results are shown in table 7. The values represent the mean of three independent experiments.

TABLE 7

| cccDNA immunoprecipitated with a FUBP1-specific antibody or control. | % cccDNA of input sample | |
|---|---|---|
| | Mean | SD |
| NoAb | 0.0043 | 0.0025 |
| FUBP1 | 0.1528 | 0.0364 |

The ChIP experiment showed significant enrichment of FUBP1 protein bound to cccDNA compared to negative control (NoAb).

Example 2: Effect of siRNAs Targeting FUBP1 on HBV Parameters in HBV Infected HepG2-NTCP Cells In the following experiment, the effect of FUBP1 knock-down on the HBV parameters, HBV pgRNA and cccDNA, was tested.

HBV infected HepG2-NTCP cells were treated with the pool of siRNAs from Dharmacon (L-011548-00) as described in the Materials and Method section "siRNA transfection and treatment protocol for HBV infected cells".

Following the 4 days-treatment, FUBP1 mRNA, cccDNA and pgRNA were measured by qPCR. FUBP1 mRNA and pgRNA RT-qPCR was described in the materials and method section "Real-time PCR for intracellular HBV pgRNA and FUBP1 RNA". For cccDNA absolute quantification in HepG2 NTCP cells, b-globin was measured using 500 ng non-digested DNA in a total volume of 50 ul of which 4 ul were used in the qPCR and used for normalization. Commercial genomic DNA was used for the standard curve for b-globin and an HBV plasmid DNA (HBV Genotype D cloned into a pGEM3Z plasmid) was used for cccDNA standard curve. The cccDNA primers used were those described in the Material and Method section "HBV DNA and cccDNA taqman qPCR". The results are shown in table 8.

TABLE 8 effect on HBV parameters following knockdown of FUBP1 with pool of siRNA

| | FUBP1 mRNA* (n = 3) | | HBV pgRNA* (n = 4) | | cccDNA/b-globin (n = 4)^ | |
|---|---|---|---|---|---|---|
| | Mean | SD | Mean | SD | Mean | SD |
| No treatment | 1.22 | 0.80 | 2.85 | 1.46 | 0.08 | 0.07 |
| siRNA control | 1.13 | 0.11 | 2.82 | 0.55 | 0.10 | 0.08 |
| FUBP1 siRNA | 0.25 | 0.27 | 1.12 | 0.55 | 0.03 | 0.04 |

*FUBP1 and HBV pgRNA were normalized to housekeeping gene Gus B.

^siRNA control was n = 3

From this it can be seen that the FUBP1 siRNA pool is capable of reducing FUBP1 mRNA as well as HBV pgRNA quite efficiently. A trend showing reduction of cccDNA is also observed, despite the short treatment time.

Example 3: Effect of siRNAs Targeting FUBP1 on HBV Parameters in HBV Infected PHH Cells In the following experiment, the effect of FUBP1 knock-down on the HBV parameters, HBV pgRNA, cccDNA and HBV DNA, was tested in HBV infected primary human hepatocytes (PHH), HBV infected PHH cells were treated with the pool of siRNAs used in Example 2 (Dharmacon L-011548-00) as well as four individual siRNA compounds FU1, FU2, FU3 and FU4 listed in the siRNA sequence and compound section of the materials and methods. The treatment was conducted as described in the materials and method section "siRNA transfection and treatment protocol for HBV infected cells".

Following the 4 days-treatment, FUBP1 mRNA, cccDNA and pgRNA were measured by qPCR in technical duplicate. FUBP1 mRNA and pgRNA RT-qPCR was described in the Materials and Method section "Real-time PCR for intracellular HBV pgRNA and FUBP1 RNA". HBV DNA was measured as described in the Materials and Methods section "HBV DNA and cccDNA taqman quantification qPCR" The HBV DNA was normalized to the housekeeping gene b-globin using the indicated Taqman primers. For cccDNA quantification, SYBR green primers for cccDNA and mitochondrial DNA (MitoDNA, housekeeping control) were performed using Fast SYBR™ green master mix (Thermo Fischer) and the following primers:

```
cccDNA:
                              (SEQ ID NO: 85)
Fwd 5'-CGTCTGTGCCTTCTCATCTGC-3;

                              (SEQ ID NO: 86)
Rev 5'-GCACAGCTTGGAGGCTTGAA-3'

MitoDNA:
                             ((SEQ ID NO: 87)
Fwd 5'-CCGTCTGAACTATCCTGCCC-3';

                              (SEQ ID NO: 88)
Rev 5'-GCCGTAGTCGGIGTACTCGT-3'
```

qPCR conditions: 95° C. 5 min, then 45 cycles of 95° C.-1 sec, 60° C.-35 sec

The results are shown in table 9 as the relative expression to non-treated cells using the comparative cycle threshold 2-ΔΔCt method (i.e. the lower the number the larger the target reduction).

TABLE 9 effect on HBV parameters following knockdown of FUBP1 with siRNA targeting FUBP1

| | FUBP1 mRNA# | | HBV pgRNA# | | cccDNA* | | HBV DNA** | |
|---|---|---|---|---|---|---|---|---|
| | Mean | SD | Mean | SD | Mean | SD | Mean | SD |
| Non-treated | 1.030 | 0.105 | 1.00 | 0.07 | 1.00 | 0.04 | 1.00 | 0.07 |
| FUBP1 siRNA pool | 0.66 | 0.04 | 0.61 | 0.04 | 0.64 | 0.06 | 0.70 | 0.04 |
| FU1 | 0.68 | 0.02 | 0.53 | 0.10 | 0.62 | 0.04 | 0.51 | 0.04 |
| FU2 | 0.72 | 0.02 | 0.43 | 0.06 | 0.61 | 0.11 | 0.96 | 0.03 |

TABLE 9-continued effect on HBV parameters following knockdown of FUBP1 with siRNA targeting FUBP1

| | FUBP1 mRNA# | | HBV pgRNA# | | cccDNA* | | HBV DNA** | |
|---|---|---|---|---|---|---|---|---|
| | Mean | SD | Mean | SD | Mean | SD | Mean | SD |
| FU3 | 0.60 | 0.01 | 0.45 | 0.02 | 0.70 | 0.03 | 0.94 | 0.03 |
| FU4 | 0.71 | 0.02 | 0.38 | 0.01 | 0.78 | 0.09 | 0.61 | 0.03 |

*cccDNA was normalized to mitochondrial DNA reference gene
**HBV DNA was normalized to b-globin housekeeping gene
#FUBP1 mRNA and HBV pgRNA was normalized to Gus B housekeeping gene.

From this it can be seen that the FUBP1 siRNA pool as well as the individual siRNA compounds are capable of reducing FUBP1 mRNA and cccDNA by 30 to 40%. The HBV pgRNA is reduced even further. HBV DNA reduction is observed for the pool of siRNA's and the individual siRNA's FU1 and FU4. The lack of reduction observed with individual siRNA's FU2 and FU3 may be due to the short treatment times since HBV DNA reduction generally require longer treatment times.

The ability of the FUBP1 siRNA pool to reduce cccDNA was confirmed by Southern blot and compared with an HBV targeting siRNA (HBx) which is known not to reduce cccDNA.

HBV infected PHH cells were treated as described in Materials and Method section "siRNA transfection and treatment protocol for HBV infected cells" and the Southern blot was performed as described in the Materials and Methods section "Southern Blot protocol".

Figure 3:
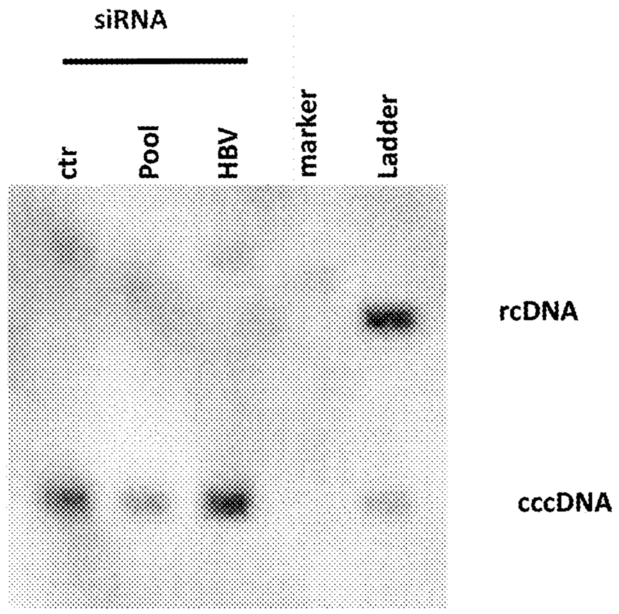
FIG. 3: Southern blot from HBV infected PPH cells treated either with control (ctr) or the pool of FUBP1 targeting siRNA's (Pool) or HBV siRNA (HBV).

The Southern blot is shown in FIG. 3 and confirms the qPCR results in this example, since it is clearly seen that the Pool of FUBP1 targeting siRNA's are capable of reducing the cccDNA band whereas the HBV targeting siRNA does (as expected) not result in any reduction of cccDNA when compared to the control.

Example 4: The Effect of FUBP1 Small Molecule Inhibitors on HBV Parameters in HBV Infected PHH Cells Several small molecules have been suggested to affect FUBP1 binding to the FUSE element on DNA. In the following we tested the effect of SN-38 (formula X herein) and GSK343 (formula VIII herein) for their ability to affect HBV parameters, HBV pgRNA, cccDNA and HBV DNA as well as FUBP1 mRNA levels.

The treatments were performed in HBV infected PHH cells (See Materials and Methods) with small molecules SN-38 (Toronto research chemical, TRC-S589960) and GSK343 (MedChemExpress, MCE-HY-13500) used at 1 μM. The treatment was performed twice weekly starting day 7 and up to day 25 post infection (i.e. treatment was performed on day 7, 11, 14, 18, 21 and 25 post infection). The cells were harvested at day 12 and day 25 post infection (5 days and 18 days of treatment). Following the 5 days or 18 days treatment, FUBP1 mRNA, cccDNA, pgRNA and HBV DNA were measured by qPCR in technical duplicate. FUBP1 mRNA and pgRNA RT-qPCR was measured as described in the materials and method section "Real-time PCR for intracellular HBV pgRNA and FUBP1 RNA". HBV DNA and cccDNA was normalized to b-globin housekeeping gene as described in the Material and Methods section "HBV DNA and cccDNA taqman qPCR".

The results are shown in table 10A and 10B as the relative expression to non-treated cells (i.e. the lower the number the larger the target reduction). The toxicity of the compounds was also tested using a standard CCK8 toxicity assay, and no cell toxicity was observed for the two compounds (data not shown).

TABLE 10A

Effect on HBV parameters after 5 days treatment with FUBP1 small molecule inhibitors in HBV infected PPH.

| | FUBP1 mRNA* | | HBV pgRNA# | | cccDNA | | HBV DNA* | |
|---|---|---|---|---|---|---|---|---|
| | Mean | SD | Mean | SD | Mean | SD | Mean | SD |
| Non-treated | 1.00 | 0.09 | 1.00 | 0.05 | 1.01 | 0.17 | 1.01 | 0.06 |
| SN-38 1 uM | 1.04 | 0.01 | 0.54 | 0.03 | 0.60 | 0.10 | 0.42 | 0.00 |
| GSK343 1 uM | 0.90 | 0.01 | 0.99 | 0.02 | 1.18 | 0.22 | 1.05 | 0.07 |

TABLE 10B

Effect on HBV parameters after 18 days treatment with FUBP1 small molecule inhibitors in HBV infected PPH

| | FUBP1 mRNA# | | HBV pgRNA# | | cccDNA* | | HBV DNA* | |
|---|---|---|---|---|---|---|---|---|
| | Mean | SD | Mean | SD | Mean | SD | Mean | SD |
| Non-treated | 1.00 | 0.06 | 1.00 | 0.00 | 1.23 | 0.95 | 1.04 | 0.32 |
| SN-38 1 uM | 0.96 | 0.06 | 0.89 | 0.15 | 0.84 | 0.02 | 0.51 | 0.01 |

TABLE 10B-continued

Effect on HBV parameters after 18 days treatment with FUBP1 small molecule inhibitors in HBV infected PPH

| | FUBP1 mRNA# | | HBV pgRNA# | | cccDNA* | | HBV DNA* | |
|---|---|---|---|---|---|---|---|---|
| | Mean | SD | Mean | SD | Mean | SD | Mean | SD |
| GSK343 1 uM | 1.27 | 0.17 | 1.34 | 0.09 | 0.34 | 0.16 | 1.29 | 0.34 |

*cccDNA HBV DNA was normalized to b-globin housekeeping gene

#FUBP1 mRNAand HBVpgRNA were normalized to Gus B housekeeping gene

From these data it can be seen that the FUBP1 small molecule inhibitors do not affect FUBP1 mRNA, which is expected since they act as antagonists of the FUBP1 protein. SN-38 has a significant effect on all three HBV parameters at day 12 at day 25 the effects on pgRNA and cccDNA seem to be rebounding. GSK343 does not have a marked effect on pgRNA and HBV DNA, the reduction of cccDNA is however more than 65% at day 25, indicating that this compound requires longer exposure to be effective, but then it is very effective on cccDNA. It remains to be shown if an even longer exposure would also lead to effects on pgRNA and HBVDNA.

Example 5: The Ability of Single Stranded LNA Antisense Oligonucleotides to Reduce FUBP In Vitro in HeLa Cells The antisense oligonucleotides listed in table 4a were tested for their ability to reduce FUBP1 in HeLa cells.

HeLa cells were cultured as described in the Materials and Method section. The cells were incubated for 24 hours before addition of oligonucleotides dissolved in PBS. Final concentration of oligonucleotides was 5 and 25 μM, the final culture volume was 100 μl/well. The cells were harvested 3 days after addition of oligonucleotide compounds. RNA was extracted using RNeasy 96 extraction kit (Qiagen) and followed by one-step RT-QPCR (Quanta Bioscience, qScript XLT 1-Step RT-qPCR ToughMix) using TaqMan assays for the target genes (FUBP1: Hs.PT.58.26883775 FAM T)) and house keeping gene (GUSB 4326320E (Thermo Fisher)) according to the manufacturer's protocols.

The relative FUBP1 mRNA expression levels are shown in table 11 as % of average control samples (PBS-treated cells) i.e. the lower the value the larger the inhibition.

TABLE 11 in vitro efficacy of anti-FUBP1 compounds (single experiment with duplex QPCR). FUBP1 mRNA levels are normalized to GUSB in HeLa cells and shown as % of control (PBS treated cells).

| CMP | % FUBP1 mRNA of control | | | | |
|---|---|---|---|---|---|
| ID | 5 μM | | 25 μM | | |
| NO | Avg | sd | Avg | sd | Compound (CMP) |
| 34_1 | 65.5 | 1.4 | 35.2 | 2.0 | ATAaccatagtcattTGA |
| 35_1 | 58.5 | 0.1 | 27.4 | 0.7 | CCCataaccatagtcAT |
| 36_1 | 81.6 | 0.1 | 57.5 | 4.9 | GAgccatctacacaTAAA |
| 37_1 | 85.7 | 2.0 | 64.6 | 0.9 | CAAgagccatctacacAT |

TABLE 11-continued in vitro efficacy of anti-FUBP1 compounds (single experiment with duplex QPCR). FUBP1 mRNA levels are normalized to GUSB in HeLa cells and shown as % of control (PBS treated cells).

| CMP | % FUBP1 mRNA of control | | | | |
|---|---|---|---|---|---|
| ID | 5 μM | | 25 μM | | |
| NO | Avg | sd | Avg | sd | Compound (CMP) |
| 38_1 | 74.8 | 4.1 | 49.9 | 0.3 | TGTCcatttaagaatcCA |
| 39_1 | 76.2 | 0.9 | 61.2 | 1.4 | TTGTgtccatttaagaAT |
| 40_1 | 78.1 | 2.7 | 64.2 | 3.1 | TACctttgctgctgAT |
| 41_1 | 88.2 | 3.9 | 66.0 | 0.8 | GActatacctttgctGC |
| 42_1 | 82.7 | 2.9 | 63.2 | 0.5 | ActttgtattcttctgtCAT |
| 43_1 | 76.3 | 1.4 | 56.3 | 0.8 | ACtttgtattcttctgTC |
| 44_1 | 89.5 | 3.9 | 69.9 | 4.9 | GattcaggtgttccagtTA |
| 45_1 | 87.3 | 4.5 | 66.3 | 5.4 | TTCaaacttactggACA |
| 46_1 | 81.1 | 3.0 | 60.3 | 0.1 | TAcatctatcccttCAT |
| 47_1 | 83.8 | 0.5 | 52.7 | 1.7 | TTacatctatccCTTC |
| 48_1 | 74.9 | 12.7 | 64.1 | 2.7 | CttcctattacaatgccaAC |
| 49_1 | 81.3 | 3.3 | 68.7 | 2.2 | ATttcttcctattacaATG |
| 50_1 | 60.9 | 9.3 | 43.2 | 5.7 | CCAtttcttcctattacAA |
| 51_1 | 69.6 | 3.1 | 50.5 | 2.4 | GTttaaaatacatTGCC |
| 52_1 | 68.5 | 0.9 | 53.3 | 1.0 | GAgtttaaaatacattGCC |
| 53_1 | 69.6 | 1.6 | 46.8 | 1.2 | GctttttatggtttcaCC |
| 54_1 | 77.5 | 1.6 | 65.9 | 3.2 | AtgctttttatggtttcaCC |
| 55_1 | 86.8 | 3.3 | 77.8 | 2.7 | AtaatcaacctgtccagCT |
| 56_1 | 85.0 | 6.1 | 82.6 | 0.0 | AtaatcaacctgtccaGC |
| 57_1 | 84.2 | 0.9 | 71.8 | 1.0 | AtaatcaacctgtCCAG |
| 58_1 | 82.1 | 1.3 | 73.3 | 1.2 | TAtaatcaacctgtcCAG |
| 59_1 | 81.4 | 0.6 | 71.2 | 0.1 | GtataatcaacctgtcCAG |
| 60_1 | 86.2 | 1.6 | 64.8 | 2.1 | AtaatcaacctgTCCA |
| 61_1 | 86.0 | 1.3 | 66.4 | 1.5 | TataatcaacctgTCCA |
| 62_1 | 79.3 | 2.5 | 59.5 | 0.6 | GtataatcaacctgtCCA |
| 64_1 | 88.9 | 7.2 | 56.6 | 1.5 | GTAtaatcaacctgtCC |

TABLE 11-continued in vitro efficacy of anti-FUBP1 compounds (single experiment with duplex QPCR). FUBP1 mRNA levels are normalized to GUSB in HeLa cells and shown as % of control (PBS treated cells).

| CMP | % FUBP1 mRNA of control | | | | |
|---|---|---|---|---|---|
| ID | 5 µM | | 25 µM | | |
| NO | Avg | sd | Avg | sd | Compound (CMP) |
| 63_1 | 68.8 | 9.1 | 33.7 | 1.0 | TAtaatcaacctGTCC |
| 65_1 | 63.0 | 1.2 | 37.7 | 1.8 | CCcattttcttgtagTA |
| 66_1 | 87.4 | 1.4 | 67.9 | 1.9 | AcccattttcttgtagTA |
| 67_1 | 88.8 | 3.7 | 81.2 | 1.1 | TacccattttcttgtagTA |
| 68_1 | 94.7 | 3.1 | 84.9 | 0.3 | AtacccattttcttgtagTA |
| 69_1 | 87.1 | 1.8 | 64.6 | 0.1 | AtacccattttcttgTAG |
| 70_1 | 83.6 | 6.8 | 81.3 | 0.7 | CAtacccattttcttgtAG |
| 71_1 | 90.2 | 4.9 | 85.6 | 2.4 | CAtacccattttcttgTA |
| 72_1 | 76.8 | 1.9 | 62.8 | 1.5 | TGgagctaattcaggaGT |
| 73_1 | 82.6 | 1.1 | 66.9 | 0.5 | AAAtggagctaattcagGAG |
| 74_1 | 73.3 | 0.8 | 67.5 | 2.5 | TtgtccacttcttatTATT |
| 75_1 | 75.9 | 1.0 | 47.2 | 0.9 | CCccacacaatgaagcAA |
| 76_1 | 75.2 | 0.1 | 53.0 | 3.4 | TtcatcaagtcgtctgcAT |
| 77_1 | 55.2 | 3.9 | 35.2 | 2.2 | GatcttcatcaagtcgTC |
| 78_1 | 83.5 | 3.6 | 69.2 | 0.5 | AtattaacctcctatcAGT |
| 79_1 | 66.5 | 0.4 | 45.7 | 0.2 | AATattaacctcctatCAG |
| 80_1 | 63.0 | 2.7 | 30.2 | 3.0 | ATttatatcacaaagCATC |
| 81_1 | 61.2 | 1.3 | 36.9 | 2.5 | AAGTacatttatatcaCA |
| 82_1 | 84.6 | 0.9 | 68.5 | 0.5 | CAtttattgtaaagcaCAAA |
| 83_1 | 61.7 | 0.5 | 40.4 | 1.8 | ATcatttattgtaaAGCA |

From these data is can be seen that 80% of the single stranded antisense oligonucleotides tested are capable of reducing FUBP1 by at least 30% at the 25 µM dose.

Example 6: The Ability of Single Stranded LNA Antisense Oligonucleotides to Reduce FUBP1 In Vitro in PMH Cells The oligonucleotides screened in Example 5 also target mouse FUBP1. To verify that the reduction of FUBP1 observed in the human HeLa cells also translates to hepatocytes, which is the cell type to be targeted in the treatment of HBV, the same library was tested in primary mouse hepatocytes (PMH).

The screening in PMH cells was conducted as described in the "Materials and Methods" section under "Primary mouse Hepatocytes" using 5 µM and 25 µM oligonucleotide, the final culture volume was 100 p/well.

RNA isolation and qPCR to measure FUBP1 mRNA expression levels were conducted as described in example 5 using the following mouse specific primers instead Fubp1: Mm.PT.58.7603777 FAM-MGB (IDT), and a house keeping gene (GusB Mm_01197698_ml VIC-MGB (IDT) (Thermo Fisher).

The relative FUBP1 mRNA expression levels are shown in table 12 as % of average control samples (PBS-treated cells) i.e. the lower the value the larger the inhibition.

TABLE 12 in vitro efficacy of anti-FUBP1 compounds (single experiment with duplex QPCR). FUBP1 mRNA levels are normalized to GUSB in HeLa cells and shown as % of control (PBS treated cells).

| CMP | % FUBP1 mRNA of control | | | | |
|---|---|---|---|---|---|
| ID | 5 µM | | 25 µM | | |
| NO | Avg | sd | Avg | sd | Compound (CMP) |
| 34_1 | 46.1 | 2.5 | 25.2 | 0.5 | ATAaccatagtcattTGA |
| 35_1 | 48.0 | 0.1 | 29.0 | 1.1 | CCCataaccatagtcAT |
| 36_1 | 32.7 | 0.7 | 52.9 | 1.6 | GAgccatctacacaTAAA |
| 37_1 | 50.0 | 1.4 | 48.2 | 0.4 | CAAgagccatctacacAT |
| 38_1 | 48.4 | 1.6 | 35.4 | 0.7 | TGTCcatttaagaatcCA |
| 39_1 | 41.6 | 0.7 | 41.5 | 1.5 | TTGTgtccatttaagaAT |
| 40_1 | 59.2 | 1.1 | 52.8 | 0.5 | TACctttgctgctgAT |
| 41_1 | 88.5 | 1.1 | 59.6 | 0.9 | GActatacctttgctGC |
| 42_1 | 75.8 | 2.0 | 66.9 | 1.9 | ActttgtattcttctgtCAT |
| 43_1 | 71.0 | 2.1 | 59.4 | 0.5 | ACtttgtattcttctgTC |
| 44_1 | 71.4 | 1.4 | 56.7 | 1.2 | GattcaggtgttccagtTA |
| 45_1 | 60.5 | 1.7 | 41.1 | 1.0 | TTCaaacttactggACA |
| 46_1 | 57.5 | 0.3 | 41.5 | 1.2 | TAcatctatcccttCAT |
| 47_1 | 44.5 | 0.5 | 38.3 | 0.5 | TTacatctatccCTTC |
| 48_1 | 58.7 | 0.1 | 45.2 | 0.3 | CttcctattacaatgccaAC |
| 49_1 | 65.0 | 3.6 | 48.2 | 1.4 | ATttcttcctattacaATG |
| 50_1 | 11.7 | 3.2 | 9.0 | 2.6 | CCAtttcttcctattacAA |
| 51_1 | 64.5 | 0.8 | 48.1 | 0.9 | GTttaaaatacatTGCC |
| 52_1 | 68.1 | 1.2 | 51.9 | 1.5 | GAgtttaaaatacattGCC |
| 53_1 | 46.1 | 1.3 | 33.2 | 0.5 | GctttttatggtttcaCC |
| 54_1 | 62.3 | 1.6 | 46.9 | 2.3 | AtgctttttatggtttcaCC |
| 55_1 | 77.8 | 0.1 | 66.3 | 1.6 | AtaatcaacctgtccagCT |
| 56_1 | 78.0 | 2.9 | 60.4 | 1.7 | AtaatcaacctgtccaGC |
| 57_1 | 51.1 | 1.7 | 29.2 | 0.8 | AtaatcaacctgtCCAG |
| 58_1 | 53.7 | 2.6 | 37.7 | 0.4 | TAtaatcaacctgtcCAG |
| 59_1 | 62.8 | 0.1 | 37.0 | 2.1 | GtataatcaacctgtcCAG |
| 60_1 | 51.6 | 0.3 | 40.3 | 0.8 | AtaatcaacctgTCCA |
| 61_1 | 55.3 | 2.0 | 38.1 | 0.8 | TataatcaacctgTCCA |
| 62_1 | 38.5 | 0.9 | 26.4 | 0.1 | GtataatcaacctgtCCA |
| 64_1 | 58.2 | 2.4 | 39.7 | 0.8 | GTAtaatcaacctgtCC |
| 63_1 | 24.7 | 1.0 | 12.6 | 0.4 | TAtaatcaacctGTCC |
| 65_1 | 29.8 | 0.8 | 19.1 | 0.3 | CCcattttcttgtagTA |

TABLE 12-continued in vitro efficacy of anti-FUBP1 compounds (single experiment with duplex QPCR). FUBP1 mRNA levels are normalized to GUSB in HeLa cells and shown as % of control (PBS treated cells).

| CMP ID NO | % FUBP1 mRNA of control | | | | Compound (CMP) |
|---|---|---|---|---|---|
| | 5 µM | | 25 µM | | |
| | Avg | sd | Avg | sd | |
| 66_1 | 71.9 | 0.1 | 54.9 | 0.3 | AcccattttcttgtagTA |
| 67_1 | 77.4 | 1.2 | 75.0 | 0.2 | TacccattttcttgtagTA |
| 68_1 | 80.5 | 4.0 | 84.1 | 1.0 | AtacccattttcttgtagTA |
| 69_1 | 67.4 | 0.9 | 49.2 | 1.1 | AtacccattttcttgTAG |
| 70_1 | 77.7 | 0.1 | 67.7 | 2.8 | CAtacccattttcttgtAG |
| 71_1 | 80.1 | 2.6 | 76.3 | 2.5 | CAtacccattttcttgTA |
| 72_1 | 64.5 | 2.7 | 47.1 | 0.8 | TGgagctaattcaggaGT |
| 73_1 | 59.1 | 0.9 | 47.8 | 0.8 | AAAtggagctaattcagGAG |
| 74_1 | 59.1 | 1.1 | 43.2 | 2.2 | TtgtccacttcttatTATT |
| 75_1 | 45.0 | 0.9 | 50.2 | 0.8 | CCccacacaatgaagcAA |
| 76_1 | 52.9 | 1.2 | 40.7 | 0.6 | TtcatcaagtcgtctgcAT |
| 77_1 | 41.5 | 0.1 | 14.8 | 0.1 | GatcttcatcaagtcgTC |
| 78_1 | 68.4 | 2.9 | 54.4 | 0.8 | AtattaacctcctatcAGT |
| 79_1 | 51.4 | 0.8 | 34.7 | 0.3 | AATattaacctcctatCAG |
| 80_1 | 40.3 | 0.8 | 26.3 | 1.2 | ATttatatcacaaagCATC |
| 81_1 | 36.6 | 1.2 | 24.2 | 1.1 | AAGTacatttatatcaCA |
| 82_1 | 51.3 | 5.7 | 45.9 | 0.9 | CAtttattgtaaagcaCAAA |
| 83_1 | 56.0 | 2.6 | 30.6 | 1.4 | ATcatttattgtaaAGCA |

From these data it can be seen that single stranded LNA gapmer oligonucleotides tested in PMH generally are capable of reducing FUBP1 mRNA in hepatocytes and with a higher efficacy than observed in the HeLa cells.

Example 7: The Effect of a Single Stranded LNA Antisense Oligonucleotide on HBV Parameters in HBV Infected PHH Cells Based on the hepatocyte screening in Example 6 the LNA antisense oligonucleotide with CMP ID NO: 50_1 was selected to confirm that the FUBP1 reduction also resulted in an effect on cccDNA in HBV infected PHH cells.

The HBV infected PPH cells (see Materials and Methods section "HBV infected PHH cells") were treated twice weekly for 2 weeks (i.e. the treatment was performed on day 4, 8, 11, 15, 18, 22 post infection) with 10 µM of FUBP1 LNA in PHH medium and cells were harvested at day 18 and day 25 post infection (14 and 21 days of treatment respectively) for FUBP1 mRNA knockdown and cccDNA qPCR measurement compared to the non-treated group.

The HBV cccDNA and FUBP1 mRNA reduction was measured at day 14 and day 21 following treatment. The results are shown in table 13

TABLE 13

FUBP1 mRNA and cccDNA reduction following treatment with a single stranded LNA antisense oligonucleotide.

| | FUBP1 mRNA | | cccDNA | |
|---|---|---|---|---|
| | Mean | SD | Mean | SD |
| D14 | | | | |
| Non treated | 1.005 | 0.09291573 | 1.054 | 0.36328887 |
| CMP ID NO: 50_1 | 0.395 | 0.0212132 | 0.337 | 0.02969848 |
| D21 | | | | |
| Non treated | 1.016125 | 0.19331428 | 1.0275 | 0.28483972 |
| CMP ID NO: 50_1 | 0.3975 | 0.02505328 | 0.3945 | 0.0205061 |

From this it can be seen that the oligonucleotide of CMP ID NO: 50_1 can reduce cccDNA by 60%.

In summary the examples of the present application show that a double stranded siRNA molecules, FUBP1 small molecule inhibitors, and single stranded antisense oligonucleotides targeting FUBP1 all are capable of reducing cccDNA in HBV infected cells confirming the relevance of FUBP1 in maintaining cccDNA stability.

The invention claimed is:

1. A method of treating Hepatitis B virus (HBV) infection in a subject suffering from HBV infection, the method comprising administering a therapeutically effective amount of a FUBP1 inhibitor, a pharmaceutically acceptable salt thereof, or a pharmaceutical composition thereof to the subject suffering from HBV infection, wherein:

the FUBP1 inhibitor is a nucleic acid molecule of 12 to 60 nucleotides in length comprising or consisting of a contiguous nucleotide sequence of 12 to 30 nucleotides in length that is at least 95 percent complementary to a mammalian FUBP1 target nucleic acid and is capable of reducing FUBP1 mRNA when administered to the subject suffering from HBV infection; and the nucleic acid molecule is selected from (a) a single stranded antisense oligonucleotide, (b) a siRNA molecule; and (c) a shRNA molecule.

2. The method of claim 1, wherein the subject suffering from HBV infection is suffering from a chronic HBV infection.

3. The method of claim 1, wherein the FUBP1 inhibitor is capable of reducing cccDNA and/or pgRNA in an infected cell of the subject.

4. The method of claim 1, wherein the FUBP1 inhibitor prevents or reduces the FUBP1/FUSE interaction in the subject.

5. The method of claim 1, wherein the mammalian FUBP1 target nucleic acid is selected from SEQ ID NOs: 1 to 8.

6. The method of claim 1, wherein the contiguous nucleotide sequence is at least 98% complementary to the target nucleic acid of SEQ ID NO: 1 and SEQ ID NO: 5.

7. The method of claim 1, wherein the cccDNA in an HBV infected cell is reduced by at least 60% when compared to a control.

8. The method of claim 1, wherein the FUBP1 mRNA is reduced by at least 60% when compared to a control.

9. The method of claim 1, wherein the contiguous nucleotide sequence is complementary to a target sequence selected from the group consisting of position 14200-14218, 14413-14431, 14966-14984 and 30344-30362 on SEQ ID NO: 1.

10. An in vivo or in vitro method for modulating FUBP1 expression in a target cell which is expressing FUBP1, said method comprising administering a nucleic acid molecule in an effective amount to said cell, wherein:

the nucleic acid molecule is of 12 to 60 nucleotides in length and comprises or consists of a contiguous nucleotide sequence of 12 to 30 nucleotides in length;

wherein the contiguous nucleotide sequence has at least 95% complementarity to a mammalian FUBP1 target nucleic acid;

the contiguous nucleotide sequence is complementary to a target sequence selected from the group consisting of position 14200-14218, 14413-14431, 14966-14984 and 30344-30362 on SEQ ID NO: 1; and wherein the target cell is a liver cell.

* * * * *